(12) United States Patent
Mao et al.

(10) Patent No.: US 11,021,486 B2
(45) Date of Patent: Jun. 1, 2021

(54) COUMARIN-LIKE CYCLIC COMPOUND AS MEK INHIBITOR AND USE THEREOF

(71) Applicants: CSTONE PHARMACEUTICALS, Grand Cayman (KY); CSTONE PHARMACEUTICALS (SUZHOU) CO., LTD., Jiangsu (CN); CSTONE PHARMACEUTICALS (SHANGHAI) CO., LTD., Shanghai (CN)

(72) Inventors: Qinghua Mao, Shanghai (CN); Chengde Wu, Shanghai (CN); Yong Huang, Shanghai (CN); Zhen Gong, Shanghai (CN); Jian Li, Shanghai (CN); Shuhui Chen, Shanghai (CN)

(73) Assignees: CSTONE PHARMACEUTICALS, Grand Cayman (KY); CSTONE PHARMACEUTICAL (SUZHOU) CO., LTD., Suzhou (CN); CSTONE PHARMACEUTICALS (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 16/625,258

(22) PCT Filed: Jun. 22, 2018

(86) PCT No.: PCT/CN2018/092457
§ 371 (c)(1),
(2) Date: Dec. 20, 2019

(87) PCT Pub. No.: WO2018/233696
PCT Pub. Date: Dec. 27, 2018

(65) Prior Publication Data
US 2020/0148695 A1     May 14, 2020

(30) Foreign Application Priority Data

Jun. 23, 2017 (CN) .......... 201710488401.X
Jun. 11, 2018 (CN) .......... 201810596587.5

(51) Int. Cl.
*C07D 491/052* (2006.01)
*A61P 35/00* (2006.01)

(52) U.S. Cl.
CPC .......... *C07D 491/052* (2013.01); *A61P 35/00* (2018.01)

(58) Field of Classification Search
None
See application file for complete search history.

(56) References Cited

U.S. PATENT DOCUMENTS

2010/0004233 A1  1/2010  Iikura et al.
2016/0244410 A1  8/2016  Tu et al.

FOREIGN PATENT DOCUMENTS

| CN | 102964326 A | 3/2013 |
|---|---|---|
| CN | 105153142 A | 12/2015 |
| CN | 105287509 A | 2/2016 |
| CN | 106810558 A | 6/2017 |
| JP | 2016155776 A | 9/2016 |
| RU | 2428420 C2 | 9/2011 |
| WO | WO-2007096259 A1 | 8/2007 |
| WO | WO-2008079814 A2 | 7/2008 |
| WO | WO-2008127274 A2 | 10/2008 |
| WO | WO-2010003022 A1 | 1/2010 |
| WO | WO-2012162293 A1 | 11/2012 |
| WO | WO-2014169843 A1 | 10/2014 |
| WO | WO-2015058589 A1 | 4/2015 |

OTHER PUBLICATIONS

Office Action issued in the counterpart Canadian Patent Application No. 3,067,941 dated Feb. 12, 2020.
Office Action issued in the counterpart Japanese Patent Application No. 2019-571352 dated Jun. 9, 2020.
Office Action issued in the counterpart Russian Patent Application No. 2020100608/04 dated Aug. 17, 2020.
Extended European Search Report issued in the counterpart European Patent Application No. 18819636.4 dated Mar. 20, 2020.
Office Action issued in the counterpart Israeli Patent Application No. 271550 dated Apr. 23, 2020.
Han, Shunlin et al. "Identification of Coumarin Derivatives as a Novel Class of Allosteric MEKI Inhibitors" Bioorganic & Medical Chemistry Letters, vol. 15, Sep. 30, 2005 (Sep. 30, 2005), pp. 5467-5473.
Nikam, B.P. "Synthesis of Acetyl and Iodo Derivatives of 4-Hydroxy-6-phenyl-6H-pyrano[3, 2-c]pyridine-2, 5-diones and 4-Hydroxy-1-Phenylpyridin-2(1H)-Ones", *J.Heterocyclic Chem.*, vol. 54, Apr. 26, 2016 (Apr. 26, 2016), pp. 546-551.

(Continued)

*Primary Examiner* — Emily A Bernhardt
*Assistant Examiner* — Laura M Daniel
(74) *Attorney, Agent, or Firm* — Harness, Dickey & Pierce, P.L.C.

(57) ABSTRACT

Disclosed are a class of coumarin-like cyclic compounds as MEK inhibitors and pharmaceutical compositions comprising the compounds, and the use of same in the preparation of a drug for treating MEK-related diseases. Particularly disclosed are compounds as shown in formula (I) and pharmaceutically acceptable salts thereof or tautomers thereof.

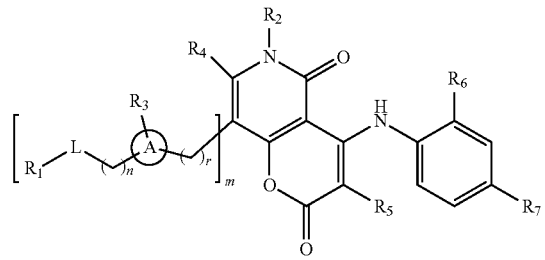

24 Claims, No Drawings

(56) References Cited

OTHER PUBLICATIONS

A. V. Khokhlatchev et al., "Phosphorylation of the MAP kinase ERK2 promotes its homodimerization and nuclear translocation", Cell, 1998, vol. 93, p. 605-615.
T. S. Lewis et al., "Identification of novel MAP kinase pathway signaling targets by functional proteomics and mass spectrometry", Molecular Cell, 2000, vol. 6, p. 1343-1354.
H. Davies et al., "Mutations of the BRAF gene in human cancer", Nature, 2002, vol. 417, p. 949-954.
R. Hoshino et al., "Constitutive activation of the 41-/43-kDa mitogen-activated protein kinase signaling pathway in human tumors", Oncogene, 1999, vol. 18, p. 813-822.
International Search Report and Written Opinion of PCT/CN2018/092457 dated Sep. 21, 2018.
N. G. Ahn et al., "Pharmacologic inhibitors of MKK1 and MKK2", Methods in Enzymology, 2001, vol. 332, p. 417-431.
Written Opinion issued in the counterpart Singaporean Patent Application No. 11201912997T dated Sep. 24, 2020.

COUMARIN-LIKE CYCLIC COMPOUND AS MEK INHIBITOR AND USE THEREOF

CROSS-REFERENCE TO RELATED APPLICATIONS

This application is a 371 National Phase of International Application No. PCT/CN2018/092457, filed Jun. 22, 2018, which claims the benefit of Chinese Patent Application No. CN201710488401.X, filed Jun. 23, 2017 and Chinese Patent Application No. CN201810596587.5, filed Jun. 11, 2018. The entire disclosures of the above applications are incorporated herein by reference.

FIELD OF THE INVENTION

The present disclosure relates to a class of coumarin-like cyclic compounds as MEK inhibitors and a pharmaceutical composition containing the same, and a use thereof in manufacturing a medicament for treating a MEK-related disease, particularly relates to a compound represented by formula (I) and a pharmaceutically acceptable salt thereof.

BACKGROUND OF THE INVENTION

MAPK pathway is involved in a series of cellular processes such as cell proliferation, differentiation, apoptosis and stress response. There are four known MAPK pathways: ERK1/2, JNK, p38 and ERK5. One of the most important and widely known MAPK pathways is the Ras/Raf kinase pathway. In this pathway, firstly extracellular growth factors (i.e., PDGF or EGF, etc.) combine with transmembrane receptors (i.e., PDGFR or EGFR or ErbB2, etc.), activating the receptors, and the activated receptors induce the intramembranous Ras to combine with GTP and be activated via a guanylate exchange factor (e.g., SOS); the activated Ras further indirectly phosphorylates and activates Raf (MAPKKK in this pathway); then, the activated Raf induces the phosphorylation of the two serine residues of MEK1/2 (MAPKK in this pathway) (MEK1 corresponds to S218 and S222; MEK2 corresponds to S222 and S226) (Ahn et al., *Methods in Enzymology*, 2001, 332, 417-431). The phosphorylated ERK dimerizes and accumulates in the nucleus (Khokhlatchev et al., *Cell*, 1998, 93, 605-615). The ERK in the nucleus involves in many cellular functions, including but not limited to nuclear transport, signal transduction, DNA repair, nucleosome assembly and migration, and mRNA processing and translation (Ahn et al., *Molecular Cell*, 2000, 6, 1343-1354).

The RAF-MEK-ERK pathway can transmit proliferation and anti-apoptotic signals from growth factors and oncogenic factors, thereby promoting cell growth, development and metastasis; the mutations of the genes involved in the pathway or the overexpression of the growth factors, downstream signaling proteins or the protein kinases will lead to uncontrolled cell proliferation and eventually tumorigenesis. For example, mutations in cancer cells cause overexpression of growth factors, leading to continuous activation of the internal MAPK pathway; or the inability to deactivate the activated Ras complexes due to mutations also will cause continuous activation of the MAPK pathway; recently, bRaf mutations have been identified in more than 60% of melanomas (Davies, H. et al., *Nature*, 2002, 417, 949-954). These bRaf mutations lead to spontaneous activation of the MAPK cascade. Spontaneous or excessive activation of the MAPK pathway has also been observed in studies of primary tumor samples and cell lines such as pancreatic cancer, colon cancer, lung cancer, ovarian cancer and kidney cancer (Hoshino, R. et al., *Oncogene*, 1999, 18, 813-822). Therefore, there is a strong correlation between overactive MAPK pathway due to gene mutations and cancer.

As the MAPK pathway locates at the central position of cell proliferation and differentiation, inhibition of this pathway will be beneficial for the treatment of a variety of hyperproliferative diseases, and MEK located downstream of Ras and Raf in the pathway has become a key role in this pathway. In addition, currently known substrates that can be phosphorylated and activated by MEK are only MAPK, namely ERK1 and ERK2. This strict selectivity and the unique ability of its bifunctional kinase make it become an attractive drug target, with potential and widespread therapeutic applications, such as malignant and benign hyperproliferative diseases, immune regulation and inflammation.

Targeting at the MAPK signaling pathway, multiple Raf and MEK inhibitors are currently developed in clinical and launching stages. For example, Sorafenib (Bay 43-9006) approved by the FDA in December 2005 is a non-specific serine/threonine and tyrosine kinase inhibitor, its targets include Raf, MEK, VEGFR2/3, Flt-3, PDGFR, c-Kit, etc. B-Raf specific inhibitors such as Dabrafenib (GSK21 18436) and Vemurafenib (PLX4032) have good clinical efficacy, but the duration is short, and clinical studies have found that the long-term treatment with B-Raf inhibitors can lead to acquired drug resistance of the patients. Therefore, MEK inhibitors are usually used in combination with B-Raf inhibitors clinically. Trametinib (GSK-1 120212), a specific inhibitor of MEK1/2, was approved by the FDA in May 2013, and was approved in January 2014 for the treatment of advanced melanoma in combination with Dabrafenib; Cobimetinib is an inhibitor that specifically inhibits MEK1/2 and was approved by the FDA in 2015 for the treatment of melanoma in combination with Vemurafenib. Binimetinib was applied to the FDA in 2016 for use in the treatment of N-RAS mutant melanoma. In addition, there are MEK1/2 inhibitors such as Selumetinib and Refametinibd in clinical stage.

Currently, a series of patent applications relating to MEK inhibitors are disclosed, including WO2007/096259, WO2010/003022, WO2012/162293, WO2014/169843, WO2015/058589, etc.

SUMMARY OF THE INVENTION

The present disclosure provides a compound represented by formula (I), a pharmaceutically acceptable salt thereof or a tautomer thereof:

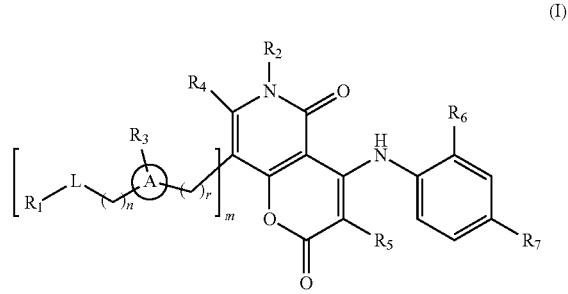

(I)

wherein,
n is selected form 0, 1 or 2;
r is selected from 0, 1, 2 or 3;

m is selected from 0 or 1; when m is 0, then

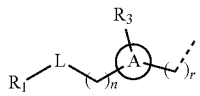

is H;

ring A is selected from phenyl or 5-6 membered heteroaryl;

L is selected from a single bond, —S(=O)—, —S(=O)$_2$—, —C(=O)—, —NH—, —NH—C(=O)—, —NH—C(=O)—O—, —NH—S(=O)$_2$—, —NH—S(=O)— and —NH—C(=O)—NH—, wherein the —NH—, —NH—C(=O)—, —NH—C(=O)—O—, —NH—S(=O)$_2$—, —NH—S(=O)— and —NH—C(=O)—NH— are each optionally substituted by 1, 2 or 3 R;

$R_1$ is selected from H, NH$_2$, C$_{1-6}$ alkyl, 3-6 membered heterocycloalkyl, C$_{3-6}$ cycloalkyl and C$_{1-3}$ heteroalkyl, wherein the NH$_2$, C$_{1-6}$ alkyl, 3-6 membered heterocycloalkyl, C$_{3-6}$ cycloalkyl and C$_{1-3}$ heteroalkyl are each optionally substituted by 1, 2 or 3 R;

$R_2$ is selected from H, C$_{1-6}$ alkyl, C$_{1-6}$ heteroalkyl, C$_{3-6}$ cycloalkyl and 5-6 membered heterocycloalkyl, wherein the C$_{1-6}$ alkyl, C$_{1-6}$ heteroalkyl, C$_{3-6}$ cycloalkyl and 5-6 membered heterocycloalkyl are each optionally substituted by 1, 2 or 3 R;

$R_3$ is selected from H, F, Cl, Br, I, C$_{1-3}$ alkyl, C$_{1-3}$ alkoxy, C$_{1-4}$ alkynyl, C$_{1-4}$ alkenyl and phenyl, wherein the C$_{1-3}$ alkyl, C$_{1-3}$ alkoxy, C$_{1-4}$ alkynyl, C$_{1-4}$ alkenyl and phenyl are each optionally substituted by 1, 2 or 3 R;

$R_4$ and $R_5$ are independently selected from H, F, Cl, Br, I, NH$_2$, OH, C$_{1-6}$ alkyl and C$_{1-3}$ alkoxy, wherein the C$_{1-6}$ alkyl and C$_{1-3}$ alkoxy are each optionally substituted by 1, 2 or 3 R;

or, $R_3$ and $R_4$ are linked together to form a 5-7 membered cycloalkyl, 5-7 membered heterocycloalkyl, 5-7 membered aryl or 5-7 membered heteroaryl;

$R_6$ and $R_7$ are independently selected from H, F, Cl, Br, I, CH$_3$, Et, CH$_3$—O— and CH$_3$—CH$_2$—O—;

R is selected from F, Cl, Br, I, OH, NH$_2$, C$_{1-3}$ alkyl and C$_{1-3}$ heteroalkyl, wherein the NH$_2$, C$_{1-3}$ alkyl and C$_{1-3}$ heteroalkyl are each optionally substituted by 1, 2 or 3 R';

R' is selected from F, Cl, Br, I, NH$_2$ or C$_{1-3}$ alkyl;

each of the "hetero" in the 5-6 membered heteroaryl, 5-6 membered heterocycloalkyl, 3-6 membered heterocycloalkyl, C$_{1-3}$ heteroalkyl, 5-7 membered heterocycloalkyl, 5-7 membered heterocycloalkyl, 5-7 membered aryl and 5-7 membered heteroaryl is independently selected from —NH—, N, —O—, —S(=O)$_2$—, —S(=O)$_2$—NH—, —NH—S(=O)$_2$—NH—, —C(=O)—NH—, —S(=O)—, —C(=O)—, —S(=O)—NH— and —O—C(=O)—NH—;

in any of the above cases, the number of the heteroatom or heteroatomic group is independently selected from 1, 2, 3 or 4.

In some embodiments of the present disclosure, R' is selected from F, Cl, Br, I, NH$_2$ or CH$_3$.

In some embodiments of the present disclosure, R is selected from F, Cl, Br, I, OH, NH$_2$, methyl, ethyl, C$_{1-3}$ alkyl-S(=O)$_2$—NH—, C$_{1-3}$ alkyl-S(=O)$_2$—, C$_{1-3}$ alkyl-C(=O)—NH— and C$_{1-3}$ alkyl-O—, wherein the NH$_2$, methyl, ethyl, C$_{1-3}$ alkyl-S(=O)$_2$—NH—, C$_{1-3}$ alkyl-S(=O)$_2$—, C$_{1-3}$ alkyl-C(=O)—NH— and C$_{1-3}$ alkyl-O— are each optionally substituted by 1, 2 or 3 R'.

In some embodiments of the present disclosure, R is selected from F, Cl, Br, I, OH, NH$_2$, CH$_3$,

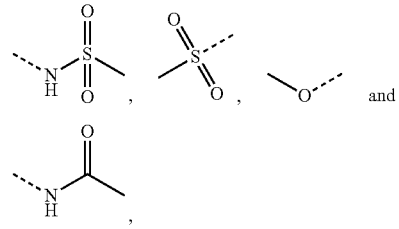

wherein the NH$_2$, CH$_3$,

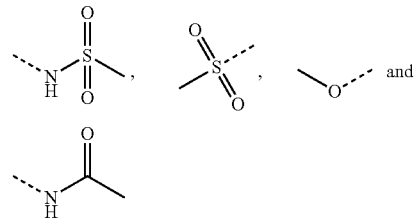

are each optionally substituted by 1, 2 or 3 R'.

In some embodiments of the present disclosure, R is selected from F, Cl, Br, I, OH, NH$_2$, CH$_3$,

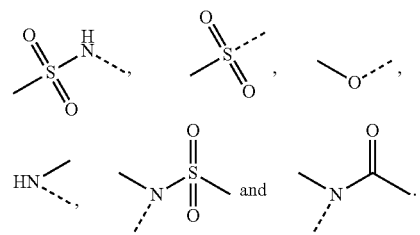

In some embodiments of the present disclosure, ring A is selected from phenyl, pyridyl or pyrazinyl.

In some embodiments of the present disclosure, ring A is selected from

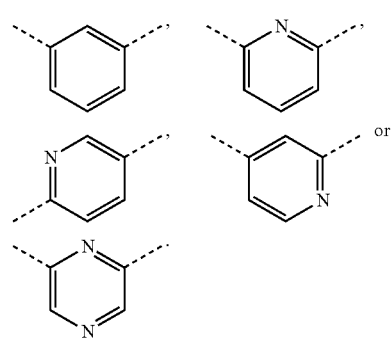

In some embodiments of the present disclosure, L is selected from a single bond, —NH—, —N(CH$_3$)—,

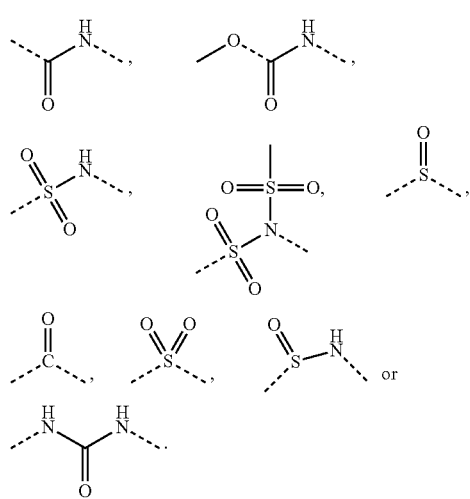

In some embodiments of the present disclosure, $R_1$ is selected from H, $NH_2$, methyl, ethyl, isobutyl, oxetanyl, morpholinyl, cyclopropyl and $CH_3-O-$, wherein the $NH_2$, methyl, ethyl, isobutyl, oxetanyl, morpholinyl, cyclopropyl and $CH_3-O-$ are each optionally substituted by 1, 2 or 3 R.

In some embodiments of the present disclosure, $R_1$ is selected from H, $NH_2$, Me, Et,

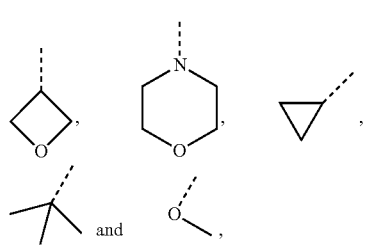

wherein the $NH_2$, Me, Et,

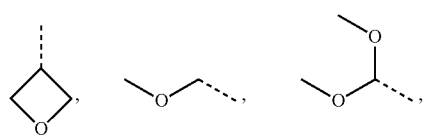

are each optionally substituted by 1, 2 or 3 R.

In some embodiments of the present disclosure, $R_1$ is selected from H, $NH_2$, $CH_3$, $CF_3$, Et,

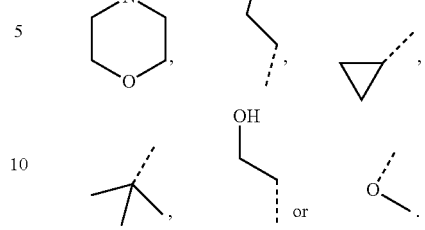

In some embodiments of the present disclosure, $R_2$ is selected from H, methyl, ethyl, propyl, cyclopropyl and tetrahydropyranyl, wherein the methyl, ethyl, propyl, cyclopropyl and tetrahydropyranyl are each optionally substituted by 1, 2 or 3 R.

In some embodiments of the present disclosure, $R_2$ is selected from H, $CH_3$,

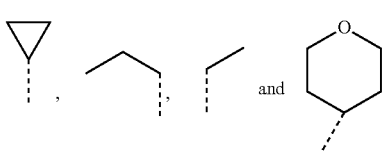

wherein the $CH_3$,

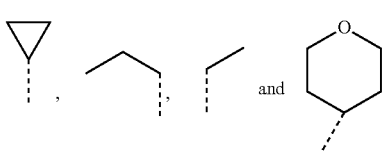

are each optionally substituted by 1, 2 or 3 R.

In some embodiments of the present disclosure, $R_2$ is selected from H, $CH_3$,

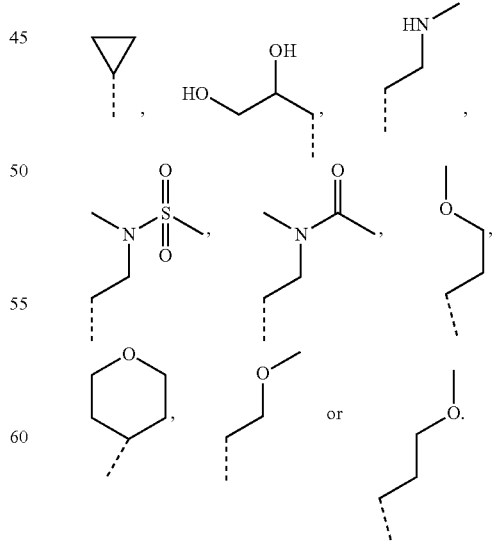

In some embodiments of the present disclosure, $R_3$ is selected from H, F, Cl, Br, I, $CH_3$, $CF_3$ or $CH_3-O-$.

In some embodiments of the present disclosure, $R_4$ and $R_5$ are independently selected from H, F, Cl, Br, I, $CH_3$, $CH_3CH_2$— and $CH_3$—O—.

In some embodiments of the present disclosure, the structural unit

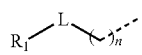

is selected from H, $CH_3$, $NH_2$,

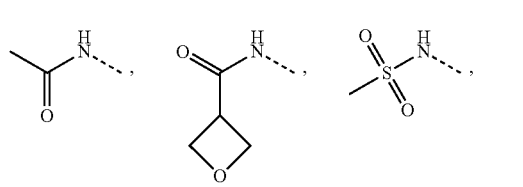

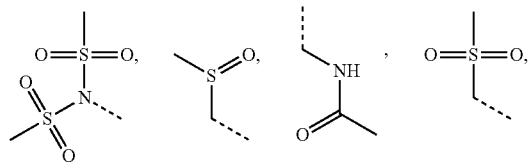

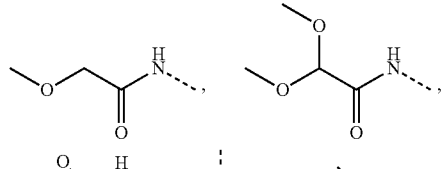

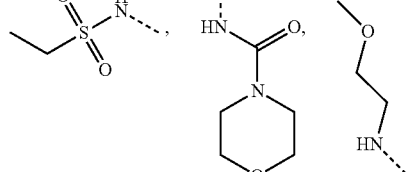

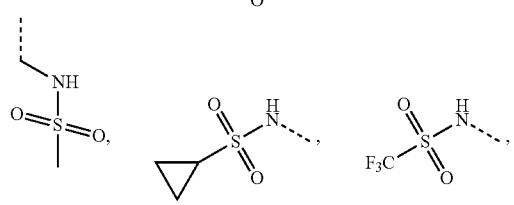

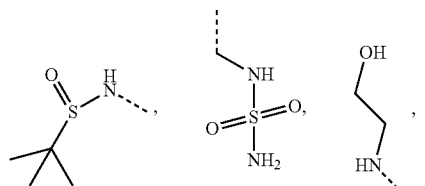

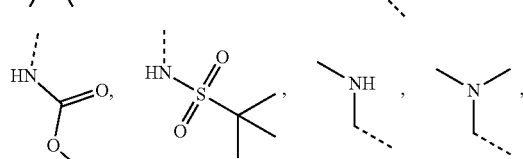

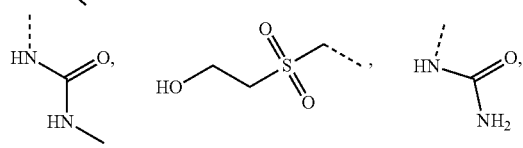

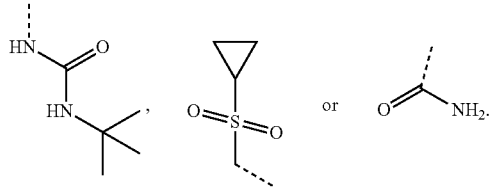

In some embodiments of the present disclosure, the structural unit

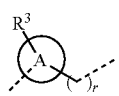

is selected from

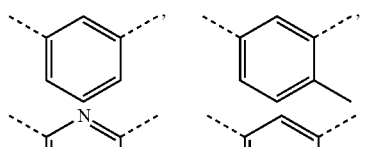

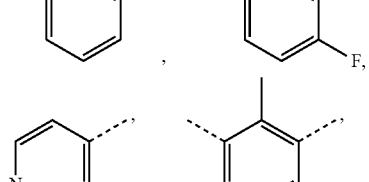

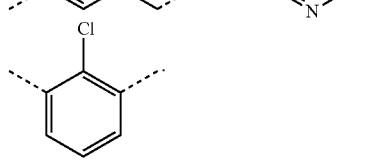

In some embodiments of the present disclosure, R' is selected from F, Cl, Br, I, $NH_2$ or $CH_3$, other variants are as defined in the present disclosure.

In some embodiments of the present disclosure, R is selected from F, Cl, Br, I, OH, $NH_2$, methyl, ethyl, $C_{1-3}$ alkyl-S(=O)$_2$—NH—, $C_{1-3}$ alkyl-S(=O)$_2$—, $C_{1-3}$ alkyl-C(=O)—NH— and $C_{1-3}$ alkyl-O—, wherein the $NH_2$, methyl, ethyl, $C_{1-3}$ alkyl-S(=O)$_2$—NH—, $C_{1-3}$ alkyl-S(=O)$_2$—, $C_{1-3}$ alkyl-C(=O)—NH— and $C_{1-3}$ alkyl-O— are each optionally substituted by 1, 2 or 3 R', other variants are as defined in the present disclosure.

In some embodiments of the present disclosure, R is selected from F, Cl, Br, I, OH, $NH_2$, $CH_3$, -continued

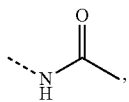

wherein the NH$_2$, CH$_3$,

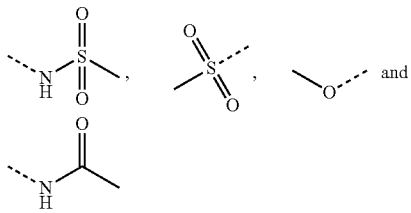

are each optionally substituted by 1, 2 or 3 R', other variants are as defined in the present disclosure.

In some embodiments of the present disclosure, R is selected from F, Cl, Br, I, OH, NH$_2$, CH$_3$,

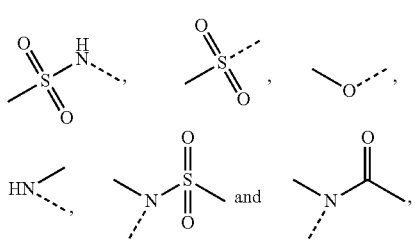

other variants are as defined in the present disclosure.

In some embodiments of the present disclosure, ring A is selected from phenyl, pyridyl or pyrazinyl, other variants are as defined above.

In some embodiments of the present disclosure, ring A is selected from

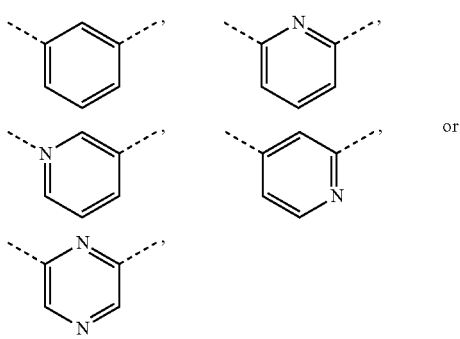

or other variants are as defined in the present disclosure.

In some embodiments of the present disclosure, L is selected from a single bond, —NH—, —N(CH$_3$)—,

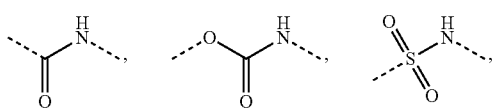

-continued

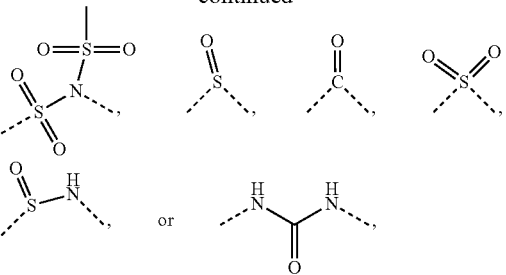

or other variants are as defined in the present disclosure.

In some embodiments of the present disclosure, R$_1$ is selected from H, NH$_2$, methyl, ethyl, isobutyl, oxetanyl, morpholinyl, cyclopropyl and CH$_3$—O—, wherein the NH$_2$, methyl, ethyl, isobutyl, oxetanyl, morpholinyl, cyclopropyl and CH$_3$—O— are each optionally substituted by 1, 2 or 3 R, other variants are as defined in the present disclosure.

In some embodiments of the present disclosure, R$_1$ is selected from H, NH$_2$, Me, Et,

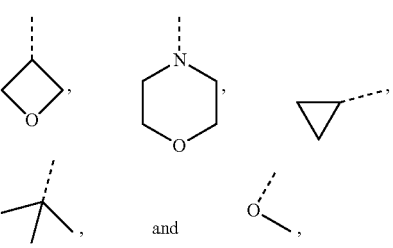

wherein the NH$_2$, Me, Et,

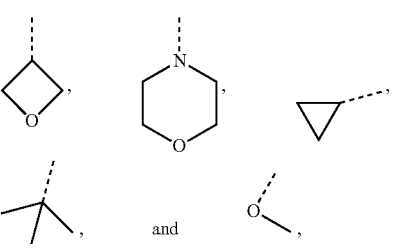

are each optionally substituted by 1, 2 or 3 R, other variants are as defined in the present disclosure.

In some embodiments of the present disclosure, R$_1$ is selected from H, NH$_2$, CH$_3$, CF$_3$, Et,

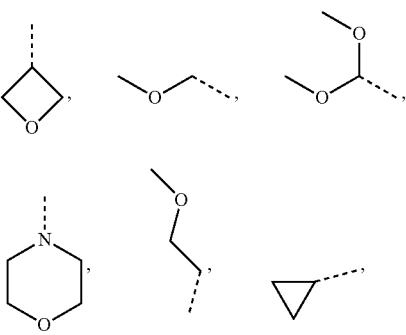

-continued

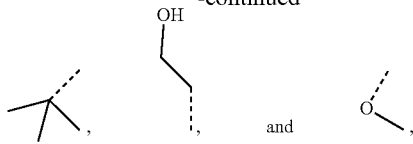

other variants are as defined in the present disclosure.

In some embodiments of the present disclosure, $R_2$ is selected from H, methyl, ethyl, propyl, cyclopropyl and tetrahydropyranyl, wherein the methyl, ethyl, propyl, cyclopropyl and tetrahydropyranyl are each optionally substituted by 1, 2 or 3 R, other variants are as defined in the present disclosure.

In some embodiments of the present disclosure, $R_2$ is selected from H, $CH_3$,

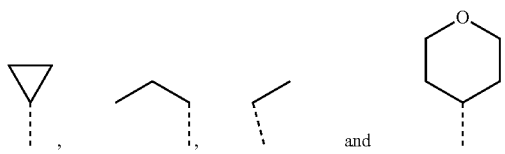

wherein the $CH_3$,

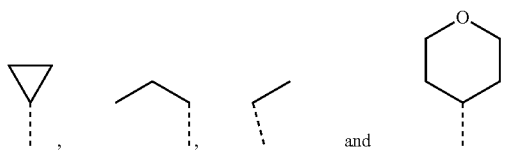

and are each optionally substituted by 1, 2 or 3 R, other variants are as defined in the present disclosure.

In some embodiments of the present disclosure, $R_2$ is selected from H, $CH_3$,

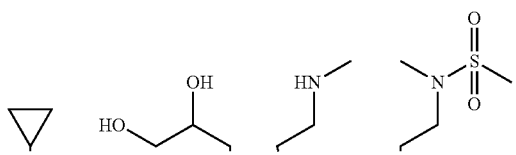

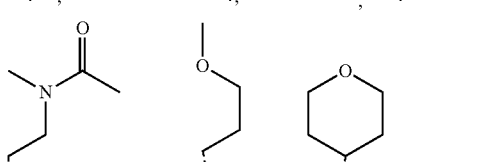

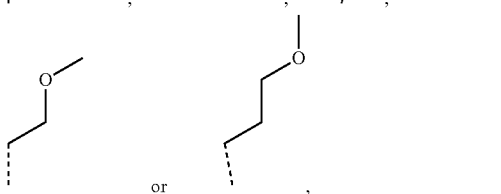

other variants are as defined in the present disclosure.

In some embodiments of the present disclosure, $R_3$ is selected from H, F, Cl, Br, I, $CH_3$, $CF_3$ or $CH_3$—O—, other variants are as defined in the present disclosure.

In some embodiments of the present disclosure, $R_4$ and $R_5$ are independently selected from H, F, Cl, Br, I, $CH_3$, $CH_3CH_2$—, $CH_3$—O—, other variants are as defined in the present disclosure.

In some embodiments of the present disclosure, the structural unit

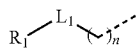

is selected from H, $CH_3$, $NH_2$,

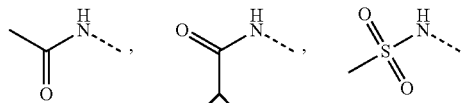

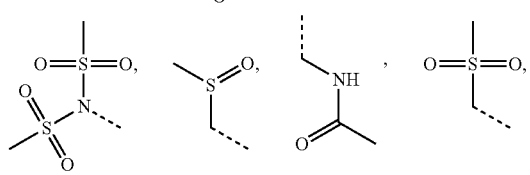

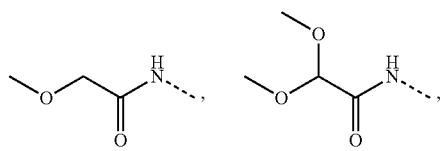

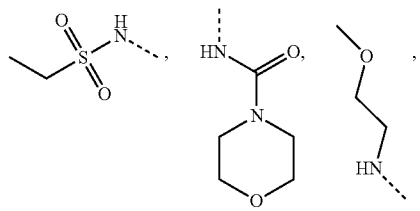

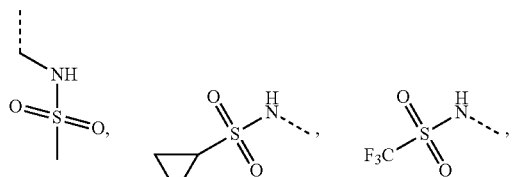

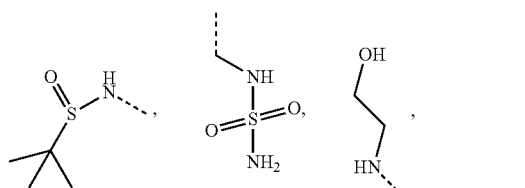

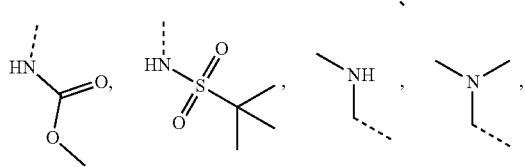

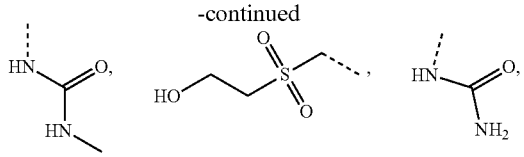

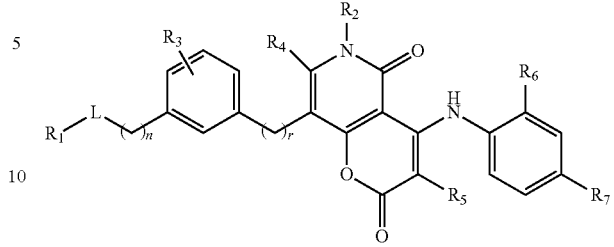

(I-1)

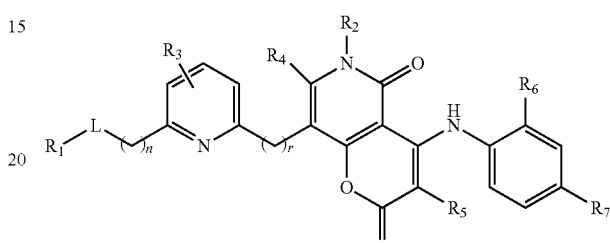

(I-2)

other variants are as defined in the present disclosure.

In some embodiments of the present disclosure, the structural unit

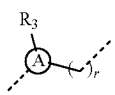

is selected from

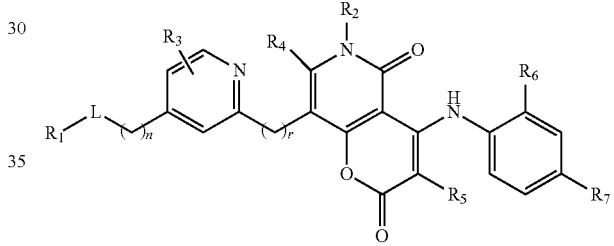

(I-3)

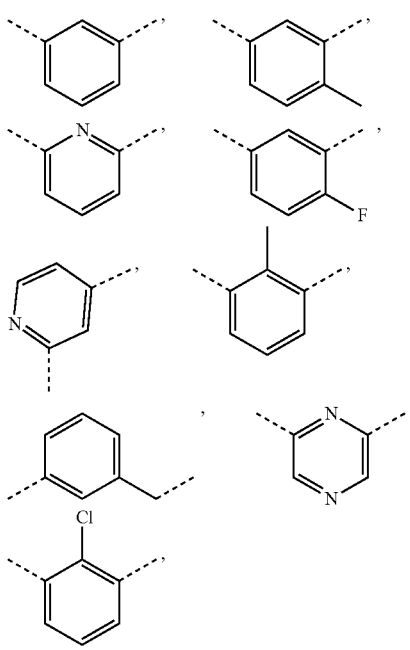

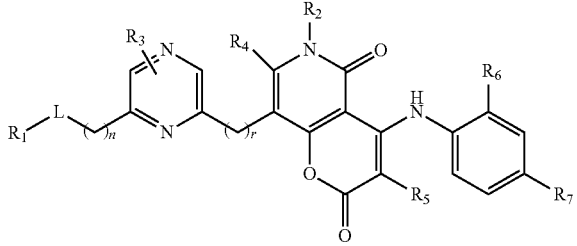

(I-4)

other variants are as defined in the present disclosure.

Other embodiments of the present disclosure are obtained by arbitrary combinations of the above variants.

In some embodiments of the present disclosure, the compound, the pharmaceutically acceptable salt thereof and the isomer thereof, which is selected from

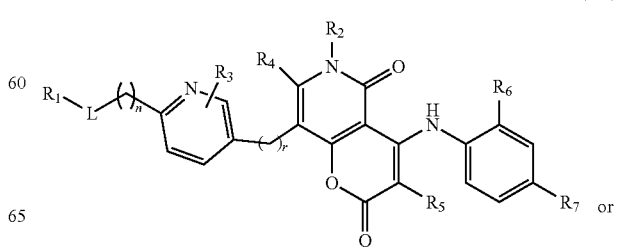

(I-5)

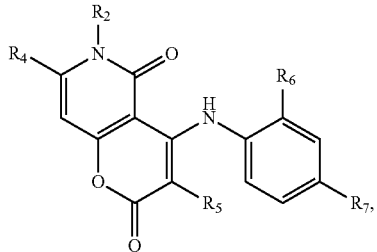
(I-6)
wherein, $R_1$, $R_2$, $R_3$, $R_4$, $R_5$, $R_6$, $R_7$, L, r and n are as defined in the present disclosure.
The present disclosure also provides a compound represented by the formula below, a pharmaceutically acceptable salt thereof or a tautomer thereof, wherein the compound is selected from
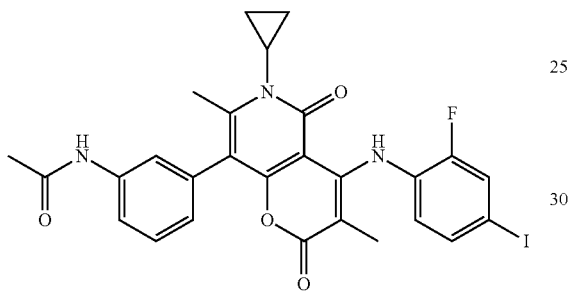
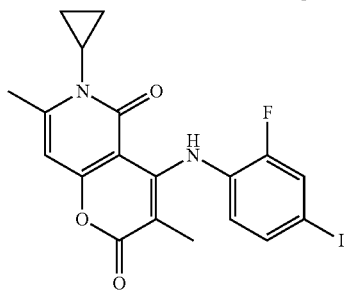
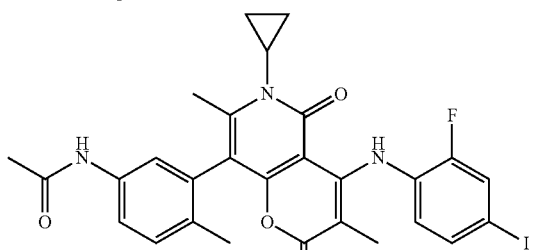
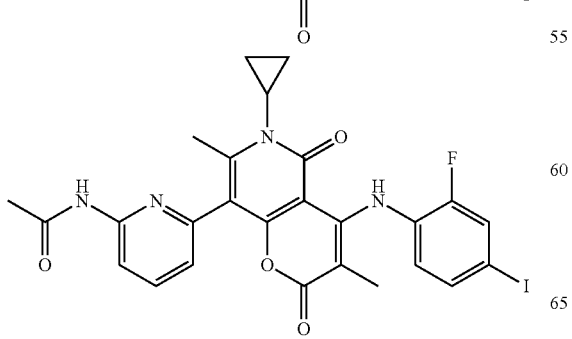
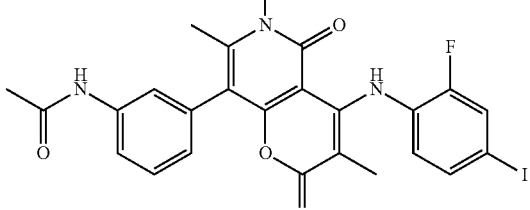
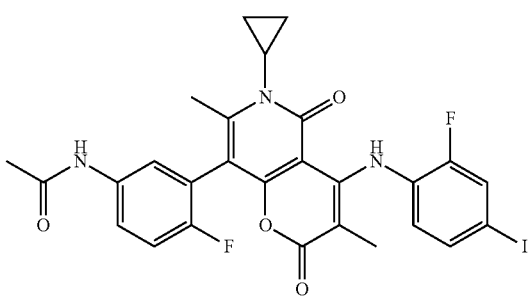
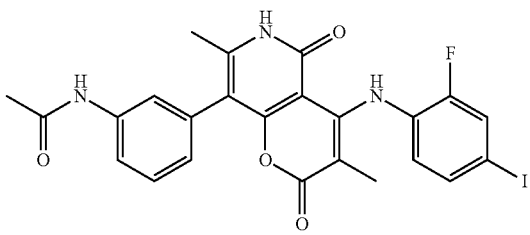
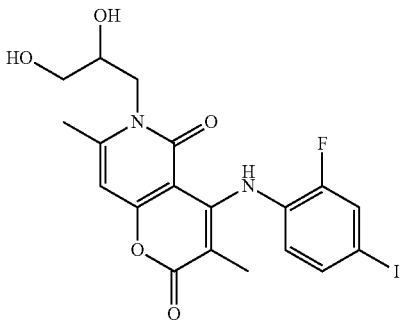
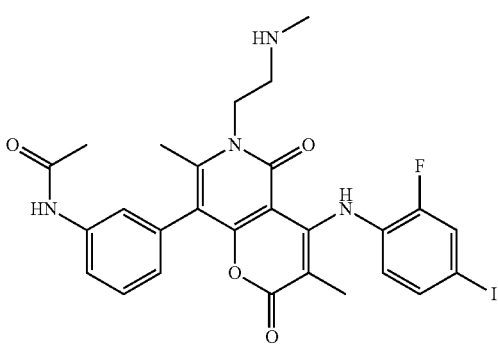

17
-continued
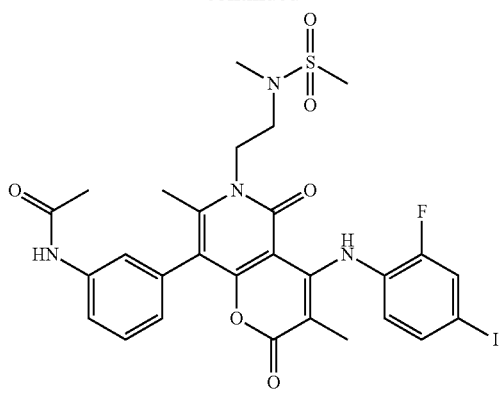
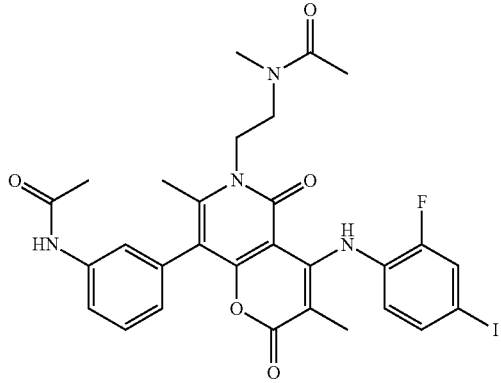
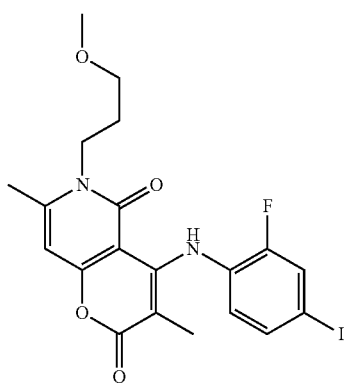
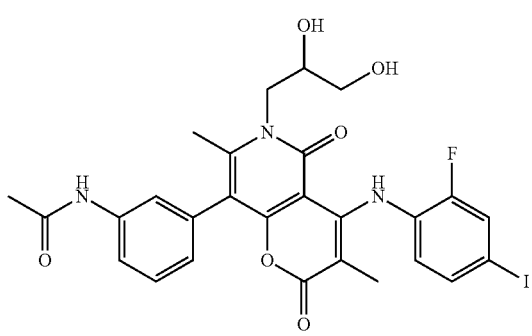
18
-continued
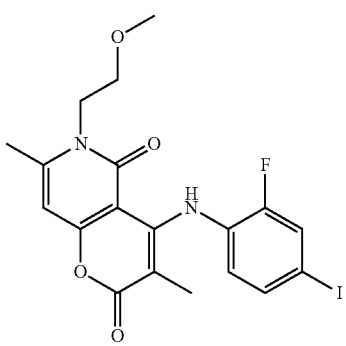
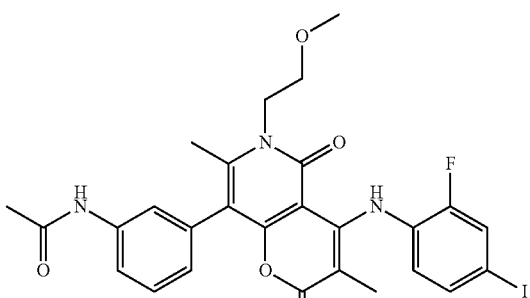
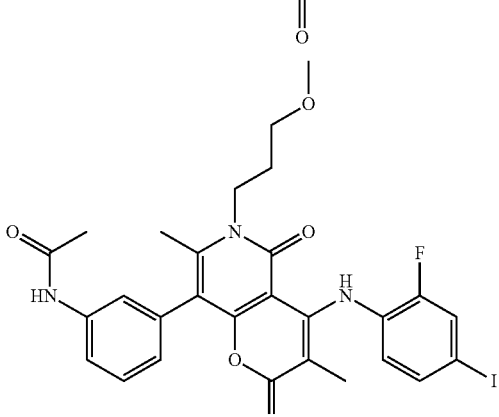
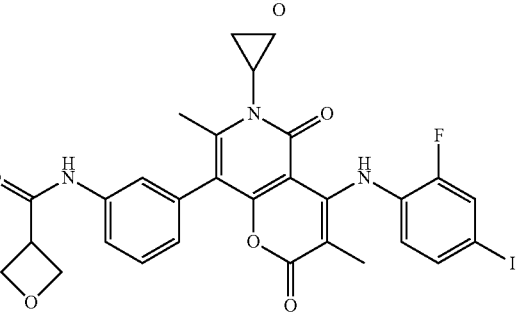

-continued
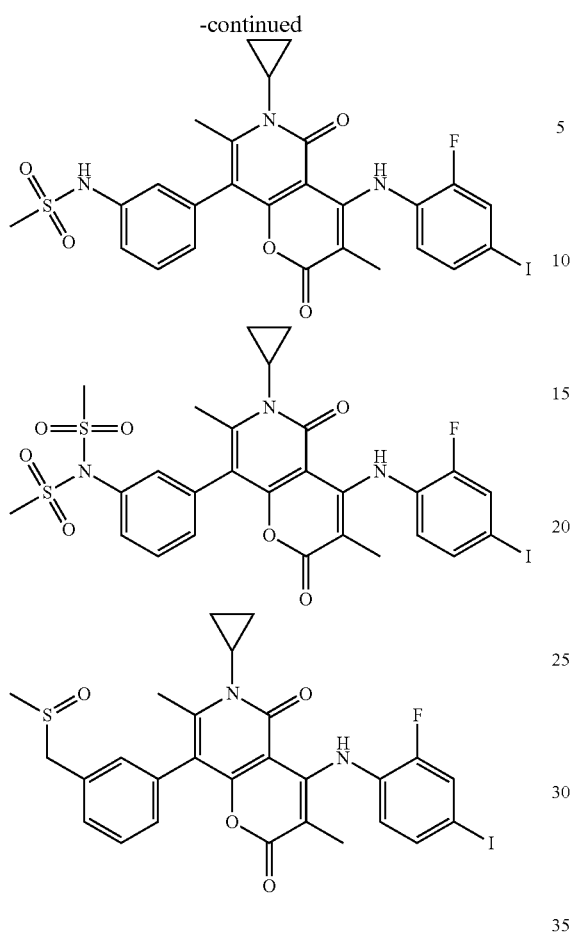
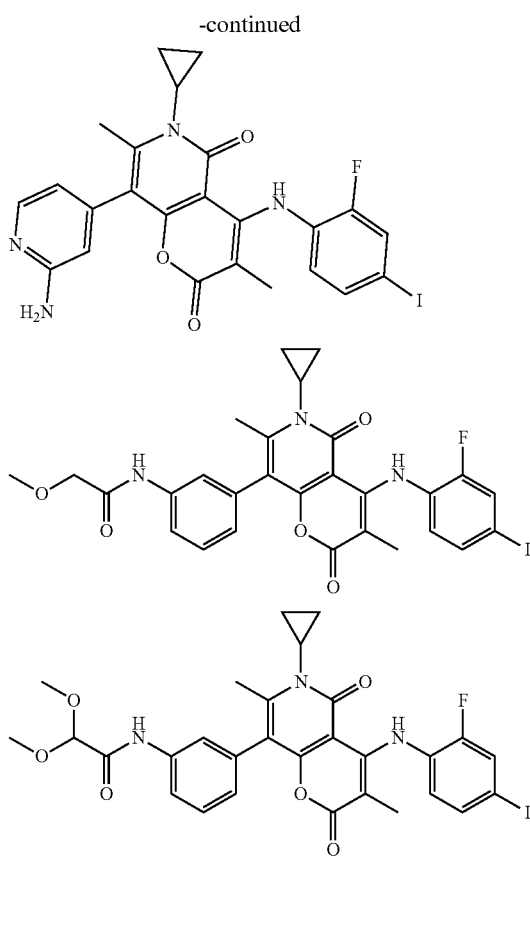
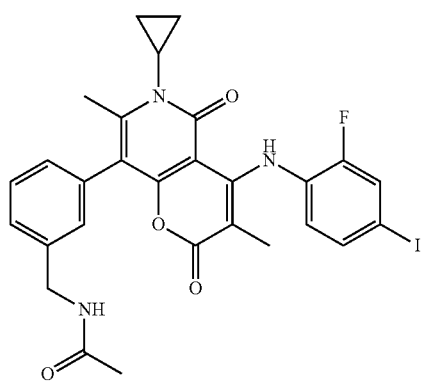
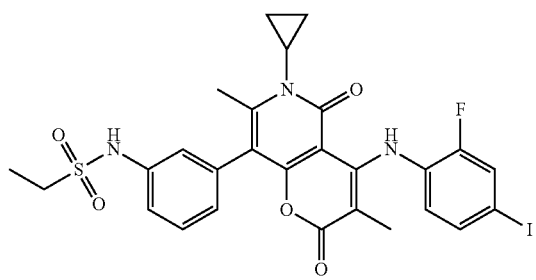
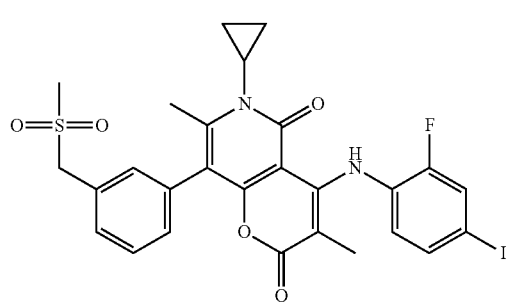
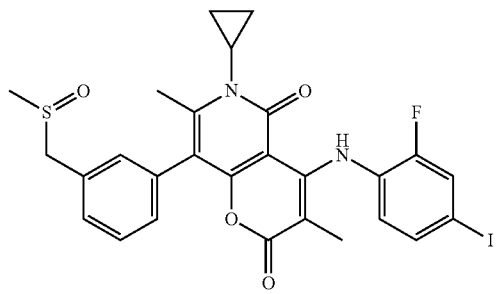

21
-continued
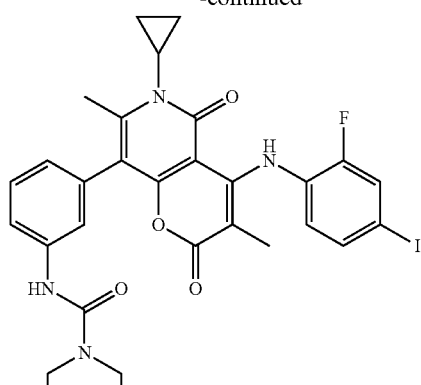
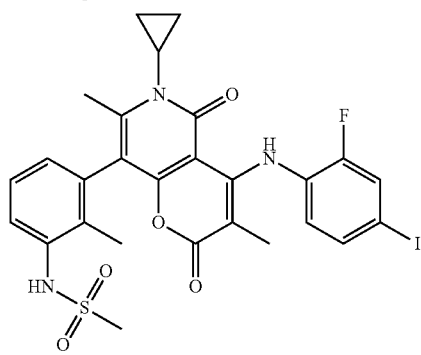
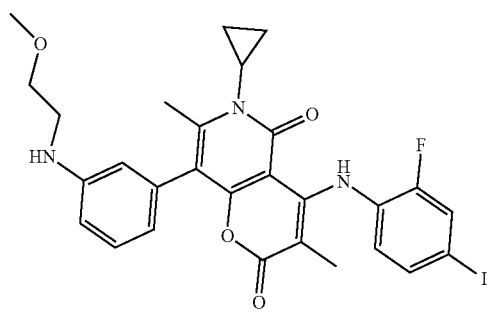
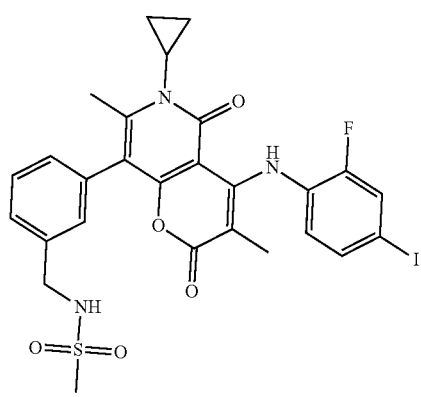
22
-continued
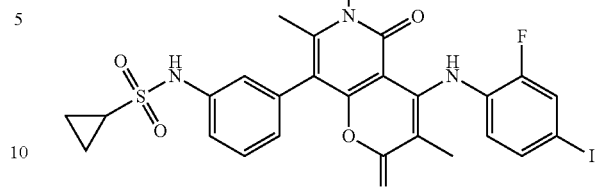
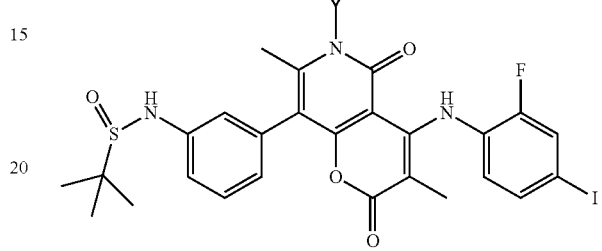
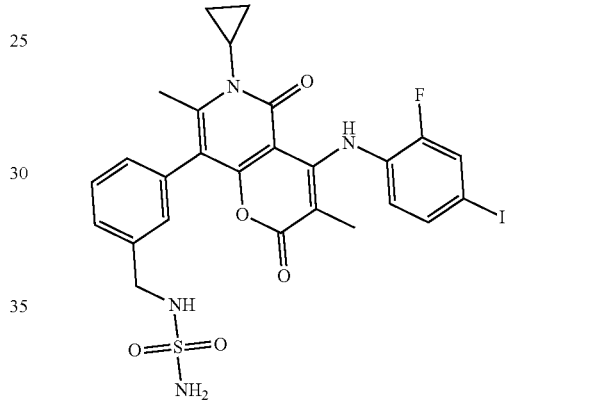
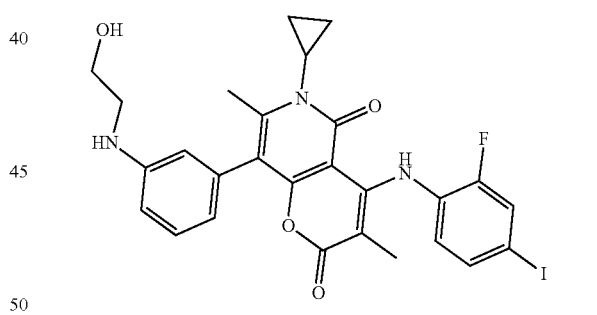
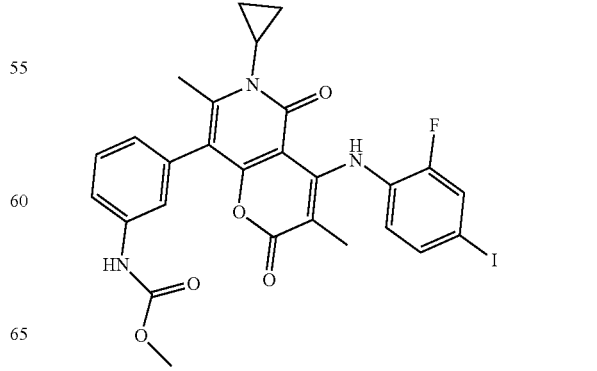

23
-continued
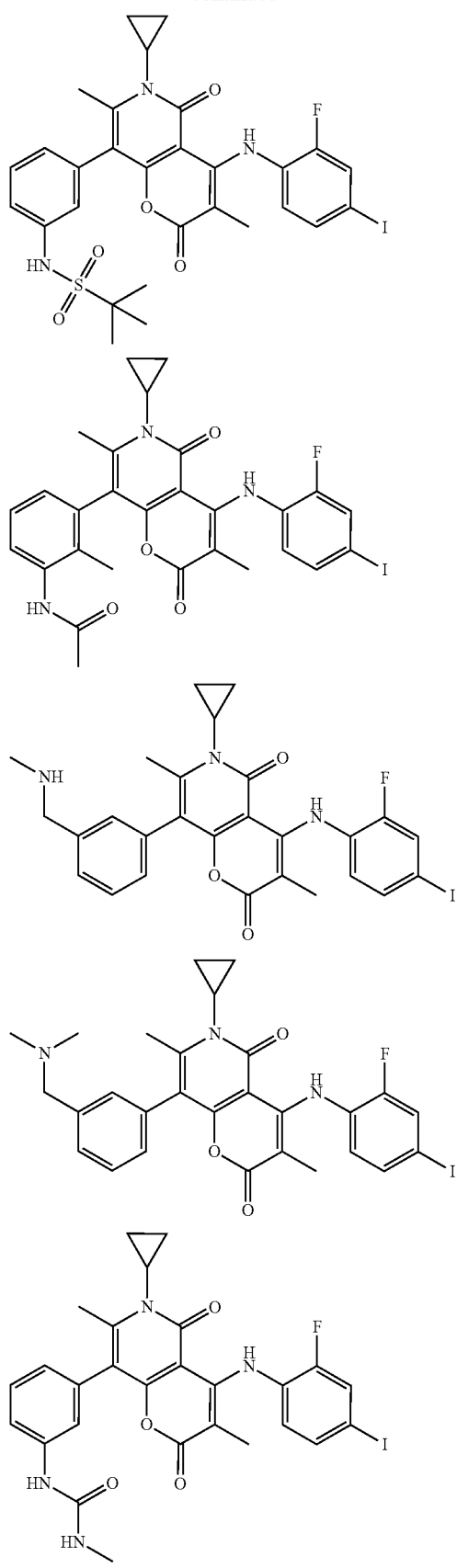
24
-continued
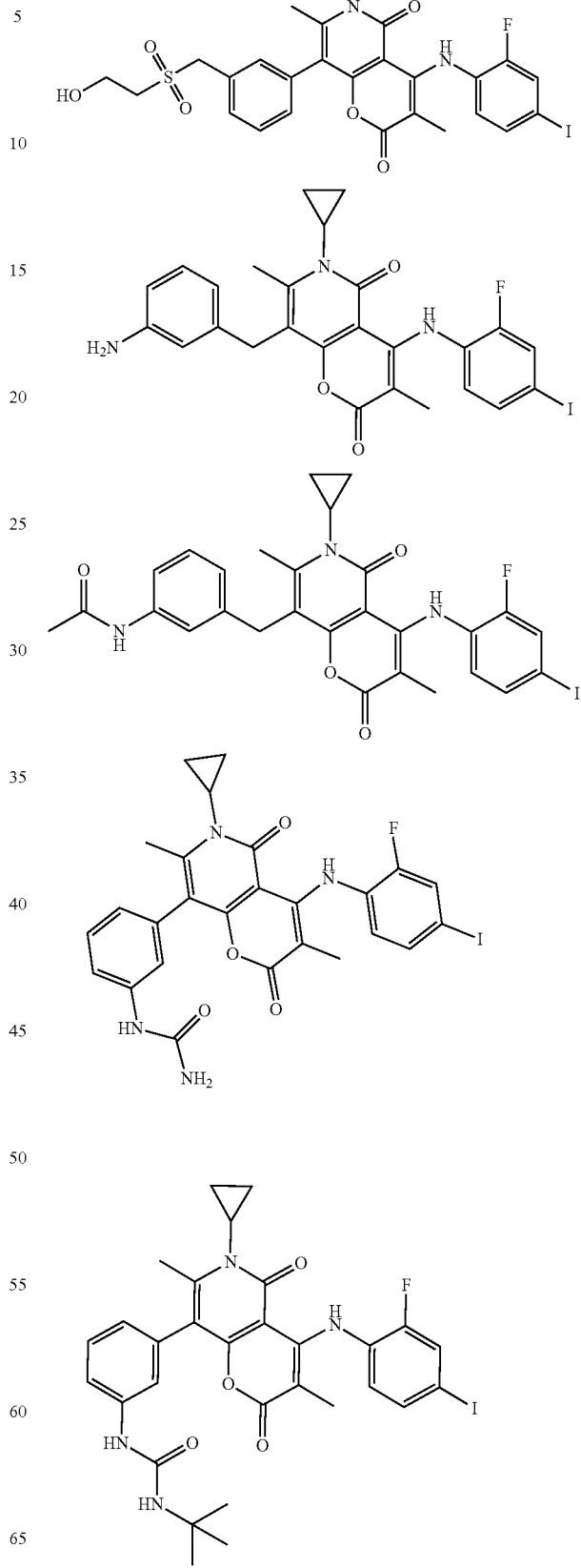

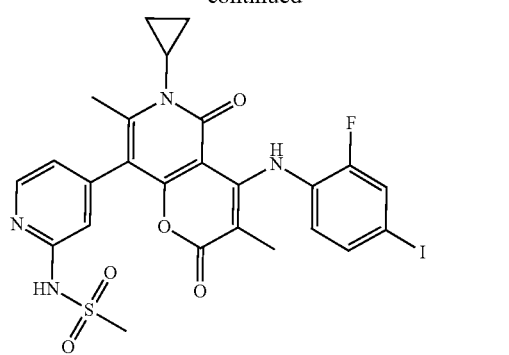
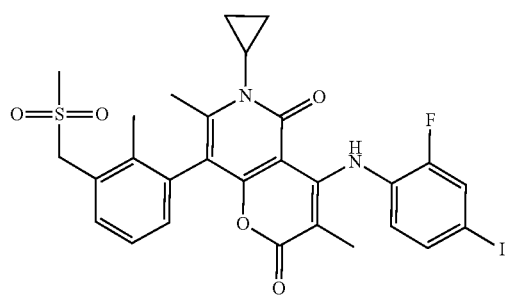
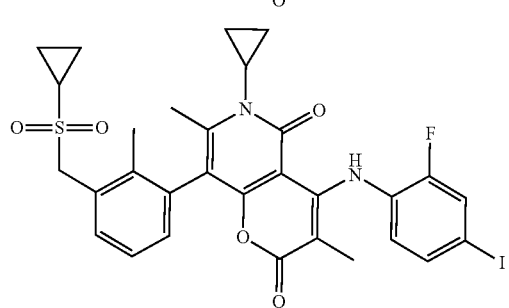
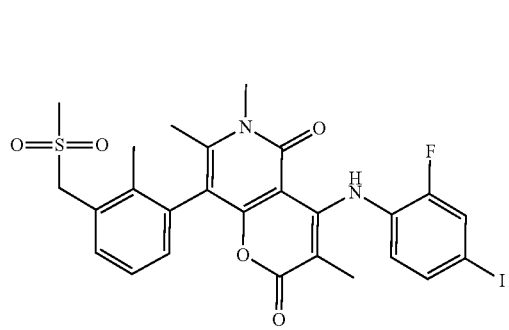
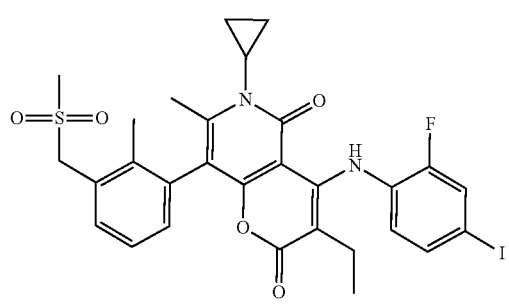
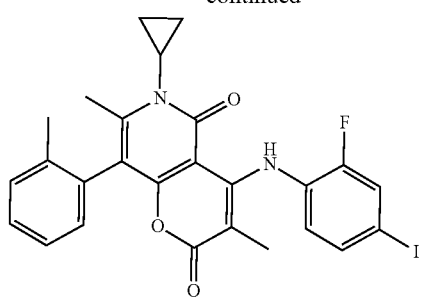
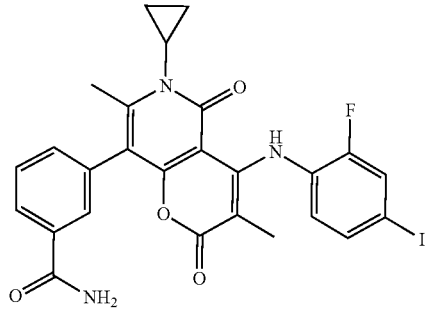
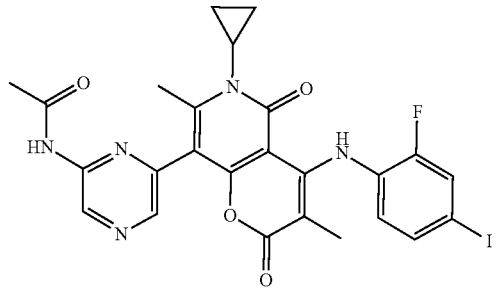
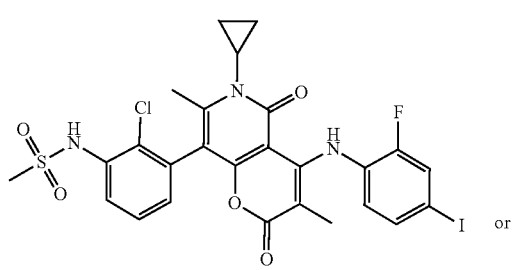
or
In some embodiments of the present disclosure, the compound is selected from

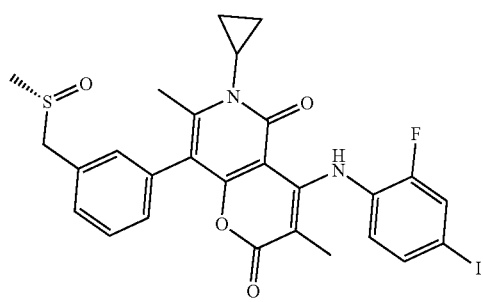
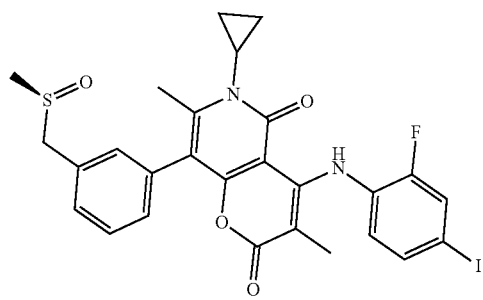
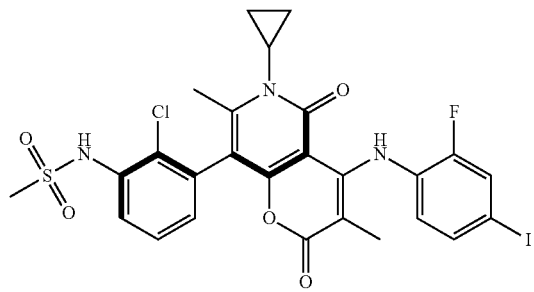
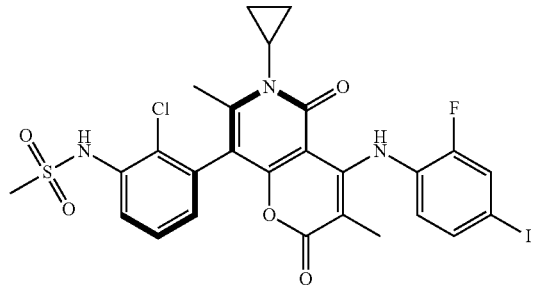
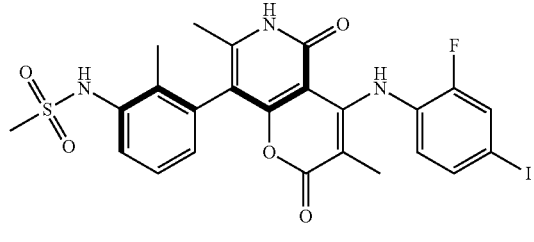
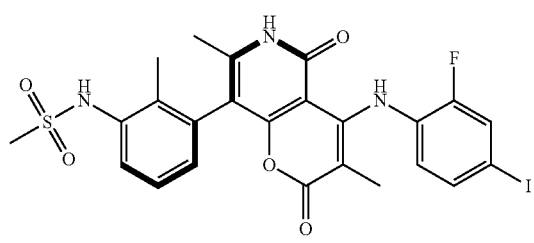
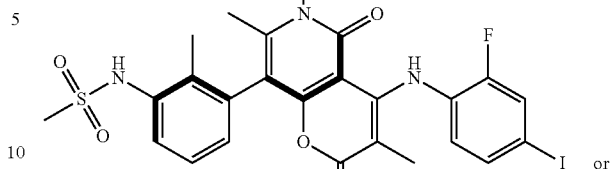
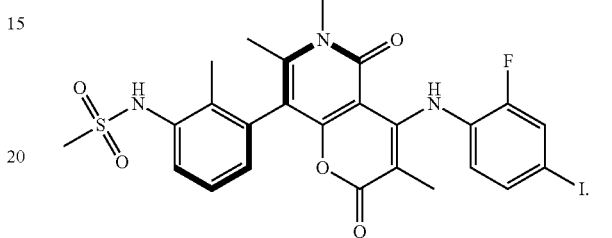
In some embodiments of the present disclosure, the salt is selected from hydrochloride or formate.
In some embodiments of the present disclosure, the hydrochloride is selected from
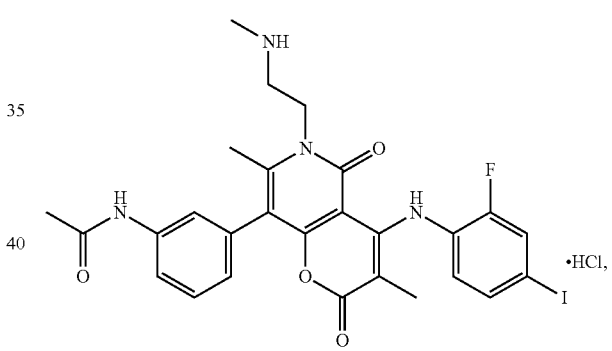
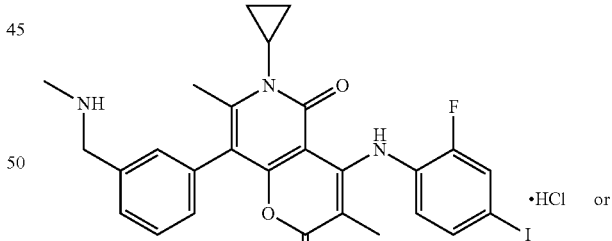
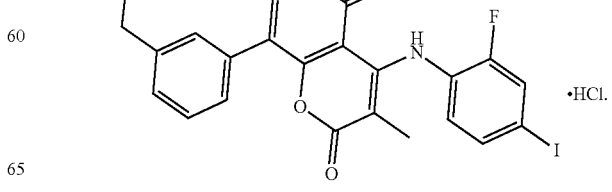

The present disclosure also provides a pharmaceutical composition comprising a therapeutically effective amount of the compound or the pharmaceutically acceptable salt thereof as the active ingredient and a pharmaceutically acceptable carrier.

The present disclosure also provides a use of the compound or the pharmaceutically acceptable salt thereof or the composition in manufacturing a medicament for treating a MEK-related disease.

Definition and Description

Unless otherwise indicated, the following terms when used in the descriptions and the claims of the present disclosure have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (e.g. arginine and the like), and a salt of an organic acid such as glucuronic acid and the like. Certain specific compounds of the present disclosure that contain both basic and acidic functional groups can be converted to any base or acid addition salt.

Preferably, salt is contacted with a base or acid in a conventional manner, and the parent compound is then isolated to regenerate the neutral form of the compound. The parent form of a compound differs from its various salt forms in certain physical properties, such as different solubility in polar solvents.

As used herein, the "pharmaceutically acceptable salt" is a derivative of the compound of the present disclosure, wherein the parent compound is modified by forming a salt with an acid or with a base. Examples of pharmaceutically acceptable salts include, but are not limited to, base such as inorganic or organic acid salts of amines, acid such as alkali or organic salt of carboxylic acid, and the like. Pharmaceutically acceptable salts include conventional non-toxic salts or quaternary ammonium salts of the parent compound, such as salts formed from non-toxic inorganic or organic acids. Conventional non-toxic salts include, but are not limited to, those derived from inorganic and organic acids selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodate, hydroxyl, hydroxynaphthalene, isethionate, lactic acid, lactose, dodecylsulfonic acid, maleic acid, malic acid, mandelic acid, methanesulfonic acid, nitric acid, oxalic acid, panic acid, pantothenic acid, phenylacetic acid, phosphoric acid, polygalactaldehyde, propionic acid, salicylic acid, stearic acid, acetic acid, succinic acid, aminosulfonic acid, p-aminobenzenesulfonic acid, sulfuric acid, tannin, tartaric acid and p-toluenesulfonic acid.

The pharmaceutically acceptable salts of the present disclosure can be synthesized from the parent compound containing an acid or a base by a conventional chemical method.

Generally, such salts are prepared by reacting these compounds in the form of a free acid or base with a stoichiometric appropriate base or acid in water or an organic solvent or a mixture of both. Generally, a non-aqueous medium such as ether, ethyl acetate, ethanol, isopropanol, or acetonitrile is preferred.

Certain compounds of the present disclosure may have asymmetric carbon atoms (optical centers) or double bonds. Racemates, diastereomers, geometric isomers and individual isomers are all included within the scope of the present disclosure.

Unless otherwise specified, the absolute configuration of a stereogenic center is represented by a wedged solid bond (  ) and a wedged dashed bond (  ), a wave line (  ) represents a wedged solid bond (  ) or a wedged dashed bond (  ), and the relative configuration of a stereogenic center is represented by a straight solid bond (  ) an a straight dashed bond (  ). When the compounds described herein contain olefinic double bonds or other centers of geometric asymmetry, unless otherwise specified, they include E, Z geometric isomers. Likewise, all tautomeric forms are included within the scope of the disclosure.

The term "enriched in one isomer" refers to the content of one of the isomers is <100%, and ≥60%, preferably ≥70%, preferably ≥80%, preferably ≥90%, preferably ≥95%, preferably ≥96%, preferably ≥97%, preferably ≥98%, preferably ≥99%, preferably ≥99.5%, preferably ≥99.6%, preferably ≥99.7%, preferably ≥99.8%, preferably ≥99.9%.

The excess of isomer refers to the difference between the relative percentages of the two isomers. For example, wherein, the content of one of the isomers is 90%, and the other one is 10%, then the excess of isomer is 80%.

"(+)" stands for dextrorotation, "(−)" stands for levorotation, or "(±)" stands for racemization.

The compounds of the present disclosure may exist in specific geometric or stereoisomeric forms. This disclosure contemplates all such compounds, including cis and trans isomers, (−)- and (+)-enantiomers, (R)- and (S)-enantiomers, diastereomer isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included in the scope of the present disclosure.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (e.g., amino) or an acidic functional group (e.g., carboxy), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (e.g., carbamate generated from amine).

The compound of the present disclosure may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). All of the transformations formed by the isotopic compositions of the present disclosure, whether radioactive or not, are included within the scope of the present disclosure.

The term "substituted" means one or more than one hydrogen atom(s) on a specific atom is(are) substituted with the substituent, including deuterium and hydrogen variants, as long as the valence of the specific atom is normal and the substituted compound is stable. When the substituent is an oxygen (i.e. =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (e.g., R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist, for example, when X is vacant in A-X, the structure of A-X is actually A. When a substituent can be attached to more than one atoms on a ring, the substituent can be bonded to any of the atom on the ring, for example, the structural unit

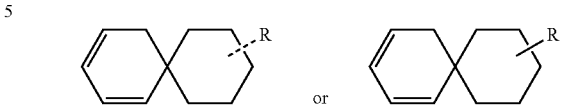

represents for the substitution by the substituent R can take place at any position on the cyclohexyl or cyclohexadiene. When the enumerated substituents do not indicate through which atom they are attached to the substituted group, such substituents may be bonded through any one of the atoms, for example, pyridyl as a substituent can be attached to the substituted group through any one of the carbon atom on the pyridine ring. When the enumerative linking group does not indicate the direction for linking, the direction for linking is arbitrary, for example, the linking group L contained in

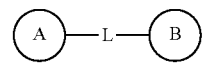

is -M-W—, then -M-W— can link ring A and ring B to form

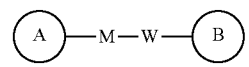

in the direction same as left-to-right reading order, and form

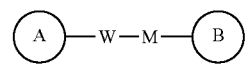

in the direction contrary to left-to-right reading order. Combinations of the linking groups, substituents and/or variants thereof are permissible only if such combinations result in stable compounds.

Unless otherwise specified, the term "hetero" represents a heteroatom or a heteroatomic group (e.g., an atomic group containing a heteroatom), including the atom except carbon (C) and hydrogen (H) and the atomic group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so called ring includes a single ring, a double ring, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclyl" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and $S(O)_p$, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment. The total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and $S(O)_p$, p is 1 or 2). It is worth noting that the total number of S and O atom of an aromatic heterocycle is not more than one. The bridged ring is also included in the definition of the heterocycle. Abridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, Benzodihydropyranyl, chromene, cinnolinyl decahydroquinolinyl, 2H,6H-1,5,2-dithiazinyl, dihydrofuro[2,3-b] tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1H-1,2,3-triazolyl, 2H-1,2,3-triazolyl, 1H-1,2,4-triazolyl, 4H-1,2,4-triazolyl and xanthenyl. Also included are fused-ring compounds and spiro compounds.

Unless otherwise specified, the term "hydrocarbyl" or its hyponyms (e.g., alkyl, alkenyl, alkynyl, and aryl, etc.), by itself or as part of another substituent, refers to a linear, branched chain or cyclic hydrocarbon radical or any combination thereof, they can be fully saturated (e.g., alkyl), mono- or polyunsaturated (e.g., alkenyl, alkynyl, and aryl), can be mono-, di- or poly-substituted, can be monovalent (e.g., methyl), divalent (e.g., methylene) or multivalent (e.g., methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl, the aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, isobutyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—CH₃, —CH₂—CH₂—S(O)₂—CH₃, —CH=CH—O—CH₃, —CH₂—CH=N—OCH₃ and —CH=CH—N(CH₃)—CH₃. Up to two consecutive heteroatoms can be present, such as, —CH₂—NH—OCH₃.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g., heteroalkyl, and heterocycloalkyl), one heteroatom can occupy the position where the heterocycle attaches to the remainder position of the molecule. Examples of the cyclohydrocarbyl include, but are not limited to, cyclopentyl, cyclohexyl, 1-cyclohexenyl, 3-cyclohexenyl, cycloheptyl and the like. Non-limiting examples of heterocyclyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g., —CH₂F) or poly-substituted (e.g., —CF₃), can be monovalent (e.g., methyl), divalent (e.g., methylene) or multivalent (e.g., methenyl). Examples of alkyl include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl) and the like.

Unless otherwise specified, "alkenyl" refers to an alkyl group having one or more carbon-carbon double bonds at any position on the chain, which may be mono- or poly-substituted, and may be monovalent, divalent, or polyvalent. Examples of alkenyl include vinyl, propenyl, butenyl, pentenyl, hexenyl, butadienyl, pentadienyl, hexadienyl, etc.

Unless otherwise specified, "alkynyl" refers to an alkyl group having one or more carbon-carbon triple bonds at any position on the chain, which may be mono- or poly-substituted, and may be monovalent, divalent, or polyvalent. Examples of alkynyl include ethynyl, propynyl, butynyl, pentynyl, etc.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, the term "halo" or "halogen" refers to fluorine, chlorine, bromine or iodine atom by itself or as part of another substituent. Furthermore, the term "haloalkyl" is intended to include monohaloalkyl and polyhaloalkyl. For example, the term "halo (C₁-C₄) alkyl" is intended to include, but is not limited to, trifluoromethyl, 2,2,2-trifluoroethyl, 4-chlorobutyl, 3-bromopropyl, and the like. Unless otherwise specified, examples of haloalkyl include, but are not limited to, trifluoromethyl, trichloromethyl, pentafluoroethyl, and pentachloroethyl.

The term "alkoxy" represents any alkyl defined above having a specified number of carbon atoms attached by an oxygen bridge. Unless otherwise specified, C₁₋₆ alkoxy includes C₁, C₂, C₃, C₄, C₅ and C₆ alkoxy. Examples of alkoxy include, but not limited to, methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g., one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when aryl combines with other terms (such as aryloxy, arylthio, arylalkyl), the aryl includes the aryl and heteroaryl ring as defined above. Thus, the term "aralkyl" is meant to include the group (e.g., benzyl, phenethyl, pyridylmethyl, etc.) where an aryl is attached to an alkyl, including an alkyl where the carbon atom (e.g., methylene) has been replaced by an atom such as oxygen, for example, phenoxymethyl, 2-pyridyloxy, 3-(1-naphthyloxy)propyl, and the like.

The compound of the present disclosure can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present disclosure.

The solvent used in the present disclosure is commercially available. The present disclosure employs the following abbreviations: aq stands for water; HATU stands for O-(7-azabenzotriazol-1-yl)-N,N,N,N'-tetramethyluronium hexafluorophosphate; EDC stands for N-(3-dimethylaminopropyl)-N-ethylcarbodiimide hydrochloride; m-CPBA stands for 3-chloroperoxybenzoic acid; eq stands for equivalent, equivalent; CDI stands for carbonyldiimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc stands for ethyl acetate; EtOH stands for ethanol; MeOH for methanol; CBz stands for benzyloxycarbonyl, an amine protecting group; BOC stands for t-butylcarbonyl, an amine protecting group; HOAc stands for acetic acid; NaCNBH₃ stands for sodium cyanoborohydride; r.t. stands for room temperature; O/N stands for overnight; THF stands for tetrahydrofuran; Boc₂O stands for di-tert-butyldicarbonate; TFA stands for trifluoroacetic acid; DIPEA stands for diisopropylethylamine; SOCl₂ stands for thionyl chloride; CS₂ stands for carbon disulfide; TsOH stands for p-toluenesulfonic acid; NFSI stands for N-fluoro- N-(phenylsulfonyl)benzenesulfonamide; NCS stands for 1-chloropyrrolidine-2,5-dione; n-Bu$_4$NF stands for tetrabutylammonium fluoride; iPrOH stands for 2-propanol; mp stands for melting point; LDA stands for diisopropylamino lithium; Pd(OAc)$_2$ stands for palladium acetate; Pd$_2$(dba)$_3$ stands for tris(dibenzylideneacetone)dipalladium; DPPP stands for bis(diphenylphosphino)propane; NIS stands for N-iodosuccinimide; SPhos stands for 2-dicyclohexylphosphino-2',6'-dimethoxybiphenyl; TBAF stands for tetrabutylammonium fluoride; Pd(PPh$_3$)$_2$Cl$_2$ stands for dichlorobis(triphenylphosphine)palladium; DMAP stands for dimethylaminopyridine; NBS stands for N-bromosuccinimide; RuPhos stands for 2-biscyclohexylphosphino-2',6'-diisopropoxybiphenyl; EA stands for ethyl acetate; Pd(dppf)Cl$_2$.CH$_2$Cl$_2$ stands for [1,1-bis(dibenzylphosphino)ferrocene] palladium dichloride dichloromethane complex; PBr$_3$ stands for phosphorus tribromide; DEA stands for diethanolamine; EDTA stands for ethylenediamine tetraacetic acid.

Compounds are named manually or by ChemDraw® software, the commercially available compounds use their vendor directory names.

Technical Effect

As a new MEK inhibitor, the compounds of the present disclosure have good MEK biological activity and cell growth inhibitory activity on tumor cells that are related to this signaling pathway.

DETAILED DESCRIPTION OF THE EMBODIMENTS

The following examples further illustrate the present disclosure, but the present disclosure is not limited thereto. The present disclosure has been described in detail in the text, and its specific embodiments have also been disclosed, for those skilled person in the art, it is obvious to modify and improve the embodiments of the present disclosure within the spirit and scope of the present disclosure.

The reaction methods commonly used in the present disclosure are as follows:

I. Suzuki Reaction

Substrate+borate ester/boric acid+Pd(dppf)Cl$_2$.CH$_2$Cl$_2$+SPhos+base+solvent→product　　Method A:

The substrate (1.00 eq) and borate ester/boric acid (1.00-2.00 eq) were dissolved in the solvent, then Pd(dppf)Cl$_2$.CH$_2$Cl$_2$ (0.10 eq) and the base (2.00-3.00 eq) were added under nitrogen protection at 20° C., the reaction was stirred at 85-100° C. After completion of the reaction, the reaction mixture was cooled to room temperature, diluted with water, and extracted with dichloromethane/EtOAc. The organic phase was collected, washed with saturated sodium chloride solution, dried over anhydrous sodium sulfate, filtered, and evaporated to dryness by rotary evaporation to give a crude product. The crude product was purified by column chromatography to give the target compound.

Substrate+borate ester/boric acid+Pd(dppf)Cl$_2$.CH$_2$Cl$_2$+base+solvent→product　　Method B:

The substrate (1.00 eq) and borate ester/boric acid (1.00-2.00 eq) were added into the solvent, then Pd(dppf)Cl$_2$.CH$_2$Cl$_2$ (0.10 eq) and the base (2.00-5.00 eq) were added, the reaction was stirred at 60-110° C. under nitrogen protection. After completion of the reaction, the reaction mixture was diluted with water and extracted with EtOAc/dichloromethane. The organic phases were combined and dried over anhydrous sodium sulfate, filtered and evaporated to dryness by rotary evaporation to give a crude product. The crude product was purified by column chromatography to give the target compound.

Substrate+borate ester/boric acid+Pd$_2$(dba)$_3$+RuPhos+base+solvent→product　　Method C:

The substrate (1.00 eq) was added into the solvent at 15° C., then borate ester/boric acid (1.20 eq), Pd$_2$(dba)$_3$ (0.10 eq), RuPhos (0.10 eq) and the base (2.00 eq) were added. The reaction was stirred at 130° C. After completion of the reaction, the reaction mixture was cooled to room temperature, diluted with water and extracted with EtOAc/dichloromethane. The organic phase was collected, washed with saturated sodium chloride solution, dried over anhydrous sodium sulfate, and evaporated to dryness by rotary evaporation to give a crude product. The crude product was purified by column chromatography to give the target compound.

Substrate+borate ester/boric acid+Pd$_2$(dba)$_3$+SPhos+base+solvent→product　　Method D:

The substrate (1.00 eq) and borate ester/boric acid (2.00 eq) were dissolved in the solvent, then SPhos (0.10 eq), Pd$_2$(dba)$_3$ (0.05 eq) and the base (2.00-2.50 eq) were added under nitrogen protection. The reaction was stirred at 110-120° C. After completion of the reaction, the reaction mixture was diluted with water and extracted with dichloromethane/EtOAc. The organic phase was collected, evaporated to dryness by rotary evaporation, and purified by column chromatography to give the target compound.

II. Iodination Reaction

Substrate+trifluoroacetic acid+N-iodosuccinimide+solvent→product

The substrate (1.00 eq) was dissolved in N,N-dimethylformamide, trifluoroacetic acid and N-iodosuccinimide (1.50-3.00 eq) were added at 0° C. under nitrogen protection. The reaction was stirred at 30° C. After completion of the reaction, the reaction solution was sequentially quenched with saturated sodium thiosulfate solution and extracted with EtOAc/dichloromethane. The combined organic phase was dried over anhydrous sodium sulfate, filtered and the filter cake was evaporated to dryness by rotary evaporation. The filter cake was triturated with a solvent of methyl tert-butyl ether/PE=1/1. After filtration, the filter cake was washed with petroleum ether (PE) to give the target compound.

Reference Example 1: Fragment BA-1

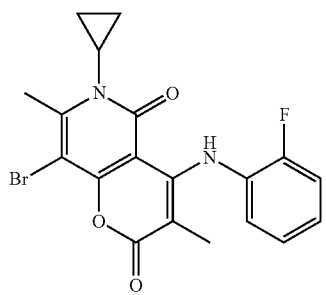 [SMILES: Cc1c(Nc2ccccc2F)c2c(=O)n(C3CC3)c(C)c(Br)c2oc1=O]

Synthetic Route:

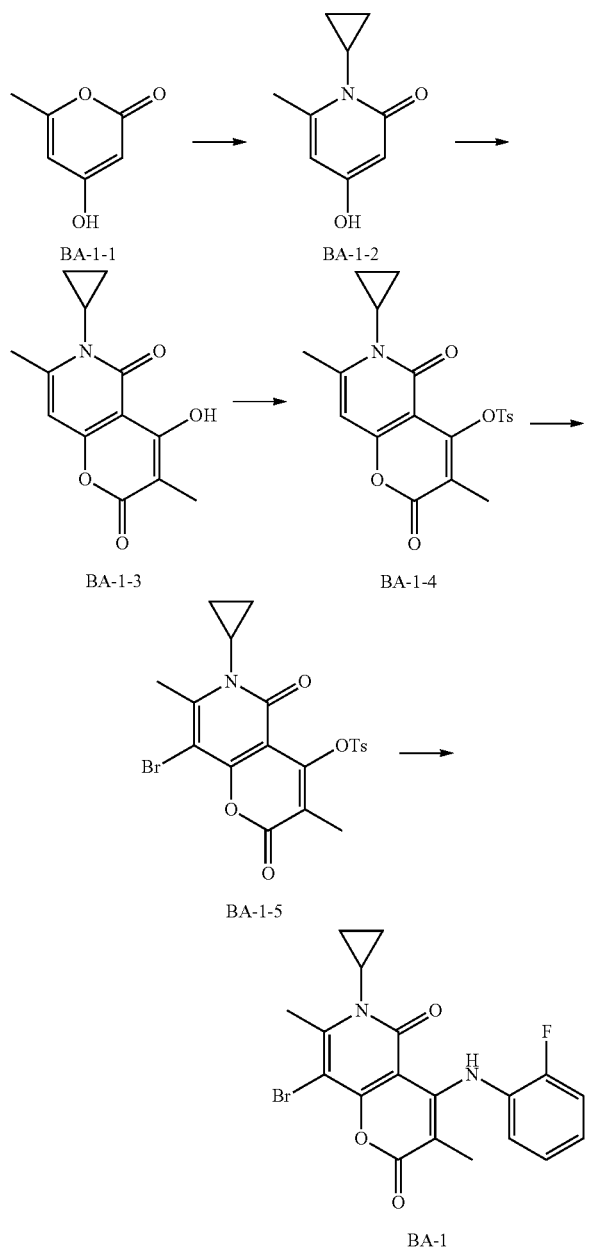

Step 1: Synthesis of the Compound BA-1-2

The compound BA-1-1 (249.70 g, 1.98 mol, 1.00 eq) was dissolved in water (500.00 mL), and cyclopropylamine (113.04 g, 1.98 mol, 1.00 eq) was added at 60-80° C. The reaction temperature was raised to 100° C. and the reaction was stirred for 6 hours, and a precipitate formed. After completion of the reaction, the reaction mixture was cooled to room temperature. Then methanol (100 mL) was added and the mixture was stirred for 30 minutes.

After filtration, the filter cake was collected, washed with EtOAc (50 mL*3), and evaporated to dryness by rotary evaporation to give the compound BA-1-2. MS m/z: 205.0 [M+H]$^+$

Step 2-Method A: Synthesis of the Compound BA-1-3

The compound BA-1-2 (31.85 g, 192.81 mmol, 1.00 eq) and methylmalonic acid (33.59 g, 192.81 mmol, 1.00 eq) were mixed in diphenyl ether (180.00 mL), the reaction temperature was raised to 220-230° C. under nitrogen protection, and the reaction was stirred for 6 hours. After completion of the reaction, the reaction solution was cooled down and diluted with petroleum ether (1 L). The filter cake was collected, washed with petroleum ether (50 mL*3), evaporated to dryness by rotary evaporation and then stirred in dichloromethane (500 mL) for 30 minutes. The mixture was filtered and the filter cake was washed with dichloromethane (50 mL*3). The organic phases were combined and evaporated to dryness by rotary evaporation to give a crude product, which was purified by column chromatography (DCM/EA=1/1) to give the target compound BA-1-3. $^1$H NMR (400 MHz, CDCl$_3$-d) δ 12.85 (s, 1H), 6.25 (s, 1H), 2.91-2.89 (m, 1H), 2.60 (s, 3H), 1.99 (s, 3H), 1.37-1.35 (m, 2H), 1.00-0.99 (m, 2H). MS m/z: 247.9 [M+H]$^+$

Step 2-Method B: Synthesis of the Compound BA-1-3

The compound BA-1-2 (13.60 g, 82.33 mmol, 1.00 eq) was dissolved in acetic anhydride (60.00 mL), followed by addition of diethyl methylmalonate (14.58 g, 123.49 mmol, 1.50 eq) at 10° C. The reaction temperature was raised to 80° C. and the reaction was stirred for 0.5 hour. After completion of the reaction, the reaction mixture was filtered and the filter cake was collected. The filter cake was washed with methyl tert-butyl ether (100 mL) to give the target compound BA-1-3.

$^1$H NMR (400 MHz, CDCl$_3$-d) δ 13.42 (s, 1H), 6.607 (s, 1H), 3.31-2.98 (m, 1H), 2.57 (s, 3H), 1.81 (s, 3H), 1.19-1.16 (m, 2H), 0.96-0.92 (m, 2H). MS m/z: 247.9 [M+H]$^+$

Step 3: Synthesis of the Compound BA-1-4

The compound BA-1-3 (4.83 g, 19.53 mmol, 1.00 eq), triethylamine (3.95 g, 39.06 mmol, 2.00 eq) and DMAP (47.72 mg, 390.60 μmol, 0.02 eq) were dissolved in dichloromethane (120.00 mL), followed by addition of 4-Methylbenzenesulfonyl chloride (3.72 g, 19.53 mmol, 1.00 eq) at 15° C. The reaction was stirred at 15° C. for 16 hours. After completion of the reaction, the reaction solution was washed sequentially with water (50 mL) and saturated sodium chloride solution (50 mL), then dried over anhydrous sodium sulfate, and evaporated to dryness by rotary evaporation to give a crude product. The crude product was purified by column chromatography (DCM, DCM/EA=5/1) to give the target compound BA-1-4. $^1$H NMR (400 MHz, CDCl$_3$-d) δ 7.96-7.94 (m, 2H), 7.41-7.39 (m, 2H), 6.07 (s, 1H), 2.85 (s, 1H), 2.54 (m, 3H), 2.49 (s, 3H), 1.67 (s, 3H), 1.32-1.30 (m, 2H), 0.87-0.86 (m, 2H).

Step 4: Synthesis of the Compound BA-1-5

The compound BA-1-4 (6.97 g, 17.36 mmol, 1.00 eq) was dissolved in acetonitrile (25.00 mL) and dichloromethane (25.00 mL), N-bromosuccinimide (4.63 g, 26.04 mmol, 1.50 eq) was added in batches. The reaction was stirred at 15° C. for 1 hour. After completion of the reaction, the reaction solution was evaporated to dryness by rotary evaporation to give a crude product. The crude product was triturated with acetonitrile (50 mL) for 30 minutes, filtered and washed with acetonitrile (10 mL*3). The filter cake was collected and evaporated to dryness by rotary evaporation to give the target compound BA-1-5. $^1$H NMR (400 MHz, CDCl$_3$-d) δ 7.92-7.90 (m, 2H), 7.40-7.38 (m, 2H), 2.95 (m, 1H), 2.75 (s, 3H), 2.47 (s, 3H), 1.64 (s, 3H), 1.40-1.30 (m, 2H), 0.87-0.85 (m, 2H). MS m/z: 481.9 [M+H]$^+$ Step 5: Synthesis of the Compound BA-1

The compound BA-1-5 (5.30 g, 11.03 mmol, 1.00 eq) and 2-fluoroaniline (5.30 g, 47.65 mmol, 4.32 eq) were dissolved in ethanol (120.00 mL). The reaction temperature was raised to 85° C. and the reaction was stirred for 16 hours. After completion of the reaction, the reaction solution was cooled down and filtered, the filter cake was washed with ethanol (30 mL*3). The filter cake was collected and evaporated to dryness by rotary evaporation to give the target compound BA-1. $^1$H NMR (400 MHz, CDCl$_3$-d) δ 11.01 (s, 1H), 7.12-7.10 (m, 3H), 7.03-7.01 (m, 1H), 2.97 (s, 3H), 1.61 (m, 3H), 1.38-1.36 (t, 3H), 0.91-0.90 (t, 3H). MS m/z: 420.8 [M+H]$^+$ Reference Example 2: Fragment BA-2

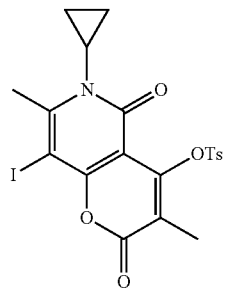 [SMILES: Cc1ccc(S(=O)(=O)Oc2c(C)c(=O)oc3c(I)c(C)n(C4CC4)c(=O)c23)cc1]

Synthetic Route:

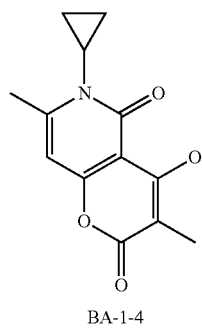 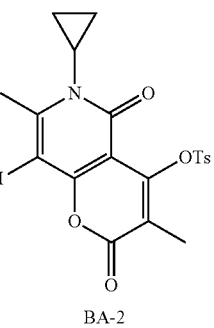

BA-1-4 BA-2

Step 1: Synthesis of the Compound BA-2

The compound BA-1-4 (3.00 g, 7.47 mmol, 1.00 eq) was dissolved in acetonitrile (40.00 mL) and dichloromethane (20.00 mL), N-iodosuccinimide (2.52 g, 11.21 mmol, 1.50 eq) was added under nitrogen protection. The reaction was stirred at 15° C. for 16 hours.

After completion of the reaction, the reaction solution was evaporated to dryness by rotary evaporation to give a crude product. The crude product was triturated with ethanol (150 mL) at 20° C. for 16 hours, then filtered and washed with ethanol (20 mL). The filter cake was collected and evaporated to dryness by rotary evaporation to give the target compound BA-2. $^1$H NMR (400 MHz, CDCl$_3$-d) δ 7.86-7.84 (d, J=8.4 Hz, 2H), 7.33-7.31 (d, J=8.0 Hz, 2H), 2.93-2.87 (m, 1H), 2.81 (s, 3H), 2.41 (s, 3H), 1.58 (s, 3H), 1.57-1.25 (m, 2H), 0.81-0.76 (m, 2H). MS m/z: 527.9 [M+H]$^+$ Reference Example 3: Fragment BA-3

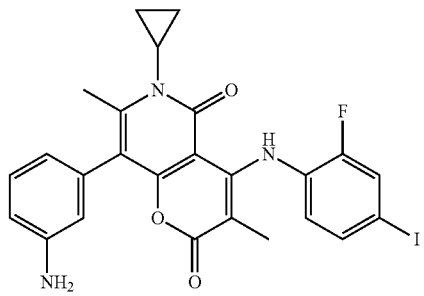 [SMILES: Cc1c(Nc2ccc(I)cc2F)c2c(=O)n(C3CC3)c(C)c(-c3cccc(N)c3)c2oc1=O]

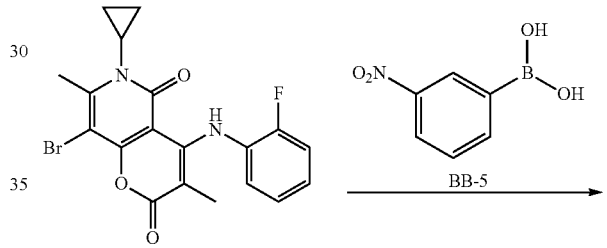

BA-1

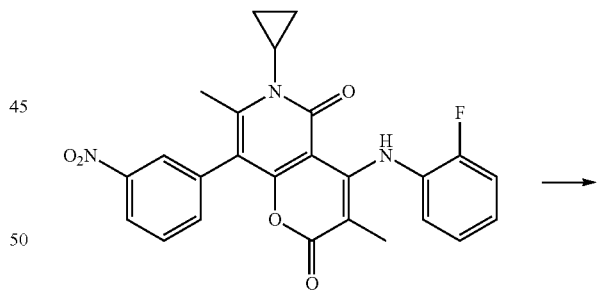

BA-3-1

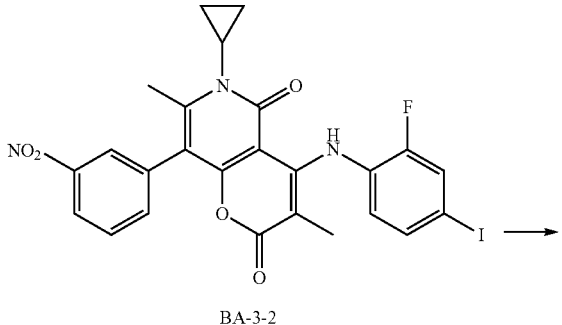

BA-3-2

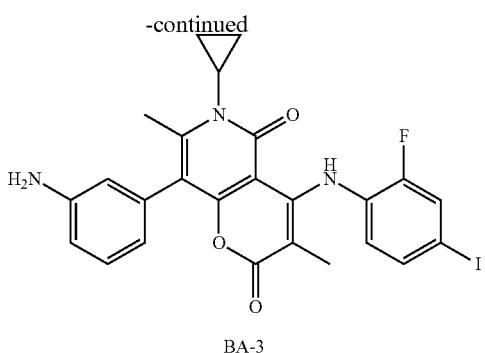

BA-3

Step 1: Synthesis of the Compound BA-3-1

The compound BA-1 (4.50 g, 10.73 mmol, 1.00 eq), the compound BB-5 (2.15 g, 12.88 mmol, 1.20 eq) and sodium bicarbonate solution (1 M, 21.47 mL, 2.00 eq) were dissolved in dioxane (300.00 mL), then the compound Pd(dppf)Cl$_2$.CH$_2$Cl$_2$ (876.56 mg, 1.07 mmol, 0.10 eq) was added under nitrogen protection. Under nitrogen protection, the reaction temperature was raised to 100° C. and the reaction was stirred for 16 hours. After completion of the reaction, the mixture was evaporated to dryness by rotary evaporation, dissolved in dichloromethane (300 mL) and stirred for 30 minutes. The mixture was then filtered by column chromatography (1 CM) and washed with dichloromethane/EtOAc=1/1 (200 mL). The organic phase was removed by rotary evaporation, dichloromethane (10 mL) was added, then ethanol (200 mL) was added slowly under stirring. The generated precipitate was collected, washed with ethanol (20 mL) and evaporated to dryness by rotary evaporation to give the compound BA-3-1. $^1$H NMR (400 MHz, CDCl$_3$-d) δ 11.06 (s, 1H), 8.31 (m, 1H), 8.29 (m, 1H), 7.99 (m, 1H), 7.97 (m, 1H), 7.69-7.60 (s, 3H), 7.12-7.02 (m, 1H), 2.96 (m, 1H), 2.39 (s, 3H), 1.59-1.58 (s, 3H), 1.38-1.42 (m, 2H), 0.99-0.98 (m, 2H). MS m/z: 484.1 [M+Na]$^+$ Step 2: Synthesis of the Compound BA-3-2

The compound BA-3-1 (3.76 mg, 8.15 mmol, 1.00 eq) was dissolved in N,N-dimethylformamide (25.00 mL), trifluoroacetic acid (7.00 mL) and N-iodosuccinimide (3.67 g, 16.30 mmol, 2.00 eq) were added at 20° C. The reaction was stirred at 20° C. for 16 hours. After completion of the reaction, water (400 mL) was added to quench the reaction. The solid was collected and washed with water (200 mL*2), and then dried. The obtained solid was triturated with ethanol (50 mL) twice, each time 30 minutes. After filtration, the filter cake was collected. The filter cake was triturated with methyl tert-butyl ether (100 mL) for 2 hours and filtered. The crude product was collected, washed with methyl tert-butyl ether (20 mL) and evaporated to dryness by rotary evaporation to give the compound BA-3-2. $^1$H NMR (400 MHz, CDCl$_3$-d) δ 11.03 (s, 1H), 8.31 (m, 1H), 8.29 (m, 1H), 8.1 (m, 1H), 7.69-7.59 (m, 1H), 7.47-7.41 (m, 2H), 6.72-6.68 (m, 1H), 2.95 (s, 3H), 2.39 (s, 3H), 1.60 (s, 3H), 1.40-1.38 (m, 2H), 0.99-0.98 (m, 2H). MS m/z: 587.9 [M+H]$^+$ Step 3: Synthesis of the Compound BA-3

The compound BA-3-2 (1.80 mg, 3.06 mmol, 1.00 eq) was dissolved in acetic acid (25.00 mL), followed by addition of zinc powder (3.00 g, 45.87 mmol, 14.99 eq). The reaction was stirred at 10° C. for 3 hours. After completion of the reaction, the reaction mixture was filtered and the filter cake was washed with dichloromethane (30 mL*3). The filtrate was collected, and then washed sequentially with water (30 mL*3), saturated sodium bicarbonate solution (30 mL*3) and saturated sodium chloride solution (30 mL). The organic phase was dried over anhydrous sodium sulfate, and evaporated to dryness by rotary evaporation to give a crude product. The crude product was purified by column chromatography (DCM, DCM/EA=10/1) to give the target compound BA-3. $^1$H NMR (400 MHz, CDCl$_3$-d) δ 11.17 (s, 1H), 7.47-7.46 (m, 1H), 7.46-7.44 (m, 1H), 7.21-7.19 (m, 1H), 6.73-6.69 (m, 2H), 6.58 (m, 1H), 6.56-6.52 (m, 1H), 2.94-2.92 (m, 1H), 2.38 (s, 3H), 2.38 (s, 3H), 1.36-1.35 (m, 2H), 0.95-0.94 (m, 2H). MS m/z: 587.9 [M+H]$^+$ Reference Example 4: Fragment BA-4

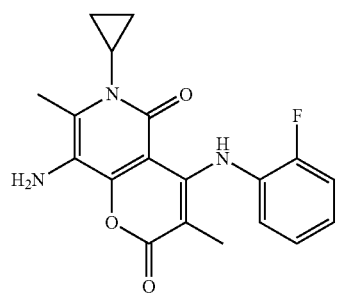 [SMILES: Cc1c(Nc2ccccc2F)c2c(=O)n(C3CC3)c(C)c(N)c2oc1=O]

Synthetic Route:

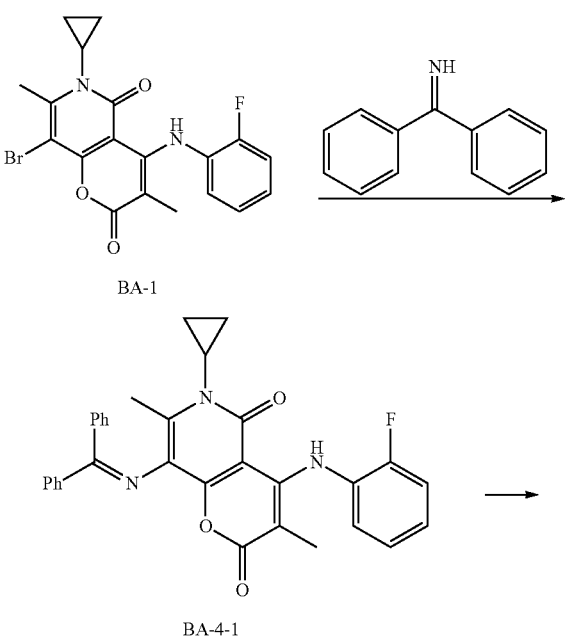

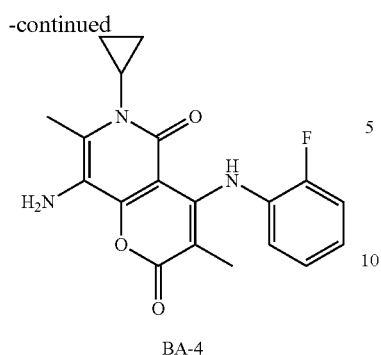

BA-4

Step 1: Synthesis of the Compound BA-4-1

The compound BA-1 (5.00 g, 11.93 mmol, 1.00 eq) and benzophenone imine (3.24 g, 17.90 mmol, 1.50 eq) were added into toluene (10.00 mL), then cesium carbonate (8.55 g, 26.25 mmol, 2.20 eq), $Pd_2(dba)_3$ (1.09 g, 1.19 μmol, 0.10 eq) and SPhos (1.04 g, 1.79 mmol, 0.15 eq) were added under nitrogen protection. The reaction temperature was raised to 110° C. and the reaction was stirred for 12 hours. After completion of the reaction, the reaction mixture was diluted with water (50 mL) and extracted with EtOAc (50 mL*3). The organic phase was collected, washed with saturated sodium chloride solution (100 mL), dried over anhydrous sodium sulfate, and evaporated to dryness by rotary evaporation to give a crude product. The crude product was purified by column chromatography (PE/EA=5/1) to give the compound BA-4-1. $^1$H NMR (400 MHz, $CDCl_3$-d) δ 11.16 (s, 1H), 7.82 (m, 2H), 7.80 (m, 1H), 7.45-7.43 (m, 3H), 7.33-7.31 (m, 3H), 7.20-7.19 (m, 2H), 7.07-7.06 (m, 3H), 6.93 (m, 1H), 2.89-2.84 (m, 1H), 2.43 (s, 3H), 1.57 (s, 3H), 1.54 (m, 2H), 1.20 (m, 2H). MS m/z: 520.3 $[M+H]^+$

Step 2: Synthesis of the Compound BA-4

The compound BA-4-1 (2.10 g, 4.04 mmol, 1.00 eq) was dissolved in 1 M aqueous hydrochloric acid solution (20.00 mL) and acetonitrile (10.00 mL), the reaction was stirred at 20° C. under nitrogen atmosphere for 0.5 hour. After completion of the reaction, the solvent was removed by rotary evaporation, then saturated sodium bicarbonate solution (30 mL) was added and a solid formed. After filtration, the filter cake was collected, triturated with methyl tert-butyl ether (50 mL), and evaporated to dryness by rotary evaporation to give the target compound BA-4.

$^1$H NMR (400 MHz, $CDCl_3$-d) δ 11.76 (s, 1H), 7.31-7.28 (m, 1H), 7.80 (m, 1H), 7.20-7.17 (m, 2H), 7.13-7.11 (m, 1H), 4.36 (s, 2H), 3.00-2.94 (m, 1H), 2.47 (s, 3H), 1.47 (s, 3H), 1.21-1.16 (m, 2H), 0.81-0.77 (m, 2H). MS m/z: 356.1 $[M+H]^+$

Reference Example 5: Fragment BA-5

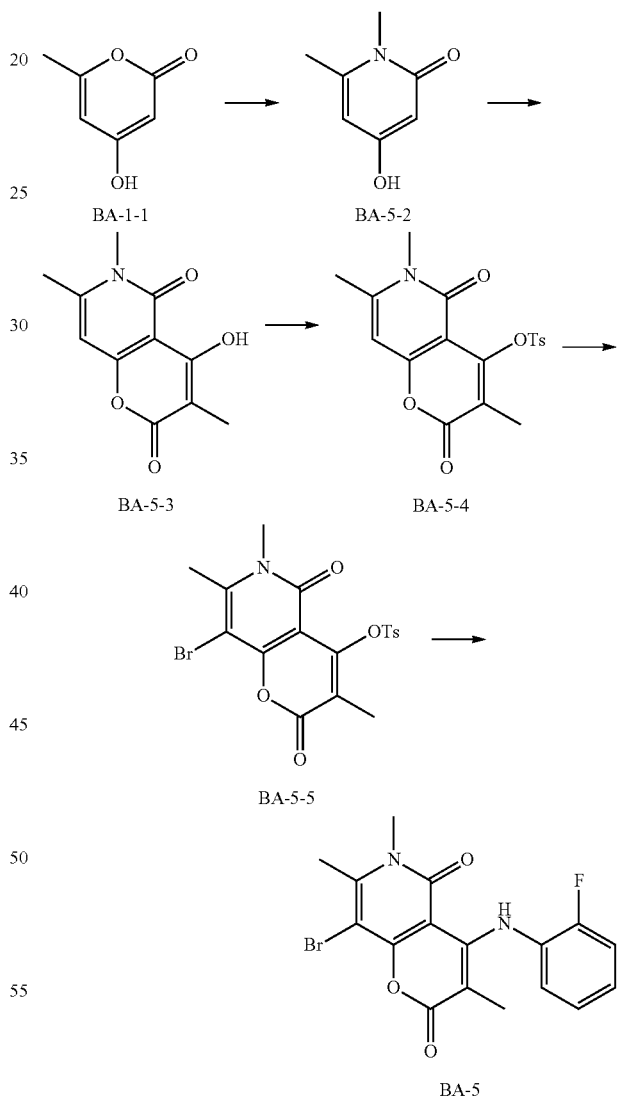

Synthetic Route:

Step 1: Synthesis of the Compound BA-5-2

The compound BA-1-1 (20.00 g, 158.59 mmol, 1.00 eq) was dissolved in methylamine (30%) (150.00 g, 1.45 mol, 9.14 eq), the reaction was stirred at 100° C. for 2 hours. After completion of the reaction, the reaction mixture was cooled to room temperature, the solvent was removed by rotary evaporation. The crude product was added into acetonitrile (200 mL) and the mixture was filtered. The filter cake was collected to give the target compound BA-5-2. $^1$H NMR (400 MHz, CDCl$_3$-d) δ 10.22 (s, 1H), 5.76 (s, 1H), 5.49 (s, 1H), 3.30 (s, 3H), 2.27 (s, 3H). MS m/z: 139.8 [M+H]$^+$ Step 2: Synthesis of the Compound BA-5-3

The compound BA-5-2 (5.00 g, 35.93 mmol, 1.00 eq) and methylmalonic acid (6.26 g, 35.93 mmol, 6.14 mL, 1.00 eq) were dissolved in diphenyl ether (100.00 mL), the reaction was stirred under reflux for 2 hours. After completion of the reaction, the reaction solution was cooled to room temperature, and a precipitate formed. The mixture was filtered, and the filter cake was collected to give the target compound BA-5-3. $^1$H NMR (400 MHz, CDCl$_3$-d) δ 13.35 (s, 1H), 6.64 (s, 1H), 3.54 (s, 1H), 2.52 (s, 3H), 1.84 (s, 3H). MS m/z: 221.9 [M+H]$^+$ Step 3: Synthesis of the Compound BA-5-4

The compound BA-5-3 (4.80 g, 21.70 mmol, 1.00 eq) was dissolved in dichloromethane (10.00 mL), triethylamine (4.39 g, 43.40 mmol, 6.02 mL, 2.00 eq) was added, then p-toluenesulfonyl chloride (4.96 g, 26.04 mmol, 1.20 eq) was added at 25° C. The reaction was stirred at 25° C. for 15 hours. After completion of the reaction, the solvent was removed by rotary evaporation, the crude product was triturated with ethanol and filtered. The filter cake was collected to give the target compound BA-5-4. $^1$H NMR (400 MHz, CDCl$_3$-d) δ 7.90-7.85 (s, 2H), 7.49-7.47 (m, 2H), 6.39 (m, 1H), 3.36 (m, 6H), 2.45-2.44 (m, 6H). MS m/z: 376.1 [M+H]$^+$ Step 4: Synthesis of the Compound BA-5-5

The compound BA-5-4 (2.80 g, 7.46 mmol, 1.00 eq) was dissolved in dichloromethane (30 mL) and acetonitrile (60 mL), N-bromosuccinimide (1.99 g, 11.19 mmol, 1.50 eq) was added slowly. The reaction was stirred at 25° C. for 15 hours. After completion of the reaction, the solvent was removed by rotary evaporation, the crude product was triturated with ethanol (100 mL) and filtered. The filter cake was collected to give the target compound BA-5-5. $^1$H NMR (400 MHz, CDCl$_3$-d) δ 7.93-7.91 (d, J=8.4, 2H), 7.40-7.27 (d, J=8.0, 2H), 3.63 (s, 3H), 2.68 (s, 3H), 2.48 (s, 3H), 1.63 (s, 3H). MS m/z: 456.0 [M+H]$^+$ Step 5: Synthesis of the Compound BA-5

The compound BA-5-5 (1.00 g, 2.20 mmol, 1.00 eq) and 2-fluoroaniline (4.89 g, 44.00 mmol, 4.25 mL, 20.00 eq) were dissolved in ethanol (10.00 mL), and the reaction was stirred under vigorous reflux for 15 hours. After completion of the reaction, the reaction solution was cooled to room temperature, and a solid appeared. The mixture was filtered, and the filter cake was collected to give the target compound BA-5. $^1$H NMR (400 MHz, CDCl$_3$-d) δ 11.10 (s, 1H), 7.13-7.12 (d, J=5.6, 3H), 7.11 (s, 1H), 3.69 (s, 3H), 2.74 (s, 3H). MS m/z: 394.9 [M+H]$^+$ Reference Example 6: Fragment BA-6

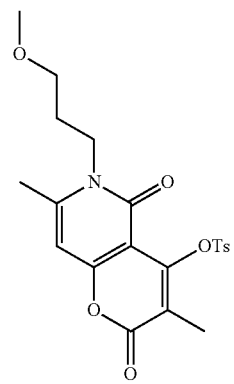 [SMILES: COCCCn1c(C)cc2oc(=O)c(C)c(OS(=O)(=O)c3ccc(C)cc3)c2c1=O]

Synthetic Route:

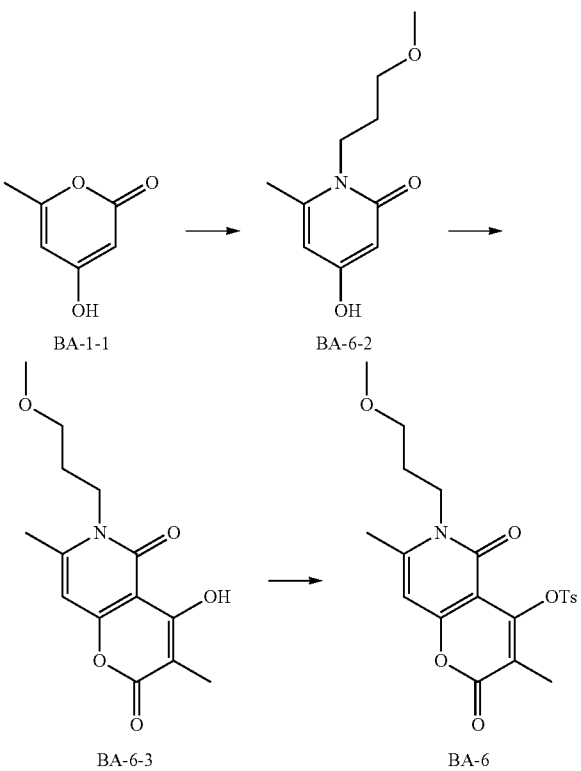

Step 1: Synthesis of the Compound BA-6-2

The compound BA-1-1 (10.00 g, 79.30 mmol, 1.00 eq) and methoxypropylamine (7.07 g, 79.30 mmol, 8.13 mL, 1.00 eq) were dissolved in water (100.00 mL), the reaction mixture was heated to reflux and stirred for 1 hour. After completion of the reaction, the mixture was cooled to room temperature, the solvent was removed by rotary evaporation, the crude product was triturated with methyl tert-butyl ether (150 mL) and filtered. The filter cake was collected to give the target compound BA-6-2. MS m/z: 527.9 [M+H]$^+$

Step 2: Synthesis of the Compound BA-6-3

The compound BA-6-2 (13.70 g, 69.46 mmol, 1.00 eq) and methylmalonic acid (12.30 g, 104.19 mmol, 8.42 mL, 1.50 eq) were dissolved in acetic anhydride (200.00 mL). The reaction was stirred at 100° C. for 1 hour. After completion of the reaction, the mixture was cooled to room temperature, and methyl tert-butyl ether (200 mL) was added. After 15 hours, a white solid formed and the mixture was filtered. The filter cake was collected to give the target compound BA-6-3. MS m/z: 279.9 [M+H]$^+$

Step 3: Synthesis of the Compound BA-6

The compound BA-6-3 (10.00 g, 35.81 mmol, 1.00 eq) was dissolved in dichloromethane (150.00 mL), followed by addition of triethylamine (7.25 g, 71.62 mmol, 9.93 mL, 2.00 eq) and p-toluenesulfonyl chloride (13.65 g, 71.62 mmol, 2.00 eq). The reaction was stirred at 15° C. for 15 hours. After completion of the reaction, the solvent was removed by rotary evaporation, the crude product was triturated with methyl tert-butyl ether (200 mL) and filtered. The filter cake was collected to give the target compound BA-6. MS m/z: 434.1 [M+H]$^+$

Reference Example 7: Fragment BB-1

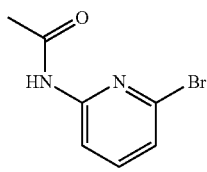

Synthetic Route:

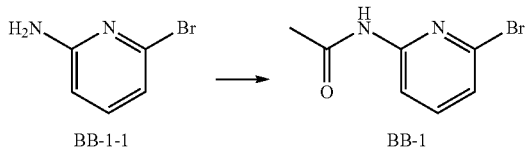

Step 1: Synthesis of the Compound BB-1

The compound BB-1-1 (3.50 g, 20.23 mmol, 1.00 eq) was dissolved in dichloromethane (40.00 mL), followed by addition of acetic anhydride (6.55 g, 64.13 mmol, 3.17 eq). The reaction was stirred at 20° C. for 16 hours. After completion of the reaction, the reaction mixture was evaporated to dryness by rotary evaporation to give a crude product.

The crude product was dissolved in EtOAc (100 mL), and washed sequentially with water (200 mL), saturated sodium bicarbonate solution (200 mL) and saturated sodium chloride solution (100 mL), dried over anhydrous sodium sulfate, and evaporated to dryness by rotary evaporation to give the target compound BB-1. $^1$H NMR (400 MHz, CDCl$_3$-d) δ 8.15 (d, J=8.0 Hz, 1H), 8.08 (br. s., 1H), 7.55 (t, J=8.0 Hz, 2H), 8.15 (d, J=7.6 Hz, 1H), 2.20 (s, 3H).

Reference Example 8: Fragment BB-2

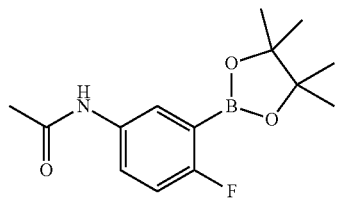 [SMILES: CC(=O)Nc1ccc(F)c(B2OC(C)(C)C(C)(C)O2)c1]

Synthetic Route:

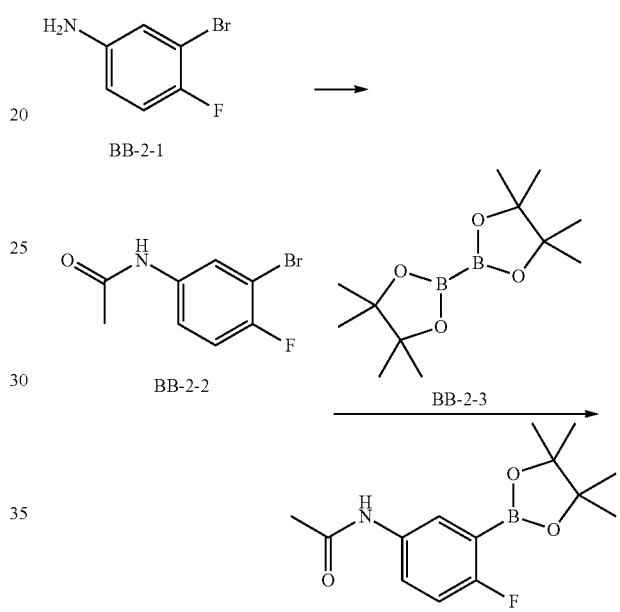

Step 1: Synthesis of the Compound BB-2-2

The compound BB-2-1 (5.00 g, 26.31 mmol, 1.00 eq) was dissolved in dichloromethane (120.00 mL), triethylamine (3.19 g, 31.57 mmol, 1.20 eq) was added, then acetyl chloride (2.07 g, 26.31 mmol, 1.00 eq) was added dropwise at 0° C. The reaction temperature was raised to 25° C., and the reaction was stirred for 3 hours. After completion of the reaction, the reaction solution was washed sequentially with saturated sodium bicarbonate solution (80 mL*3), water (100 mL*2) and saturated sodium chloride solution (80 mL). The organic phase was collected, dried over anhydrous sodium sulfate, evaporated to dryness by rotary evaporation to give a crude product. The crude product was triturated with petroleum ether (30 mL), filtered and evaporated to dryness by rotary evaporation to give the compound BB-2-2. $^1$H NMR (400 MHz, CDCl$_3$-d) δ 7.81-7.79 (m, 1H), 7.40-7.36 (m, 2H), 7.06 (t, J=8.6 Hz, 1H), 2.18 (s, 3H). MS m/z: 231.8 [M+H]$^+$

Step 2: Synthesis of the Compound BB-2

The compound BB-2-2 (1.00 g, 4.31 mmol, 1.00 eq) was dissolved in anhydrous dioxane (20.00 mL), the compound BB-2-3 (1.42 g, 5.60 mmol, 1.30 eq), potassium acetate (1.27 g, 12.93 mmol, 3.00 eq) and Pd(dppf)Cl$_2$ (157.68 mg, 215.50 μmol, 0.05 eq) were added sequentially at 25° C. under nitrogen protection. The reaction temperature was raised to 100° C., and the reaction was stirred for 15 hours. After completion of the reaction, the solid was removed by filtration and washed with dichloromethane (25 mL*3). The filtrate was collected and evaporated to dryness by rotary evaporation to give a crude product. The crude product was purified by column chromatography (PE/EA=8/1-2/1) to give the target compound BB-2. $^1$H NMR (400 MHz, CDCl$_3$-d) δ 7.84-7.81 (m, 1H), 7.56-7.54 (m, 1H), 7.22 (br. s., 1H), 7.00 (t, J=8.8 Hz, 1H), 2.15 (s, 3H), 1.35 (s, 12H). MS m/z: 279.9 [M+H]$^+$ Reference Example 9: Fragment BB-3

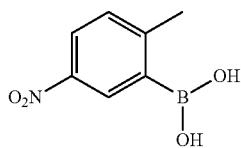

Synthetic Route:

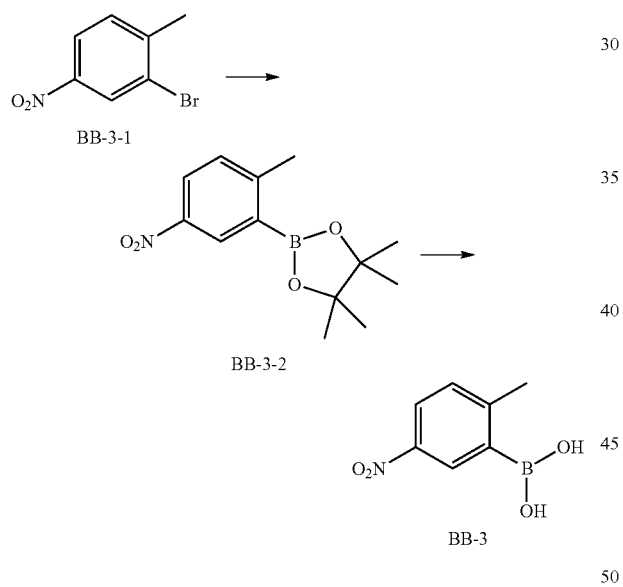

Step 1: Synthesis of the Compound BB-3-2

The compound BB-3-1 (20.00 g, 92.58 mmol, 1.00 eq), the compound BB-2-3 (28.21 g, 111.10 mmol, 1.20 eq), potassium acetate (27.26 g, 277.74 mmol, 3.00 eq) and Pd(dppf)Cl$_2$.CH$_2$Cl$_2$ (3.78 g, 4.63 mmol, 0.05 eq) were dissolved in dioxane (150.00 mL).

The reaction temperature was raised to 100° C. and the reaction was stirred under nitrogen atmosphere for 16 hours. After completion of the reaction, the reaction mixture was dissolved in EtOAc (350 mL), washed sequentially with water (100 mL*3) and saturated sodium chloride solution (200 mL*2), dried over anhydrous sodium sulfate and evaporated to dryness by rotary evaporation. The residue was triturated with petroleum ether (50 mL) for 30 minutes, then filtered and collected. The crude product was washed with petroleum ether (20 mL) and evaporated to dryness by rotary evaporation to give the compound BB-3-2. $^1$H NMR (400 MHz, CDCl$_3$-d) δ 8.61 (d, J=2.0 Hz, 1H), 8.15 (dd, J=8.2 Hz, J=2.6 Hz, 1H), 7.32 (d, J=8.4 Hz, 1H), 2.65 (s, 3H), 1.38 (s, 12H).

Step 2: Synthesis of the Compound BB-3

The compound BB-3-2 (16.00 g, 60.81 mmol, 1.00 eq) was dissolved in THF (400.00 mL) and water (200.00 mL), followed by addition of sodium periodate (39.02 g, 182.43 mmol, 3.00 eq). The reaction was stirred at 20° C. for 1 hour, then hydrochloric acid (1 M, 200.06 mL, 3.29 eq) was added, and the reaction was stirred for 16 hours. After completion of the reaction, the reaction solution was extracted with EtOAc (250 mL*3). The organic phase was washed sequentially with water (200 mL*3) and saturated sodium chloride solution (200 mL), dried over anhydrous sodium sulfate and evaporated to dryness by rotary evaporation to give a crude product. The crude product was triturated with methyl tert-butyl ether (100 mL) for 1 hour, then filtered to give the target compound BB-3. $^1$H NMR (400 MHz, MeOD) δ 8.16 (s, 1H), 8.11 (d, J=8.0 Hz, 1H), 7.42 (d, J=8.0 Hz, 1H), 2.46 (s, 3H).

Reference Example 10: Fragment BB-4

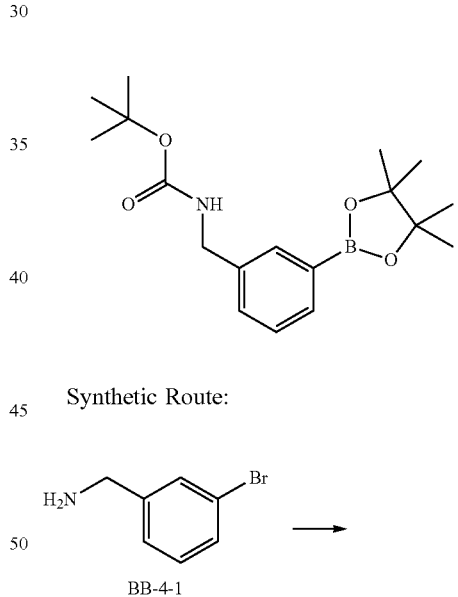

Synthetic Route:

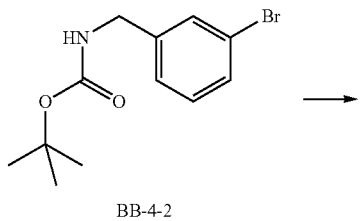

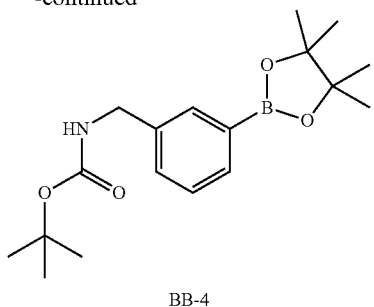

BB-4

Step 1: Synthesis of the Compound BB-4-2

The compound BB-4-1 (4.50 g, 24.19 mmol, 1.00 eq) was dissolved in dioxane (45.00 mL), saturated sodium bicarbonate solution (45 mL) was added, then Boc$_2$O (7.92 g, 36.28 mmol, 1.50 eq) was added at 0° C. The reaction temperature was raised to 20° C. and the reaction was stirred for 1 hour. After completion of the reaction, EtOAc (50 mL*2) was added.

The organic phase was washed with saturated sodium chloride solution (100 mL), dried over anhydrous sodium sulfate, and evaporated to dryness by rotary evaporation to give a crude product. The crude product was purified by column chromatography (PE/EA=50/1-10/1), and evaporated to dryness by rotary evaporation to give the compound BB-4-2. $^1$H NMR (400 MHz, CDCl$_3$-d) δ 7.44 (s, 1H), 7.42-7.39 (m, 1H), 7.21 (d, J=6.4 Hz, 2H), 7.00 (t, J=8.8 Hz, 1H), 4.86 (br. s., 1H), 4.30 (d, J=5.6 Hz, 2H), 1.47 (s, 9H). MS m/z: 231.8 [M+H]$^+$

Step 2: Synthesis of the Compound BB-4

The compound BB-2-3 (7.45 g, 29.36 mmol, 1.50 eq) and the compound BB-4-2 (5.60 g, 19.57 mmol, 1.00 eq), potassium acetate (3.84 g, 39.14 mmol, 2.00 eq) and Pd(dppf)Cl$_2$·CH$_2$Cl$_2$ (1.60 g, 1.96 mmol, 0.10 eq) were dissolved in dioxane (110.00 mL). Under nitrogen protection, the reaction temperature was raised to 80° C. and the reaction was stirred for 3 hours. After completion of the reaction, the reaction solution was filtered through diatomaceous earth, the filtrate was evaporated to dryness by rotary evaporation to give a crude product. The crude product was purified by column chromatography (PE/EA=5/1) to give the target compound BB-4. $^1$H NMR (400 MHz, CDCl$_3$-d) δ 7.72 (d, J=6.0 Hz, 2H), 7.44-7.40 (m, 1H), 7.35 (t, J=8.0 Hz, 1H), 4.81 (br. s., 1H), 4.31 (d, J=5.6 Hz, 2H), 1.47 (s, 9H), 1.35 (s, 12H). MS m/z: 233.9 [M-Boc+H]$^+$

Reference Example 11: Fragment BB-6

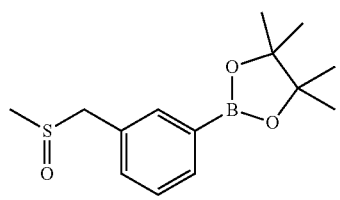

Synthetic Route:

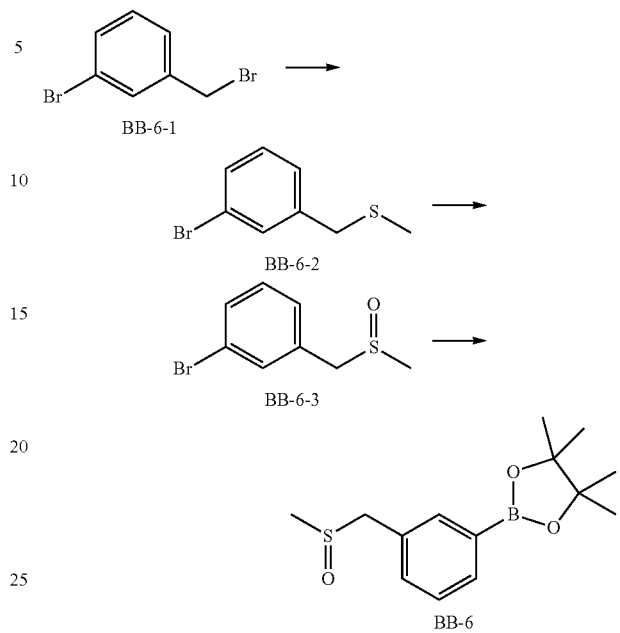

Step 1: Synthesis of the Compound BB-6-2

At 0° C. under nitrogen protection, sodium thiomethoxide (1.34 g, 18.16 mmol, 1.22 mL, 2.27 eq) was dissolved in N,N-dimethylformamide (5.00 mL), followed by addition of the compound BB-6-1 (2.00 g, 8.00 mmol, 1.00 eq). The reaction temperature was raised to 15° C. and the reaction was stirred for 16 hours. After completion of the reaction, the reaction mixture was diluted with water (20 mL) and extracted with EtOAc (30 mL*2). The organic phase was washed with saturated sodium chloride solution (30 mL), dried over anhydrous sodium sulfate, filtered and evaporated to dryness by rotary evaporation to give the compound BB-6-2. $^1$H NMR (400 MHz, CDCl$_3$-d) δ 7.40 (s, 1H), 7.31 (d, J=7.6 Hz, 1H), 7.16 (d, J=7.6 Hz, 1H), 7.11 (t, J=7.8 Hz, 1H), 3.56 (s, 2H), 1.93 (s, 3H).

Step 2: Synthesis of the Compound BB-6-3

The compound BB-6-2 (1.70 g, 7.83 mmol, 1.00 eq) was dissolved in hexafluoroisopropanol (2.00 mL), followed by addition of hydrogen peroxide (1.78 g, 15.66 mmol, 1.50 mL, 2.00 eq). The reaction was stirred at 25° C. for 2 hours. After completion of the reaction, the reaction mixture was diluted with water (10 mL) and extracted with EtOAc (20 mL*2). The organic phases were combined and washed with saturated sodium chloride solution (30 mL), dried over anhydrous sodium sulfate, filtered, and evaporated to dryness by rotary evaporation to give a crude product. The crude product was stirred in petroleum ether (10 mL) for 0.5 hour, then filtered to give the compound BB-6-3. $^1$H NMR (400 MHz, CDCl$_3$-d) δ 7.52 (d, J=7.2 Hz, 1H), 7.48 (s, 1H), 7.29-7.26 (m, 2H), 3.98 (d, J=12.8 Hz, 1H), 3.92 (d, J=12.8 Hz, 1H), 2.51 (s, 3H).

Step 3: Synthesis of the Compound BB-6

Potassium acetate (1.52 g, 15.44 mmol, 2.00 eq) and Pd(dppf)Cl$_2$ (564.95 mg, 772.00 μmol, 0.10 eq) were added to a solution of the compound BB-6-3 (1.80 g, 7.72 mmol, 1.00 eq) and the compound BB-2-3 (2.94 g, 11.58 mmol, 1.50 eq) in dioxane (10.00 mL). The reaction was stirred at 80° C. under nitrogen atmosphere for 16 hours. After completion of the reaction, the mixture was filtered and evaporated to dryness by rotary evaporation to give a crude product.

The crude product was purified by column chromatography (DCM/MeOH=1/0-30/1) to give the target compound BB-6. $^1$H NMR (400 MHz, CDCl$_3$-d) δ 7.82-7.78 (m, 1H), 7.71 (s, 1H), 7.44-7.39 (m, 2H), 4.13 (d, J=12.8 Hz, 1H), 3.94 (d, J=12.8 Hz, 1H), 2.48 (s, 3H), 1.37 (s, 12H). MS m/z: 281.1 [M+H]$^+$ Reference Example 12: Fragment BB-7

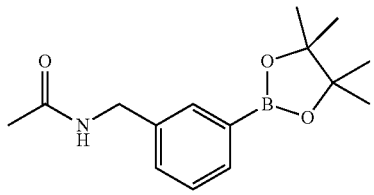 [SMILES: CC(=O)NCc1cccc(B2OC(C)(C)C(C)(C)O2)c1]

Synthetic Route:

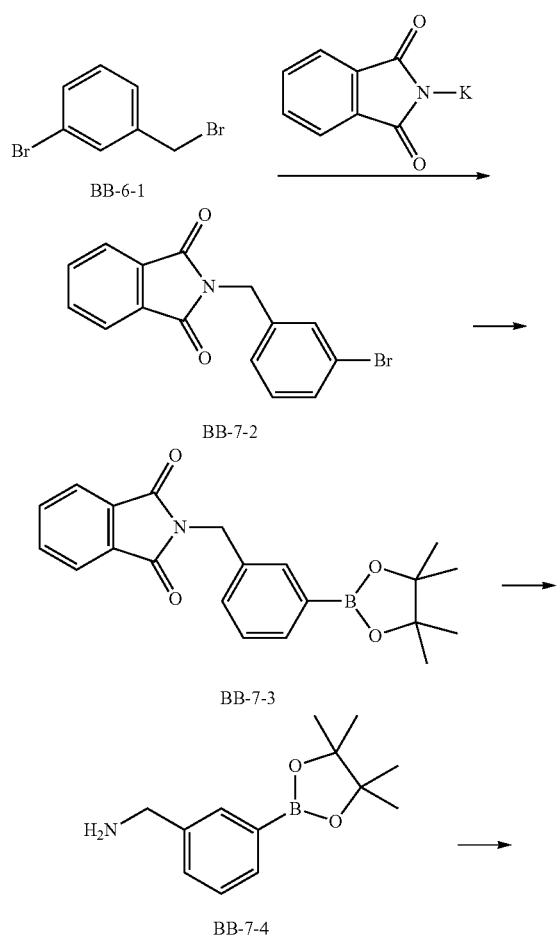

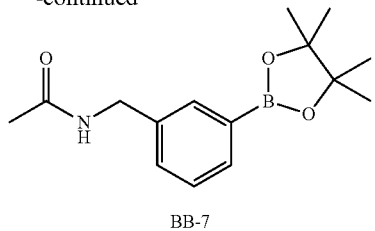

BB-7

Step 1: Synthesis of the Compound BB-7-2

The compound BB-6-1 (1.00 g, 4.00 mmol, 1.00 eq) and phthalimide potassium (643.20 mg, 3.47 mmol, 0.87 eq) were dissolved in N,N-dimethylformamide (5.00 mL), the reaction was protected for dryness with calcium chloride and stirred at 100° C. for 12 hours. After completion of the reaction, the reaction mixture was diluted with water (15 mL) and extracted with EtOAc (40 mL*2). The organic phases were combined and washed with saturated sodium chloride solution (20 mL*3), dried over anhydrous sodium sulfate, filtered, and evaporated to dryness by rotary evaporation to give a crude product. The crude product was stirred in petroleum ether (10 mL) for 0.5 hour, then filtered and evaporated to dryness by rotary evaporation to give the compound BB-7-2. $^1$H NMR (400 MHz, CDCl$_3$-d) δ 7.90-7.87 (m, 2H), 7.76-7.74 (m, 2H), 7.60 (s, 1H), 7.46-7.35 (m, 2H), 7.21 (t, J=5.2 Hz, 1H), 4.83 (s, 2H). MS m/z: 315.9 [M+H]$^+$ Step 2: Synthesis of the Compound BB-7-3

The compound BB-7-2 (700.00 mg, 2.21 mmol, 1.00 eq) and the compound BB-2-3 (673.45 mg, 2.65 mmol, 1.20 eq) were dissolved in dioxane (10.00 mL), then potassium acetate (433.78 mg, 4.42 mmol, 2.00 eq) and Pd(dppf)Cl$_2$ (161.71 mg, 221.00 μmol, 0.10 eq) were added. The reaction was stirred at 80° C. under nitrogen atmosphere for 16 hours. After completion of the reaction, the reaction mixture was filtered, evaporated to dryness by rotary evaporation to give a crude product. The crude product was purified by column chromatography (PE/EA=10/1-2/1) to give the compound BB-7-3. $^1$H NMR (400 MHz, CDCl$_3$-d) δ 7.89-7.86 (m, 3H), 7.74-7.71 (m, 3H), 7.53 (d, J=6.4 Hz, 1H), 7.34 (t, J=8.0 Hz, 1H), 4.88 (s, 2H), 1.36 (s, 12H). MS m/z: 364.0 [M+H]$^+$ Step 3: Synthesis of the Compound BB-7-4

The compound BB-7-3 (600.00 mg, 1.65 mmol, 1.00 eq) was dissolved in THF (5.00 mL), then hydrazine hydrate (253.15 mg, 4.96 mmol, 3.00 eq) was added. The reaction was stirred at 80° C. under nitrogen atmosphere for 12 hours. After completion of the reaction, the reaction mixture was filtered and evaporated to dryness by rotary evaporation to give the compound BB-7-4. $^1$H NMR (400 MHz, CDCl$_3$-d) δ 7.77 (m, 1H), 7.73-7.71 (m, 1H), 7.45-7.43 (m, 1H), 7.39-7.35 (s, 1H), 3.90 (s, 2H), 1.37 (m, 12H).

Step 4: Synthesis of the Compound BB-7

The compound BB-7-4 (500.00 mg, 1.34 mmol, 1.00 eq) and triethylamine (271.19 mg, 2.68 mmol, 2.00 eq) were dissolved in dichloromethane (10 mL), followed by addition of acetyl chloride (157.79 mg, 2.01 mmol, 1.50 eq) at 0° C. The reaction was stirred at room temperature under nitrogen atmosphere for 20 minutes. After completion of the reaction, the reaction mixture was diluted with water (10 mL) and extracted with EtOAc (20 mL*3). The organic phases were combined, washed with water (30 mL), dried over anhydrous sodium sulfate, filtered and evaporated to dryness by rotary evaporation to give a crude product. The crude product was purified by column chromatography (PE/EA=5/1-1/1) to give the target compound BB-7. $^1$H NMR (400 MHz, CDCl$_3$-d) δ 7.67-7.64 (m, 2H), 7.34-7.26 (m, 2H), 4.37 (d, J=6.0 Hz, 2H), 1.95 (s, 3H), 1.28 (s, 12H). MS m/z: 276.2 [M+H]$^+$ Reference Example 13: Fragment BB-8

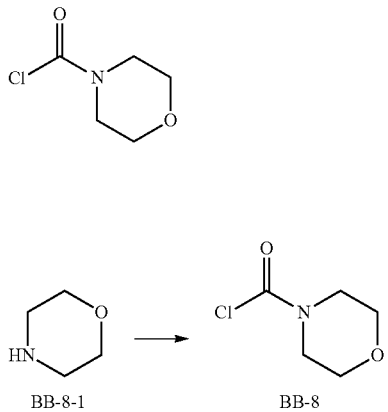

Step 1: Synthesis of the Compound BB-8

The compound BB-8-1 (60.00 mg, 688.71 μmol, 1.00 eq) and triphosgene (214.59 mg, 723.15 μmol, 1.05 eq), pyridine (163.43 mg, 2.07 mmol, 3.00 eq) were added into dichloromethane (2.00 mL), the reaction was stirred at 0° C. under nitrogen atmosphere for 1 hour. After completion of the reaction, the reaction mixture was evaporated to dryness by rotary evaporation to give the target compound BB-8.

Reference Example 14: Fragment BB-9

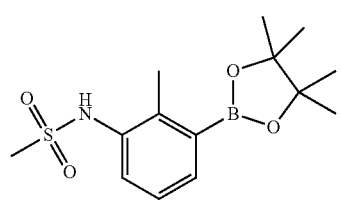

Synthetic Route:

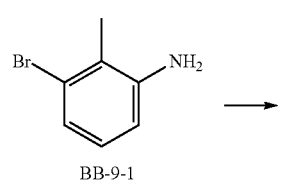

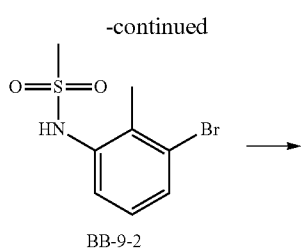

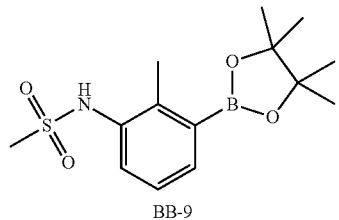

Step 1: Synthesis of the Compound BB-9-2

The compound BB-9-1 (5.00 g, 26.87 mmol, 1.00 eq) was dissolved in pyridine (100.00 mL), then methanesulfonyl chloride (11.87 g, 103.62 mmol, 3.86 eq) was added at 0° C. under nitrogen protection. The reaction temperature was raised to 60° C. and the reaction was stirred for 1 hour. After completion of the reaction, the solvent was removed by rotary evaporation. The residue was dissolved in dichloromethane (100 mL), washed with hydrochloric acid (1 M, 100 mL) and saturated sodium bicarbonate solution (100 mL). The organic phase was dried over anhydrous sodium sulfate, filtered and evaporated to dryness by rotary evaporation to give a crude product. The crude product was purified by column chromatography (PE/EA=10/1-2/1) to give the compound BB-9-2. $^1$H NMR (400 MHz, CDCl$_3$-d) δ 7.47 (d, J=8.0 Hz, 1H), 7.43 (d, J=8.0 Hz, 1H), 7.10 (t, J=8.0H, 1H), 6.39 (s, 1H), 3.03 (s, 3H), 2.45 (s, 3H). MS m/z: 264.0 [M+H]$^+$ Step 2: Synthesis of the Compound BB-9

The compound BB-9-2 (3.00 g, 11.36 mmol, 1.00 eq) and the compound BB-2-3 (4.33 g, 17.04 mmol, 1.50 eq) were dissolved in dioxane (60.00 mL), then Pd(dppf)Cl$_2$.CH$_2$Cl$_2$ (927.51 mg, 1.14 mmol, 0.10 eq) and potassium acetate (3.34 g, 34.08 mmol, 3.00 eq) were added at 20° C. under nitrogen protection. The reaction temperature was raised to 85° C. and the reaction was stirred for 3 hours. After completion of the reaction, the reaction mixture was cooled to room temperature, diluted with water (100 mL) and extracted with dichloromethane (100 mL*2). The organic phase was collected, washed with saturated sodium chloride solution (100 mL), dried over anhydrous sodium sulfate, filtered, and evaporated to dryness by rotary evaporation to give a crude product. The crude product was purified by preparative TLC (PE/EA=1/1) to give the compound BB-9. $^1$H NMR (400 MHz, CDCl$_3$-d) δ 7.70-7.65 (m, 1H), 7.61-7.56 (m, 1H), 7.25 (t, J=7.6 Hz, 1H), 6.29 (s, 1H), 3.00 (s, 3H), 2.55 (s, 3H), 1.37 (s, 12H). MS m/z: 311.9 [M+H]$^+$

Reference Example 15: Fragment BB-10

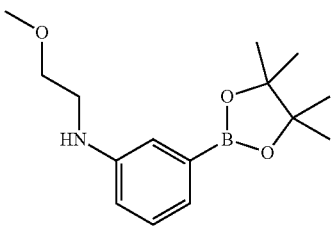

Synthetic Route:

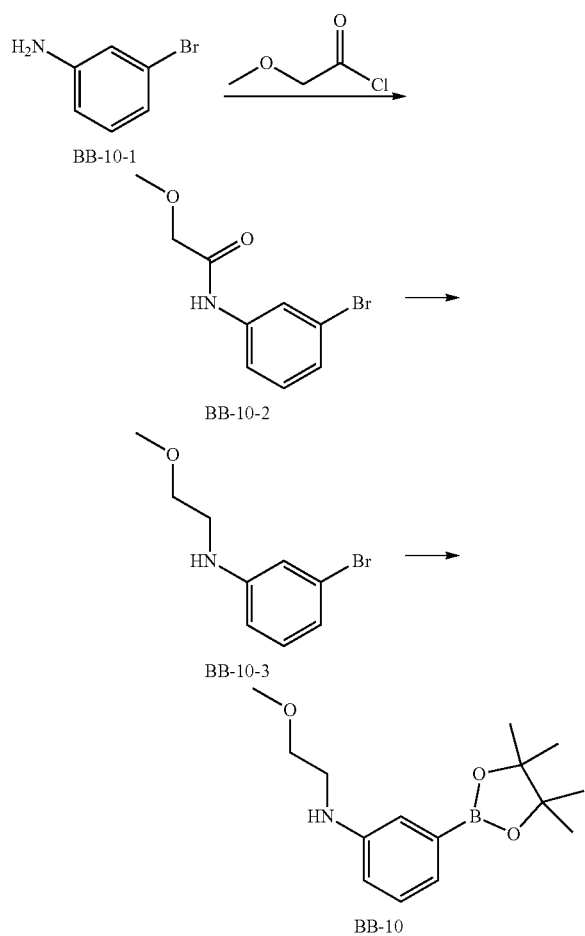

Step 1: Synthesis of the Compound BB-10-2

The compound BB-10-1 (6.00 g, 34.88 mmol, 1.00 eq) was dissolved in dichloromethane (60.00 mL), then triethylamine (7.06 g, 69.76 mmol, 9.67 mL, 2.00 eq) was added, and a solution of methoxy acetyl chloride (3.97 g, 36.62 mmol, 1.05 eq) dissolved in dichloromethane (60 mL) was added dropwise at 0° C. The reaction temperature was raised to 15° C. and the reaction was stirred for 2 hours. After completion of the reaction, water (120 mL) was added to quench the reaction. The organic phase was washed sequentially with saturated sodium bicarbonate solution (100 mL*2) and water (100 mL). The aqueous phase was extracted with dichloromethane (100 mL*2), and the organic phases were combined. The combined organic phase was dried over anhydrous sodium sulfate and evaporated to dryness by rotary evaporation to give a crude product. The crude product was triturated with methyl tert-butyl ether (10 mL) and petroleum ether (10 mL) to give the compound BB-10-2. $^1$H NMR (400 MHz, CDCl$_3$-d) δ 8.25 (br. s., 1H), 7.84-7.82 (m, 1H), 7.50 (d, J=7.2 Hz, 1H), 7.26 (d, J=4.0 Hz, 1H), 7.20 (t, J=8.0 Hz, 1H), 4.01 (s, 2H), 3.51 (s, 3H). MS m/z: 245.9 [M+H]$^+$

Step 2: Synthesis of the Compound BB-10-3

The compound BB-10-2 (5.07 g, 20.77 mmol, 1.00 eq) was dissolved in THF (80.00 mL), a solution of borane (8.92 g, 103.85 mL, 1 M, 5.00 eq) dissolved in THF was added dropwise at 0° C., then the temperature was recovered to 15° C. The reaction was stirred at 80° C. for 17 hours. After completion of the reaction, the temperature was lowered to 0° C., and the reaction was quenched slowly with methanol (150 mL), then the solvent was removed by rotary evaporation. The crude product was diluted by EtOAc (200 mL), and washed with hydrochloric acid (3 M, 100 mL*3). The aqueous phase was extracted with EtOAc (100 mL).

The aqueous phase was adjusted to pH=7 with saturated sodium bicarbonate solution, and then extracted with EtOAc (150 mL*3). The organic phases were combined, dried over anhydrous sodium sulfate and evaporated to dryness by rotary evaporation to give the compound BB-10-3. $^1$H NMR (400 MHz, CDCl$_3$-d) δ 7.01 (t, J=8.2 Hz, 1H), 6.82 (d, J=7.6 Hz, 1H), 6.76 (s, 1H), 6.54 (dd, J=8.0 Hz, J=2.0 Hz, 1H), 4.44 (br. s., 1H), 3.60 (t, J=5.2 Hz, 2H), 3.39 (s, 3H), 3.26 (t, J=5.2 Hz, 2H). MS m/z: 231.7 [M+H]$^+$

Step 3: Synthesis of the Compound BB-10

The compound BB-10-3 (3.94 g, 17.12 mmol, 1.00 eq) was dissolved in dioxane (80.00 mL), the compound BB-2-3 (5.65 g, 22.26 mmol, 1.30 eq) and potassium acetate (5.04 g, 51.36 mmol, 3.00 eq) were added, then Pd(dppf)Cl$_2$.CH$_2$Cl$_2$ (1.40 g, 1.71 mmol, 0.10 eq) was added at 15° C. under nitrogen protection. The reaction temperature was raised to 120° C. and the reaction was stirred for 18 hours. After completion of the reaction, the mixture was filtered and the filter cake was washed with dichloromethane (50 mL*4). The filtrate was collected, evaporated to dryness by rotary evaporation, dissolved in EtOAc (150 mL) and then washed with water (120 mL*3). The aqueous phases were combined and extracted with EtOAc (80 mL*3). The organic phases were combined, dried over anhydrous sodium sulfate and evaporated to dryness by rotary evaporation. The crude product was purified by column chromatography (PE/EA=20/1-5/1) to give the target compound BB-10. $^1$H NMR (400 MHz, CDCl$_3$-d) δ 7.27 (s, 1H), 7.19 (t, J=8.0 Hz, 1H), 7.09 (d, J=2.0 Hz, 1H), 6.76-6.74 (m, 1H), 4.03 (br. s., 1H), 3.61 (t, J=4.8 Hz, 2H), 3.39 (s, 3H), 3.33 (t, J=4.8 Hz, 2H), 1.34 (s, 12H). MS m/z: 278.0 [M+H]$^+$

Reference Example 16: Fragment BB-12

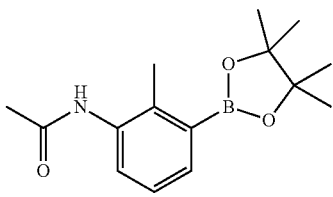 [SMILES: CC(=O)Nc1cccc(B2OC(C)(C)C(C)(C)O2)c1C]

Synthetic Route:

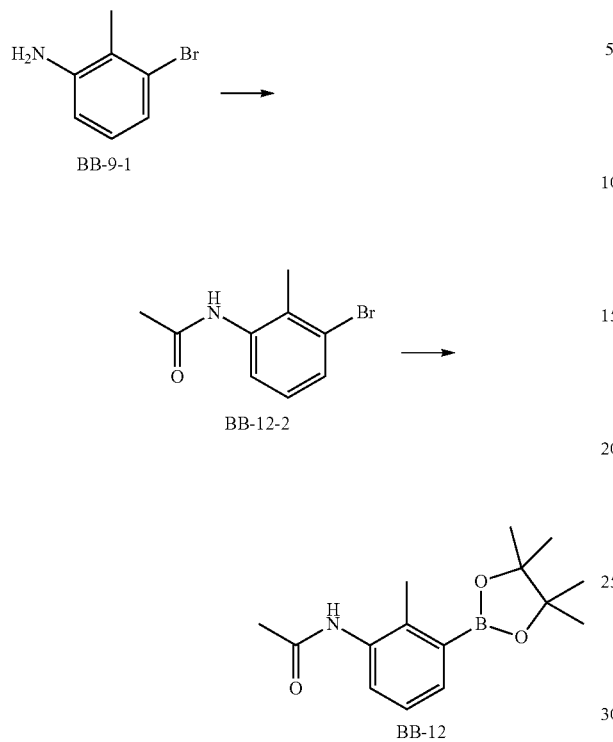

Step 1: Synthesis of the Compound BB-12-2

The compound BB-9-1 (5.00 g, 26.87 mmol, 1.00 eq) was added into pyridine (50.00 mL) and chloroform (100.00 mL), then acetyl chloride (2.74 g, 34.93 mmol, 1.30 eq) was added at 0° C. under nitrogen protection. The reaction was stirred at 25° C. for 2 hours. After completion of the reaction, the reaction mixture was evaporated to dryness by rotary evaporation to give a crude product. The crude product was purified by column chromatography (PE/EA=1/1, Rf=0.5) to give the compound BB-12-2. $^1$H NMR (400 MHz, CDCl$_3$-d) δ 7.64 (br. s., 1H), 7.43 (d, J=7.6 Hz, 1H), 7.09 (t, J=8.0 Hz, 2H), 2.37 (s, 3H), 2.24 (s, 3H). MS m/z: 229.7 [M+H]$^+$

Step 2: Synthesis of the Compound BB-12

The compound BB-12-2 (3.00 g, 13.15 mmol, 1.00 eq) and the compound BB-2-3 (5.01 g, 19.72 mmol, 1.50 eq) were added into dioxane (60.00 mL), then Pd(dppf)Cl$_2$.CH$_2$Cl$_2$ (1.07 g, 1.32 mmol, 0.10 eq) and potassium acetate (3.87 g, 39.45 mmol, 3.00 eq) were added at 20° C. under nitrogen protection. The reaction was stirred at 85° C. for 3 hours. After completion of the reaction, the reaction mixture was diluted with water (100 mL) and extracted with dichloromethane (100 mL*2). The organic phase was collected and washed with saturated sodium chloride solution (100 mL), dried over anhydrous sodium sulfate, filtered and evaporated to dryness by rotary evaporation. The crude product was purified by column chromatography (PE/EA=2/1) to give the target compound BB-12. $^1$H NMR (400 MHz, CDCl$_3$-d) δ 7.85 (d, J=8.0 Hz, 1H), 7.30 (d, J=7.2 Hz, 1H), 7.23 (t, J=7.4 Hz, 1H), 6.98 (br. s., 1H), 2.48 (s, 3H), 2.24 (s, 3H), 1.37 (s, 12H). MS m/z: 276.0 [M+H]$^+$

Reference Example 17: Fragment BB-13

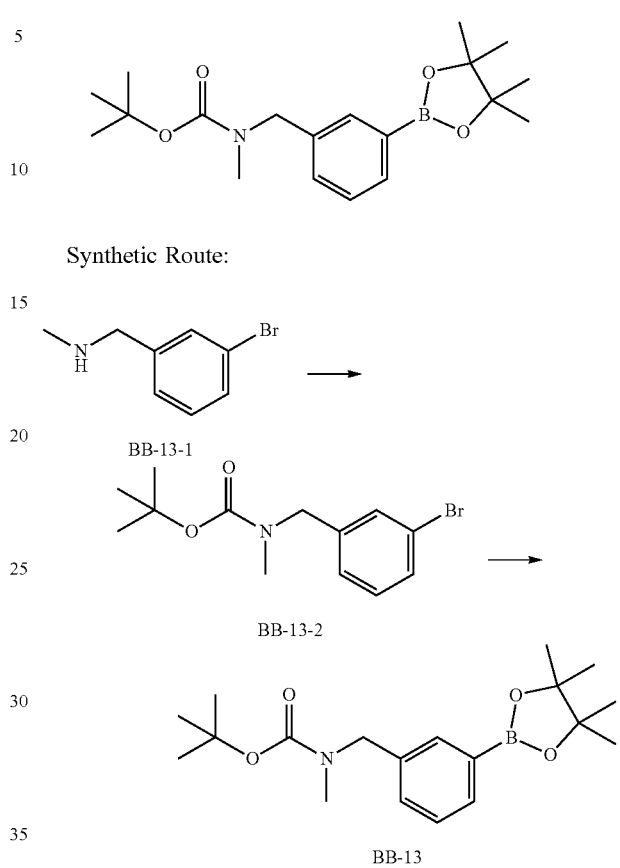

Step 1: Synthesis of the Compound BB-13-2

The compound BB-13-1 (5.00 g, 24.99 mmol, 1.00 eq) was dissolved in dioxane (50.00 mL) and saturated sodium bicarbonate solution (50.00 mL), followed by addition of Boc$_2$O (8.18 g, 37.49 mmol, 1.50 eq) at 0° C. The reaction was stirred at 20° C. for 10 hours.

After completion of the reaction, the reaction mixture was evaporated to dryness by rotary evaporation to give a crude product. The crude product was purified by column chromatography (PE/EA=10/1) to give the compound BB-13-2. $^1$H NMR (400 MHz, CDCl$_3$-d) δ 7.43-7.39 (m, 2H), 7.25-7.17 (m, 2H), 4.40 (br. s., 2H), 2.88-2.81 (m, 3H), 1.49 (s, 9H). MS m/z: 245.8 [M+H]$^+$

Step 2: Synthesis of the Compound BB-13

The compound BB-2-3 (6.34 g, 24.99 mmol, 1.50 eq), the compound BB-13-2 (5.00 g, 16.66 mmol, 1.00 eq), potassium acetate (3.27 g, 33.32 mmol, 2.00 eq) and Pd(dppf)Cl$_2$.CH$_2$Cl$_2$ (1.36 g, 1.67 mmol, 0.10 eq) were added into a dried reaction flask, and dioxane (100.00 mL) was added. The reaction temperature was raised to 80° C. and the reaction was stirred for 3 hours. After completion of the reaction, the reaction solution was filtered through diatomaceous earth. The filtrate was collected and evaporated to dryness by rotary evaporation to give a crude product. The crude product was purified by column chromatography (PE/EA=5/1) to give the target compound BB-13.

¹H NMR (400 MHz, CDCl₃-d) δ 7.73-7.68 (m, 2H), 7.37-7.33 (m, 2H), 4.42 (br. s., 2H), 2.85-2.76 (m, 3H), 1.49 (s, 9H), 1.35 (s, 12H). MS m/z: 291.9 [M+H]⁺

Reference Example 18: Fragment BB-14

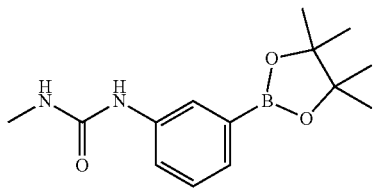

Synthetic Route:

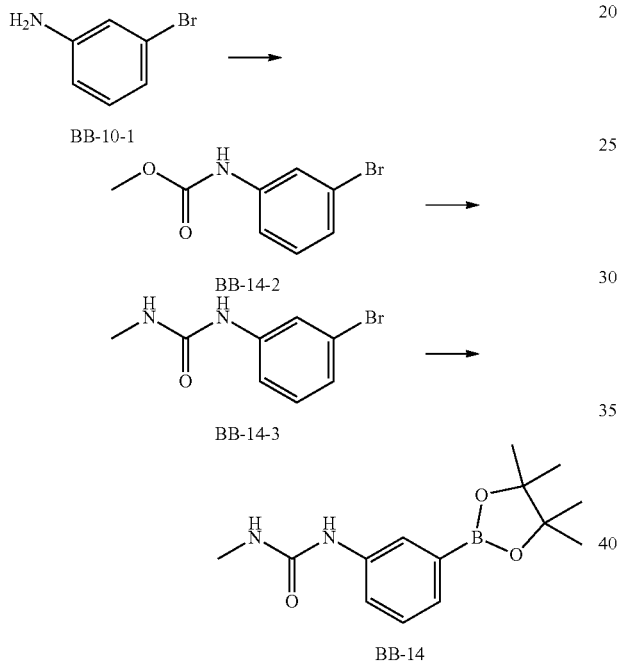

Step 1: Synthesis of the Compound BB-14-2

Methyl chloroformate (22.90 g, 242.33 mmol, 5.21 eq) was dissolved in dichloromethane (100.00 mL), then a solution of the compound BB-10-1 (8.00 g, 46.51 mmol, 1.00 eq) and triethylamine (14.12 g, 139.53 mmol, 3.00 eq) dissolved in dichloromethane (60.00 mL) were added at −10° C. The reaction was stirred at −10° C. for 2 hours. After completion of the reaction, the reaction mixture was diluted with methyl tert-butyl ether (500 mL) and a solid formed. The solid was filtered and washed with methyl tert-butyl ether (50 mL*3), the filtrate was collected and evaporated to dryness by rotary evaporation. The crude product was diluted with methyl tert-butyl ether (200 mL), then washed sequentially with 0.5 M hydrochloric acid solution (100 mL*2), saturated sodium bicarbonate solution (100 mL*2) and saturated sodium chloride solution (80 mL). The organic phase was collected, dried over anhydrous sodium sulfate and evaporated to dryness by rotary evaporation to give the compound BB-14-2. ¹H NMR (400 MHz, CDCl₃-d) δ 7.64 (s, 1H), 7.30-7.25 (m, 1H), 7.20-7.15 (m, 2H), 6.67 (br. s., 1H), 3.78 (s, 3H). MS m/z: 231.8 [M+H]⁺

Step 2: Synthesis of the Compound BB-14-3

The compound BB-14-2 (1.04 g, 4.52 mmol, 1.00 eq) and methylamine (6.60 g, 53.12 mmol, 11.75 eq) were added into a sealed tube, the temperature was raised to 100° C. and the reaction was stirred for 40 hours. After completion of the reaction, the reaction mixture was evaporated to dryness by rotary evaporation to give a crude product. The crude product was triturated with petroleum ether (20 mL) and methyl tert-butyl ether (4 mL), filtered and evaporated to dryness by rotary evaporation to give the compound BB-14-3. ¹H NMR (400 MHz, CDCl₃-d) δ 7.51 (s, 1H), 7.43 (s, 1H), 7.19 (d, J=8.0 Hz, 1H), 7.14-7.09 (m, 2H), 5.54 (d, J=3.6 Hz, 1H), 2.78 (d, J=4.8 Hz, 3H). MS m/z: 230.8 [M+H]⁺

Step 3: Synthesis of the Compound BB-14

The compound BB-14-3 (1.31 g, 5.72 mmol, 1.00 eq) was dissolved in dioxane (25.00 mL), then the compound BB-2-3 (1.74 g, 6.86 mmol, 1.20 eq), potassium acetate (1.68 g, 17.16 mmol, 3.00 eq) and Pd(dppf)Cl₂.CH₂Cl₂ (467.02 mg, 572.00 μmol, 0.10 eq) were added sequentially at 25° C. under nitrogen protection. The temperature was raised to 100° C. and the reaction was stirred for 3 hours. After completion of the reaction, the reaction solution was evaporated to dryness by rotary evaporation and diluted with EtOAc (50 mL), washed sequentially with water (30 mL*2) and saturated sodium chloride solution (20 mL). The organic phase was dried over anhydrous sodium sulfate, filtered and evaporated to dryness by rotary evaporation to give a crude product. The crude product was triturated with methyl tert-butyl ether (20 mL), filtered and evaporated to dryness by rotary evaporation to give the target compound BB-14. ¹H NMR (400 MHz, CDCl₃-d) δ 7.64 (s, 1H), 7.55-7.51 (m, 2H), 7.33 (t, J=7.6 Hz, 1H), 6.88 (s, 1H), 5.12 (d, J=4.0 Hz, 1H), 2.80 (d, J=4.4 Hz, 3H), 1.34 (s, 12H). MS m/z: 276.9 [M+H]⁺

Reference Example 19: Fragment BB-15

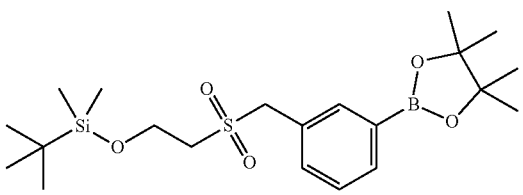 [SMILES: CC1(C)OB(c2cccc(CS(=O)(=O)CCO[Si](C)(C)C(C)(C)C)c2)OC1(C)C]

Synthetic Route:

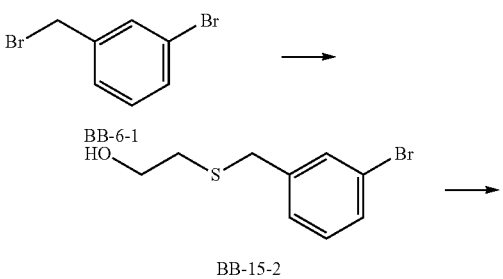

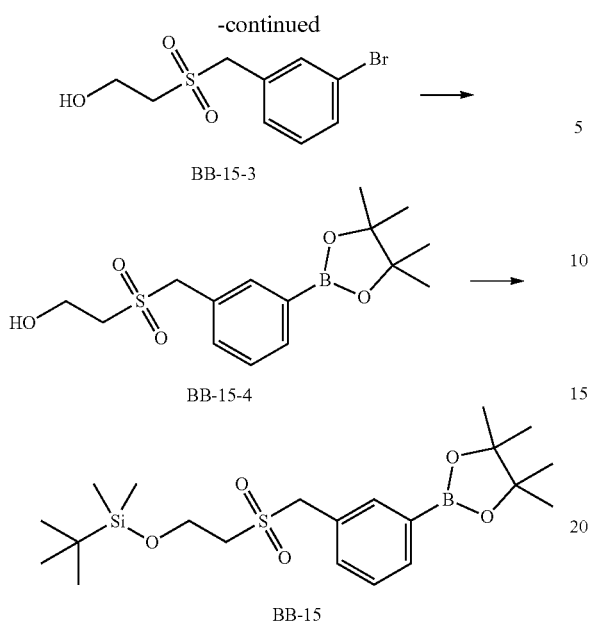

Step 1: Synthesis of the Compound BB-15-2

2-Mercaptoethanol (2.19 g, 28.08 mmol, 1.96 mL, 2.34 eq) was dissolved in methanol (30.00 mL), then sodium methoxide (1.32 g, 24.00 mmol, 98% purity, 2.00 eq) was added at 20° C. under nitrogen protection. The reaction was stirred at 20° C. for 1 hour, then the compound BB-6-1 (3.00 g, 12.00 mmol, 1.00 eq) was added, and the reaction was stirred at 20° C. for another 3 hours. After completion of the reaction, the methanol was removed by rotary evaporation and water (10 mL) was added to quench the reaction. The aqueous phase was extracted with EtOAc (30 mL*2). The organic phases were combined and washed with saturated sodium chloride solution (10 mL). The organic phase was collected, dried over anhydrous sodium sulfate and evaporated to dryness by rotary evaporation to give a crude product. The crude product was purified by column chromatography (PE/EA=20/1-5/1) to give the compound BB-15-2. $^1$H NMR (400 MHz, CDCl$_3$-d) δ 7.50 (s, 1H), 7.41 (d, J=7.6 Hz, 1H), 7.27 (d, J=8.4 Hz, 1H), 7.21 (t, J=7.6 Hz, 1H), 3.76-3.62 (m, 4H), 2.66 (t, J=5.8 Hz, 2H).

Step 2: Synthesis of the Compound BB-15-3

The compound BB-15-2 (2.90 g, 11.73 mmol, 1.00 eq) was dissolved in THF (30.00 mL) and water (30.00 mL), then potassium bisulfate complex salt (21.64 g, 17.60 mmol, 50% purity, 1.50 eq) was added at 20° C. under nitrogen protection. The reaction was stirred at 20° C. for 6 hours. After completion of the reaction, saturated sodium sulfite solution (20 mL) was added and the mixture was extracted with EtOAc (30 mL*3). The organic phases were combined and washed with saturated sodium chloride solution (15 mL), dried over anhydrous sodium sulfate and evaporated to dryness by rotary evaporation to give the compound BB-15-3.
$^1$H NMR (400 MHz, CDCl$_3$-d) δ 7.62 (s, 1H), 7.55 (d, J=8.0 Hz, 1H), 7.41 (d, J=7.6 Hz, 1H), 7.29 (t, J=8.0 Hz, 1H), 4.33 (s, 2H), 4.14 (q, J=4.8 Hz, 2H), 3.11 (t, J=5.0 Hz, 2H).

Step 3: Synthesis of the Compound BB-15-4

The compound BB-15-3 (3.00 g, 10.75 mmol, 1.00 eq) and the compound BB-2-3 (4.09 g, 16.12 mmol, 1.50 eq) were dissolved in dioxane (10.00 mL), then Pd(dppf)Cl$_2$.CH$_2$Cl$_2$ (877.64 mg, 1.07 mmol, 0.10 eq) and potassium acetate (2.11 g, 21.49 mmol, 2.00 eq) were added at 20° C. under nitrogen protection. The temperature was raised to 80° C. and the reaction was stirred for 16 hours. After completion of the reaction, the solvent was removed by rotary evaporation to give a crude product, which was purified by column chromatography (DCM/MeOH=1/0-20/1) to give the compound BB-15-4. $^1$H NMR (400 MHz, CDCl$_3$-d) δ 7.87-7.80 (m, 2H), 7.58 (d, J=7.6 Hz, 1H), 7.42 (t, J=7.6 Hz, 1H), 4.35 (s, 2H), 4.12-4.05 (m, 2H), 3.14-3.07 (m, 2H), 1.35 (s, 12H).

Step 4: Synthesis of the Compound BB-15

The compound BB-15-4 (2.93 g, 8.98 mmol, 1.00 eq) was dissolved in N,N-dimethylformamide (20.00 mL), then tert-butyldimethylsilyl chloride (2.03 g, 13.47 mmol, 1.65 mL, 1.50 eq) and imidazole (1.53 g, 22.45 mmol, 2.50 eq) were added at 25° C. under nitrogen protection. The reaction was stirred at 25° C. for 2 hours. After completion of the reaction, the solvent was removed by rotary evaporation to give a crude product, which was purified by column chromatography (DCM/MeOH=20/1) to give the target compound BB-15. $^1$H NMR (400 MHz, CDCl$_3$-d) δ 7.88 (s, 1H), 7.84 (d, J=7.2 Hz, 1H), 7.60 (d, J=8.0 Hz, 1H), 7.43 (t, J=7.6 Hz, 1H), 4.37 (s, 2H), 4.12 (t, J=5.4 Hz, 2H), 3.08 (t, J=5.4 Hz, 2H), 1.36 (s, 12H), 0.98 (s, 9H), 0.19 (s, 6H).

Reference Example 20: Fragment BB-16

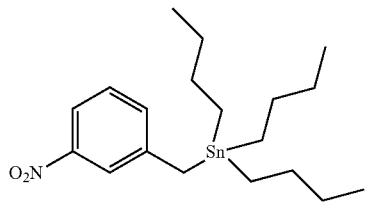 [SMILES: CCC[CH2][Sn]([CH2]CCC)([CH2]CCC)[CH2]c1cccc([N+](=O)[O-])c1]

Synthetic Route:

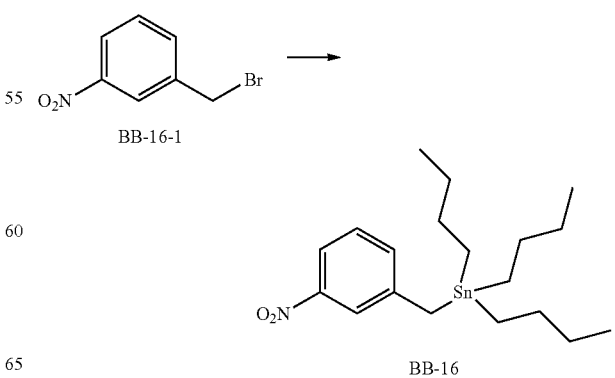

Step 1: Synthesis of the Compound BB-16

The compound BB-16-1 (5.00 g, 23.14 mmol, 1.00 eq) was dissolved in toluene (125.00 mL), then hexabutyldistannane (18.79 g, 31.74 mmol, 16.20 mL, 98% purity, 1.37 eq) and Pd(PPh$_3$)$_4$ (267.45 mg, 231.40 μmol, 0.01 eq) were added at 20° C. under nitrogen protection. The temperature was raised to 100° C. and the reaction was stirred for 16 hours. After completion of the reaction, the reaction mixture was washed with 20% potassium fluoride aqueous solution (15 mL). The aqueous phase was extracted with EtOAc (40 mL*2). The organic phases were combined and washed with saturated sodium chloride solution (20 mL), dried over anhydrous sodium sulfate, and evaporated to dryness by rotary evaporation to give a crude product. The crude product was purified by column chromatography (PE/EA=1/0) to give the target compound BB-16. $^1$H NMR (400 MHz, CDCl$_3$-d) δ 7.78-7.73 (m, 2H), 7.27-7.19 (m, 2H), 2.33 (s, 2H), 1.46-1.30 (m, 6H), 1.25-1.13 (m, 6H), 0.85-0.73 (m, 15H).

Reference Example 21: Fragment BB-17

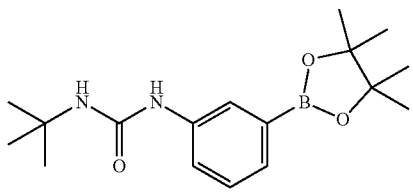 [SMILES: CC(C)(C)NC(=O)Nc1cccc(B2OC(C)(C)C(C)(C)O2)c1]

Synthetic Route:

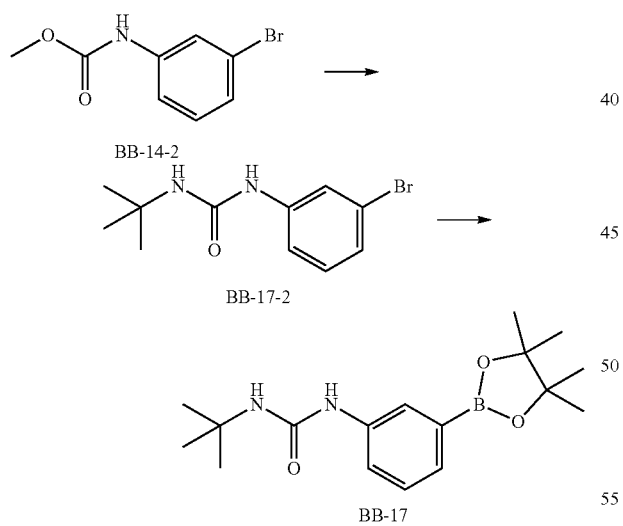

Step 1: Synthesis of the Compound BB-17-2

The compound BB-14-2 (3.15 g, 13.69 mmol, 1.00 eq) and tert-butylamine (17.40 g, 237.90 mmol, 25.00 mL, 17.38 eq) was added into a pot, the reaction was heated to 100° C. and stirred for 65 hours. After LCMS indicated that the reaction was incomplete, the reaction was stirred for another 22 hours at 100° C. After LCMS indicated that the reaction was incomplete, the reaction was stirred for another 22 hours at 100° C. After completion of the reaction, the reaction solution was evaporated to dryness by rotary evaporation to give a crude product.

The crude product was triturated with petroleum ether (20 mL) and methyl tert-butyl ether (4 mL), and purified to give the compound BB-17-2. $^1$H NMR (400 MHz, CDCl$_3$-d) δ 7.56 (s, 1H), 7.22 (s, 1H), 7.20-7.14 (m, 1H), 7.10-7.05 (m, 2H), 5.30 (s, 1H), 1.35 (s, 9H). MS m/z: 272.8 [M+H]$^+$

Step 2: Synthesis of the Compound BB-17

The compound BB-17-2 (3.25 g, 11.99 mmol, 1.00 eq) and the compound BB-2-3 (3.65 g, 14.39 mmol, 1.20 eq) were dissolved in dioxane (65.00 mL), Pd(dppf)Cl$_2$.CH$_2$Cl$_2$ (978.82 mg, 1.20 mmol, 0.10 eq) and potassium acetate (3.53 g, 35.97 mmol, 3.00 eq) were added at 25° C. under nitrogen protection. The reaction temperature was raised to 100° C. and the reaction was stirred for 3 hours. After completion of the reaction, the solvent was removed by rotary evaporation, and the crude product was diluted with EtOAc (60 mL). After filtration, the filter cake was washed with EtOAc (20 mL*3). The organic phases were combined, washed sequentially with water (80 mL*2) and saturated sodium chloride solution (50 mL). The organic phase was dried over anhydrous sodium sulfate, filtered and evaporated to dryness by rotary evaporation to give a crude product. The crude product was dissolved in dichloromethane (100 mL), then petroleum ether (150 mL) was added and a solid formed. After filtration, the filter cake was washed with dichloromethane (15 mL*4) and collected, then evaporated to dryness by rotary evaporation to give the target compound BB-17. $^1$H NMR (400 MHz, CDCl$_3$-d) δ 7.57 (s, 1H), 7.54-7.49 (m, 2H), 7.34 (t, J=7.6 Hz, 1H), 6.19 (s, 1H), 4.64 (s, 1H), 1.38 (s, 9H), 1.35 (s, 12H). MS m/z: 319.1 [M+H]$^+$

Reference Example 22: Fragment BB-18

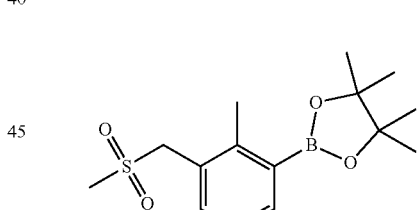

Synthetic Route:

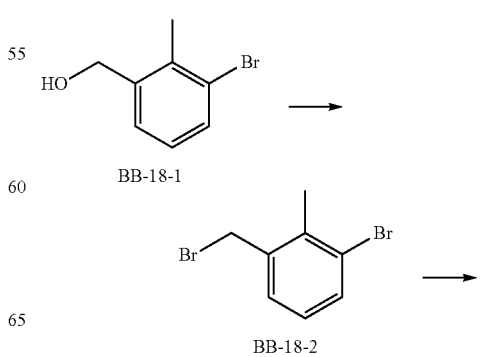

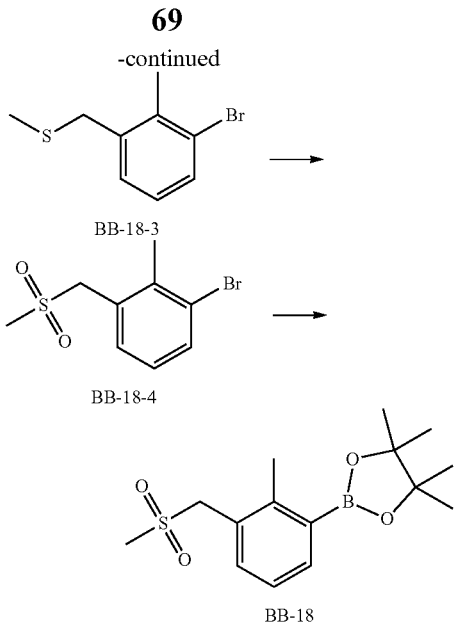

Step 1: Synthesis of the Compound BB-18-2

BB-18-1 (15.00 g, 74.60 mmol, 1.00 eq) was dissolved in dichloromethane (300.00 mL), PBr$_3$ (13.13 g, 48.49 mmol, 4.61 mL, 0.65 eq) was added dropwise at 0° C., then the reaction was stirred at 25° C. for 15 hours. After completion of the reaction, the mixture was cooled to 0° C., and quenched by methanol (20 mL). The mixture was washed sequentially with saturated sodium bicarbonate solution (100 mL*3) and water (100 mL*2). The organic phase was collected, dried over anhydrous sodium sulfate, and evaporated to dryness by rotary evaporation to give the compound BB-18-2. $^1$H NMR (400 MHz, CDCl$_3$-d) δ 7.53 (d, J=8.0 Hz, 1H), 7.26 (d, J=6.0 Hz, 1H), 7.03 (t, J=7.8 Hz, 1H), 4.52 (s, 2H), 2.49 (s, 3H).

Step 2: Synthesis of the Compound BB-18-3

The compound BB-18-2 (20.26 g, 76.75 mmol, 1.00 eq) was dissolved in N,N-dimethylformamide (250.00 mL), sodium thiomethoxide (5.40 g, 77.04 mmol, 1.00 eq) was added, then the reaction was stirred at 0° C. for 3 hours. After completion of the reaction, the reaction solution was poured into water (500 mL) and extracted with EtOAc (150 mL*3). The organic phases were combined, washed sequentially with water (300 mL*3) and saturated sodium chloride solution (250 mL). The organic phase was dried over anhydrous sodium sulfate, and evaporated to dryness by rotary evaporation to give the compound BB-18-3. $^1$H NMR (400 MHz, CDCl$_3$-d) δ 7.49 (d, J=8.0 Hz, 1H), 7.13 (d, J=7.2 Hz, 1H), 7.00 (t, J=7.6 Hz, 1H), 3.73 (s, 2H), 2.49 (s, 3H), 2.05 (s, 3H).

Step 3: Synthesis of the Compound BB-18-4

The compound BB-18-3 (17.30 g, 74.84 mmol, 1.00 eq) was dissolved in dichloromethane (350.00 mL), m-chloroperbenzoic acid (35.52 g, 164.65 mmol, 2.20 eq) was added at 0° C. in batches, then the temperature was raised slowly to 25° C. and the reaction was stirred for 16 hours. After completion of the reaction, the temperature was cooled to 0° C., and saturated sodium sulfite solution (150 mL) was added to quench the reaction. The dichloromethane was removed by rotary evaporation, and the mixture was filtered. The filter cake was washed with methanol (30 mL*4) to give a crude product 1. The filtrate was concentrated and extracted with EtOAc (100 mL*3), the organic phases were combined and washed sequentially with saturated sodium sulfite solution (100 mL*2), saturated sodium bicarbonate solution (100 mL*3), water (100 mL) and saturated sodium chloride solution (100 mL), then dried over anhydrous sodium sulfate and evaporated to dryness by rotary evaporation to give a crude product 2. The crude product 1 and the crude product 2 were combined and triturated with petroleum ether (100 mL) to give the compound BB-18-4. $^1$H NMR (400 MHz, CDCl$_3$-d) δ 7.61 (d, J=8.0 Hz, 1H), 7.29 (d, J=7.6 Hz, 1H), 7.10 (t, J=7.8 Hz, 1H), 4.39 (s, 2H), 2.84 (s, 3H), 2.54 (s, 3H).

Step 4: Synthesis of the Compound BB-18

The compound BB-18-4 (10.00 g, 38.00 mmol, 1.00 eq) was dissolved in dioxane (100.00 mL), then the compound BB-2-3 (11.58 g, 45.60 mmol, 1.20 eq), potassium acetate (11.19 g, 114.00 mmol, 3.00 eq) and Pd(dppf)Cl$_2$·CH$_2$Cl$_2$ (3.10 g, 3.80 mmol, 0.10 eq) were added sequentially. The reaction was stirred at 100° C. under nitrogen atmosphere for 14 hours. After completion of the reaction, the reaction solution was cooled to room temperature and the solvent was removed by rotary evaporation. The residue was dissolved with EtOAc (500 mL). The organic phase was washed sequentially with water (250 mL*2) and saturated sodium chloride solution (200 mL). The organic phases were combined, dried over anhydrous sodium sulfate, and evaporated to dryness by rotary evaporation to give a crude product. The crude product was purified by column chromatography (PE/EA=25/1-5/1) to give the target compound BB-18. $^1$H NMR (400 MHz, CDCl$_3$-d) δ 7.72 (d, J=7.2 Hz, 1H), 7.35 (dd, J=7.6 Hz, J=1.2 Hz, 1H), 7.15 (t, J=7.6 Hz, 1H), 4.30 (s, 2H), 2.71 (s, 3H), 2.57 (s, 3H), 1.28 (s, 12H).

Reference Example 23: Fragment BB-19

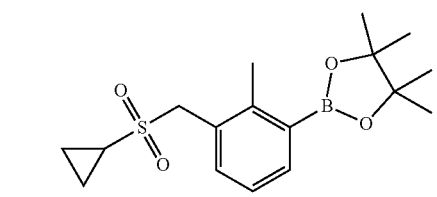 [SMILES: Cc1c(CS(=O)(=O)C2CC2)cccc1B1OC(C)(C)C(C)(C)O1]

Synthetic Route:

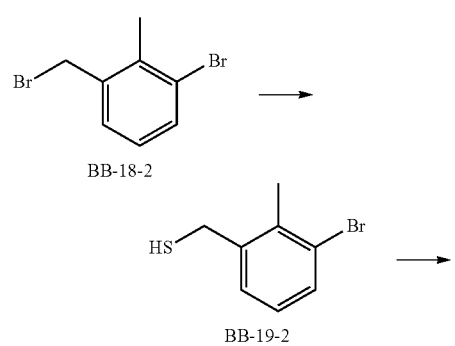

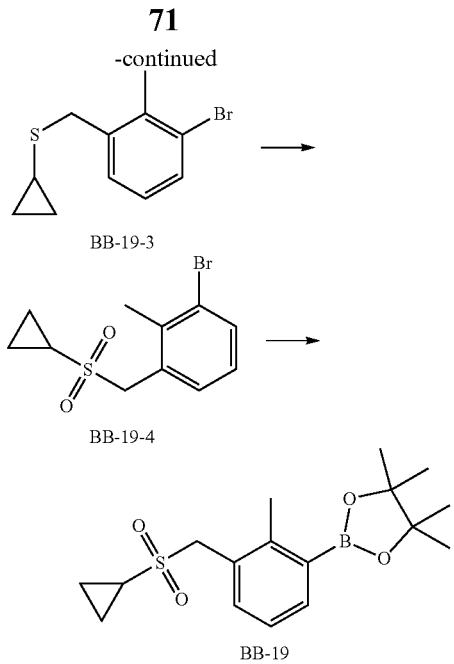

BB-19-3

BB-19-4

BB-19

Step 1: Synthesis of the Compound BB-19-2

The compound BB-18-2 (10.00 g, 37.88 mmol, 1.00 eq) was dissolved in methanol (50.00 mL), then potassium carbonate (6.28 g, 45.46 mmol, 1.20 eq) and thioacetic acid (3.46 g, 45.46 mmol, 1.20 eq) were added sequentially under nitrogen protection. After the mixture was stirred at 25° C. for 30 minutes, potassium carbonate (6.28 g, 45.46 mmol, 1.20 eq) was added and the reaction was stirred for 30 minutes. After completion of the reaction, the reaction mixture was poured into water (80 mL), the aqueous phase was extracted with EtOAc (100 mL*2). The organic phases were combined, washed with saturated sodium chloride solution (60 mL), dried over anhydrous sodium sulfate, and evaporated to dryness by rotary evaporation to give the compound BB-19-2. $^1$H NMR (400 MHz, CDCl$_3$-d) δ 7.51-7.49 (m, 1H), 7.01-6.97 (m, 2H), 4.47 (s, 2H), 3.41 (s, 3H).

Step 2: Synthesis of the Compound BB-19-3

The compound BB-19-2 (5.00 g, 23.03 mmol, 1.00 eq) and potassium tert-butoxide (2.58 g, 23.03 mmol, 1.00 eq) were dissolved in dimethyl sulfoxide (30.00 mL), cyclopropyl bromide (3.06 g, 25.33 mmol, 1.10 eq) was added under nitrogen protection. The temperature was raised to 90° C. and the reaction was stirred for 16 hours. After completion of the reaction, water was added (80 mL) and the aqueous phase was extracted with EtOAc (80 mL*2). The organic phases were combined, washed with saturated sodium chloride solution (30 mL), dried over anhydrous sodium sulfate and evaporated to dryness by rotary evaporation to give a crude product of the compound BB-19-3.

Step 3: Synthesis of the Compound BB-19-4

The compound BB-19-3 (5.20 g, 20.22 mmol, 1.00 eq) was dissolved in THF (50.00 mL) and water (50.00 mL), potassium hydrogen sulfate (37.29 g, 30.33 mmol, 50% purity, 1.50 eq) was added under nitrogen protection. The reaction was stirred at 25° C. for 4 hours. After completion of the reaction, saturated sodium sulfite solution (10 mL) was added. The aqueous phase was extracted with EtOAc (20 mL*3). The organic phases were combined, washed with saturated sodium chloride solution (10 mL), dried over anhydrous sodium sulfate, and evaporated to dryness by rotary evaporation to give a crude product. The crude product was purified by column chromatography (PE/EA=20/1-3/1) to give the compound BB-19-4. $^1$H NMR (400 MHz, CDCl$_3$-d) δ 7.60 (d, J=8.0 Hz, 1H), 7.40 (d, J=7.6 Hz, 1H), 7.08 (t, J=8.0 Hz, 1H), 4.41 (s, 2H), 2.55 (s, 3H), 2.34-2.28 (m, 1H), 1.20-1.16 (m, 2H), 1.02-1.00 (m, 2H).

Step 4: Synthesis of the Compound BB-19

The compound BB-19-4 (2.20 g, 7.61 mmol, 1.00 eq) and the compound BB-2-3 (2.90 g, 11.41 mmol, 1.50 eq) were added into dioxane (20.00 mL), then Pd(dppf)Cl$_2$·CH$_2$Cl$_2$ (621.26 mg, 760.75 μmol, 0.10 eq) and potassium acetate (1.49 g, 15.21 mmol, 2.00 eq) were added under nitrogen protection. The temperature was raised to 90° C. and the reaction was stirred for 16 hours. After completion of the reaction, the reaction mixture was evaporated to dryness by rotary evaporation to give a crude product, which was purified by column chromatography (PE/EA=20/1-5/1) to give the target compound BB-19. $^1$H NMR (400 MHz, CDCl$_3$-d) δ 7.78 (d, J=7.6 Hz, 1H), 7.46 (d, J=7.6 Hz, 1H), 7.21 (t, J=7.6 Hz, 1H), 4.40 (s, 2H), 2.66 (s, 3H), 2.30-2.25 (m, 1H), 1.36 (s, 12H), 1.17-1.15 (m, 2H), 0.98-0.95 (m, 2H).

Reference Example 24: Fragment BB-20

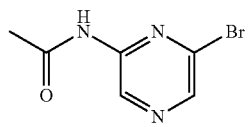

Synthetic Route:

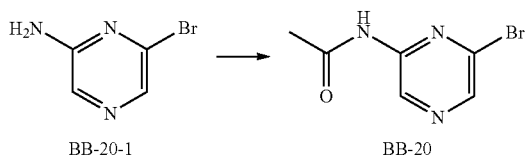

BB-20-1                BB-20

Step 1: Synthesis of the Compound BB-20

The compound BB-20-1 (500.00 mg, 2.87 mmol, 1.00 eq) was added into acetic anhydride (5.45 g, 53.38 mmol, 5.00 mL, 18.60 eq), then the reaction was stirred at 25° C. for 5 hours. The reaction solution was concentrated and diluted with dichloromethane (50 mL).

The organic phase was washed sequentially with saturated sodium carbonate solution (50 mL*3) and saturated sodium chloride solution (50 mL), dried over anhydrous sodium sulfate, and evaporated to dryness by rotary evaporation to give the target compound BB-20. $^1$H NMR (400 MHz, CDCl$_3$-d) δ 9.45 (s, 1H), 8.44 (s, 1H), 8.00 (br. s., 1H), 2.26 (s, 3H). MS m/z: 217.7 [M+H]$^+$

Reference Example 25: Fragment BB-21

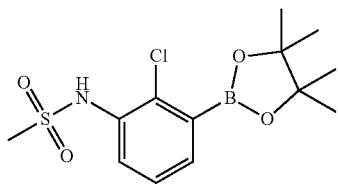

Synthetic Route:

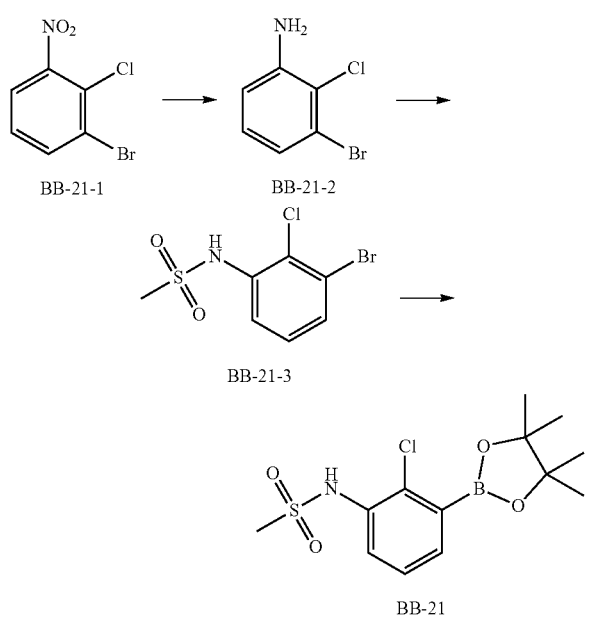

Step 1: Synthesis of the Compound BB-21-2

The compound BB-21-1 (4.80 g, 20.30 mmol, 1.00 eq) was dissolved in ethanol (100.00 mL), then stannous dichloride dihydrate (22.90 g, 101.50 mmol, 8.45 mL, 5.00 eq) was added. The temperature was raised to 80° C. and the reaction was stirred for 2 hours.

After completion of the reaction, the reaction mixture was cooled to room temperature and diluted with water (50 mL). The mixture was adjusted to pH=8-9 with saturated sodium bicarbonate solution, then the aqueous phase was extracted with EtOAc (50 mL*3). The organic phases were combined, dried over anhydrous sodium sulfate, and evaporated to dryness by rotary evaporation to give the compound BB-21-2. $^1$H NMR (400 MHz, CDCl$_3$-d) δ 6.92 (d, J=7.6 Hz, 1H), 6.83 (t, J=7.8 Hz, 1H), 6.62 (dd, J=8.0 Hz, J=1.2 Hz, 1H), 4.14 (br. s., 2H). MS m/z: 207.9 [M+H]$^+$

Step 2: Synthesis of the Compound BB-21-3

At 0° C., the compound BB-21-2 (2.75 g, 13.32 mmol, 1.00 eq) was dissolved in dichloromethane (20.00 mL), then pyridine (1.05 g, 13.32 mmol, 1.08 mL, 1.00 eq) and methanesulfonyl chloride (2.29 g, 19.98 mmol, 1.55 mL, 1.50 eq) were added. Under nitrogen protection, the temperature was raised to 12° C. and the reaction was stirred for 16 hours. After completion of the reaction, the reaction was quenched with saturated sodium bicarbonate solution (20 mL) at room temperature, then the mixture was diluted with water (30 mL) and extracted with dichloromethane (30 mL*3). The organic phases were combined, dried over anhydrous sodium sulfate, and evaporated to dryness by rotary evaporation to give the compound BB-21-3. $^1$H NMR (400 MHz, CDCl$_3$-d) δ 7.57 (dd, J=8.4 Hz, J=1.6 Hz, 1H), 7.40 (dd, J=8.0 Hz, J=1.2 Hz, 1H), 7.11 (t, J=8.0 Hz, 1H), 6.94 (br. s., 1H), 2.96 (s, 3H).

Step 3: Synthesis of the Compound BB-21

The compound BB-21-3 (500.00 mg, 1.76 mmol, 1.00 eq) was dissolved in dioxane (4.00 mL), the compound BB-2-3 (581.01 mg, 2.29 mmol, 1.30 eq), potassium acetate (207.27 mg, 2.11 mmol, 1.20 eq) and Pd(dppf)Cl$_2$ (257.56 mg, 352.00 μmol, 0.20 eq) were added sequentially. Under nitrogen protection, the temperature was raised to 100° C. and the reaction was stirred for 4 hours. After completion of the reaction, the reaction mixture was cooled to room temperature, diluted with EtOAc (20 mL), washed sequentially with water (20 mL*3) and saturated sodium chloride solution (20 mL). The organic phase was dried over anhydrous sodium sulfate, and evaporated to dryness by rotary evaporation to give a crude product. The crude product was purified by column chromatography (PE/EA=1/1) to give the target compound BB-21.

$^1$H NMR (400 MHz, CDCl$_3$-d) δ 7.66 (dd, J=8.0 Hz, J=1.6 Hz, 1H), 7.48 (dd, J=7.6 Hz, J=1.6 Hz, 1H), 7.23 (t, J=7.8 Hz, 1H), 6.84 (br. s., 1H), 2.89 (s, 3H), 1.31 (s, 12H).

Reference Example 26: Fragment BB-22

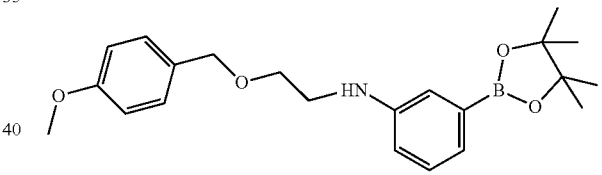

Synthetic Route:

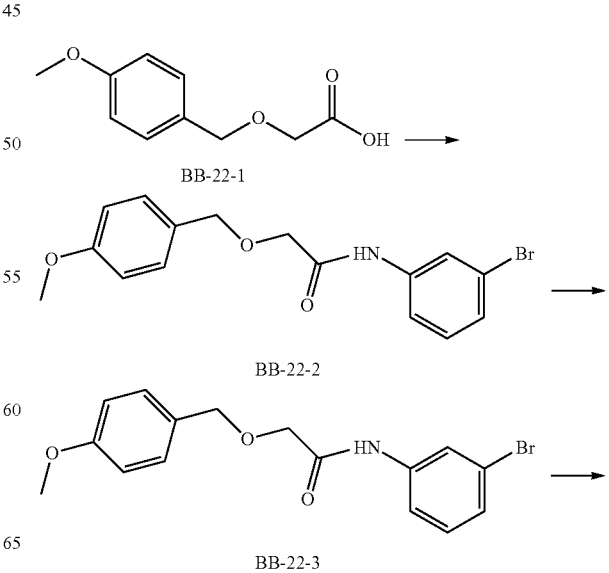

75

-continued

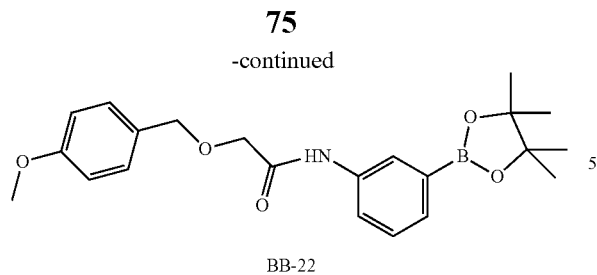

BB-22

Step 1: Synthesis of the Compound BB-22-2

The compound BB-22-1 (4.5 g, 22.94 mmol, 1.00 eq) was dissolved in DMF (90 mL), then DIPEA (8.89 g, 68.82 mmol, 12.01 mL, 3.00 eq) and HATU (15.70 g, 41.29 mmol, 1.80 eq) were added under nitrogen protection at 0° C. The reaction solution was reacted at 20° C. for 0.5 hour and then 3-bromoaniline (5.92 g, 34.41 mmol, 3.75 mL, 1.50 eq) was added. The reaction was stirred at 20° C. for 12 hours. After completion of the reaction, water (200 mL) was added to quench the reaction and the mixture was extracted with EtOAc (200 mL) twice. The organic phase was washed with saturated brine (200 mL), dried over anhydrous sodium sulfate, and evaporated to dryness by rotary evaporation to give a crude product, which was purified by column chromatography (EA/PE=5/1-1/1) to give the compound BB-22-2. $^1$H NMR (400 MHz, CDCl$_3$-d) δ 8.28 (s, 1H), 7.78 (s, 1H), 7.46 (d, J=8.0 Hz, 1H), 7.30 (m, 3H), 7.18 (m, 1H), 6.94 (m, 2H), 4.59 (s, 1H), 4.07 (d, J=4.0 Hz, 1H), 3.83 (s, 3H). MS m/z: 350 [M+H]+

Step 2: Synthesis of the Compound BB-22-3

At 0° C., under nitrogen protection, borane dimethyl sulfide solution (10 M, 5.57 mL, 3.00 eq) was added into a solution of compound BB-22-2 (6.5 g, 18.56 mmol, 1.00 eq) in anhydrous THF (130 mL). The temperature was slowly raised to 65° C. and the reaction was stirred at 65° C. for 12 hours. After completion of the reaction, the reaction was cooled to 0° C. and quenched by methanol (100 mL). After quenching, the mixture was stirred at 20° C. for 1 hour, then concentrated to dryness by rotary evaporation. The residue was dissolved in dichloromethane (100.00 mL), washed with water (100 mL), dried over anhydrous sodium sulfate and evaporated to dryness by rotary evaporation to give the compound BB-22-3. MS m/z: 337 [M+H]+

Step 3: Synthesis of the Compound BB-22

The compound BB-22-3 (5.1 g, 15.17 mmol, 1.00 eq) and the compound BB-2-3 (5.78 g, 22.76 mmol, 1.50 eq) was mixed in dioxane (100 mL), then potassium acetate (3.72 g, 37.92 mmol, 2.5 eq) and Pd(dppf)Cl$_2$.CH$_2$Cl$_2$ (1.24 g, 1.52 μmol, 0.10 eq) were added sequentially. Under nitrogen protection, the temperature was raised to 80° C. and the reaction was stirred for 2 hours. After completion of the reaction, the mixture was cooled to room temperature, the reaction solution was filtered by short silica column. The filtrate was concentrated and purified by column chromatography (PE/EA=10/1-5/1) to give the compound BB-22. $^1$H NMR (400 MHz, CDCl$_3$-d) δ 7.66 (dd, J=8.0 Hz, J=1.6 Hz, 1H), 7.48 (dd, J=7.6 Hz, J=1.6 Hz, 1H), 7.23 (t, J=7.8 Hz, 1H), 6.84 (br. s., 1H), 2.89 (s, 3H), 1.31 (s, 12H). MS m/z: 384 [M+H]+

76

Embodiment 1: WX040

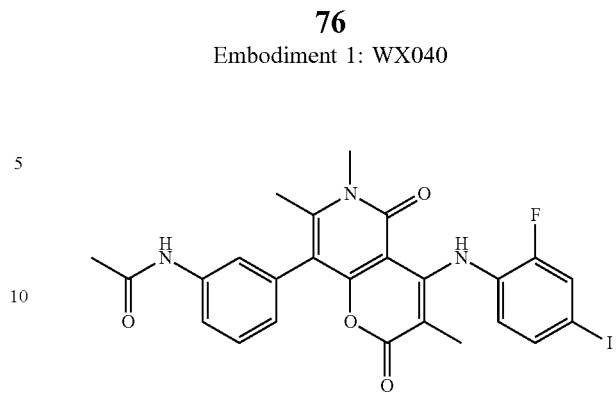

Synthetic Route:

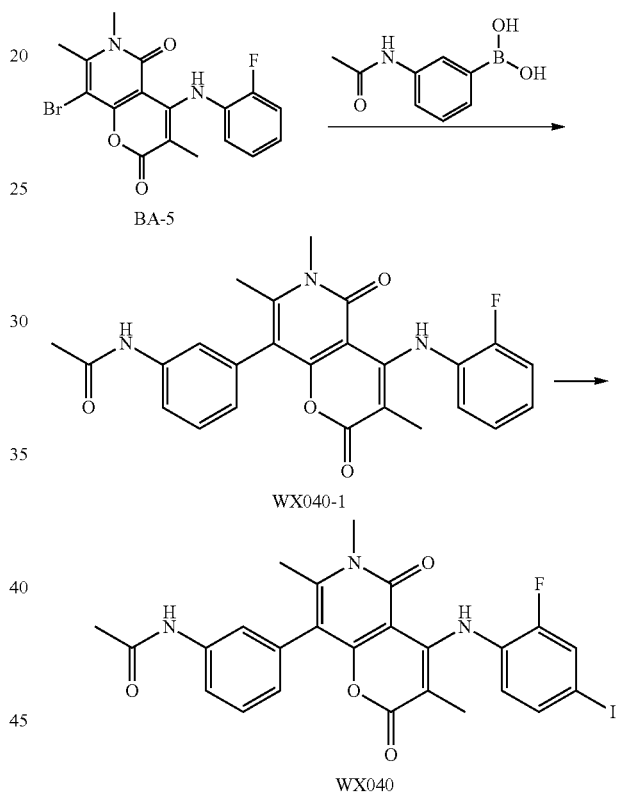

Step 1: Synthesis of the Compound WX040

The compound BA-5 (500.00 mg, 1.27 mmol, 1.00 eq) and 3-acetaminophenylboronic acid (454.61 mg, 2.54 mmol, 2.00 eq) were dissolved in dioxane (20.00 mL), then Pd(dppf)Cl$_2$.CH$_2$Cl$_2$ (103.71 mg, 127.00 μmol, 0.10 eq) was added into the reaction solution, and a solution of sodium carbonate (269.21 mg, 2.54 mmol, 2.00 eq) dissolved in water (5.00 mL) was added into the reaction solution. The temperature was raised to 100° C. and the reaction was stirred for 15 hours. After completion of the reaction, the reaction solution was cooled to room temperature and filtered. The filtrate was collected and evaporated to dryness by rotary evaporation to give a crude product, which was purified by column chromatography (EA/PE=10%-50%) to give the target compound WX040-1. $^1$H NMR (400 MHz, DMSO-d$_6$) δ 11.41 (s, 1H), 10.08 (s, 1H), 7.64-7.58 (m, 2H), 7.43 (t, J=7.6 Hz, 1H), 7.35-7.28 (m, 1H), 7.22-7.12 (m, 3H), 6.96 (d, J=7.2 Hz, 1H), 3.61 (s, 3H), 2.26 (s, 3H), 2.01 (s, 3H), 1.44 (s, 3H). MS m/z: 448.0 [M+H]$^+$ Step 2: Synthesis of the Compound WX040

The compound WX040-1 (100.00 mg, 223.48 mol, 1.00 eq) was dissolved in N,N-dimethylformamide (2.00 mL), then trifluoroacetic acid (76.44 mg, 670.45 mol, 49.64 μL, 3.00 eq) was added, and N-iodosuccinimide (125.70 mg, 558.70 μmol, 2.50 eq) was added into the reaction solution. The reaction was stirred at 25° C. for 15 hours. After completion of the reaction, the reaction mixture was purified by HPLC to give the target compound WX040. $^1$H NMR (400 MHz, DMSO-d$_6$) δ 11.34 (s, 1H), 10.06 (s, 1H), 7.70 (dd, J=10.2 Hz, J=1.8 Hz, 1H), 7.60-7.54 (m, 2H), 7.51 (d, J=8.0 Hz, 1H), 7.40 (t, J=8.0 Hz, 1H), 6.93 (d, J=7.6 Hz, 1H), 6.87 (t, J=8.0 Hz, 1H), 3.58 (s, 3H), 2.24 (s, 3H), 2.04 (s, 3H), 1.44 (s, 3H). MS m/z: 574.1 [M+H]$^+$ Embodiment 2: WX049

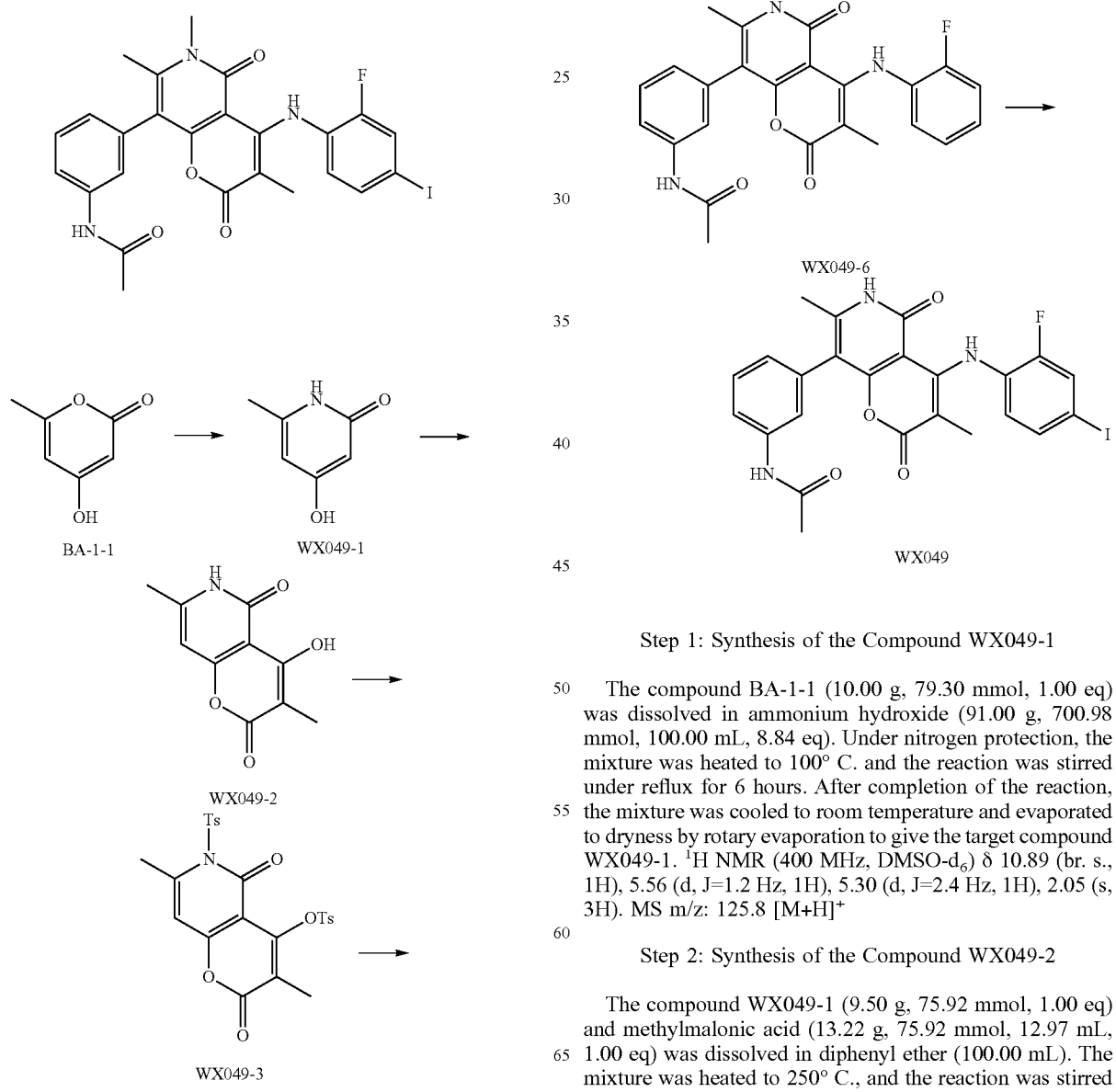

Step 1: Synthesis of the Compound WX049-1

The compound BA-1-1 (10.00 g, 79.30 mmol, 1.00 eq) was dissolved in ammonium hydroxide (91.00 g, 700.98 mmol, 100.00 mL, 8.84 eq). Under nitrogen protection, the mixture was heated to 100° C. and the reaction was stirred under reflux for 6 hours. After completion of the reaction, the mixture was cooled to room temperature and evaporated to dryness by rotary evaporation to give the target compound WX049-1. $^1$H NMR (400 MHz, DMSO-d$_6$) δ 10.89 (br. s., 1H), 5.56 (d, J=1.2 Hz, 1H), 5.30 (d, J=2.4 Hz, 1H), 2.05 (s, 3H). MS m/z: 125.8 [M+H]$^+$ Step 2: Synthesis of the Compound WX049-2

The compound WX049-1 (9.50 g, 75.92 mmol, 1.00 eq) and methylmalonic acid (13.22 g, 75.92 mmol, 12.97 mL, 1.00 eq) was dissolved in diphenyl ether (100.00 mL). The mixture was heated to 250° C., and the reaction was stirred under reflux for 2 hours until the methanol gas no longer formed. After completion of the reaction, water (30 mL) was added, and then the mixture was extracted with EtOAc (30 mL*3). The organic phase was collected and evaporated to dryness by rotary evaporation to give the target compound WX049-2. $^1$H NMR (400 MHz, DMSO-d$_6$) δ 13.26 (s, 1H), 12.75 (br. s., 1H), 6.45 (s, 1H), 2.31 (s, 3H), 1.82 (s, 3H). MS m/z: 207.8 [M+H]$^+$ Step 3: Synthesis of the Compound WX049-3

The compound WX049-2 (7.00 g, 33.79 mmol, 1.00 eq) was dissolved in dichloromethane (200.00 mL), then triethylamine (10.26 g, 101.37 mmol, 14.05 mL, 3.00 eq) and dimethylaminopyridine (206.39 mg, 1.69 mmol, 0.05 eq) were added, followed by addition of p-toluenesulfonyl chloride (14.17 g, 74.34 mmol, 2.20 eq). The reaction was stirred at 25° C. for 12 hours. After completion of the reaction, the reaction solution was evaporated to dryness by rotary evaporation, then triturated with ethanol (100 mL) and filtered. The filter cake was triturated with chloroform (100 mL) and filtered. The filtrate was collected, and evaporated to dryness by rotary evaporation to give a crude product of the target compound WX049-3. $^1$H NMR (400 MHz, CDCl$_3$-d) δ 7.96 (d, J=8.4 Hz, 2H), 7.89 (d, J=8.4 Hz, 2H), 7.39 (d, J=8.4 Hz, 2H), 7.34 (d, J=8.0 Hz, 2H), 6.94 (s, 1H), 2.49 (s, 3H), 2.46 (s, 3H), 2.42 (s, 3H), 1.81 (s, 3H). MS m/z: 538.1 [M+Na]$^+$ Step 4: Synthesis of the Compound WX049-4

The compound WX049-3 (11.00 g, 21.34 mmol, 1.00 eq) was dissolved in THF (100.00 mL) and acetonitrile (100.00 mL), then N-bromosuccinimide (7.59 g, 42.68 mmol, 2.00 eq) was added. The mixture was heated to 80° C. and the reaction was stirred for 15 hours.

Some of the raw material was left. Additional N-bromosuccinimide (7.59 g, 42.68 mmol, 2.00 eq) was added and the reaction was stirred at 80° C. for 5 hours. After completion of the reaction, the reaction mixture was cooled to room temperature, filtered, and the filter cake was collected to give the target compound WX049-4. $^1$H NMR (400 MHz, DMSO-d$_6$) δ 12.33 (s, 1H), 7.88 (d, J=8.8 Hz, 2H), 7.46 (d, J=8.0 Hz, 2H), 2.42 (s, 3H), 2.37 (s, 3H), 1.50 (s, 3H). MS m/z: 442.0 [M+H]$^+$ Step 5: Synthesis of the Compound WX049-5

The compound WX049-4 (7.50 g, 17.04 mmol, 1.00 eq) and 2-fluoroaniline (18.93 g, 170.40 mmol, 16.46 mL, 10.00 eq) were dissolved in ethanol (100.00 mL). The reaction was stirred under reflux for 15 hours. After completion of the reaction, the reaction solution was cooled to room temperature, filtered, and the filter cake was collected to give the target compound WX049-5. $^1$H NMR (400 MHz, DMSO-d$_6$) δ 12.84 (s, 1H), 11.17 (s, 1H), 7.32-7.17 (m, 4H), 2.45 (s, 3H), 1.46 (s, 3H). MS m/z: 442.0 [M+H]$^+$ Step 6: Synthesis of the Compound WX049-6

The compound WX049-5 (500.00 mg, 1.32 mmol, 1.00 eq) and 3-acetaminophenylboronic acid (472.02 mg, 2.64 mmol, 2.00 eq) were dissolved in dioxane (10.00 mL) and water (5.00 mL). Under nitrogen protection, SPhos (54.13 mg, 131.86 μmol, 0.10 eq), Pd$_2$(dba)$_3$ (37.91 mg, 65.93 μmol, 0.05 eq) and potassium phosphate (699.77 mg, 3.30 mmol, 2.50 eq) were added. The temperature was raised to 110° C. and the reaction was stirred for 15 hours. After completion of the reaction, the reaction mixture was diluted with water (20 mL) and extracted with dichloromethane (20 mL*3). The organic phase was collected, evaporated to dryness by rotary evaporation, then purified by column chromatography (PE/EA=5/1-0/1) to give the target compound WX049-6. MS m/z: 434.1 [M+H]$^+$ Step 7: Synthesis of the Compound WX049

The compound WX049-6 (250.00 mg, 576.79 μmol, 1.00 eq) was dissolved in dimethylsulfoxide (2.00 mL), then trifluoroacetic acid (197.30 mg, 1.73 mmol, 128.12 μL, 3.00 eq) and N-iodosuccinimide (389.30 mg, 1.73 mmol, 3.00 eq) were added. The mixture was heated to 25° C. and the reaction was stirred for 15 hours. After completion of the reaction, the reaction solution was diluted with water (20 mL) and extracted with EtOAc (20 mL*2). The organic phase was collected, dried over anhydrous sodium sulfate, evaporated to dryness by rotary evaporation, and purified by preparative HPLC to give the compound WX049. $^1$H NMR (400 MHz, DMSO-d$_6$) δ 12.56 (s, 1H), 11.28 (s, 1H), 10.08 (s, 1H), 7.73 (dd, J=10.0 Hz, J=1.6 Hz, 1H), 7.72-7.53 (m, 3H), 7.40 (t, J=8.8 Hz, 1H), 6.99 (d, J=7.2 Hz, 1H), 6.92 (t, J=8.8 Hz, 1H), 2.11 (s, 3H), 2.06 (s, 3H), 1.45 (s, 3H). MS m/z: 560.0 [M+H]$^+$ Embodiment 3: WX053

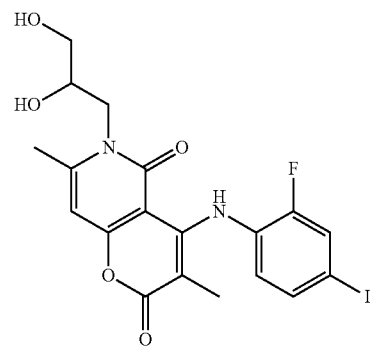 [SMILES: Cc1c(Nc2ccc(I)cc2F)c2c(=O)n(CC(O)CO)c(C)cc2oc1=O]

Synthetic Route:

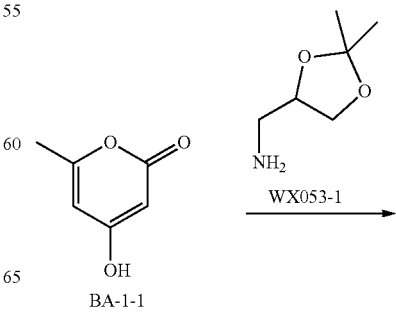

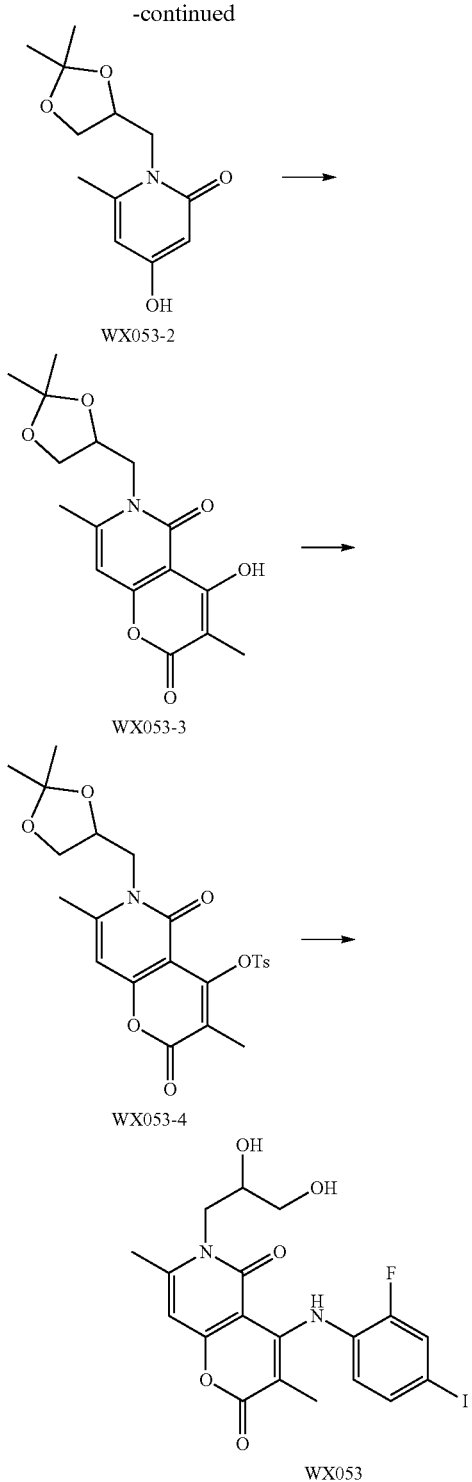

mL), dried at 45° C. until the weight became constant, to give the target compound WX053-2.

$^1$H NMR (400 MHz, CDCl$_3$-d) δ 5.96 (d, J=2.4 Hz, 1H), 5.90 (d, J=2.0 Hz, 1H), 4.44 (m, 1H), 4.34 (dd, J=14.0, 2.8 Hz, 1H), 4.16 (dd, J=8.8, 6.4 Hz, 1H), 3.91 (dd, J=14.0, 7.2 Hz, 1H), 3.69 (dd, J=8.4, 7.2 Hz, 1H), 2.45 (s, 3H), 1.40 (s, 3H), 1.31 (s, 3H). MS m/z: 239.9 [M+H]$^+$

Step 2: Synthesis of the Compound WX053-3

The compound WX053-2 (200 mg, 835.88 μmol, 1.00 eq) and diethyl methylmalonate (218 mg, 1.25 mmol, 214.12 μL, 1.50 eq) were mixed in diphenyl ether (5.00 mL). The temperature was raised to 250° C. and the reaction was stirred under reflux for 2 hours until no more ethanol was steamed out. After completion of the reaction, the reaction solution was cooled down and methyl tert-butyl ether (10 mL) and petroleum ether (10 mL) were added, then a solid formed. After completion of the reaction, the mixture was filtered. The filter cake was washed with methyl tert-butyl ether (2 mL) and petroleum ether (2 mL), and evaporated to dryness by rotary evaporation to give the target compound WX053-3. $^1$H NMR (400 MHz, CDCl$_3$-d) δ 6.28 (s, 1H), 4.46-4.54 (m, 1H), 4.42 (dd, J=14.0, 2.8 Hz, 1H), 4.21 (dd, J=8.8, 6.8 Hz, 1H), 4.00 (dd, J=14.0, 7.6 Hz, 1H), 3.74 (dd, J=8.8, 6.8 Hz, 1H), 2.60 (s, 3H), 2.00 (s, 3H), 1.42 (s, 3H), 1.32 (s, 3H). MS m/z: 322.1 [M+H]$^+$ Step 3: Synthesis of the Compound WX053-4

The compound WX053-3 (1.80 g, 5.60 mmol, 1.00 eq) was dissolved in dichloromethane (20 mL), then triethylamine (1.70 g, 16.80 mmol, 2.33 mL, 3.00 eq), DMAP (34.22 mg, 280 μmol, 0.05 eq) and p-toluenesulfonyl chloride (1.60 g, 8.40 mmol, 1.50 eq) were added. The reaction was stirred at 25° C. for 12 hours. After completion of the reaction, the reaction mixture was evaporated to dryness by rotary evaporation to give a crude product, which was purified by column chromatography (PE/EA=5/1-1/1) to give the target compound WX053-4. $^1$H NMR (400 MHz, CDCl$_3$-d) δ 7.91 (d, J=8.4 Hz, 2H), 7.39 (d, J=8.0 Hz, 2H), 6.13 (s, 1H), 4.42-4.53 (m, 2H), 4.19 (dd, J=8.8, 6.4 Hz, 1H), 3.90-3.97 (m, 1H), 3.71 (dd, J=8.8, 7.2 Hz, 1H), 2.56 (s, 3H), 2.48 (s, 3H), 1.54 (s, 3H), 1.41 (s, 3H), 1.31 (s, 3H). MS m/z: 476.2 [M+H]$^+$ Step 4: Synthesis of the Compound WX053

The compound WX053-4 (200 mg, 420.60 mol, 1.00 eq) was dissolved in ethanol (4.00 mL), then 2-fluoro-4-iodoaniline (299 mg, 1.26 mmol, 3.00 eq) was added at 25° C. under nitrogen protection. The reaction temperature was raised to 80° C. and the reaction was stirred for 36 hours. After completion of the reaction, the reaction mixture was evaporated to dryness by rotary evaporation to give a crude product. The crude product was purified by preparative HPLC to give the compound WX053. $^1$H NMR (400 MHz, DMSO-d$_6$) δ 11.21 (s, 1H), 7.73 (d, J=10.0 Hz, 1H), 7.54 (d, J=8.4 Hz, 1H), 6.90 (t, J=8.4 Hz, 1H), 6.51 (s, 1H), 5.05 (d, J=4.8 Hz, 1H), 4.78 (t, J=5.6 Hz, 1H), 4.27 (d, J=11.2 Hz, 1H), 3.79-3.92 (m, 2H), 3.39-3.49 (m, 2H), 2.56 (s, 3H), 1.49 (s, 3H). MS m/z: 501.1 [M+H]$^+$ Step 1: Synthesis of the Compound WX053-2

The compound BA-1-1 (2.50 g, 19.82 mmol, 1.00 eq) was dissolved in water (30.00 mL), then the compound WX053-1 (2.86 g, 2.83 mL, 1.10 eq) was added at 25° C. The reaction temperature was raised to 100° C. and the reaction was stirred for 2 hours, and a precipitate formed. After completion of the reaction, the reaction mixture was filtered. The filter cake was collected, washed with water (20

Embodiment 4: WX054
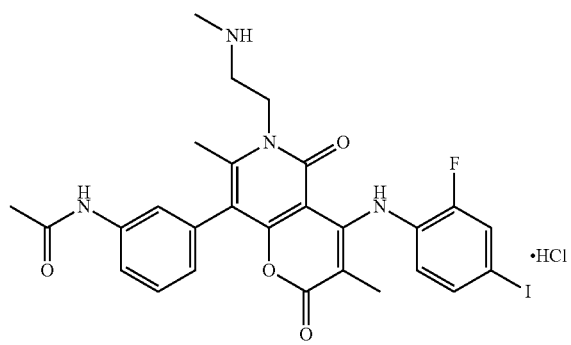 [SMILES: CNCCn1c(C)c(-c2cccc(NC(C)=O)c2)c2oc(=O)c(C)c(Nc3ccc(I)cc3F)c2c1=O ; Cl]
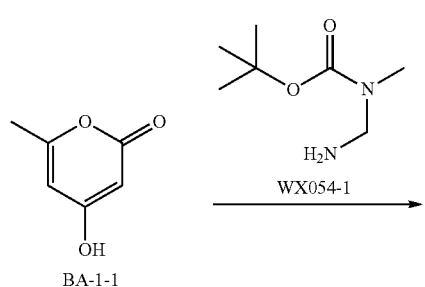
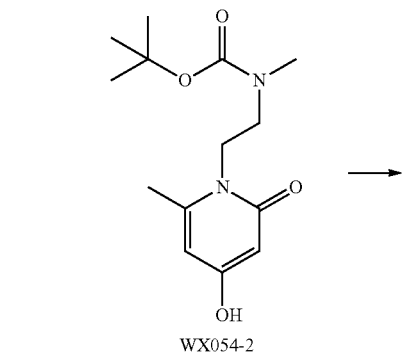
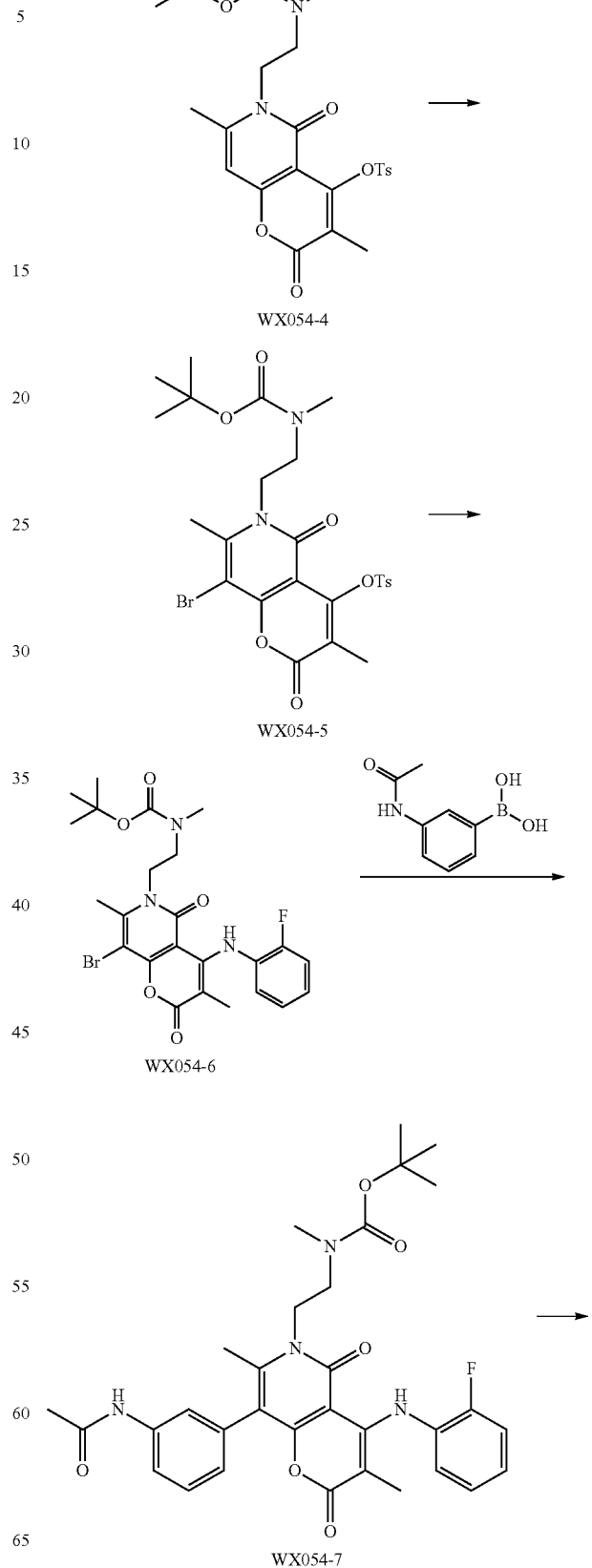

-continued

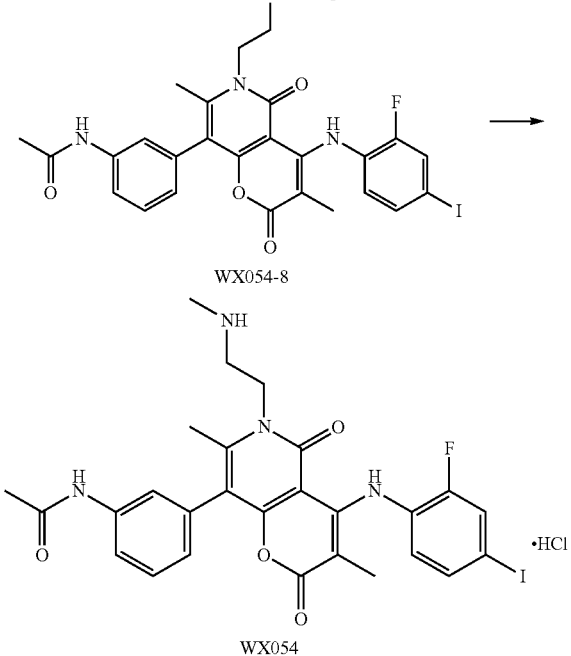

WX054-8

WX054

Step 1: Synthesis of the Compound WX054-2

The compound BA-1-1 (6.70 g, 53.13 mmol, 1.00 eq) was dissolved in water (250.00 mL), then the compound WX054-1 (9.26 g, 53.13 mmol, 9.45 mL, 1.00 eq) was added at room temperature. The reaction solution was heated to reflux and the reaction was stirred for 1 hour, and a solid formed. After completion of the reaction, the mixture was filtered and the filter cake was collected to give the target compound WX054-2. $^1$H NMR (400 MHz, DMSO-$d_6$) δ 10.34 (s, 1H), 5.75 (d, J=2.0 Hz, 1H), 5.48 (d, J=2.4 Hz, 1H), 3.96 (s, 2H), 3.38 (s, 2H), 2.76 (s, 3H), 2.27 (s, 3H), 1.31 (s, 9H). MS m/z: 282.9 [M+H]$^+$

Step 2: Synthesis of the Compound WX054-3

The compound WX054-2 (4.60 g, 16.29 mmol, 1.00 eq) and methylmalonic acid (2.89 g, 24.44 mmol, 1.50 eq) were added into acetic anhydride (50.00 mL). The temperature was raised to 100° C. and the reaction was stirred for 1 hour. After completion of the reaction, the reaction solution was cooled to room temperature, methyl tert-butyl ether (200 mL) was added. After the mixture was allowed to stand for 15 hours, a precipitate formed and was filtered. The filter cake was collected to give the target compound WX054-3. $^1$H NMR (400 MHz, DMSO-$d_6$) δ 13.24 (s, 1H), 6.66 (s, 1H), 4.20 (s, 2H), 3.56-3.50 (m, 2H), 2.80 (s, 3H), 1.82 (s, 3H), 1.26 (s, 3H), 1.16 (s, 9H). MS m/z: 365.0 [M+H]$^+$

Step 3: Synthesis of the Compound WX054-4

The compound WX054-3 (4.40 g, 12.07 mmol, 1.00 eq) was dissolved in dichloromethane (100.00 mL), then triethylamine (2.44 g, 24.14 mmol, 3.35 mL, 2.00 eq) and DMAP (294.92 mg, 2.41 mmol, 0.20 eq) were added, followed by addition of p-toluenesulfonyl chloride (3.45 g, 18.11 mmol, 1.50 eq) at 0° C. The reaction solution was heated to 20° C. and stirred for 15 hours. After completion of the reaction, the reaction solution was washed with water (200 mL) and the liquid was separated. The organic phase was dried over anhydrous sodium sulfate and then evaporated to dryness by rotary evaporation. The solid was triturated with methyl tert-butyl ether (200 mL) and filtered, the filter cake was collected to give the target compound WX054-4. MS m/z: 541.1 [M+Na]$^+$

Step 4: Synthesis of the Compound WX054-5

The compound WX054-4 (2.70 g, 5.21 mmol, 1.00 eq) was added into a mixed solvent of dichloromethane (20.00 mL) and acetonitrile (40.00 mL), then N-bromosuccinimide (1.39 g, 7.82 mmol, 1.50 eq) was added. The reaction solution was stirred at 20° C. for 15 hours. After completion of the reaction, the reaction solution was directly evaporated to dryness by rotary evaporation to give a crude product, which was subjected to column chromatography (PE/EA=3/1, Rf=0.3) to give WX054-5.
MS m/z: 621.1 [M+Na]$^+$

Step 5: Synthesis of the Compound WX054-6

The compound WX054-5 (2.70 g, 4.52 mmol, 1.00 eq) was dissolved in ethanol (50.00 mL), then 2-fluoroaniline (3.01 g, 27.12 mmol, 2.62 mL, 6.00 eq) was added. The reaction solution was heated to reflux and stirred for 15 hours, then a solid formed. After completion of the reaction, the mixture was filtered and the filter cake was collected to give the target compound WX054-6. MS m/z: 536.1 [M+H]$^+$

Step 6: Synthesis of the Compound WX054-7

The compound WX054-6 (700.00 mg, 1.31 mmol, 1.00 eq) and 3-acetaminophenylboronic acid (422.03 mg, 2.36 mmol, 1.80 eq) were added into dioxane (20.00 mL) and water (5.00 mL), then Pd(dppf)Cl$_2$.CH$_2$Cl$_2$ (106.98 mg, 131.00 μmol, 0.10 eq) and sodium bicarbonate (550.27 mg, 6.55 mmol, 5.00 eq) were added. Under nitrogen protection, the reaction was heated to 110° C. and stirred for 1.5 hours. After completion of the reaction, the reaction mixture was diluted with water (20 mL) and extracted with EtOAc (10 mL*3).
The organic phases were combined, dried over anhydrous sodium sulfate, filtered and evaporated to dryness by rotary evaporation to give a crude product, which was purified by column chromatography (PE/EA=2/1-0/1, Rf=0.31) to give the target compound WX054-7. MS m/z: 591.2 [M+H]$^+$

Step 7: Synthesis of the Compound WX054-8

The compound WX054-7 (500.00 mg, 846.54 μmol, 1.00 eq) was dissolved in dimethyl sulfoxide (10.00 mL), trifluoroacetic acid (289.57 mg, 2.54 mmol, 188.03 μL, 3.00 eq) was added, followed by addition of N-iodosuccinimide (571.36 mg, 2.54 mmol, 3.00 eq) at 15° C. in dark condition. The reaction was stirred for 15 hours in dark place. After completion of the reaction, the reaction solution was diluted with water (30 mL) and extracted with EtOAc (10 mL*3). The organic phases were combined, dried over anhydrous sodium sulfate and filtered. The filtrate was evaporated to dryness by rotary evaporation to give a crude product, which was purified by preparative HPLC (preparative separation to give the target compound WX054-8. $^1$H NMR (400 MHz, CDCl$_3$-d) δ 11.23 (d, J=8.4 Hz, 1H), 7.89 (s, 1H), 7.68 (s, 1H), 7.49-7.43 (m, 2H), 7.35-7.25 (m, 1H), 6.89 (d, J=7.2 Hz, 1H), 6.74 (t, J=7.2 Hz, 1H), 4.25 (s, 1H), 2.93 (s, 2H), 2.36 (s, 2H), 2.09 (s, 3H), 1.62 (s, 3H), 1.57 (s, 9H), 1.42 (s, 3H), 1.40 (s, 3H). MS m/z: 717.1 [M+H]$^+$ Step 8: Synthesis of the Compound WX054

The compound WX054-8 (160.00 mg, 223.30 μmol, 1.00 eq) was dissolved in dichloromethane (5.00 mL), a solution of hydrogen chloride in EtOAc (4M, 10.00 mL, 179.13 eq) was added. The reaction was stirred 15° C. for 1 hour. After completion of the reaction, the reaction mixture was evaporated to dryness by rotary evaporation to give the target compound WX054. $^1$H NMR (400 MHz, DMSO-d$_6$) δ 11.18 (s, 1H), 10.19 (s, 1H), 8.64 (br. s., 1H), 7.73 (d, J=10.8 Hz, 1H), 7.68 (s, 1H), 7.56 (t, J=9.2 Hz, 2H), 7.44 (t, J=8.0 Hz, 1H), 6.96 (d, J=7.6 Hz, 1H), 6.90 (t, J=8.0 Hz, 1H), 4.42 (br. s., 2H), 3.24 (br. s., 2H), 2.55 (s, 3H), 2.32 (s, 3H), 2.07 (s, 3H), 1.48 (s, 3H). MS m/z: 617.1 [M+H-HCl]$^+$ Embodiment 5: WX055

Synthetic Route:

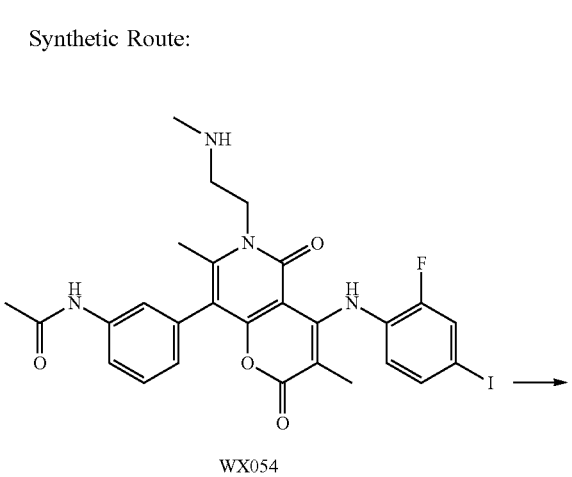

WX054

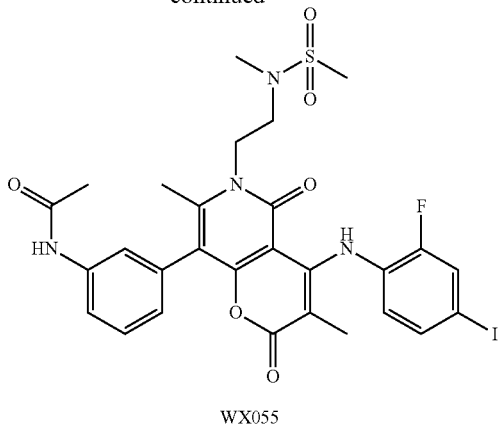

WX055

Step 1: Synthesis of the Compound WX055

The compound WX054 (30.00 mg, 45.95 μmol, 1.00 eq) was dissolved in dichloromethane (5.00 mL), triethylamine (18.60 mg, 183.80 μmol, 25.48 μL, 4.00 eq) was added, followed by addition of methanesulfonyl chloride (800.00 mg, 6.98 mmol, 540.54 μL, 151.99 eq) at 15° C. The reaction was stirred at 15° C. for 1 hour. After completion of the reaction, the reaction mixture was evaporated to dryness by rotary evaporation and purified by preparative TLC (EA, Rf=0.3) to give the target compound WX055. $^1$H NMR (400 MHz, CDCl$_3$-d) δ 11.16 (s, 1H), 8.22 (s, 1H), 7.78 (br. s., 1H), 7.50-7.43 (m, 2H), 7.27 (d, J=4.8 Hz, 1H), 7.15 (d, J=8.0 Hz, 1H), 6.87 (d, J=8.0 Hz, 1H), 6.75 (t, J=8.8 Hz, 1H), 4.36 (t, J=6.4 Hz, 2H), 3.47 (t, J=6.8 Hz, 2H), 3.00 (s, 3H), 2.84 (s, 3H), 2.34 (s, 3H), 2.05 (s, 3H), 1.62 (s, 3H). MS m/z: 694.9 [M+H]$^+$ Embodiment 6: WX056

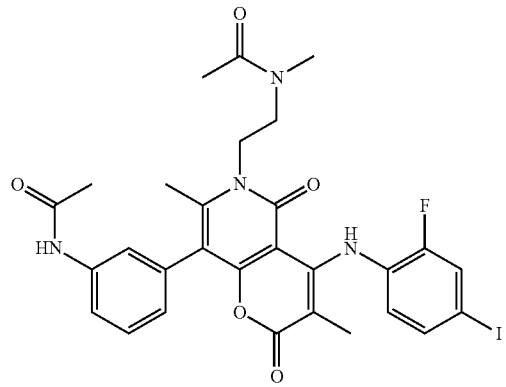 [SMILES: CC(=O)Nc1cccc(-c2c(C)n(CCN(C)C(C)=O)c(=O)c3c(Nc4ccc(I)cc4F)c(C)c(=O)oc23)c1]

Synthetic Route:

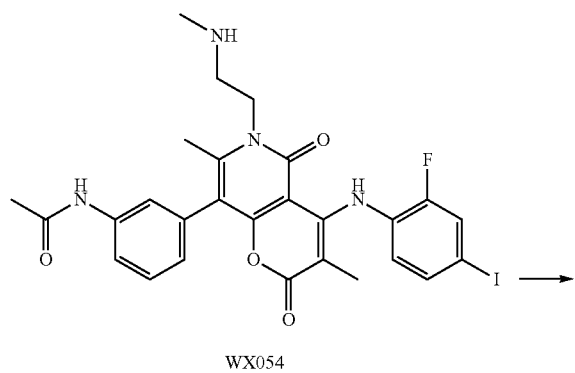

WX054

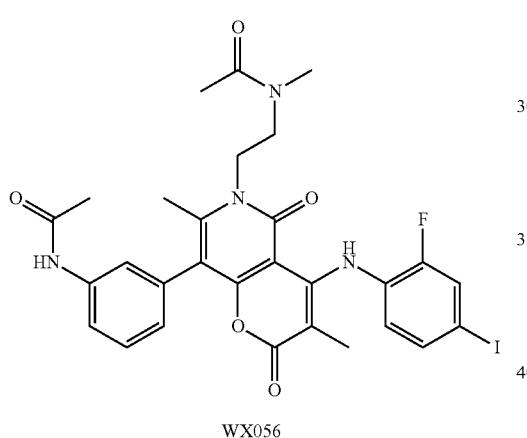

WX056

Step 1: Synthesis of the Compound WX056

The compound WX054 (30.00 mg, 45.95 μmol, 1.00 eq) was dissolved in dichloromethane (5.00 mL), triethylamine (18.60 mg, 183.80 μmol, 25.48 μL, 4.00 eq) was added, followed by addition of acetyl chloride (10.82 mg, 137.85 μmol, 9.84 μL, 3.00 eq). The reaction was stirred at 15° C. for 1 hour. After completion of the reaction, the reaction mixture was evaporated to dryness by rotary evaporation and purified by preparative TLC (EA, Rf=0.2) to give the target compound WX056. $^1$H NMR (400 MHz, CDCl$_3$-d) δ 11.24 (s, 1H), 8.29 (s, 1H), 7.79 (br. s., 1H), 7.50-7.43 (m, 2H), 7.26 (d, J=4.8 Hz, 1H), 7.14 (d, J=8.0 Hz, 1H), 6.86 (d, J=6.8 Hz, 1H), 6.76 (t, J=8.0 Hz, 1H), 4.28 (d, J=7.2 Hz, 2H), 3.64 (t, J=7.2 Hz, 2H), 3.14 (s, 3H), 2.39 (s, 3H), 2.09 (s, 3H), 2.04 (s, 3H), 1.63 (s, 3H). MS m/z: 659.0 [M+H]$^+$ Embodiment 7: WX057

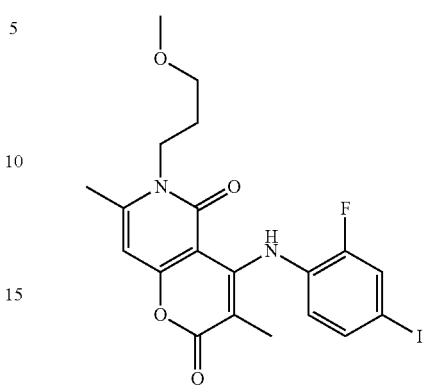

Synthetic Route:

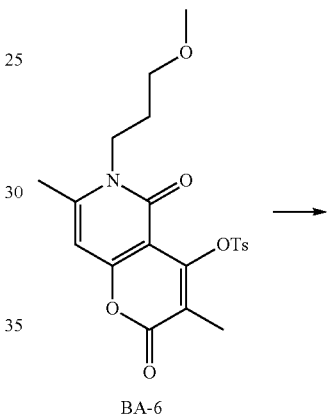

BA-6

WX057

Step 1: Synthesis of the Compound WX057

The compound BA-6 (2.00 g, 2.86 mmol, 1.00 eq) and 2-fluoro-4-iodoaniline (3.39 g, 14.30 mmol, 5.00 eq) were dissolved in ethanol (20.00 mL), the mixture was heated to reflux and stirred for 15 hours. The reaction mixture was evaporated to dryness by rotary evaporation and the residue was triturated with methyl tert-butyl ether (200 mL*2). The mixture was filtered, then the filter cake was collected and purified by column chromatography (PE/EA=1/1, Rf=0.25) twice. The obtained crude product was further purified by preparative HPLC to give the compound WX057. $^1$H NMR (400 MHz, DMSO-d$_6$) δ 11.16 (s, 1H), 7.72 (dd, J=10.0 Hz, J=2.0 Hz, 1H), 7.53 (d, J=8.0 Hz, 1H), 6.89 (t, J=8.6 Hz, 1H), 6.53 (s, 1H), 4.07 (t, J=7.6 Hz, 2H), 3.39 (t, J=5.8 Hz, 2H), 3.24 (s, 3H), 2.53 (s, 3H), 1.91-1.83 (m, 2H), 1.47 (s, 3H). MS m/z: 498.9 [M+H]$^+$ Embodiment 8: WX058

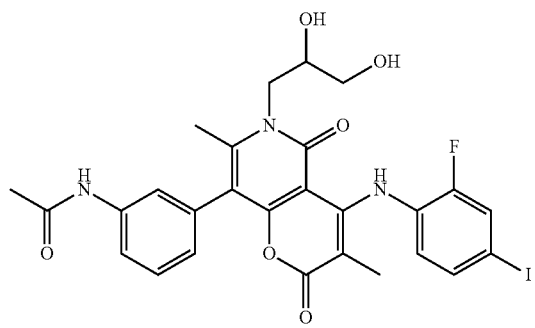 [SMILES: CC(=O)Nc1cccc(-c2c(C)n(CC(O)CO)c(=O)c3c(Nc4ccc(I)cc4F)c(C)c(=O)oc23)c1]

Synthetic Route:

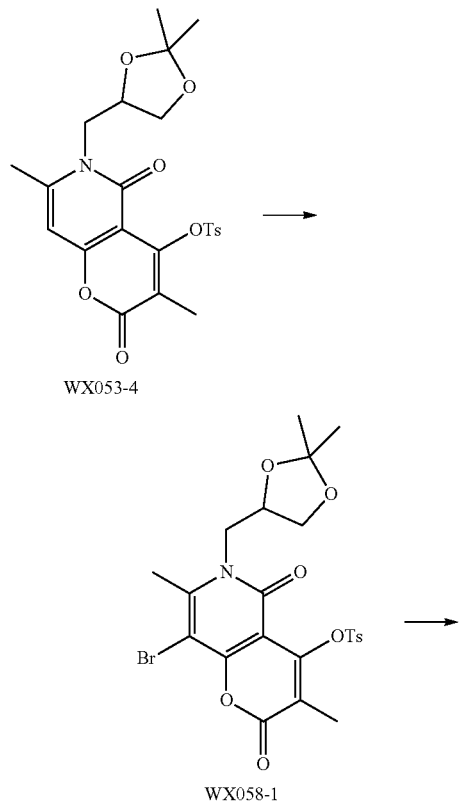

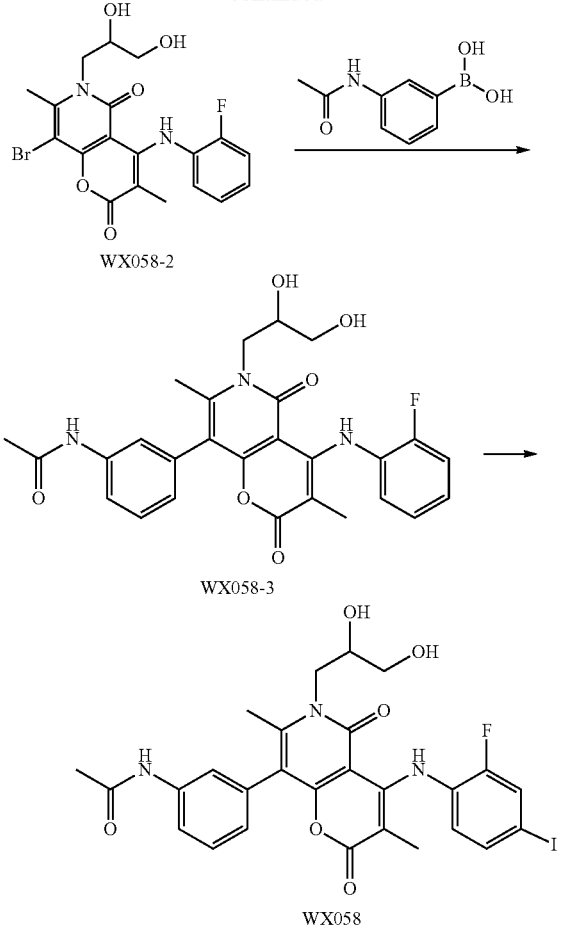

Step 1: Synthesis of the Compound WX058-1

The compound WX053-4 (1 g, 2.1 mmol, 1.00 eq) was added into dichloromethane (10 mL) and acetonitrile (20 mL), then sodium bicarbonate (176.42 mg, 2.1 mmol, 1.00 eq) and N-bromosuccinimide (747.52 mg, 4.2 mmol, 2.00 eq) were added at 25° C. under nitrogen protection. The reaction was stirred at 25° C. for 12 hours. After completion of the reaction, the reaction mixture was evaporated to dryness by rotary evaporation. The crude product was purified by column chromatography (PE/EA=1/1, Rf=0.6) to give the target compound WX058-1. $^1$H NMR (400 MHz, CDCl$_3$-d) δ 7.88 (d, J=8.4 Hz, 2H), 7.38 (d, J=8.0 Hz, 2H), 4.58 (dd, J=14.2 Hz, J=2.6 Hz, 1H), 4.50-4.48 (m, 1H), 4.19 (dd, J=8.8 Hz, J=6.4 Hz, 1H), 4.05 (dd, J=14.4 Hz, J=7.6 Hz, 1H), 3.71 (dd, J=8.8 Hz, J=6.8 Hz, 1H), 2.96 (s, 3H), 2.48 (s, 3H), 1.53 (s, 3H), 1.41 (s, 3H), 1.30 (s, 3H). MS m/z: 555.8 [M+H]$^+$ Step 2: Synthesis of the Compound WX058-2

The compound WX058-1 (600 mg, 1.08 mmol, 1.00 eq) was dissolved in ethanol (6.00 mL), then 2-fluoroaniline (360.03 mg, 3.24 mmol, 313.07 μL, 3.00 eq) was added at 20° C.

The reaction temperature was raised to 80° C. and the reaction was stirred for 24 hours. After completion of the reaction, the reaction mixture was evaporated to dryness by rotary evaporation. The crude product was triturated with methyl tert-butyl ether (10 mL) and then filtered to give the target compound WX058-2. ¹H NMR (400 MHz, DMSO-d₆) δ 11.26 (s, 1H), 7.37-7.28 (m, 1H), 7.23-7.12 (m, 3H), 5.11 (d, J=4.8 Hz, 1H), 4.81 (t, J=5.8 Hz, 1H), 4.40 (dd, J=14.0 Hz, J=2.8 Hz, 1H), 4.05-3.96 (m, 1H), 3.93-3.84 (m, 1H), 3.50-3.38 (m, 2H), 2.81 (s, 3H), 1.49 (s, 3H). MS m/z: 477.2 [M+Na]⁺

Step 3: Synthesis of the Compound WX058-3

The compound WX058-2 (250 mg, 551.56 μmol, 1.00 eq) and 3-acetaminophenylboronic acid (148.08 mg, 827.34 μmol, 1.50 eq) were added into dioxane (10.00 mL), then saturated sodium bicarbonate solution (2.00 mL, 1.00 eq) and Pd(dppf)Cl₂.CH₂Cl₂ (45.04 mg, 55.16 μmol, 0.10 eq) were added at 20° C. under nitrogen protection. The reaction temperature was raised to 80-90° C. and the reaction was stirred for 12 hours. After completion of the reaction, the reaction mixture was evaporated to dryness by rotary evaporation. The crude product was purified by preparative HPLC (trifluoroacetic acid system) to give the target compound WX058-3. ¹H NMR (400 MHz, DMSO-d₆) δ 11.43 (s, 1H), 10.09 (d, J=3.6 Hz, 1H), 7.62-7.56 (m, 2H), 7.45-7.39 (m, 1H), 7.36-7.27 (m, 1H), 7.22-7.12 (m, 3H), 6.94 (t, J=8.4 Hz, 1H), 5.12 (d, J=9.2 Hz, 1H), 4.80 (t, J=5.4 Hz, 1H), 4.44-4.34 (m, 1H), 3.95 (br. s., 2H), 3.45 (br. s., 2H), 2.34 (s, 3H), 2.06 (s, 3H) 1.45 (s, 3H). MS m/z: 508.2 [M+H]⁺

Step 4: Synthesis of the Compound WX058

At 0° C., under nitrogen protection and in dark place, the compound WX058-3 (80 mg, 157.63 μmol, 1.00 eq) and N-iodobromosuccinimide (70.93 mg, 315.26 μmol, 2.00 eq) was dissolved in N,N-dimethylformamide (2.00 mL), followed by addition of trifluoroacetic acid (35.95 mg, 315.26 μmol, 23.34 μL, 2.00 eq). The reaction was stirred at 20° C. for 12 hours. After completion of the reaction, the reaction mixture was purified by preparative HPLC to give the target compound WX058. ¹H NMR (400 MHz, DMSO-d₆) δ 11.39 (s, 1H), 10.09 (d, J=4.0 Hz, 1H), 7.73 (dd, J=10.0 Hz, J=1.6 Hz, 1H), 7.62-7.52 (m, 3H), 7.42 (t, J=8.0 Hz, 1H), 6.97-6.88 (m, 2H), 5.11 (d, J=10.0 Hz, 1H), 4.80 (br. s., 1H), 4.42-4.34 (m, 1H), 3.95 (br. s., 2H), 3.45 (br. s., 2H), 2.33 (s, 3H), 2.06 (s, 3H), 1.47 (s, 3H). MS m/z: 633.9 [M+H]⁺

Embodiment 9: WX059

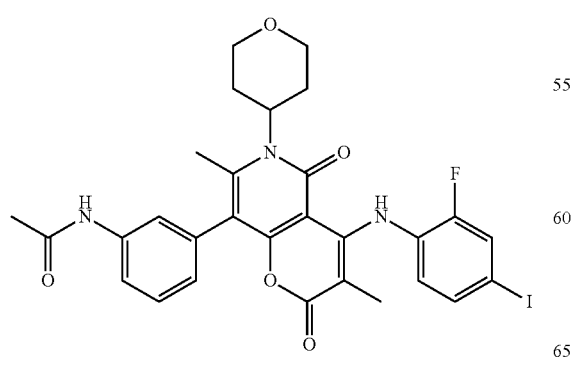

Synthetic Route:

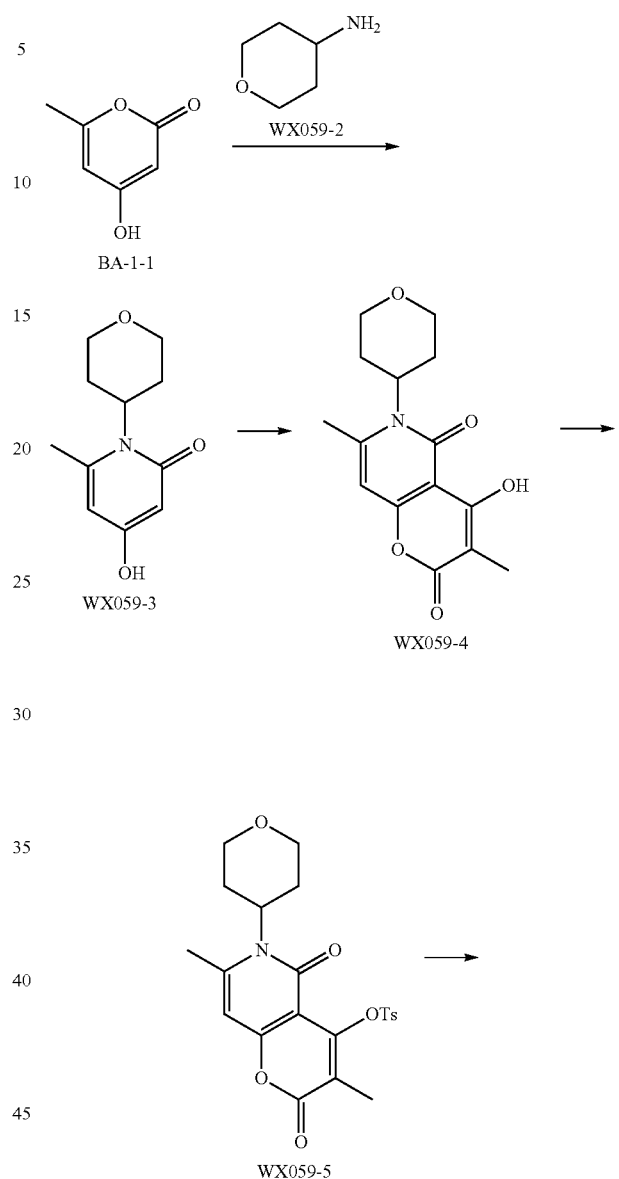

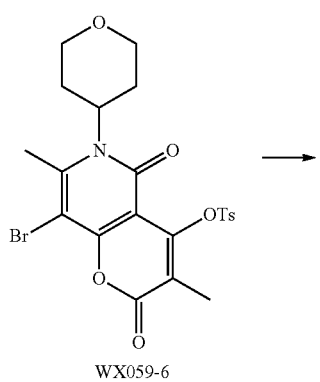

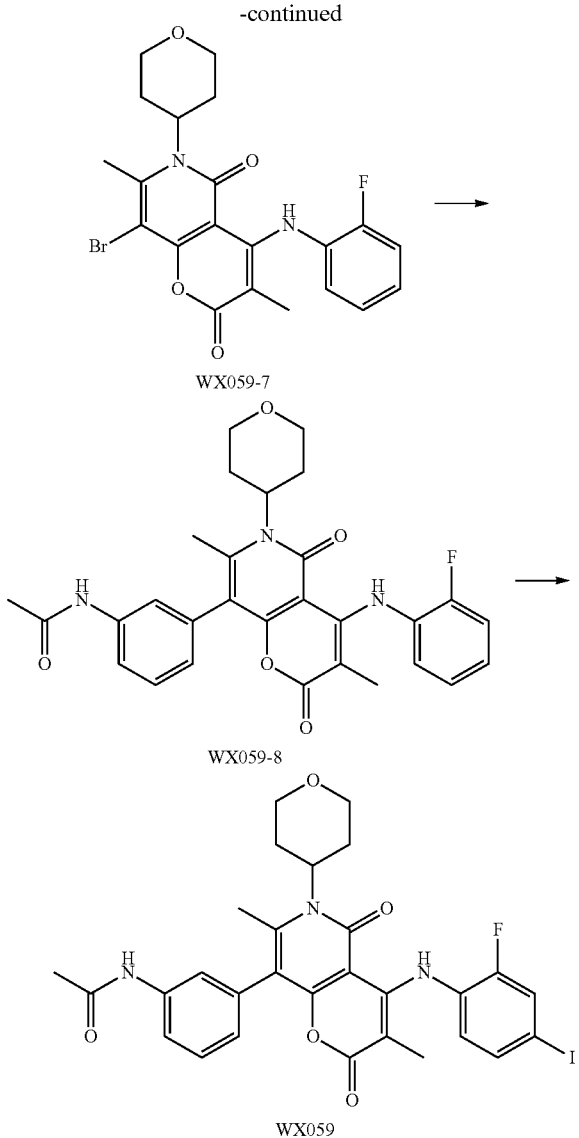

WX059-7

WX059-8

WX059

Step 1: Synthesis of the Compound WX059-3

The compound BA-1-1 (4 g, 31.72 mmol, 1.00 eq) was dissolved in H$_2$O (1.60 L), then the compound WX059-2 (3.37 g, 33.31 mmol, 1.05 eq) was added dropwise at 25° C. Under nitrogen protection, the reaction temperature was raised to 120° C. and the reaction was stirred for 36 hours. After completion of the reaction, the solvent was removed by rotary evaporation, the crude product was purified by preparative HPLC (trifluoroacetic acid system) to give the target compound WX059-3. $^1$H NMR (400 MHz, DMSO-d$_6$) δ 10.41 (br. s., 1H), 5.76 (br. s., 1H), 5.46 (br. s., 1H), 4.16 (br. s., 1H), 3.90 (dd, J=11.4 Hz, J=4.6 Hz, 2H), 3.36 (t, J=11.0 Hz, 2H), 2.89 (br. s., 2H), 2.35 (s, 3H), 1.47 (d, J=12.0 Hz, 2H). MS m/z: 210.0 [M+H]$^+$ Step 2: Synthesis of the Compound WX059-4

The compound WX059-3 (700 mg, 3.35 mmol, 1.00 eq) was dissolved in diphenyl ether, the compound diethyl methylmalonate (700.24 mg, 4.02 mmol, 686.51 μL, 1.20 eq) was added. The reaction temperature was raised to 250° C. and the reaction was stirred for 2 hours. After completion of the reaction, petroleum ether (20 mL) was added, then a solid precipitated. The solid was filtered, and the filter cake was washed with petroleum ether (5 mL) to give the target compound WX059-4. $^1$H NMR (400 MHz, CDCl$_3$-d) δ 12.98 (s, 1H), 6.23 (s, 1H), 4.28 (br. s., 1H), 4.15 (dd, J=11.4 Hz, J=4.6 Hz, 2H), 3.46 (t, J=11.8 Hz, 2H), 3.17 (br. s., 2H), 2.52 (s, 3H), 1.99 (s, 3H), 1.64-1.62 (m, 2H). MS m/z: 292.1 [M+H]$^+$ Step 3: Synthesis of the Compound WX059-5

The compound WX059-4 (1.1 g, 3.78 mmol, 1.00 eq) was dissolved in dichloromethane (20 mL), then triethylamine (1.15 g, 11.34 mmol, 1.57 mL, 3.00 eq), DMAP (46.18 mg, 378 μmol, 0.10 eq) and p-toluenesulfonyl chloride (1.08 g, 5.67 mmol, 1.50 eq) were added at 0° C. under nitrogen protection. The reaction temperature was raised to 20° C. and the reaction was stirred for 12 hours. After completion of the reaction, the solvent was removed by rotary evaporation. The crude product was purified by column chromatography (PE/EA=1/1) to give the target compound WX059-5. $^1$H NMR (400 MHz, CDCl$_3$-d) δ 7.94 (d, J=8.4 Hz, 2H), 7.40 (d, J=8.0 Hz, 2H), 6.05 (s, 1H), 4.46-4.19 (m, 1H), 4.12 (dd, J=11.4 Hz, J=4.2 Hz, 2H), 3.44 (t, J=11.2 Hz, 2H), 3.07 (s, 2H), 2.47 (s, 3H), 1.73 (s, 3H), 1.61 (s, 3H), 1.55 (d, J=12.4 Hz, 2H). MS m/z: 446.1 [M+H]$^+$ Step 4: Synthesis of the Compound WX059-6

The compound WX059-5 (950 mg, 2.13 mmol, 1.00 eq) was dissolved in acetonitrile (10 mL) and THF (10 mL), followed by addition of N-bromosuccinimide (682.38 mg, 3.83 mmol, 1.80 eq) at 0° C. Under nitrogen protection, the reaction temperature was raised to 25° C. and the reaction was stirred for 12 hours. After completion of the reaction, the solvent was removed by rotary evaporation. The crude product was triturated with methyl tert-butyl ether (20 mL) and ethanol (5 mL) and filtered. The filter cake was collected to give the target compound WX059-6. $^1$H NMR (400 MHz, DMSO-d$_6$) δ 7.87 (d, J=8.4 Hz, 2H), 7.49 (d, J=8.0 Hz, 2H), 4.41 (br. s., 1H), 3.93 (dd, J=10.8 Hz, J=4.4 Hz, 2H), 3.48-3.40 (m, 2H), 2.77 (s, 3H), 2.73-2.66 (m, 2H), 2.44 (s, 3H), 1.71 (d, J=11.6 Hz, 1H), 1.52 (br. s., 1H), 1.49 (s, 3H). MS m/z: 524.0 [M+H]$^+$ Step 5: Synthesis of the Compound WX059-7

The compound WX059-6 (650 mg, 1.24 mmol, 1.00 eq) was dissolved in ethanol (10 mL), then 2-fluoroaniline (688.94 mg, 6.20 mmol, 599.08 μL, 5.00 eq) was added at 20° C. under nitrogen protection. The reaction mixture was heated to 80° C. and the reaction was stirred for 15 hours. After completion of the reaction, the reaction mixture was filtered. The filter cake was collected and triturated with methyl tert-butyl ether (10 mL). The solid was collected by filtration to give the target compound WX059-7. $^1$H NMR (400 MHz, DMSO-d$_6$) δ 11.21 (s, 1H), 7.36-7.29 (m, 1H), 7.22-7.12 (m, 3H), 4.61 (br. s., 1H), 3.98-3.90 (m, 3H), 3.48-3.39 (m, 3H), 2.83 (s, 3H), 1.68 (d, J=10.0 Hz, 2H), 1.47 (s, 3H). MS m/z: 465.0 [M+H]$^+$ Step 6: Synthesis of the Compound WX059-8

The compound WX059-7 (260 mg, 561.19 mol, 1.00 eq) and the compound 3-acetaminophenylboronic acid (150.66 mg, 841.79 μmol, 1.50 eq) were dissolved in dioxane (10 mL), then Pd(dppf)Cl$_2$.CH$_2$Cl$_2$ (45.83 mg, 56.12 μmol, 0.10 eq) and saturated sodium bicarbonate solution (2 mL) were added at 20° C. under nitrogen protection. The reaction temperature was raised to 80-90° C. and the reaction was stirred for 12 hours. After completion of the reaction, the solvent was removed by rotary evaporation. Dichloromethane (20 mL) and water (10 mL) was added to dissolve the residue, and the liquid was partitioned. The organic phase was collected, washed with saturated sodium chloride solution, dried over anhydrous sodium sulfate, then evaporated to dryness by rotary evaporation to give a crude product. The crude product was purified by column chromatography (dichloromethane/methanol=20/1) to give the target compound WX059-8. $^1$H NMR (400 MHz, CDCl$_3$-d) δ 11.48 (s, 1H), 8.86 (s, 1H), 7.92 (s, 1H), 7.24-7.10 (m, 5H), 6.97 (d, J=8.0 Hz, 1H), 6.82 (d, J=7.6 Hz, 1H), 4.51-4.30 (m, 1H), 4.15 (d, J=10.0 Hz, 2H), 3.46 (t, J=11.6 Hz, 2H), 3.31-3.09 (m, 2H), 2.29 (s, 3H), 2.03-1.96 (m, 4H), 1.64 (br. s., 1H), 1.60 (s, 3H). MS m/z: 518.3 [M+H]$^+$ Step 7: Synthesis of the Compound WX059

The compound WX059-8 (200 mg, 386.44 μmol, 1.00 eq) was dissolved in N,N-dimethylformamide (3 mL), then trifluoroacetic acid (88.12 mg, 772.88 μmol, 57.22 μL, 2.00 eq) was added, followed by addition of N-iodosuccinimide (173.88 mg, 772.88 μmol, 2.00 eq) at 0° C. under nitrogen protection and in dark place. The reaction temperature was raised to 20° C. and the reaction was stirred for 12 hours. After completion of the reaction, the reaction mixture was diluted with water (10 mL) and extracted with dichloromethane (10 mL*2). The organic phase was washed with saturated sodium chloride solution (10 mL), dried over anhydrous sodium sulfate and evaporated to dryness by rotary evaporation. The crude product was purified by preparative HPLC to give the target compound WX059. $^1$H NMR (400 MHz, CDCl$_3$-d) δ 11.44 (br. s., 1H), 7.77 (br. s., 1H), 7.51-7.42 (m, 2H), 7.36-7.29 (m, 1H), 7.19 (br. s., 1H), 6.92 (d, J=7.6 Hz, 1H), 6.80 (br. s., 1H), 4.15 (d, J=11.6 Hz, 2H), 3.46 (t, J=11.6 Hz, 2H), 3.20 (br. s., 1H), 2.33 (s, 3H), 2.06 (s, 3H), 1.71-1.67 (m, 4H), 1.60 (s, 3H). MS m/z: 644.2 [M+H]$^+$ Embodiment 10: WX060

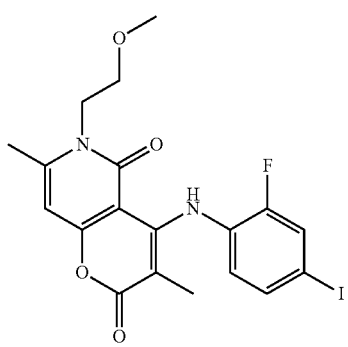 [SMILES: COCCn1c(C)cc2oc(=O)c(C)c(Nc3ccc(I)cc3F)c2c1=O]

Synthetic Route:

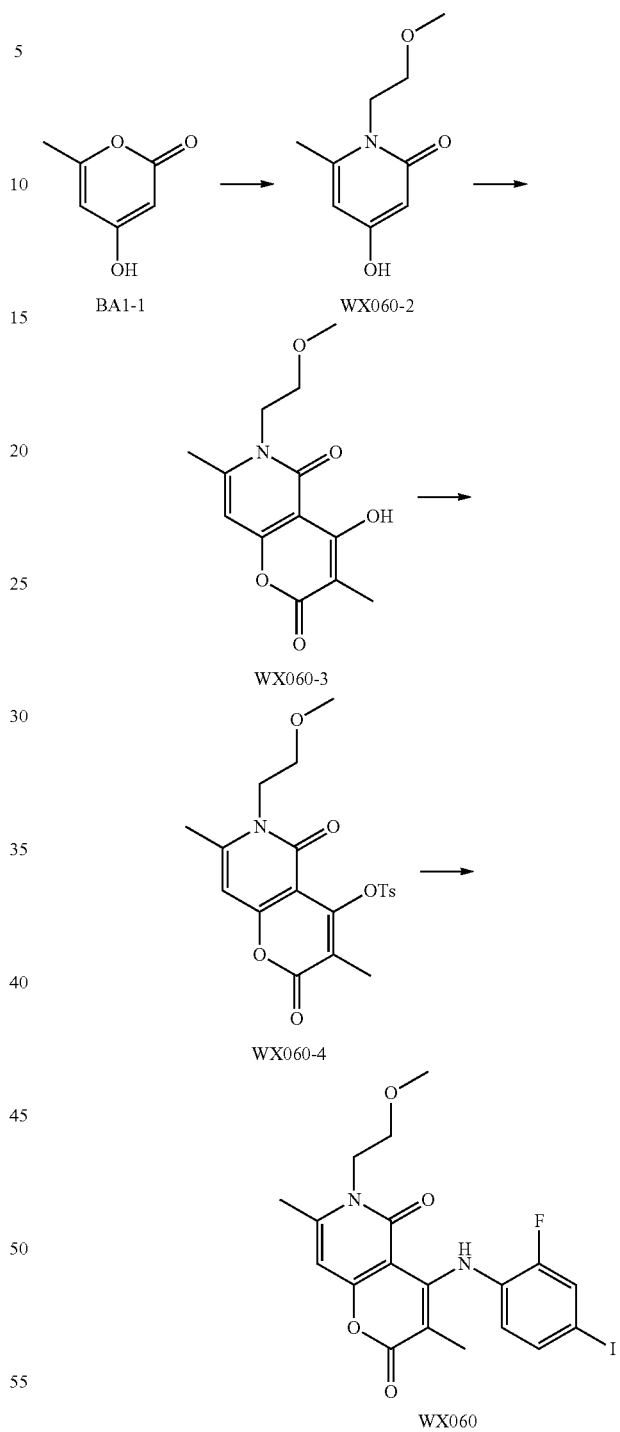

Step 1: Synthesis of the Compound WX060-2

The compound BA-1-1 (15 g, 118.94 mmol, 1.00 eq) was added into water (200 mL), followed by addition of methoxyethylamine (9.83 g, 130.83 mmol, 11.43 mL, 1.10 eq) at 20° C. The reaction was stirred at 100° C. for 1.5 hours, and a white solid formed. After completion of the reaction, the reaction mixture was filtered and the filter cake was washed with water (200 mL) to give the target compound WX060-2. ¹H NMR (400 MHz, CDCl₃-d) δ 5.97 (d, J=2.4 Hz, 1H), 5.87 (d, J=2.0 Hz, 1H), 4.15 (t, J=5.0 Hz, 1H), 3.65 (t, J=5.2 Hz, 1H), 3.30 (s, 1H), 2.40 (s, 1H). MS m/z: 205.9 [M+Na]⁺

Step 2: Synthesis of the Compound WX060-3

The compound WX060-2 (8 g, 43.67 mmol, 1.00 eq) was added into acetic anhydride (20 mL), followed by addition of methylmalonic acid (7.74 g, 65.50 mmol, 1.50 eq) at 20° C. The reaction was stirred at 20° C. for 0.5 hour, and a white solid formed. After completion of the reaction, the reaction mixture was filtered and the filter cake was washed with methyl tert-butyl ether (100 mL) to give the target compound WX060-3. ¹H NMR (400 MHz, CDCl₃-d) δ 12.78 (s, 1H), 6.25 (s, 1H), 4.26 (t, J=5.0 Hz, 1H), 3.70 (t, J=5.0 Hz, 1H), 3.31 (s, 3H), 2.54 (s, 3H), 2.00 (s, 3H). MS m/z: 265.9 [M+H]⁺

Step 3: Synthesis of the Compound WX060-4

The compound WX060-3 (10.5 g, 39.58 mmol, 1.00 eq) was added into dichloromethane (200 mL), then triethylamine (10.01 g, 98.95 mmol, 13.71 mL, 2.50 eq), DMAP (483.60 mg, 3.96 mmol, 0.10 eq) and p-toluenesulfonyl chloride (11.32 g, 59.37 mmol, 1.50 eq) were added at 0° C. under nitrogen protection. The reaction was stirred at 20° C. for 12 hours. After completion of the reaction, the reaction mixture was washed with water (200 mL*2). The organic phase was dried over anhydrous sodium sulfate, filtered and evaporated to dryness by rotary evaporation to give a crude product. The crude product was triturated with methyl tert-butyl ether (200 mL) to give the target compound WX060-4. ¹H NMR (400 MHz, CDCl₃-d) δ 7.91 (d, J=8.4 Hz, 1H), 7.38 (d, J=8.0 Hz, 1H), 6.09 (s, 1H), 4.22 (t, J=4.8 Hz, 2H), 3.68 (t, J=4.8 Hz, 2H), 3.28 (s, 3H), 2.49 (d, J=9.2 Hz, 6H), 1.55 (s, 3H). MS m/z: 442.2 [M+Na]⁺

Step 4: Synthesis of the Compound WX060

The compound WX060-4 (1 g, 2.38 mmol, 1.00 eq) was added into ethanol (10.00 mL), followed by addition of the compound 2-fluoro-4-iodoaniline (564.09 mg, 2.38 mmol, 1.00 eq) at 20° C. The reaction was stirred at 80° C. for 12 hours, and a white solid formed.

After completion of the reaction, the reaction mixture was filtered and washed with methyl tert-butyl ether (10 mL) to give the filter cake. The filter cake was triturated with a solvent of dimethylsulfoxide/acetonitrile=1/1 (10 mL), and then filtered to give the target compound WX060. ¹H NMR (400 MHz, DMSO-d₆) δ 11.10 (s, 1H), 7.73 (dd, J=10.2 Hz, 2.0 Hz, 2H), 7.54 (d, J=9.2 Hz, 1H), 6.90 (t, J=8.8 Hz, 1H), 6.52 (s, 1H), 4.22 (t, J=5.2 Hz, 2H), 3.61 (t, J=5.2 Hz, 2H), 3.24 (s, 3H), 2.54 (s, 2H), 1.48 (s, 3H). MS m/z: 485.0 [M+H]⁺

Embodiment 11: WX061

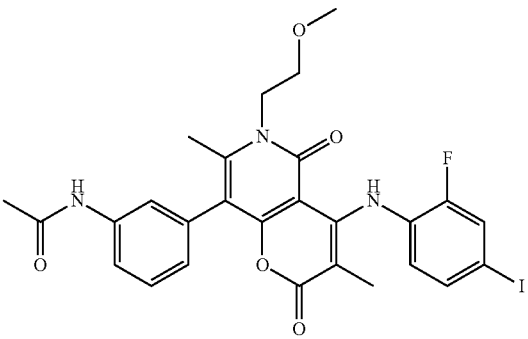 [SMILES: COCCn1c(C)c(-c2cccc(NC(C)=O)c2)c2oc(=O)c(C)c(Nc3ccc(I)cc3F)c2c1=O]

Synthetic Route:

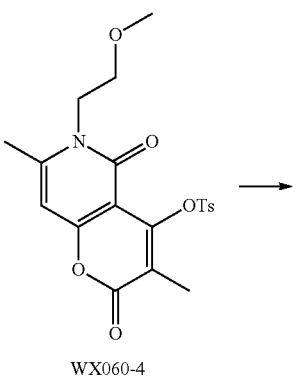
WX060-4

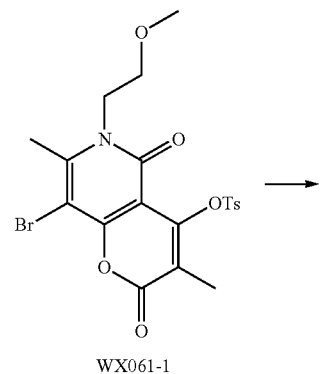
WX061-1

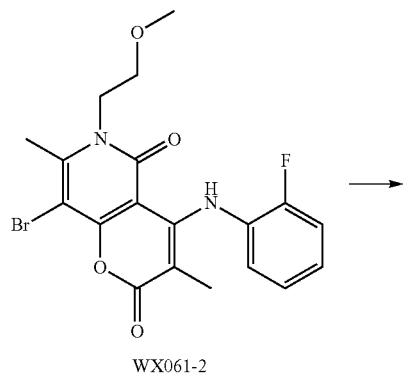
WX061-2

-continued

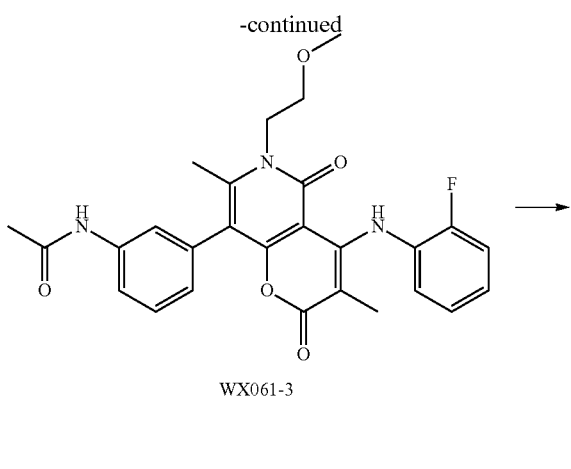

WX061-3

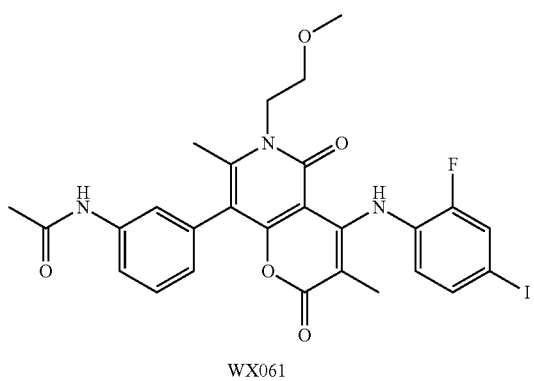

WX061

Step 1: Synthesis of the Compound WX061-1

The compound WX060-4 (12.50 g, 29.8 mmol, 1.00 eq) was added into acetonitrile (130 mL) and dichloromethane (130 mL), followed by addition of N-bromosuccinimide (7.96 g, 44.7 mmol, 1.50 eq) at 0° C. under nitrogen protection. The reaction was stirred at 20° C. for 12 hours. After completion of the reaction, the reaction mixture was evaporated to dryness by rotary evaporation to give a solid. The solid was triturated with methyl tert-butyl ether (100 mL) to give the target compound WX061-1. $^1$H NMR (400 MHz, DMSO-d$_6$) δ 7.86 (d, J=8.4 Hz, 2H), 7.46 (d, J=8.4 Hz, 2H), 4.18 (t, J=5.4 Hz, 2H), 3.52-3.45 (m, 2H), 3.24-3.18 (m, 3H), 2.70 (s, 3H), 2.42 (s, 3H), 1.46 (s, 3H). MS m/z: 521.9 [M+H]$^+$

Step 2: Synthesis of the Compound WX061-2

The compound WX061-1 (12.00 g, 24.08 mmol, 1.00 eq) was added into ethanol (200 mL), followed by addition of 2-fluoroaniline (13.38 g, 120.40 mmol, 11.63 mL, 5.00 eq) at 20° C. under nitrogen protection. The reaction was stirred at 80° C. for 12 hours, and a white solid formed. After completion of the reaction, the reaction mixture was filtered, and the filter cake was washed with methyl tert-butyl ether (100 mL) to give the target compound WX061-2.

$^1$H NMR (400 MHz, DMSO-d$_6$) δ 11.16 (s, 1H), 7.38-7.28 (m, 1H), 7.25-7.11 (m, 3H), 4.36 (t, J=5.2 Hz, 2H), 3.63 (t, J=5.2 Hz, 2H), 3.26-3.22 (m, 3H), 2.78 (s, 3H), 1.48 (s, 3H). MS m/z: 437.0 [M+H]$^+$

Step 3: Synthesis of the Compound WX061-3

The compound WX061-2 (5.00 g, 11.43 mmol, 1.00 eq) and 3-acetaminophenylboronic acid (3.07 g, 17.15 mmol, 1.50 eq) were added into dioxane (100 mL), followed by addition of saturated sodium bicarbonate solution (20 mL) and Pd(dppf)Cl$_2$.CH$_2$Cl$_2$ (933.82 mg, 1.14 mmol, 0.10 eq) at 20° C. under nitrogen protection. The reaction was stirred at 80-90° C. for 12 hours. After completion of the reaction, the reaction solution was evaporated to dryness by rotary evaporation. The crude product was purified by column chromatography (PE/EA=0/1) to give the target compound WX061-3. $^1$H NMR (400 MHz, CDCl$_3$-d) δ 11.36 (s, 1H), 8.44 (s, 1H), 7.80 (s, 1H), 7.17-7.05 (m, 5H), 6.88 (d, J=7.6 Hz, 1H), 4.35 (s, 2H), 3.75 (t, J=5.2 Hz, 2H), 3.33 (s, 3H), 2.35 (s, 3H), 2.04 (s, 3H), 1.62 (s, 3H). MS m/z: 492.2 [M+H]$^+$

Step 4: Synthesis of the Compound WX061

The compound WX061-3 (2.30 g, 4.68 mmol, 1.00 eq) was added into N,N-dimethylformamide (25 mL), then trifluoroacetic acid (1.07 g, 9.36 mmol, 693 μL, 2.00 eq) and N-iodosuccinimide (2.11 g, 9.36 mmol, 2.00 eq) were added at 0° C. under nitrogen protection and in dark place. The reaction was stirred at 20° C. for 15 hours. After completion of the reaction, water (100 mL) was added, and the mixture was extracted with dichloromethane (100 mL*2). The organic phase was washed with saturated sodium chloride solution (100 mL), dried over anhydrous sodium sulfate, filtered and evaporated to dryness by rotary evaporation. The crude product was purified by preparative HPLC, and then triturated with dichloromethane (10 mL) and methyl tert-butyl ether (10 mL) to give the target compound WX061. $^1$H NMR (400 MHz, DMSO-d$_6$) δ 11.25 (s, 1H), 10.07 (s, 1H), 7.71 (d, J=10.0 Hz, 1H), 7.59-7.49 (m, 3H), 7.40 (t, J=7.6 Hz, 1H), 6.93 (d, J=7.6 Hz, 1H), 6.88 (t, J=8.4 Hz, 1H), 4.30 (t, J=5.2 Hz, 2H), 3.64 (t, J=5.2 Hz, 2H), 3.23 (s, 3H), 2.29 (s, 3H), 2.04 (s, 3H), 1.44 (s, 3H). MS m/z: 617.9 [M+H]$^+$

Embodiment 12: WX062

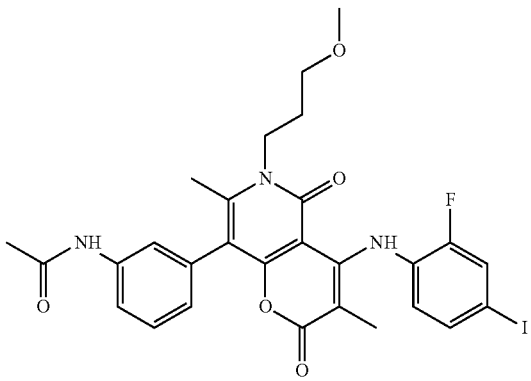 [SMILES: COCCCn1c(C)c(-c2cccc(NC(C)=O)c2)c2oc(=O)c(C)c(Nc3ccc(I)cc3F)c2c1=O]

Synthetic Route:

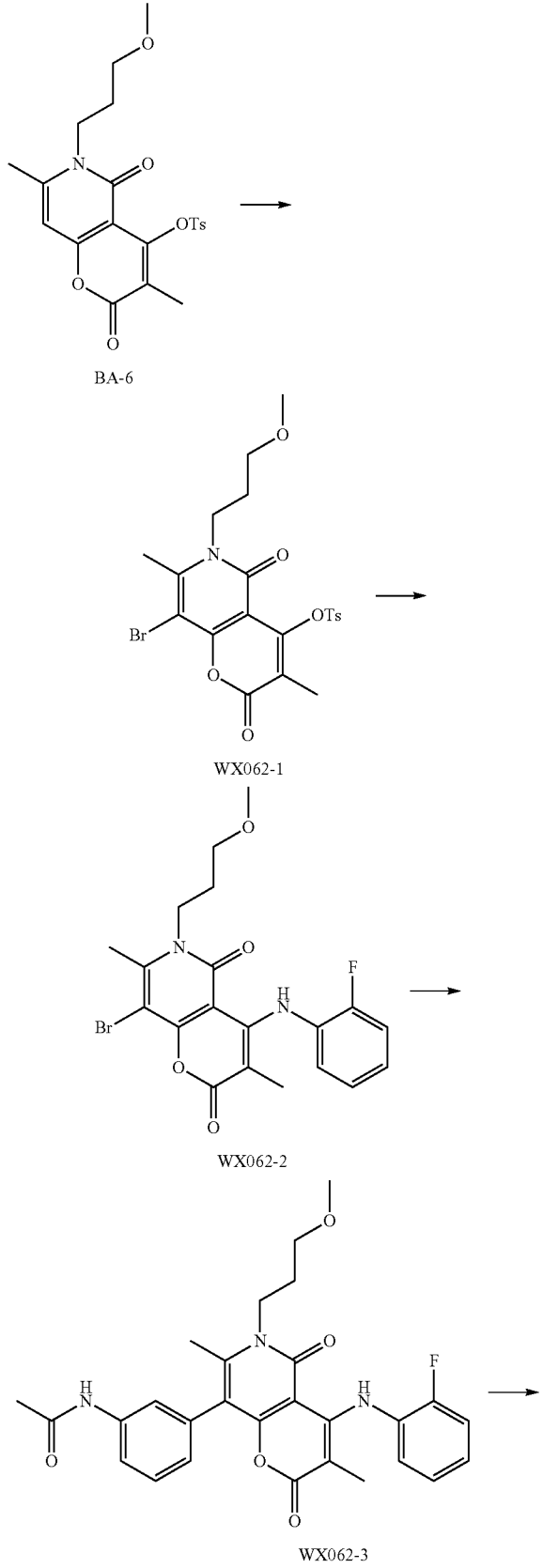

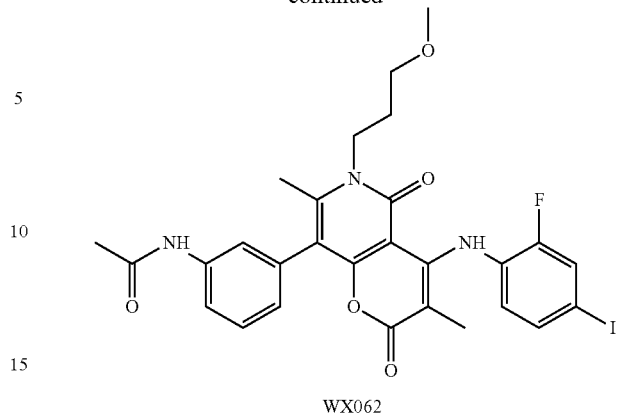

Step 1: Synthesis of the Compound WX062-1

The compound BA-6 (20.00 g, 46.14 mmol, 1.00 eq) was dissolved in acetonitrile (100.00 mL) and THF (150.00 mL), followed by addition of N-bromosuccinimide (12.32 g, 69.21 mmol, 1.50 eq). The reaction was stirred at 15° C. for 15 hours. After completion of the reaction, the mixture was evaporated to dryness by rotary evaporation. The crude product was triturated with a solvent of methyl tert-butyl ether/ethanol=2/1 (150 mL) and filtered. The filter cake was collected to give the target compound WX062-1. MS m/z: 536.0 [M+Na]$^+$ Step 2: Synthesis of the Compound WX062-2

The compound WX062-1 (7.00 g, 11.59 mmol, 1.29 eq) and 2-fluoroaniline (7.00 g, 62.99 mmol, 6.09 mL, 7.00 eq) were dissolved in ethanol (100.00 mL), the mixture was heated to reflux and stirred for 15 hours. After completion of the reaction, the reaction mixture was evaporated to dryness by rotary evaporation. The crude product was triturated with methyl tert-butyl ether (200 mL), filtered and the filter cake was collected to give the target compound WX062-2. MS m/z: 453.1 [M+H]$^+$ Step 3: Synthesis of the Compound WX062-3

The compound WX062-2 (3.00 g, 6.65 mmol, 1.00 eq) and 3-acetaminophenylboronic acid (1.79 g, 9.98 mmol, 1.50 eq) were added into dioxane (100.00 mL), then Pd(dppf)Cl$_2$ (486.59 mg, 665.00 μmol, 0.10 eq) and saturated sodium bicarbonate solution (6.65 mmol, 10.00 mL) were added sequentially. Under nitrogen protection, the reaction temperature was raised to 100° C. and the reaction was stirred for 15 hours. After completion of the reaction, water (100 mL) was added, and the mixture was extracted with dichloromethane (50 mL*3). The organic phases were combined, dried over anhydrous sodium sulfate, and evaporated to dryness by rotary evaporation to give a crude product, which was purified by column chromatography (PE/EA=1/0-1/5, Rf=0.42) to give the target compound WX062-3. MS m/z: 506.2 [M+H]$^+$ Step 4: Synthesis of the Compound WX062

The compound WX062-3 (400.00 mg, 791.23 μmol, 1.00 eq) was dissolved in N,N-dimethylformamide (10.00 mL) and dichloromethane (10.00 mL), followed by addition of N-iodosuccinimide (534.03 mg, 2.37 mmol, 3.00 eq) at 15° C. under nitrogen protection. The reaction was stirred at 15° C. for 15 hours. After LCMS indicated that the reaction was incomplete, additional N-iodosuccinimide (534.03 mg, 2.37 mmol, 3.00 eq) was added, and the reaction was stirred at 15° C. for 15 hours. After LCMS indicated that the reaction was incomplete, the reaction was stirred at 15° C. for another 48 hours. After completion of the reaction, the mixture was washed with water (50 mL) and extracted with dichloromethane (50 mL*3). The organic phases were combined, dried over anhydrous sodium sulfate and evaporated to dryness by rotary evaporation to give a crude product, which was purified by preparative HPLC to give the target compound WX062. $^1$H NMR (400 MHz, DMSO-$d_6$) δ 11.33 (s, 1H), 10.06 (s, 1H), 7.71 (dd, J=10.4 Hz, J=2.0 Hz, 1H), 7.58-7.55 (m, 2H), 7.51 (d, J=8.4 Hz, 1H), 7.40 (t, J=8.0 Hz, 1H), 6.95 (d, J=8.0 Hz, 1H), 6.88 (t, J=8.0 Hz, 1H), 4.16 (t, J=7.6 Hz, 2H), 3.40 (t, J=5.8 Hz, 2H), 3.23 (s, 3H), 2.26 (s, 3H), 2.04 (s, 3H), 1.44 (s, 3H). MS m/z: 632.0 [M+H]$^+$ Embodiment 13: WX109

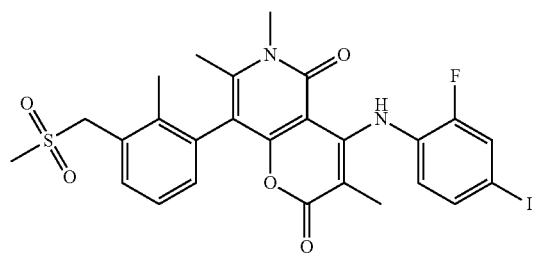 [SMILES: Cc1c(CS(C)(=O)=O)cccc1-c1c(C)n(C)c(=O)c2c(Nc3ccc(I)cc3F)c(C)c(=O)oc12]

Synthetic Route:

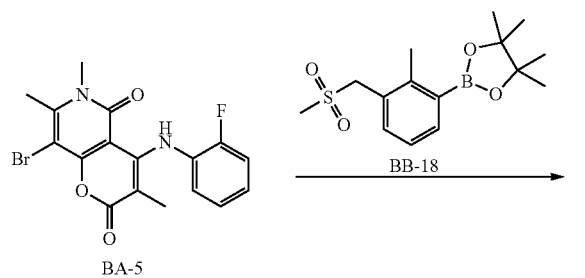

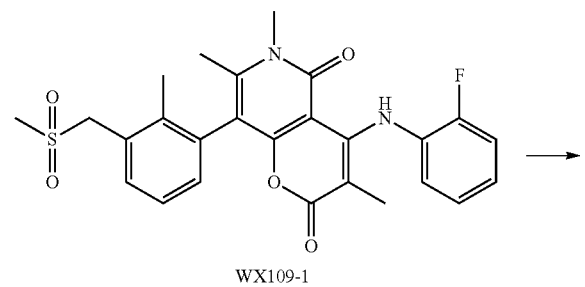

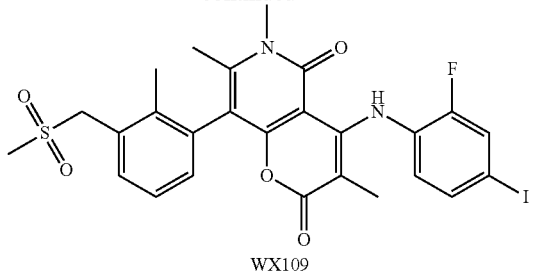

WX109

Step 1: Synthesis of the Compound WX109-1

The compound BA-5 (400.00 mg, 1.27 mmol, 0.80 eq) was dissolved in dioxane (8.00 mL) and water (4.00 mL), then the compound BB-18 (395.53 mg, 1.28 mmol, 1.00 eq), potassium phosphate (541.29 mg, 2.55 mmol, 2.00 eq), Pd(dppf)Cl$_2$·CH$_2$Cl$_2$ (104.12 mg, 127.50 μmol, 0.10 eq) and SPhos (104.69 mg, 255.00 μmol, 0.20 eq) were added into the reaction solution at 25° C. The reaction temperature was raised to 100° C. and the reaction was stirred for 7 hours. After completion of the reaction, the reaction mixture was evaporated to dryness by rotary evaporation. The residue was dissolved in EtOAc (20 mL), washed with water (10 mL*3) and saturated sodium chloride solution (5 mL). The organic phases were combined, dried over anhydrous sodium sulfate and evaporated to dryness by rotary evaporation to give a crude product. The crude product was purified by preparative HPLC to give the target compound WX109-1. $^1$H NMR (400 MHz, CDCl$_3$-d) δ 11.21 (s, 1H), 7.46 (d, J=6.8 Hz, 1H), 7.34 (t, J=8.8 Hz, 1H), 7.17-7.08 (m, 4H), 7.06-6.98 (m, 1H), 4.50-4.36 (m, 2H), 3.67 (s, 3H), 2.90 (s, 3H), 2.22 (d, J=2.4 Hz, 6H), 1.58 (s, 3H). MS m/z: 497.3 [M+H]$^+$ Step 2: Synthesis of the Compound WX109

The compound WX109-1 (50.00 mg, 100.69 μmol, 1.00 eq) was dissolved in N,N-dimethylformamide (1.00 mL), followed by addition of N-iodosuccinimide (45.31 mg, 201.38 μmol, 2.00 eq) and trifluoroacetic acid (500.00 μL) at 0° C. The reaction was stirred at 25° C. for 16 hours. After completion of the reaction, the reaction solution was dissolved in EtOAc (20 mL), washed sequentially with saturated sodium bicarbonate solution (20 mL*3), water (20 mL*2) and saturated sodium chloride solution (20 mL). The organic phase was dried over anhydrous sodium sulfate and evaporated to dryness by rotary evaporation to give a crude product. The crude product was purified by preparative HPLC to give the target compound WX109. $^1$H NMR (400 MHz, DMSO-$d_6$) δ 11.38 (s, 1H), 7.72 (d, J=10.0 Hz, 1H), 7.52 (d, J=8.4 Hz, 1H), 7.46 (d, J=8.0 Hz, 1H), 7.34 (t, J=7.6 Hz, 1H), 7.18 (d, J=7.6 Hz, 1H), 6.90 (t, J=8.4 Hz, 1H), 4.70-4.61 (m, 2H), 3.60 (s, 3H), 3.33 (s, 3H), 3.01 (s, 3H), 2.15 (s, 3H), 1.45 (s, 3H). MS m/z: 623.0 [M+H]$^+$

Embodiment 14: WX110

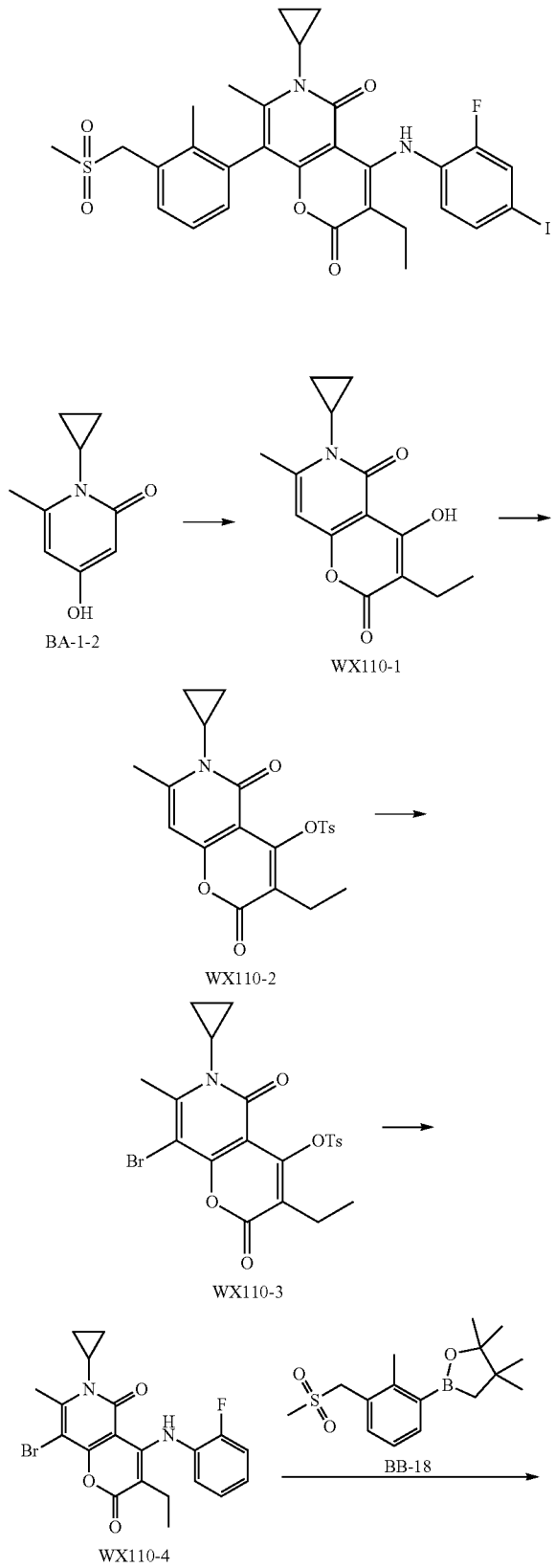

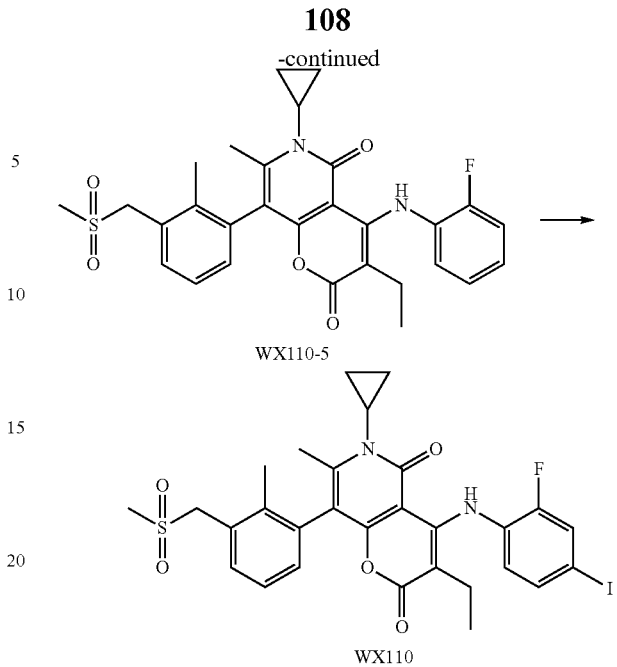

Step 1: Synthesis of the Compound WX110-1

The compound BA-1-2 (7.20 g, 42.07 mmol, 1.00 eq) was dissolved in acetic anhydride (70.00 mL), followed by addition of 2-ethylmalonic acid (8.34 g, 63.11 mmol, 1.50 eq) at 25° C. The reaction temperature was raised to 100° C. and the reaction was stirred for 0.5 hour. After completion of the reaction, the reaction mixture was cooled to 25° C. After the mixture was allowed to stand for 15 hours, a solid formed. The mixture was filtered and the filter cake was collected. The filter cake was triturated with methyl tert-butyl ether (50 mL) and dried to give the target compound WX110-1. $^1$H NMR (DMSO-$d_6$) δ 13.41 (s, 1H), 6.54 (s, 1H), 3.00-2.92 (m, 1H), 2.53 (s, 3H), 2.30 (q, J=7.6 Hz, 2H), 1.15-0.98 (d, J=5.8 Hz, 2H), 0.96 (t, J=7.2 Hz, 3H), 0.93-0.88 (m, 2H). MS m/z: 261.9 [M+H]$^+$

Step 2: Synthesis of the Compound WX110-2

The compound WX110-1 (3.70 g, 14.16 mmol, 1.00 eq) was dissolved in dichloromethane (100.00 mL), triethylamine (3.58 g, 35.40 mmol, 4.91 mL, 2.50 eq) and DMAP (432.48 mg, 3.54 mmol, 0.25 eq) were added at 0° C., followed by addition of p-toluenesulfonyl chloride (6.75 g, 35.40 mmol, 2.50 eq). The reaction temperature was allowed to warm to 25° C. and the reaction was stirred for 16 hours. After the substrate was detected as being left, additional triethylamine (1.43 g, 14.16 mmol, 1.96 mL, 1.00 eq) and DMAP (86.50 mg, 708.00 μmol, 0.50 eq) were added, followed by addition of 4-methylbenzenesulfonyl chloride (2.70 g, 14.16 mmol, 1.00 eq) at 0° C. The reaction temperature was allowed to warm to 25° C. and the reaction was stirred for 4 hours. After completion of the reaction, the reaction mixture was evaporated to dryness by rotary evaporation to give a crude product. The crude product was triturated with ethanol (100 mL), then filtered and the filter cake was collected and dried to give the compound WX110-2. $^1$H NMR (DMSO-$d_6$) δ 7.90 (d, J=8.4 Hz, 2H), 7.50 (d, J=8.4 Hz, 2H), 6.33 (s, 1H), 2.87-2.83 (m, 1H), 2.50 (s, 3H), 2.44 (s, 3H), 2.06 (q, J=7.2 Hz, 2H), 1.13 (q, J=6.8 Hz, 2H), 0.85 (t, J=7.2 Hz, 3H), 0.69 (d, J=4.0 Hz, 2H). MS m/z: 416.1 [M+H]+

Step 3: Synthesis of the Compound WX110-3

The compound WX110-2 (2.90 g, 6.98 mmol, 1.00 eq) was dissolved in dichloromethane (30.00 mL) and acetonitrile (50.00 mL), then N-bromosuccinimide (1.86 g, 10.47 mmol, 1.50 eq) was added in batches at 25° C. under nitrogen protection. The reaction was stirred at 25° C. for 15 hours. After completion of the reaction, the reaction mixture was evaporated to dryness by rotary evaporation to give a crude product. The crude product was triturated with ethanol (50 mL), filtered and the filter cake was collected to give the target compound WX110-3. $^1$H NMR (CDCl$_3$-d) δ 7.93 (d, J=8.3 Hz, 2H), 7.37 (d, J=8.0 Hz, 2H), 3.00-2.85 (m, 1H), 2.73 (s, 3H), 2.46 (s, 3H), 2.17 (q, J=7.4 Hz, 2H), 1.35-1.25 (m, 2H), 0.94 (t, J=7.6 Hz, 3H), 0.89-0.83 (m, 2H). MS m/z: 494.0 [M+H]+

Step 4: Synthesis of the Compound WX110-4

The compound WX110-3 (2.5 g, 5.06 mmol, 1.00 eq) was dissolved in ethanol (100.00 mL), then 2-fluoroaniline (5.62 g, 50.60 mmol, 10.00 eq) was added at 25° C. under nitrogen protection. The reaction temperature was raised to 100° C. and the reaction was stirred for 12 hours. After the substrate was detected as being left, additional 2-fluoroaniline (2.81 g, 25.30 mmol, 5.00 eq) was added, the reaction was stirred for another 12 hours. After completion of the reaction, the reaction solution was evaporated to dryness by rotary evaporation, the residue was triturated with ethanol (50 mL) and filtered. The filtrate was evaporated to dryness by rotary evaporation and then triturated with methyl tert-butyl ether (50 mL). The mixture was filtered and the filtrate was collected and evaporated to dryness by rotary evaporation to give a crude product. The crude product was purified by column chromatography (PE/EA=30/1-5/1), then triturated with methyl tert-butyl ether (50 mL) and filtered. The filter cake was dried to give the target compound WX110-4. $^1$H NMR (400 MHz, CDCl$_3$-d) δ 10.99 (s, 1H), 7.18-7.01 (m, 4H), 3.01-2.90 (m, 1H), 2.79 (s, 3H), 2.16 (q, J=7.4 Hz, 2H), 1.41-1.32 (m, 2H), 0.94-0.85 (m, 2H), 0.81 (t, J=7.4 Hz, 3H). MS m/z: 435.0 [M+H]+

Step 5: Synthesis of the Compound WX110-5

The compound WX110-4 (420.00 mg, 969.37 μmol, 1.00 eq) was dissolved in dioxane (8.00 mL) and water (4.00 mL), then the compound BB-18 (375.90 mg, 1.21 mmol, 1.25 eq), potassium phosphate (514.42 mg, 2.42 mmol, 2.50 eq), Pd(dppf)Cl$_2$.CH$_2$Cl$_2$ (98.95 mg, 21.17 μmol, 0.02 eq) and SPhos (99.49 mg, 242.34 μmol, 0.25 eq) were added sequentially at 25° C. under nitrogen protection. The reaction temperature was raised to 100° C. and the reaction was stirred for 15 hours. After completion of the reaction, the reaction mixture was evaporated to dryness by rotary evaporation, diluted with EtOAc (20 mL), then washed with water (10 mL*3) and saturated sodium chloride solution (5 mL). The organic phase was dried over anhydrous sodium sulfate, filtered and evaporated to dryness by rotary evaporation to give a crude product. The crude product was purified by preparative HPLC to give the target compound WX110-5. $^1$H NMR (400 MHz, CDCl$_3$-d) δ 11.13 (s, 1H), 7.44 (d, J=7.6 Hz, 1H), 7.33 (t, J=7.6 Hz, 1H), 7.16-7.10 (m, 5H), 4.49-4.44 (m, 1H), 4.41-4.33 (m, 1H), 2.97-2.91 (m, 1H), 2.89 (s, 3H), 2.30 (s, 3H), 2.21 (s, 3H), 2.10 (q, J=7.2 Hz, 2H), 1.40-1.32 (m, 2H), 0.95 (q, J=4.4 Hz, 2H), 0.76 (t, J=7.2 Hz, 3H). MS m/z: 537.3 [M+H]+

Step 6: Synthesis of the Compound WX110

The compound WX110-5 (40.00 mg, 74.54 μmol, 1.00 eq) was dissolved in N,N-dimethylformamide (1.00 mL), then N-iodosuccinimide (33.54 mg, 149.08 mol, 2.00 eq) and trifluoroacetic acid (1.00 mL) were added sequentially at 0° C. The reaction temperature was raised to 25° C. and the reaction was stirred for 16 hours. After completion of the reaction, the reaction mixture was diluted with EtOAc (10 mL), then washed sequentially with saturated sodium bicarbonate solution (10 mL*3), water (10 mL*2) and saturated sodium chloride solution (20 mL). The organic phase was dried over anhydrous sodium sulfate, filtered and evaporated to dryness by rotary evaporation to give a crude product. The crude product was purified by preparative HPLC to give the target compound WX110. $^1$H NMR (DMSO-d$_6$) δ 11.31 (s, 1H), 7.74 (d, J=9.8 Hz, 1H), 7.53 (d, J=7.6 Hz, 1H), 7.45 (d, J=7.6 Hz, 1H), 7.34 (t, J=7.4 Hz, 1H), 7.21 (d, J=8.0 Hz, 1H), 7.02 (t, J=8.4 Hz, 1H), 4.70-4.61 (m, 2H), 3.10 (m, 1H), 3.01 (s, 3H), 2.21 (s, 3H), 2.14 (s, 3H), 2.00 (d, J=7.2 Hz, 2H), 1.23 (s, 2H), 0.91 (d, J=10.8 Hz, 2H), 0.70 (t, J=7.2 Hz, 3H). MS m/z: 663.0 [M+H]+

Embodiment 15: WX118&119

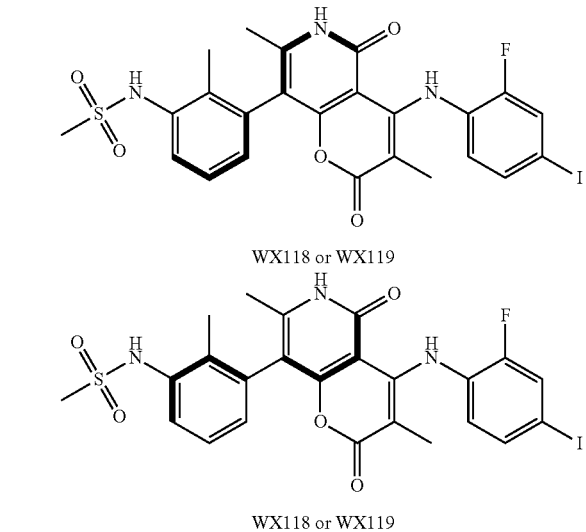

WX118 or WX119

WX118 or WX119

Synthetic Route:

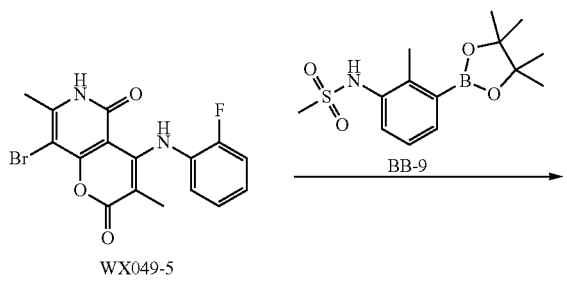

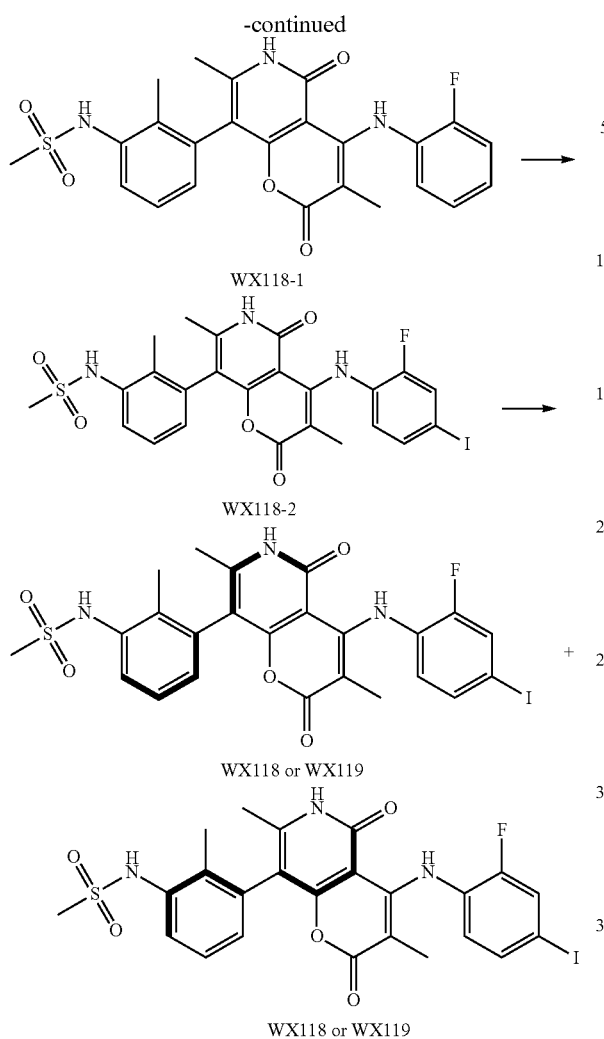

7.18-7.11 (m, 3H), 7.09 (m, 1H), 3.00 (m, 1H), 2.06 (s, 3H), 1.98 (s, 3H), 1.43-1.39 (s, 3H). MS m/z: 484.1 [M+H]$^+$

Step 2: Synthesis of the Compound WX118-2

The compound WX118-1 (0.32 g, 661.83 mol, 1.00 eq) was dissolved in dichloromethane (4.80 mL), then trifluoroacetic acid (1.48 g, 12.97 mmol, 19.59 eq) and N-iodosuccinimide (178.68 mg, 794.19 μmol, 1.20 eq) were added sequentially at 0° C. in dark place. The reaction was stirred at 15° C. for 24 hours. After completion of the reaction, the reaction solution was washed sequentially with saturated sodium bicarbonate solution (50 mL*3) and water (50 mL*2), dried over anhydrous sodium sulfate, and evaporated to dryness by rotary evaporation to give the target compound WX118-2. $^1$H NMR (DMSO-d$_6$) δ 12.23-11.34 (m, 1H), 7.72 (d, J=10.4 Hz, 1H), 7.53 (d, J=7.8 Hz, 1H), 7.42-7.35 (m, 1H), 7.34-7.26 (m, 1H), 7.10 (d, J=7.6 Hz, 1H), 6.93 (t, J=8.4 Hz, 1H), 3.01 (s, 3H), 2.67 (s, 1H), 2.33 (s, 1H), 2.06 (s, 3H), 1.99 (s, 3H), 1.43 (s, 3H). MS m/z: 609.9 [M+H]$^+$ Step 3: Synthesis of the Compound WX118 and WX119

WX118-2 was subjected to supercritical fluid chromatography (column: Chiralpak AD-3 100×4.6 mm ID, 3 μm; mobile phase: A: CO$_2$, B: ethanol (0.05% DEA); gradient: from 5% B to 40% B at a uniform speed in 4.5 minutes, then 40% B for 2.5 minutes, 5% B for 1 minute; flow rate: 2.8 mL/min; column temperature: 40° C.), to give the atropisomers WX118 and WX119, with retention times of 5.934 min and 4.958 min respectively and a ratio of 6:7.

WX118

$^1$H NMR (DMSO-d$_6$) δ 11.33 (m, 1H), 7.72-7.35 (m, 1H), 7.37-7.10 (m, 1H), 6.92 (t, J=8.4 Hz, 1H), (s, 3H), 3.01 (m, 2H), 2.50 (s, 3H), 2.06 (s, 3H), 2.00 (s, 3H), 1.43 (s, 1H). MS m/z: 609.9 [M+H]$^+$

WX119

$^1$H NMR (DMSO-d$_6$) δ 11.35-11.26 (m, 1H), 7.75-7.68 (m, 1H), 7.59-7.25 (m, 3H), 7.10 (m, 1H), 6.89-6.95 (m, 1H), 3.00 (s, 3H), 2.06 (s, 3H), 1.99 (s, 3H), 1.43 (s, 3H). MS m/z: 610.0 [M+H]$^+$

Embodiment 16: WX034

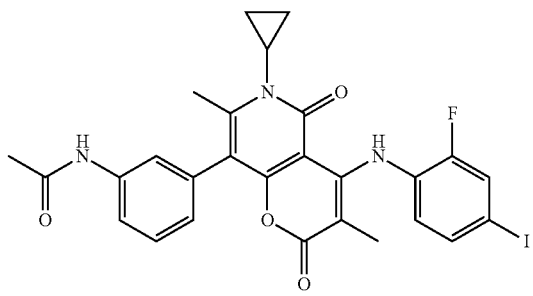

Step 1: Synthesis of the Compound WX118-1

The compound WX049-5 (3.15 g, 8.31 mmol, 1.00 eq) was dissolved in dioxane (50 mL) and water (10 mL), then the compound BB-9 (5.17 g, 16.61 mmol, 2.00 eq), SPhos (341.04 mg, 830.74 μmol, 0.10 eq), potassium phosphate (3.53 g, 16.61 mmol, 2.00 eq) and palladium acetate (93.25 mg, 415.37 μmol, 0.50 eq) were added sequentially at 15° C. The reaction temperature was raised to 100° C. and the reaction was stirred for 32 hours. After completion of the reaction, the reaction mixture was evaporated to dryness by rotary evaporation to give a crude product, which was then diluted with dichloromethane (50 mL) and filtered. The filter cake was washed with dichloromethane (15 mL*3). The organic phases were combined, washed with water (40 mL*3), dried over anhydrous sodium sulfate, filtered and evaporated to dryness by rotary evaporation to give a crude product. The crude product was purified by column chromatography (PE/EA=20/1-1/1) to give the target compound WX118-1. $^1$H NMR (DMSO-d$_6$) δ 12.57 (s, 1H), 11.32 (m, 1H), 9.18 (m, 1H), 7.38-7.36 (m, 1H), 7.31-7.28 (m, 1H), Synthetic Route:

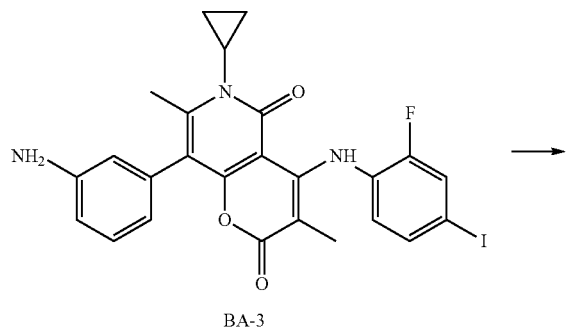

BA-3

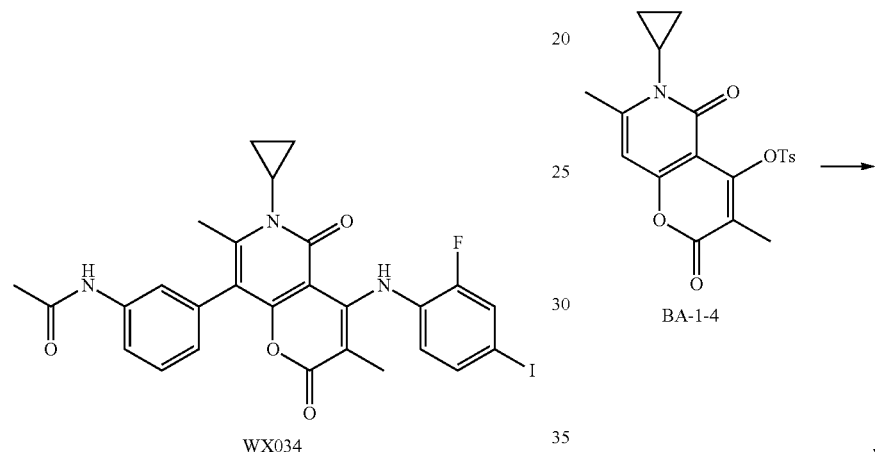

WX034

Embodiment 17: WX035

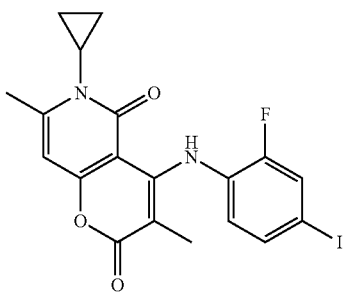 [SMILES: Cc1c(Nc2ccc(I)cc2F)c2c(=O)n(C3CC3)c(C)cc2oc1=O]

BA-1-4

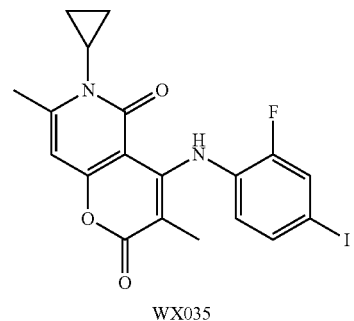

WX035

Step 1: Synthesis of the Compound WX034

The compound BA-3 (500.00 mg, 897.10 μmol, 1.00 eq) was dissolved in chloroform (5.00 mL) and N,N-dimethylformamide (5.00 mL), pyridine (4.90 g, 61.94 mmol, 69.05 eq) was added at 0° C., followed by addition of acetyl chloride (211.27 mg, 2.69 mmol, 3.00 eq) dropwise. The reaction was stirred at 20° C. for 12 hours. After completion of the reaction, the solvent was removed by rotary evaporation. The residue was diluted with water (10 mL) and extracted with EtOAc (15 mL*3). The organic phases were combined, washed sequentially with dilute hydrochloric acid (0.5 M, 10 mL*2), saturated sodium bicarbonate solution (10 mL*2), water (10 mL) and saturated sodium chloride solution (10 mL). The organic phase was dried over anhydrous sodium sulfate, and evaporated to dryness by rotary evaporation to give a crude product. The crude product was triturated with methyl tert-butyl ether (18 mL) and filtered to give a crude product. The crude product was purified by preparative HPLC to give the target compound WX034. $^1$H NMR (DMSO-$d_6$) δ 11.28 (s, 1H), 10.05 (m, 2H), 7.72-7.69 (m, 1H), 7.56 (m, 1H), 7.52 (m, 1H), 7.40 (m, 1H), 6.97 (m, 1H), 6.86 (m, 1H), 3.03 (m, 1H), 2.31 (m, 3H), 2.04 (s, 3H), 1.44 (s, 3H), 1.19 (m, 2H), 0.90 (m, 2H). MS m/z: 600.1 [M+H]$^+$ Step 1: Synthesis of the Compound WX035

The compound BA-1-4 (300.00 mg, 747.33 μmol, 1.00 eq) and 2-fluoro-4-aniline (531.37 mg, 2.24 mmol, 3.00 eq) were dissolved in ethanol (4.00 mL), the reaction was stirred at 90° C. for 16 hours. After completion of the reaction, the mixture was cooled to room temperature, filtered and the filter cake was collected. The filter cake was purified by column chromatography (methyl tert-butyl ether) to give a crude product. The crude product was further purified by preparative TLC (DCM) to give the target compound WX035. $^1$H NMR (400 MHz, CDCl$_3$-d) δ 10.99 (s, 1H), 7.48-7.42 (m, 2H), 6.74-6.20 (m, 1H), 6.22 (s, 1H), 2.91-2.88 (m, 1H), 2.59 (m, 3H), 1.64 (s, 3H), 1.36-1.34 (s, 2H), 0.94-0.93 (s, 2H).

Embodiment 18: WX039

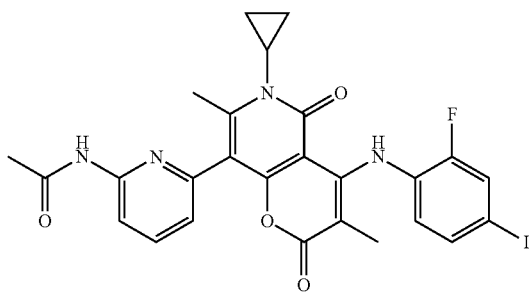 [SMILES: CC(=O)Nc1cccc(-c2c(C)n(C3CC3)c(=O)c3c(Nc4ccc(I)cc4F)c(C)c(=O)oc23)n1]

Synthetic Route:

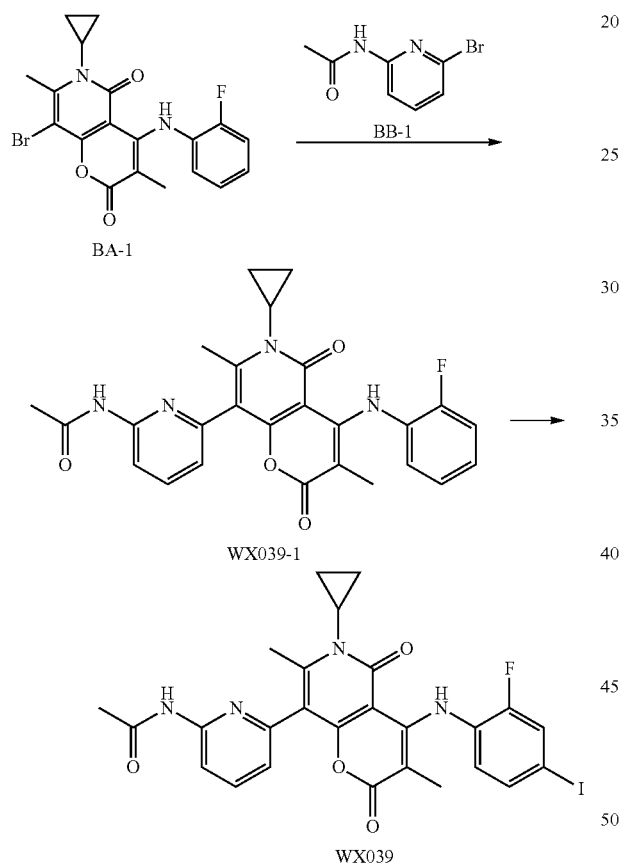

Step 1: Synthesis of the Compound WX039-1

The compound BB-1 (500.00 mg, 2.33 μmol, 1.00 eq), Pd(PPh₃)₂Cl₂ (163.54 mg, 233.00 μmol, 0.10 eq) and hexamethyldistannane (839.72 mg, 2.56 mmol, 1.10 eq) were added into anhydrous toluene (15.00 mL). The reaction temperature was raised to 110° C. under nitrogen protection and the reaction was stirred for 16 hours. The reaction was cooled to room temperature, then the compound BA-1 (976.83 mg, 2.33 mmol, 1.00 eq) and dioxane (15.00 mL) were added. Under nitrogen protection, the temperature was raised to 100° C. and the reaction was stirred for 24 hours. After completion of the reaction, the reaction mixture was cooled to room temperature, followed by addition of potassium fluoride (0.5 g). The mixture was stirred for 30 minutes and filtered, the filter cake was washed with dichloromethane (30 mL*3). The organic phase was collected and evaporated to dryness by rotary evaporation to give a crude product. The crude product was stirred in methanol (30 mL) for 30 minutes and filtered. The filter cake was washed with methanol (80 mL) and evaporated to dryness by rotary evaporation to recycle the raw material BA-1. The filtrates were combined and evaporated to dryness by rotary evaporation. The crude product was purified by column chromatography (PE/EA=3/1-0/1) to give the compound WX039-1. MS m/z: 475.2 [M+H]⁺

Step 2: Synthesis of the Compound WX039

The compound WX039-1 (44.00 mg, 60.74 μmol, 1.00 eq) was dissolved in N,N-dimethylformamide (1.00 mL), then trifluoroacetic acid (1.00 mL) and N-iodosuccinimide (45.00 mg, 200.02 μmol, 3.29 eq) were added sequentially in batches at 25° C. The reaction was stirred at 25° C. for 32 hours. After LCMS indicated the reaction was incomplete, additional N-iodosuccinimide (40.00 mg) was added, and the reaction was stirred for another 6 hours. After completion of the reaction, the reaction mixture was diluted with dichloromethane (20 mL), sodium carbonate (2 g) was added to quench the reaction until no more gas formed. The mixture was filtered and the filtrate was collected, evaporated to dryness by rotary evaporation to give a crude product. The crude product was purified by preparative HPLC and dried to give the compound WX039. ¹H NMR (400 MHz, CDCl₃-d) δ 11.04 (s, 1H), 8.27-8.25 (s, 1H), 7.95 (m, 1H), 7.87-7.83 (m, 1H), 7.49-7.47 (m, 1H), 7.46-7.42 (m, 1H), 7.11-7.09 (m, 1H), 6.73-6.70 (m, 1H), 2.98-2.92 (s, 1H), 2.40 (s, 3H), 2.24 (s, 3H), 1.62 (m, 3H), 1.43-1.38 (m, 2H), 0.98-0.97 (m, 2H). MS m/z: 601.1 [M+H]⁺

Embodiment 19: WX048

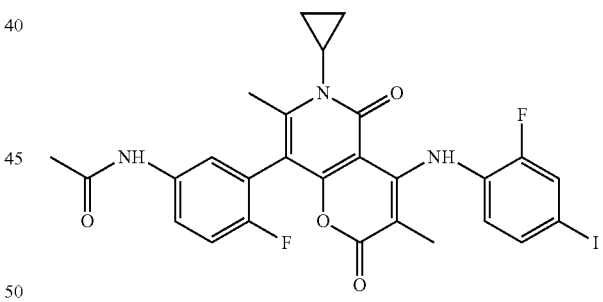

Synthetic Route:

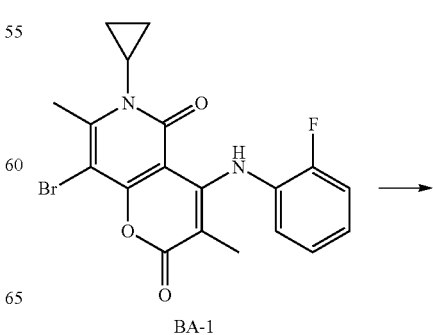

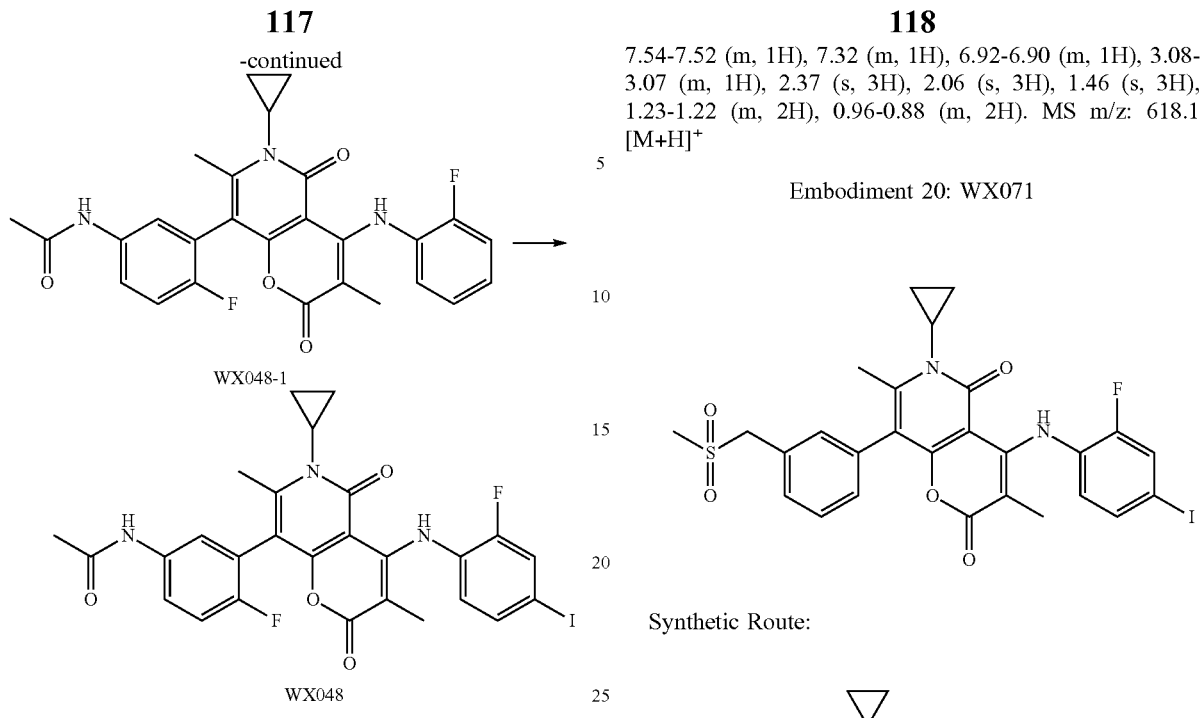

Step 1: Synthesis of the Compound WX048-1

The compound BA-1 (75.10 mg, 179.14 μmol, 1.00 eq) was dissolved in dioxane (4.00 mL) and water (1.00 mL), then Pd$_2$(dba)$_3$ (8.20 mg, 8.96 μmol, 0.05 eq), potassium phosphate (76.05 mg, 358.28 μmol, 2.00 eq), SPhos (7.35 mg, 17.91 μmol, 0.10 eq) and the compound BB-2 (100.00 mg, 358.28 μmol, 2.00 eq) were added at 25° C. under nitrogen protection. The reaction temperature was raised to 120° C. and the reaction was stirred for 21 hours. After completion of the reaction, the reaction mixture was filtered and the filter cake was washed with EtOAc (10 mL*3). The filtrates were combined, washed sequentially with water (15 mL*3) and saturated sodium chloride solution (15 mL). The combined aqueous phase was extracted with EtOAc (15 mL). The organic phases were combined, dried over anhydrous sodium sulfate and evaporated to dryness by rotary evaporation to give a crude product. The crude product was purified by preparative TLC (PE/EA=1/1) to give the compound WX048-1. MS m/z: 492.1 [M+H]$^+$ Step 2: Synthesis of the Compound WX048

The compound WX048-1 (50.00 mg, 101.73 μmol, 1.00 eq) was added into the mixture of trifluoroacetic acid (250.00 μL) and N,N-dimethylformamide (500.00 μL), followed by addition of N-iodosuccinimide (45.78 mg, 203.46 μmol, 2.00 eq) at 0° C. The reaction was stirred at 25° C. for 16 hours. After completion of the reaction, the reaction mixture was diluted with EtOAc (20 mL), washed sequentially with saturated sodium sulfite solution (20 mL*2) and saturated sodium bicarbonate solution (20 mL*2). The combined aqueous phase was extracted with EtOAc (30 mL*3). The organic phases were combined, dried over anhydrous sodium sulfate and evaporated to dryness by rotary evaporation to give a crude product. The crude product was purified by preparative HPLC and dried to give the target compound WX048. $^1$H NMR (400 MHz, CDCl$_3$-d) δ 11.22 (s, 1H), 10.13 (s, 1H), 7.75-7.72 (m, 1H), 7.65-7.64 (m, 2H), 7.54-7.52 (m, 1H), 7.32 (m, 1H), 6.92-6.90 (m, 1H), 3.08-3.07 (m, 1H), 2.37 (s, 3H), 2.06 (s, 3H), 1.46 (s, 3H), 1.23-1.22 (m, 2H), 0.96-0.88 (m, 2H). MS m/z: 618.1 [M+H]$^+$ Embodiment 20: WX071

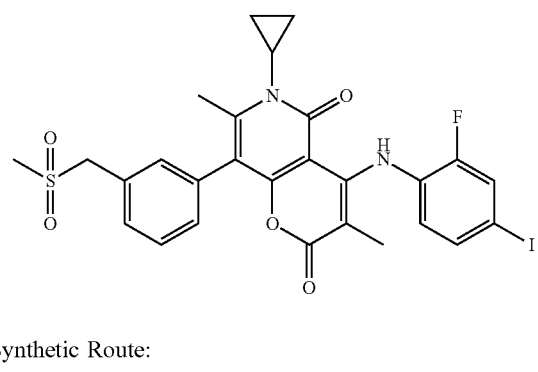

Synthetic Route:

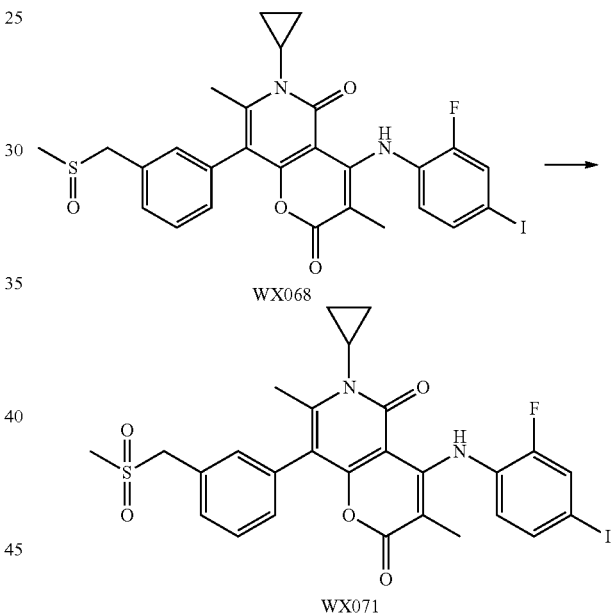

Step 1: Synthesis of the Compound WX071

The compound WX068 (55.00 mg, 88.93 mol, 1.00 eq) was dissolved in a mixed solvent of THF (2.00 mL) and water (2.00 mL), followed by addition of potassium hydrogen sulfate (54.13 mg, 177.86 μmol, 2.00 eq) under nitrogen protection. The reaction was stirred at 15° C. for 16 hours. After completion of the reaction, the reaction mixture was diluted with water (20 mL), the aqueous phase was extracted with dichloromethane (20 mL*3). The organic phase was collected and washed with saturated sodium chloride solution (10 mL), dried over anhydrous sodium sulfate, filtered and evaporated to dryness by rotary evaporation to give a crude product. The crude product was purified by preparative HPLC and lyophilized to give the target compound WX071. $^1$H NMR (400 MHz, CDCl$_3$-d) δ 11.12 (s, 1H), 7.55-7.42 (m, 2H), 7.35-7.30 (m, 2H), 6.74-6.70 (m, 1H), 4.35-4.28 (m, 1H), 2.98-2.93 (m, 1H), 2.87 (s, 3H), 2.44 (s, 3H), 1.61 (s, 3H), 1.40-1.38 (m, 2H), 0.99-0.90 (m, 2H). MS m/z: 635.0 [M+H]$^+$ Embodiment 21: WX083 & WX084

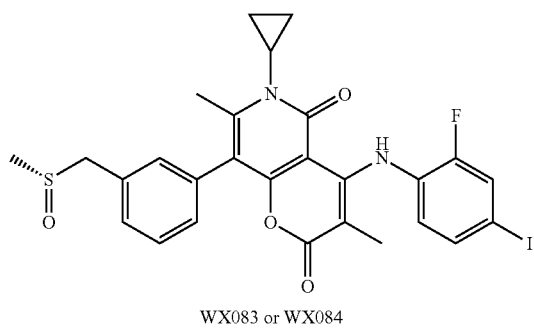

WX083 or WX084

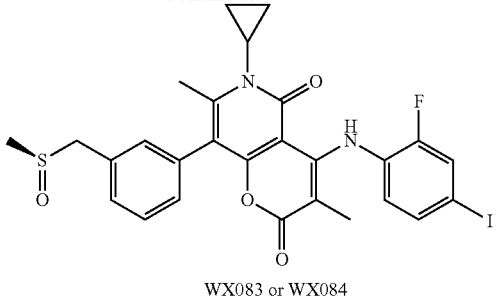

WX083 or WX084

-continued

WX083 or WX084

Step 1: Synthesis of the Compound WX083 and the Compound WX084

The compound WX068 was subjected to supercritical fluid chromatography (Chiral column: Chiralpak OD-3 150× 4.6 mm ID, 3 μm; mobile phase: A: CO$_2$, B: 40% ethanol (0.05% DEA); flow rate: 2.4 mL/min; wavelength: 220 nm), to give the atropisomers WX083 and WX084, with retention times of 5.88 min and 6.79 min respectively and a ratio of 1:1.

WX083

$^1$H NMR (400 MHz, CDCl$_3$-d) δ 11.03 (s, 1H), 7.42-7.35 (m, 2H), 7.33-7.28 (m, 2H), 7.19-7.12 (m, 2H), 6.64-6.60 (m, 1H), 4.09-3.86 (m, 2H), 2.89-2.85 (m, 1H), 2.40 (s, 3H), 2.33 (s, 3H), 1.52 (s, 2H), 1.30-1.20 (m, 2H), 1.18-1.13 (m, 1H), 0.89-0.88 (m, 2H). MS m/z: 619.1 [M+H]$^+$

WX084

$^1$H NMR (400 MHz, CDCl$_3$-d) δ 11.08 (s, 1H), 7.49-7.72 (m, 2H), 7.40-7.36 (m, 2H), 7.26-7.19 (m, 2H), 6.72-6.68 (s, 1H), 4.16-3.93 (m, 2H), 2.93 (m, 1H), 2.48 (s, 3H), 2.40 (s, 3H), 1.63-1.59 (s, 2H), 1.38-1.30 (m, 2H), 1.29-1.20 (m, 1H), 0.96 (m, 2H). MS m/z: 619.1 [M+H]$^+$

Embodiment 22: WX092

Synthetic Route:

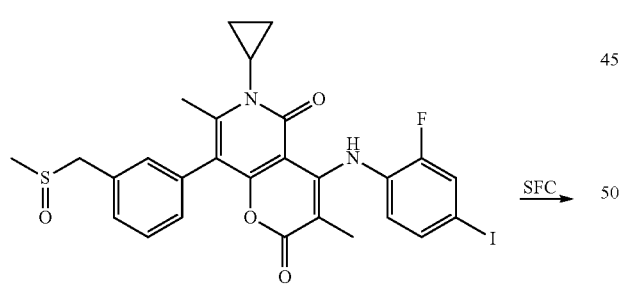

WX068

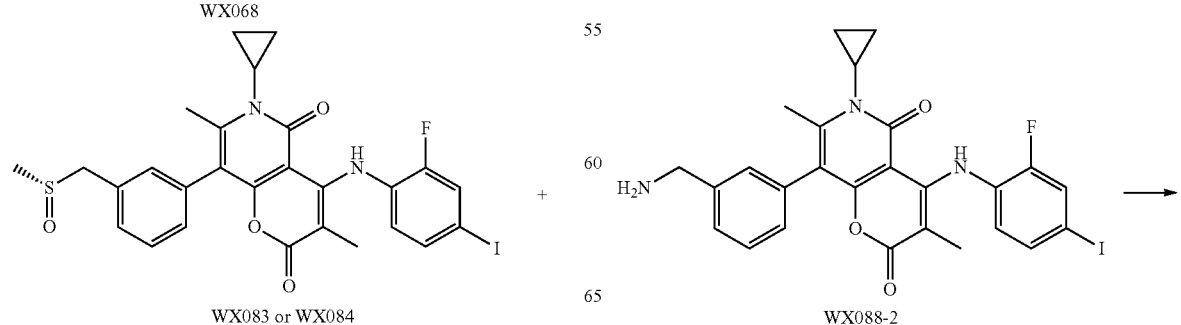

WX083 or WX084

WX088-2

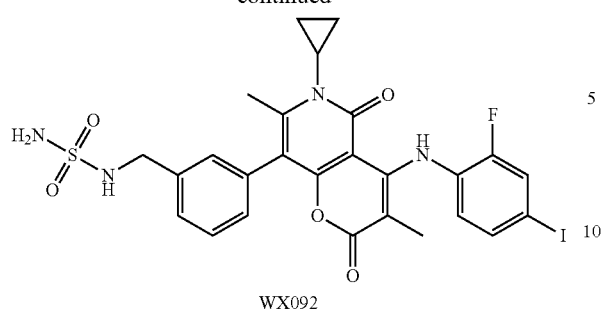

WX092

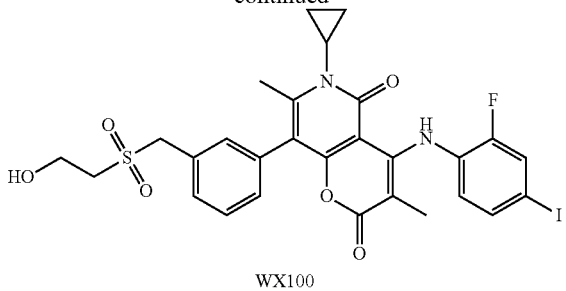

WX100

Step 1: Synthesis of the Compound WX

The compound WX088-2 (50.00 mg, 87.51 mol, 1.00 eq) was dissolved in dichloromethane (2.00 mL), then triethylamine (17.71 mg, 175.02 μmol, 2.00 eq), DMAP (2.14 mg, 17.50 μmol, 0.20 eq) and chlorosulfonamide (12.13 mg, 105.01 μmol, 1.20 eq) were added sequentially at 0° C. The reaction temperature was raised to 25° C. and the reaction was stirred for 1 hour. After completion of the reaction, the reaction mixture was evaporated to dryness by rotary evaporation to give a crude product. The crude product was purified by preparative HPLC to give the target compound WX092. $^{1}$H NMR (400 MHz, CDCl$_3$-d) δ 11.19 (s, 1H), 7.50-7.45 (m, 5H), 7.43-7.16 (m, 1H), 6.76-6.71 (m, 1H), 4.91 (m, 1H), 4.83 (s, 2H), 4.39-4.38 (s, 2H), 2.98-2.96 (m, 1H), 2.49 (s, 3H), 1.59 (s, 3H), 1.41 (m, 2H), 1.00 (m, 2H). MS m/z: 651.1 [M+H]$^{+}$ Embodiment 23: WX100

Step 1: Synthesis of the Compound WX100

The compound WX100-1 (220.00 mg, 157.71 μmol, 1.00 eq) was dissolved in THF (2.00 mL), then TBAF (1 M, 565.02 μL, 3.58 eq) was added under nitrogen protection. The reaction was stirred at 0° C. for 2 hours. After completion of the reaction, the reaction mixture was diluted with water (30 mL) and extracted with EtOAc (40 mL*3). The organic phases were combined, washed with saturated sodium chloride solution (20 mL), dried over anhydrous sodium sulfate, and evaporated to dryness by rotary evaporation to give a crude product. The crude product was purified by column chromatography (PE/EA=10/1-1/1), and further purified by preparative HPLC (formic acid system) to give the target compound WX100.

$^{1}$H NMR (400 MHz, CDCl$_3$-d) δ 11.24 (s, 1H), 7.68-7.66 (m, 1H), 7.52 (m, 1H), 7.49-7.44 (m, 2H), 7.43-7.39 (m, 1H), 7.25 (m, 1H), 6.76-6.71 (s, 1H), 4.47-4.31 (m, 2H), 4.01-3.95 (s, 3H), 3.67 (s, 1H), 3.04-2.95 (s, 1H), 2.48 (m, 2H), 1.58 (s, 3H), 1.43-1.38 (m, 2H), 0.98 (m, 2H). MS m/z: 665.3 [M+H]$^{+}$

Embodiment 24: WX102

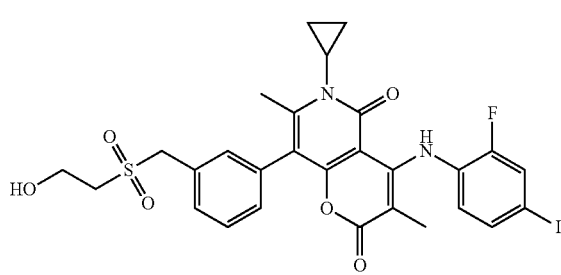 [SMILES: Cc1c(Nc2ccc(I)cc2F)c2c(=O)n(C3CC3)c(C)c(-c3cccc(CS(=O)(=O)CCO)c3)c2oc1=O]

Synthetic Route:

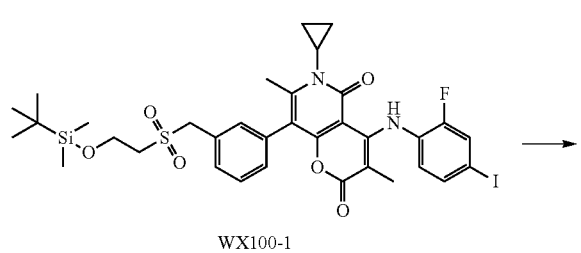

WX100-1

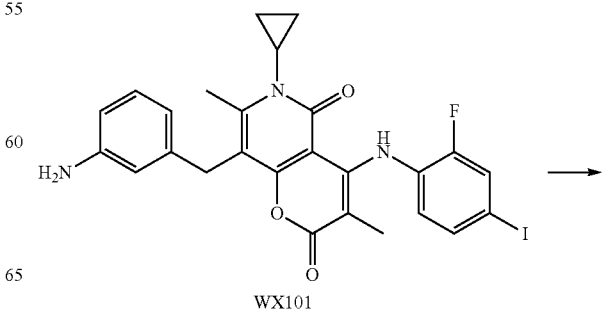

WX101

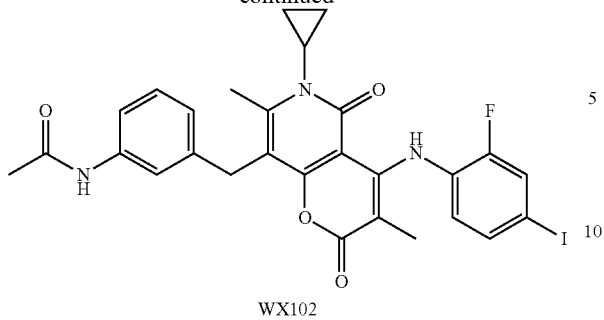

WX102

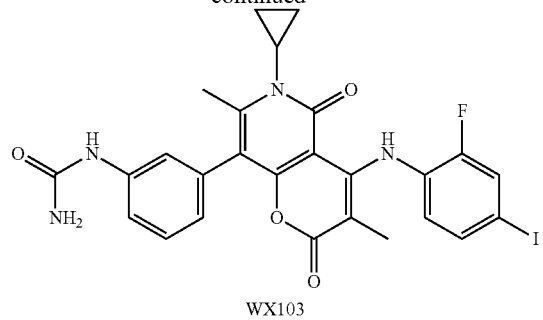

WX103

Step 1: Synthesis of the Compound WX102

The compound WX101 (100.00 mg, 175.01 μmol, 1.00 eq) was dissolved in dichloromethane (2.00 mL), then triethylamine (35.42 mg, 350.03 μmol, 2.00 eq) and acetyl chloride (20.61 mg, 262.52 μmol, 1.50 eq) were added at 0° C. under nitrogen protection. The reaction was stirred at 0° C. for 20 minutes. After completion of the reaction, the reaction mixture was added into water (20 mL), and the aqueous phase was extracted with dichloromethane (40 mL*3). The organic phases were combined, washed with saturated sodium chloride solution (10 mL*3), dried over anhydrous sodium sulfate, and evaporated to dryness by rotary evaporation to give a crude product. The crude product was purified by preparative HPLC to give the target compound WX102. $^1$H NMR (400 MHz, CDCl$_3$-d) δ 11.21 (s, 1H), 7.47-7.44 (m, 1H), 7.40-7.34 (m, 3H), 7.23 (s, 1H), 6.96 (m, 1H), 6.73-6.70 (m, 1H), 4.03 (s, 2H), 2.94-2.88 (m, 1H), 2.60 (s, 3H), 2.16 (s, 3H), 1.62 (s, 3H), 1.37-1.32 (m, 2H), 0.92-0.88 (m, 2H). MS m/z: 614.2 [M+H]$^+$ Embodiment 25: WX103

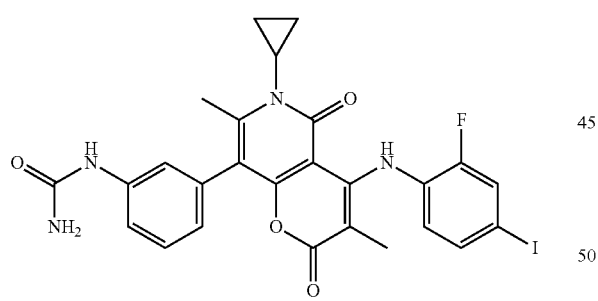

Synthetic Route:

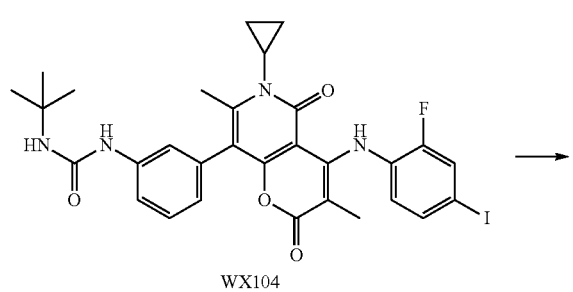

WX104

Step 1: Synthesis of the Compound WX103

The compound WX104 (120.00 mg, 129.78 μmol, 1.00 eq) was dissolved in dichloromethane (2.00 mL), then trifluoroacetic acid (2.00 mL) was added dropwise at 0° C. The reaction temperature was raised to 45° C. and the reaction was stirred for 16 hours. After completion of the reaction, the reaction mixture was diluted with EtOAc (25 mL), washed sequentially with saturated sodium bicarbonate solution (15 mL*3), water (15 mL) and saturated sodium chloride solution (10 mL). The organic phase was dried over anhydrous sodium sulfate and evaporated to dryness by rotary evaporation to give a crude product. The crude product was purified by preparative HPLC to give the target compound WX103. $^1$H NMR (400 MHz, CDCl$_3$-d) δ 11.28 (s, 1H), 8.66 (m, 1H), 7.70 (m, 1H), 7.51 (s, 1H), 7.73 (m, 3H), 6.83 (m, 2H), 5.88 (m, 2H), 3.02 (m, 1H), 2.31 (s, 3H), 1.43 (s, 3H), 1.19 (m, 2H), 0.89 (m, 2H). MS m/z: 650.5 [M+H]$^+$ Embodiment 26: WX105

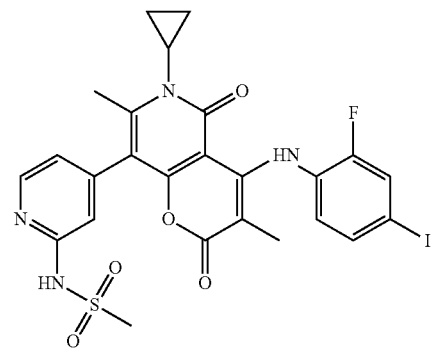 [SMILES: Cc1c(Nc2ccc(I)cc2F)c2c(=O)n(C3CC3)c(C)c(-c3ccnc(NS(C)(=O)=O)c3)c2oc1=O]

Synthetic Route:

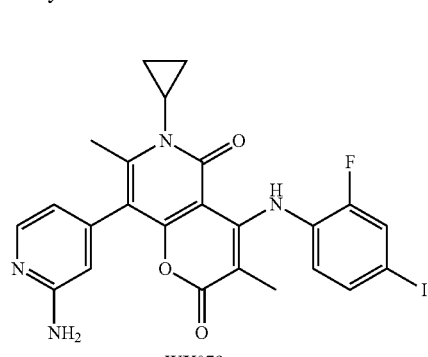
WX079

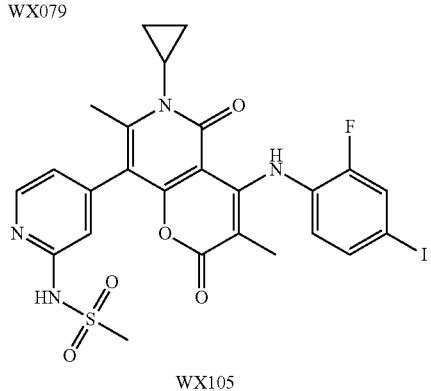
WX105

Step 1: Synthesis of the Compound WX105

The compound WX079 (65.00 mg, 116.42 μmol, 1.00 eq) was dissolved in pyridine (2.00 mL), followed by addition of methanesulfonyl chloride (200.00 mg, 1.75 mmol, 15.00 eq) at 0° C. The reaction temperature was raised to 25° C. and the reaction was stirred for 2 hours. After completion of the reaction, the reaction mixture was diluted with EtOAc (25 mL), washed sequentially with 0.5 M aqueous hydrochloric acid solution (15 mL*3), saturated ammonium bicarbonate solution (15 mL*2), water (15 mL) and saturated sodium chloride solution (10 mL). The organic phase was dried over anhydrous sodium sulfate and evaporated to dryness by rotary evaporation to give a crude product. The crude product was purified by preparative HPLC to give the target compound WX105. $^1$H NMR (DMSO-$d_6$) δ 11.18 (s, 1H), 8.34 (m, 1H), 7.72-7.69 (m, 1H), 7.52-7.50 (m, 1H), 6.99-6.98 (m, 1H), 6.90-6.87 (m, 1H), 6.85-6.83 (m, 1H), 3.31 (s, 3H), 3.02 (m, 1H), 2.35 (s, 3H), 1.44 (m, 3H), 1.21-1.18 (m, 2H), 0.90 (m, 2H). MS m/z: 637.0 [M+H]$^+$

Embodiment 27: WX036

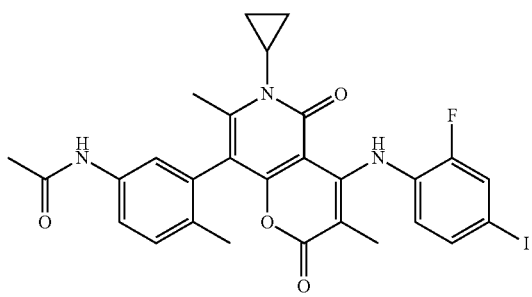 [SMILES: CC(=O)Nc1ccc(C)c(-c2c(C)n(C3CC3)c(=O)c3c(Nc4ccc(I)cc4F)c(C)c(=O)oc23)c1]

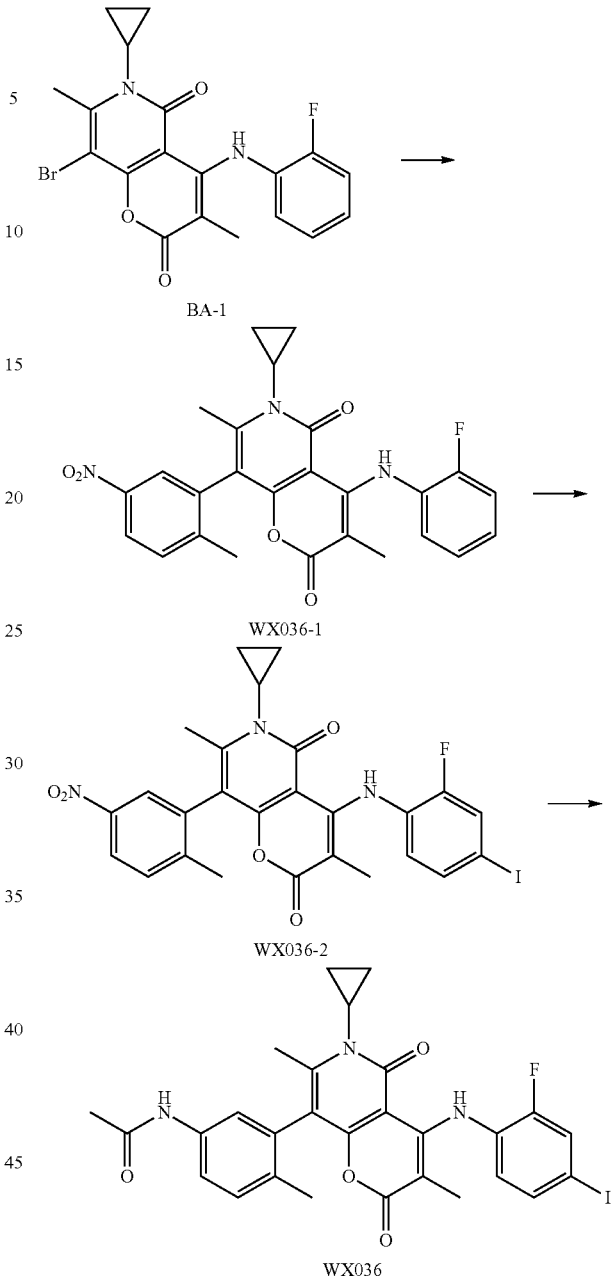

Step 1: Synthesis of the Compound WX036-1

The compound BA-1 (2.00 g, 4.77 mmol, 1.00 eq), the compound BB-3 (1.73 g, 9.54 mmol, 2.00 eq), cesium carbonate (3.11 g, 9.54 mmol, 2.00 eq), palladium acetate (107.10 g, 477.00 μmol, 0.10 eq) and SPhos (445.22 mg, 954.00 μmol, 0.20 eq) were dissolved in N,N-dimethylformamide (80.00 mL). Under nitrogen protection, the reaction temperature was raised to 100° C. and the reaction was stirred for 16 hours. The reaction mixture was filtered, and the filter cake was washed with dichloromethane (30 mL*3). The filtrate was collected and evaporated to dryness by rotary evaporation to give a crude product. The crude product was dissolved in dichloromethane (200 mL), washed with water (200 mL*3) and saturated sodium chloride solution (200 mL), dried over anhydrous sodium sulfate, and evaporated to dryness by rotary evaporation to give a crude product. The crude product was purified sequentially by column chromatography (DCM, DCM/EA=10/1) and preparative TLC (DCM) to give the compound WX036-1. MS m/z: 476.2 [M+H]$^+$ Step 2: Synthesis of the Compound WX036-2

The compound WX036-1 (99.00 mg, 208.22 mmol, 1.00 eq) was dissolved in N,N-dimethylformamide (2.00 mL), followed by addition of trifluoroacetic acid (2.00 mL) and N-iodosuccinimide (49.49 mg, 218.63 μmol, 1.05 eq) at 0° C. The reaction was stirred at 20° C. for 16 hours. After LCMS indicated the reaction was incomplete, additional N-iodosuccinimide (49.49 mg, 218.63 μmol, 1.05 eq) was added. The reaction was stirred for another 16 hours. After completion of the reaction, the reaction mixture was diluted with dichloromethane (20 mL), washed with water (10 mL*3), saturated sodium carbonate solution (20 mL*2) and saturated sodium chloride solution (20 mL), dried over anhydrous sodium sulfate, and evaporated to dryness by rotary evaporation to give the compound WX036-2. MS m/z: 602.1 [M+H]$^+$ Step 3: Synthesis of the Compound WX036

The compound WX036-2 (100.00 mg, 166.29 mmol, 1.00 eq) was dissolved in acetic acid (4.00 mL), followed by addition of zinc powder (108.74 mg, 1.66 mmol, 10.00 eq) at 10° C. The reaction was stirred at 20° C. for 1.5 hours, detection showed that intermediate formed. Acetic anhydride (2.00 mL) was added and the reaction was stirred at 20° C. for 1 hour. After completion of the reaction, the reaction mixture was filtered and the filter cake was washed with dichloromethane (30 mL). The filtrate was collected, washed sequentially with water (40 mL), saturated sodium carbonate solution (30 mL) and saturated sodium chloride solution (30 mL), dried over anhydrous sodium sulfate, and evaporated to dryness by rotary evaporation to give a crude product. The crude product was purified by preparative HPLC and further purified by preparative TLC (DCM/EA=4/1) to give the target compound WX036. $^1$H NMR (400 MHz, CDCl$_3$-d) δ 11.26 (s, 1H), 8.08 (m, 1H), 7.65 (m, 1H), 7.49-7.43 (m, 2H), 7.15-7.13 (m, 1H), 7.03-7.01 (m, 1H), 6.78-3.74 (m, 1H), 2.94 (s, 1H), 2.30 (s, 3H), 2.05-2.03 (m, 7H), 1.62 (s, 3H), 1.36 (m, 2H), 0.97-0.95 (m, 2H). MS m/z: 602.0 [M+H]$^+$ Referring to the synthesis method of steps 1-2 in Embodiment 19, the compounds or intermediates of the examples in the following table were synthesized. The structures in the following table also represent their possible isomers.

TABLE 1

Structure of the compounds

| Embodiment | Fragment 1 | Fragment 2 | Fragment 3 | Structure | Compound | Suzuki method | Suzuki Type of base | Suzuki solvent |
|---|---|---|---|---|---|---|---|---|
| 28 | BA-1 | 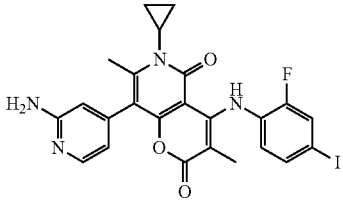 [SMILES: Cc1c(Nc2ccc(I)cc2F)c2c(=O)n(C3CC3)c(C)c(-c3ccnc(N)c3)c2oc1=O] | NIS | 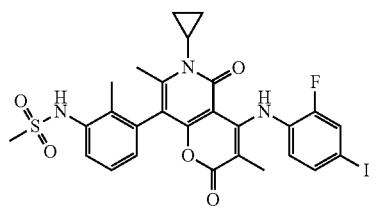 [SMILES: Cc1c(NS(C)(=O)=O)cccc1-c1c(C)n(C2CC2)c(=O)c2c(Nc3ccc(I)cc3F)c(C)c(=O)oc12] | WX079 | B | Sodium bicarbonate | Dioxane |
| 29 | BA-1 | BB-9 | NIS | 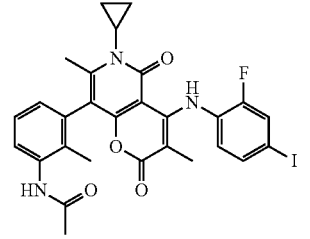 | WX086 | A | Potassium phosphate | Dioxane |
| 30 | BA-1 | BB-12 | NIS | 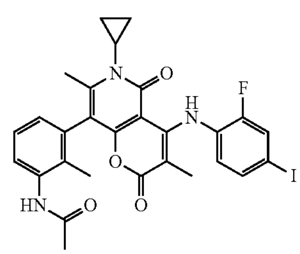 [SMILES: CC(=O)Nc1cccc(-c2c(C)n(C3CC3)c(=O)c3c(Nc4ccc(I)cc4F)c(C)c(=O)oc23)c1C] | WX096 | A | Potassium phosphate | Dioxane |

TABLE 1-continued

Structure of the compounds

| Embodiment | Fragment 1 | Fragment 2 | Fragment 3 | Structure | Compound | Suzuki method | Suzuki Type of base | Suzuki solvent |
|---|---|---|---|---|---|---|---|---|
| 31 | BA-1 | BB-18 | NIS | 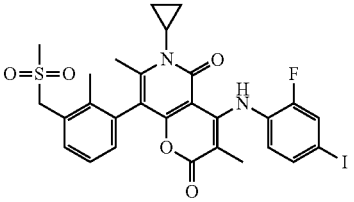 [SMILES: Cc1c(CS(C)(=O)=O)cccc1-c1c(C)n(C2CC2)c(=O)c2c(Nc3ccc(I)cc3F)c(C)c(=O)oc12] | WX106 | A | Potassium phosphate | Dioxane |
| 32 | BA-1 | BB-19 | NIS | 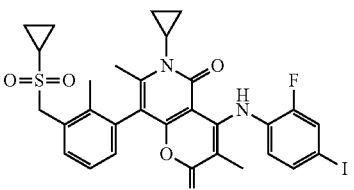 | WX108 | A | Potassium phosphate | Dioxane |
| 33 | BA-1 | 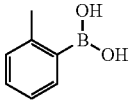 | NIS | 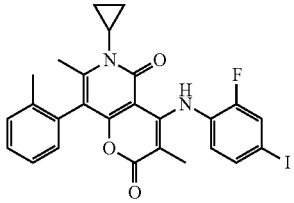 [SMILES: Cc1ccccc1-c1c(C)n(C2CC2)c(=O)c2c(Nc3ccc(I)cc3F)c(C)c(=O)oc12] | WX111 | A | Potassium phosphate | Dioxane |
| 34 | BA-1 | 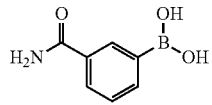 | NIS | 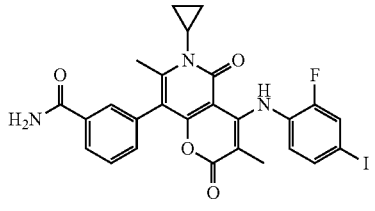 [SMILES: Cc1c(Nc2ccc(I)cc2F)c2c(=O)n(C3CC3)c(C)c(-c3cccc(C(N)=O)c3)c2oc1=O] | WX112 | A | Potassium phosphate | Dioxane |
| 35 | BA-1 | BB-21 | NIS | 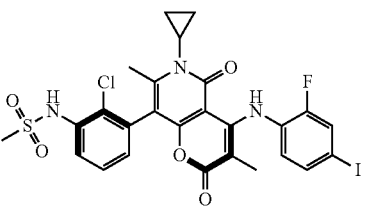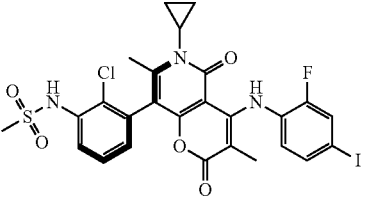 | WX116 or WX117 | A | Potassium phosphate | Dioxane |

Embodiment 36: WX115

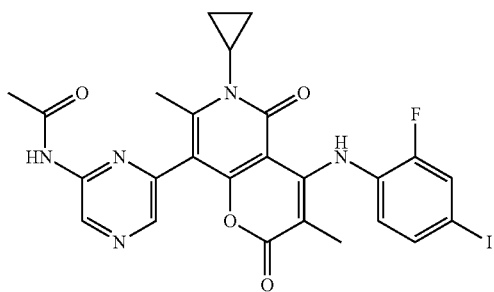 [SMILES: CC(=O)Nc1cncc(-c2c(C)n(C3CC3)c(=O)c3c(Nc4ccc(I)cc4F)c(C)c(=O)oc23)n1]

Synthetic Route:

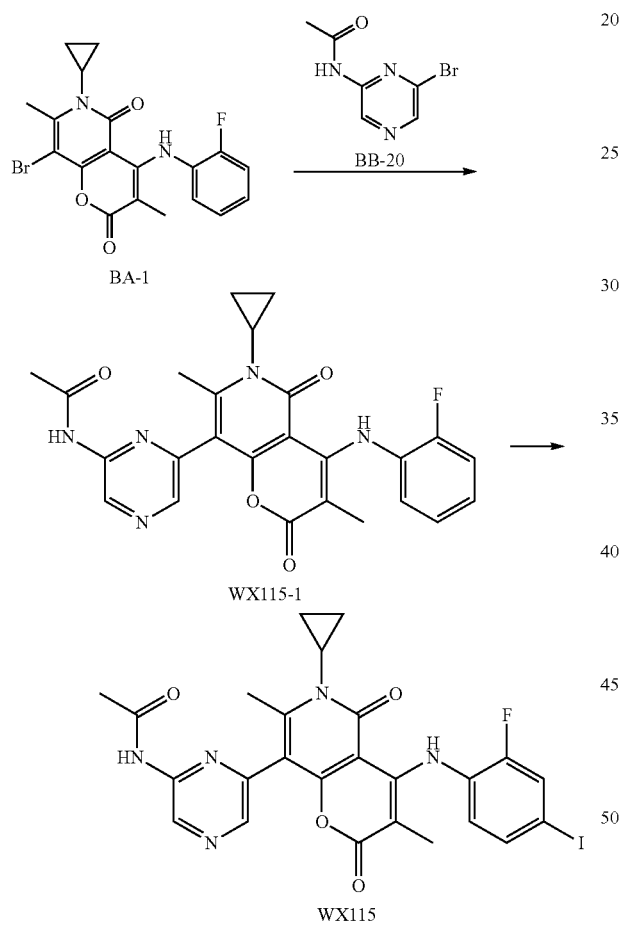

Step 1: Synthesis of the Compound WX115-1

The compound BB-20 (420.00 mg, 1.94 mmol, 1.00 eq), Pd(PPh$_3$)$_2$Cl$_2$ (272.91 mg, 388.82 μmol, 0.20 eq), hexamethyldistannane (955.41 mg, 2.92 mmol, 604.69 μL, 1.50 eq) were added into anhydrous toluene (12.00 mL). The reaction temperature was raised to 110° C. under nitrogen protection and the reaction was stirred for 20 hours. Then the compound BA-1 (650.66 mg, 1.55 mmol, 0.80 eq) and dioxane (15.00 mL) were added. Under nitrogen protection, the reaction temperature was raised to 110° C. and the reaction was stirred for 28 hours. After completion of the reaction, the reaction mixture was cooled to room temperature, followed by addition of potassium fluoride (0.5 g). The mixture was stirred for 30 minutes, diluted with dichloromethane (50 mL) and filtered. The organic phase was collected and evaporated to dryness by rotary evaporation to give a crude product. The crude product was purified by preparative HPLC to give the compound WX115-1. $^1$H NMR (400 MHz, CDCl$_3$-d) δ 11.03 (s, 1H), 9.52 (s, 1H), 8.37 (s, 1H), 8.14 (s, 1H), 7.18-7.06 (m, 3H), 7.18-6.98 (m, 1H), 3.02-2.92 (m, 1H), 2.37 (s, 3H), 2.27 (s, 3H), 1.58 (s, 3H), 1.44-1.34 (m, 2H), 1.00-0.92 (m, 2H). MS m/z: 587.1 [M+H]$^+$

Step 2: Synthesis of the Compound WX115

The compound WX115-1 (70.00 mg, 147.22 μmol, 1.00 eq) was dissolved in dichloromethane (1.00 mL), then trifluoroacetic acid (308.00 mg, 2.70 mmol, 200.00 μL, 18.35 eq) and N-iodosuccinimide (33.12 mg, 147.22 μmol, 1.00 eq) were added sequentially and in batches at 0° C. The reaction temperature was raised to 21° C. and the reaction was stirred for 2 hours in dark place. After completion of the reaction, the reaction mixture was evaporated to dryness by rotary evaporation, the residue was diluted with EtOAc (15 mL), washed sequentially with saturated bicarbonate solution (10 mL*3), saturated sodium thiosulfate solution (10 mL*2), water (10 mL*2) and saturated sodium chloride solution (10 mL). The organic phase was washed with anhydrous sodium sulfate and filtered, the filtrate was evaporated to dryness by rotary evaporation to give a crude product. The crude product was purified by preparative HPLC and dried to give the target compound WX115. $^1$H NMR (400 MHz, CDCl$_3$-d) δ 10.98 (s, 1H), 9.58 (s, 1H), 8.40 (s, 1H), 7.88 (s, 1H), 7.50-7.43 (m, 2H), 6.72 (t, J=8.6 Hz, 1H), 2.99-2.95 (m, 1H), 2.42 (s, 3H), 2.30 (s, 3H), 1.62 (s, 3H), 1.45-1.39 (m, 2H), 1.02-0.95 (m, 2H). MS m/z: 601.8 [M+H]$^+$

Embodiment 37: WX113 & WX114

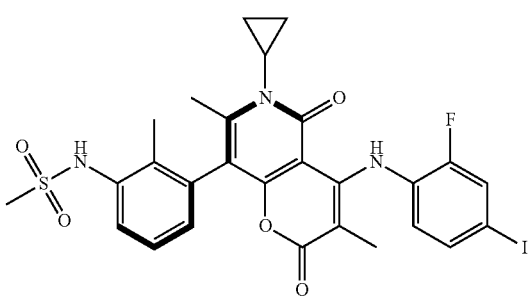

WX113 or WX114

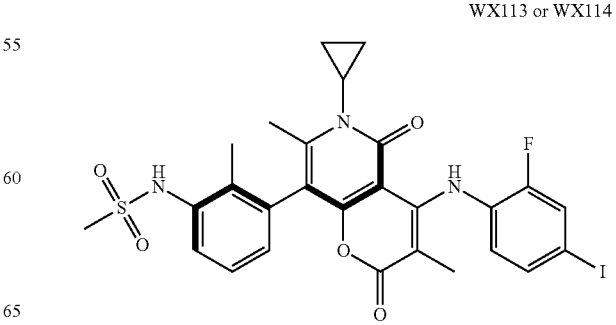

WX113 or WX114

Synthetic Route:

Embodiment 38: WX088

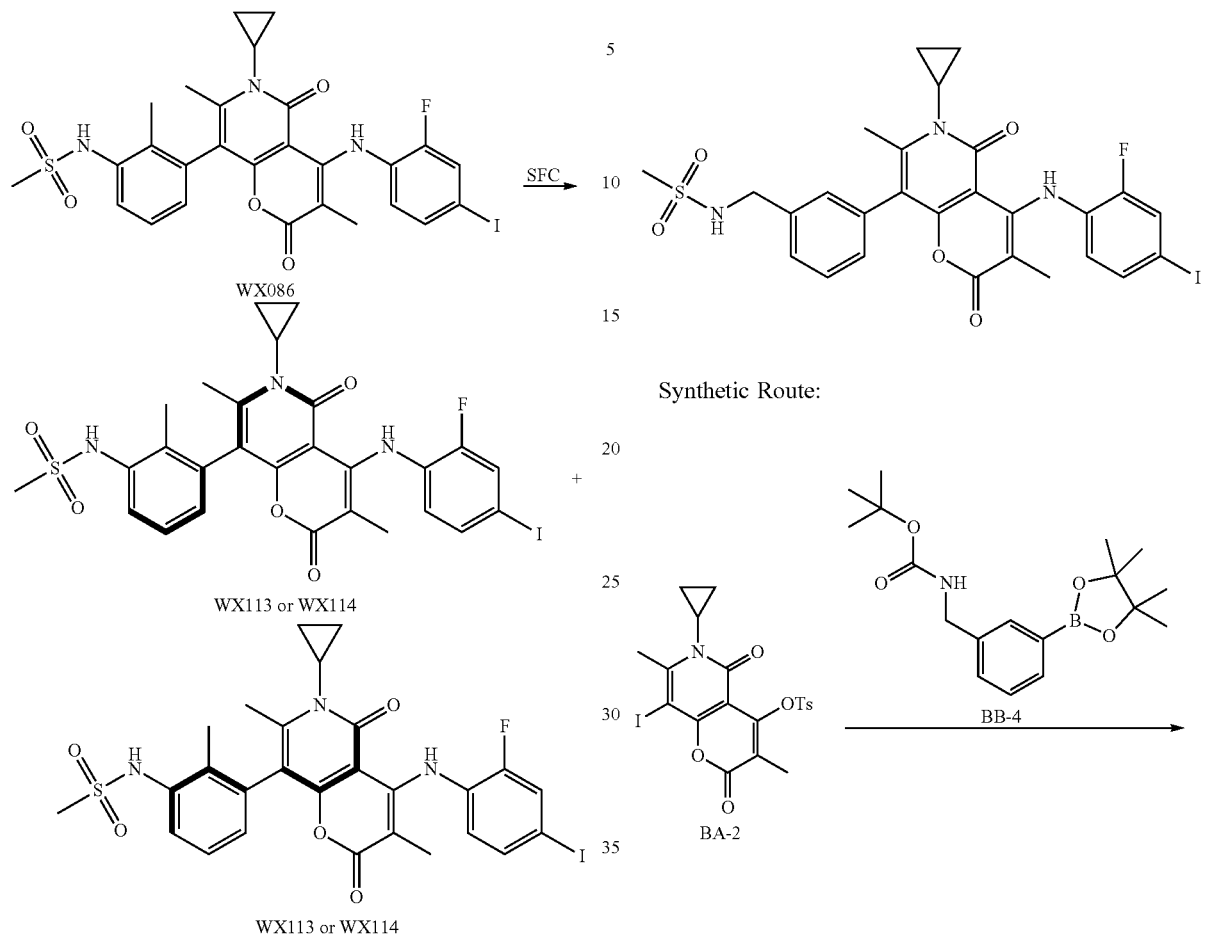

WX086

WX113 or WX114

WX113 or WX114

Step 1: Synthesis of the Compound WX113 and the Compound WX114

The compound WX086 was subjected to supercritical fluid chromatography (column: Chiralpak OJ-3 100×4.6 mm ID, 3 μm; mobile phase: A: CO$_2$ B: methanol (0.05% DEA); gradient: from 5% B to 40% B at a constant speed in 4.5 minutes, 5% B for 2.5 minutes, 5% B for 1 minute. Flow rate: 2.8 mL/min; column temperature: 40° C.), to give the atropisomers WX113 and WX114, with retention times of 4.503 min and 4.166 min respectively and a ratio of 1:1.

Compound WX113 $^1$H NMR (400 MHz, DMSO-d$_6$) δ 11.31 (s, 1H), 9.22 (s, 1H), 7.73 (dd, J=10.0 Hz, J=1.6 Hz, 1H), 7.53 (d, J=8.4 Hz, 1H), 7.43-7.38 (m, 1H), 7.36-7.30 (m, 1H), 7.12 (d, J=7.6 Hz, 1H), 6.89 (t, J=8.0 Hz, 1H), 3.08-3.04 (m, 1H), 3.02 (s, 3H), 2.24 (s, 3H), 2.07 (s, 3H), 1.45 (s, 3H), 1.27-1.16 (m, 2H), 1.00-0.86 (m, 2H). 650.0 [M+H]$^+$ Compound WX114 $^1$H NMR (400 MHz, DMSO-d$_6$) δ 11.31 (s, 1H), 9.22 (s, 1H), 7.73 (dd, J=10.4 Hz, J=2.0 Hz, 1H), 7.53 (d, J=8.8 Hz, 1H), 7.43-7.38 (m, 1H), 7.36-7.30 (m, 1H), 7.12 (d, J=7.6 Hz, 1H), 6.89 (t, J=8.4 Hz, 1H), 3.08-3.04 (m, 1H), 3.02 (s, 3H), 2.24 (s, 3H), 2.07 (s, 3H), 1.45 (s, 3H), 1.27-1.15 (m, 2H), 1.01-0.85 (m, 2H). 650.0 [M+H]$^+$ Synthetic Route:

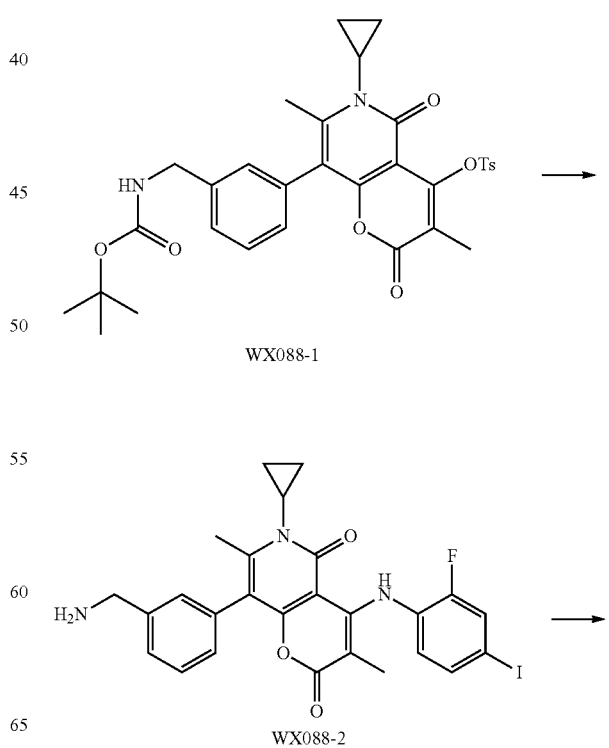

BA-2

BB-4

WX088-1

WX088-2

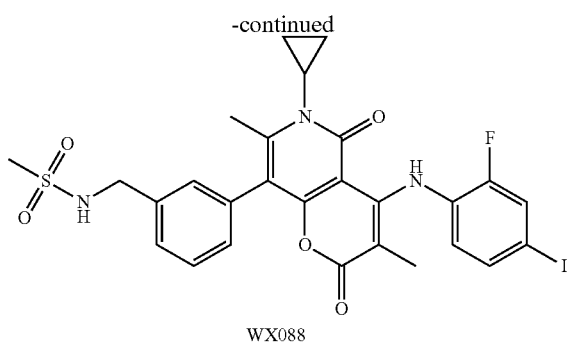

WX088

Step 1: Synthesis of the Compound WX088-1

The compound BA-2 (5.06 g, 9.60 mmol, 0.80 eq) and the compound BB-4 (4.00 g, 12.00 mmol, 1.00 eq) were dissolved in dioxane (80.00 mL), followed by addition of Pd(dppf)Cl$_2$·CH$_2$Cl$_2$ (979.97 mg, 1.20 mmol, 0.10 eq) and saturated sodium bicarbonate solution (40.00 mL). Under nitrogen protection, the reaction temperature was raised to 60° C. and the reaction was stirred for 12 hours. After completion of the reaction, the reaction solution was filtered through diatomaceous earth, and the filtrate was evaporated to dryness by rotary evaporation to give a crude product. The crude product was purified by column chromatography (PE/EA=5/1-1/1) to give the compound WX088-1. $^1$H NMR (400 MHz, CDCl$_3$-d) δ 7.99-7.94 (s, 4H), 7.41-7.40 (m, 3H), 7.13 (m, 1H), 6.07-6.05 (m, 1H), 4.38-4.37 (d, J=6.00, 2H), 2.86-2.82 (m, 1H), 2.53 (m, 3H), 2.33 (m, 3H), 1.67 (s, 3H), 1.50-1.47 (m, 9H), 0.95-0.90 (m, 2H), 0.87-0.84 (m, 2H). MS m/z: 551.1 [M+H]$^+$

Step 2: Synthesis of the Compound WX088-2

The compound WX088-1 (600.00 mg, 988.99 μmol, 1.00 eq) was dissolved in ethanol (10.00 mL), then 2-fluoro-4-iodoaniline (1.17 g, 4.94 mmol, 5.00 eq) was added sequentially under nitrogen protection. The reaction temperature was raised to 80° C. and the reaction was stirred for 12 hours. After completion of the reaction, the reaction solution was evaporated to dryness by rotary evaporation to give a crude product. The crude product was purified by column chromatography (PE/EA=5/1-1/1) to give the compound WX088-2. $^1$H NMR (400 MHz, CDCl$_3$-d) δ 10.41 (s, 1H), 8.08 (m, 2H), 7.47 (m, 1H), 7.45-7.35 (m, 3H), 7.25 (m, 1H), 7.13 (m, 1H), 6.72-6.67 (m, 1H), 4.00-3.95 (m, 2H), 3.47 (s, 3H), 2.82-2.81 (m, 1H), 2.22 (s, 3H), 1.25-1.22 (m, 2H), 0.90-0.83 (m, 2H). MS m/z: 572.0 [M+H]$^+$

Step 3: Synthesis of the Compound WX088

The compound WX088-2 (600.00 mg, 988.99 μmol, 1.00 eq) was dissolved in N,N-dimethylformamide (4.00 mL), then triethylamine (70.84 mg, 700.06 μmol, 2.00 eq) and methanesulfonyl chloride (48.12 mg, 420.04 μmol, 1.20 eq) were added sequentially at 0° C. The reaction temperature was raised to 25° C. and the reaction was stirred for 1 hour. After completion of the reaction, the reaction mixture was diluted with water (20.00 mL) and extracted with dichloromethane (20 mL*2). The organic phase was washed with saturated sodium chloride solution (20 mL), dried over anhydrous sodium sulfate, and evaporated to dryness by rotary evaporation to give a crude product. The crude product was purified by preparative HPLC to give the target compound WX088. $^1$H NMR (400 MHz, CDCl$_3$-d) δ 11.13 (s, 1H), 7.49-7.38 (m, 5H), 7.18-7.15 (m, 1H), 6.73-6.68 (m, 1H), 4.96-4.93 (m, 1H), 4.39-4.36 (m, 2H), 2.96-2.92 (m, 4H), 1.58 (s, 3H), 1.38-1.36 (m, 2H), 0.97 (m, 2H). MS m/z: 650.5 [M+H]$^+$ Referring to the synthesis method of steps 1-2 in Embodiment 38, the embodiments in the following table were synthesized. The structures in the table also represent their possible isomers.

Remarks: All reaction conditions in this table were (base: sodium bicarbonate, solvent: DMF).

TABLE 2

Structures of the compounds

| Embodiment | Fragment 1 | Fragment 2 | Fragment 3 | Structure | Compound | Suzuki method |
|---|---|---|---|---|---|---|
| 39 | BA-2 | BB-6 | (structure) | (structure) | WX068 | B |
| 40 | BA-2 | BB-7 | (structure) | (structure) | WX069 | B |

TABLE 2-continued

Structures of the compounds

| Embodiment | Fragment 1 | Fragment 2 | Fragment 3 | Structure | Compound | Suzuki method |
|---|---|---|---|---|---|---|
| 41 | BA-2 | BB-10 | | 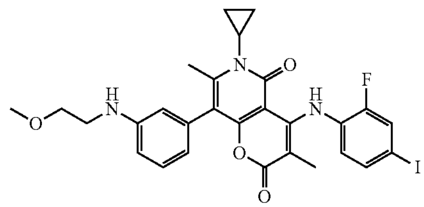 [SMILES: COCCNc1cccc(-c2c(C)n(C3CC3)c(=O)c3c(Nc4ccc(I)cc4F)c(C)c(=O)oc23)c1] | WX087 | B |
| 42 | BA-2 | BB-22 | | 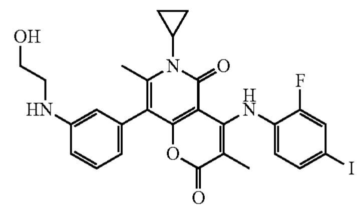 [SMILES: Cc1c(Nc2ccc(I)cc2F)c2c(=O)n(C3CC3)c(C)c(-c3cccc(NCCO)c3)c2oc1=O] | WX093 | B |
| 43 | BA-2 | BB-13 | | 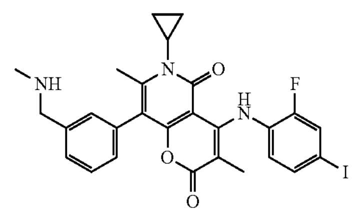 | WX097 | B |
| 44 | BA-2 | BB-14 | | 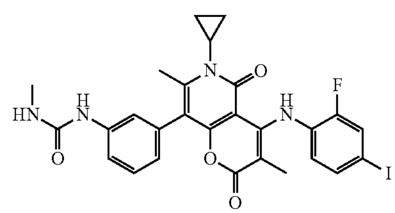 [SMILES: CNC(=O)Nc1cccc(-c2c(C)n(C3CC3)c(=O)c3c(Nc4ccc(I)cc4F)c(C)c(=O)oc23)c1] | WX099 | B |
| 45 | BA-2 | BB-17 | | 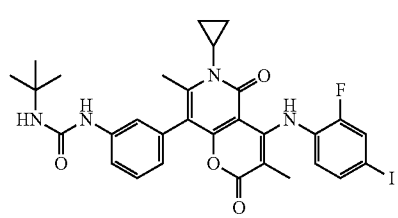 [SMILES: Cc1c(Nc2ccc(I)cc2F)c2c(=O)n(C3CC3)c(C)c(-c3cccc(NC(=O)NC(C)(C)C)c3)c2oc1=O] | WX104 | B |
| 23 | BA-2 | BB-15 | | 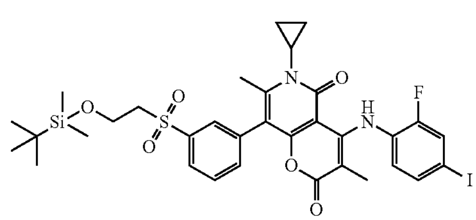 [SMILES: Cc1c(Nc2ccc(I)cc2F)c2c(=O)n(C3CC3)c(C)c(-c3cccc(S(=O)(=O)CCO[Si](C)(C)C(C)(C)C)c3)c2oc1=O] | WX100-1 | B |

139
Embodiment 46: WX098

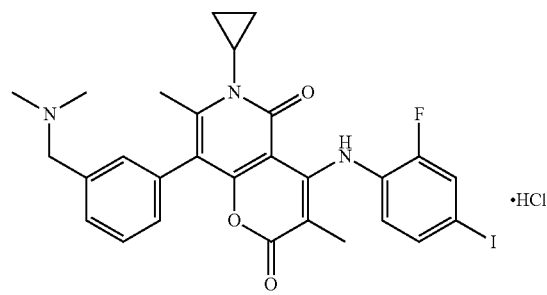 [SMILES: Cc1c(Nc2ccc(I)cc2F)c2c(=O)n(C3CC3)c(C)c(-c3cccc(CN(C)C)c3)c2oc1=O ; Cl]

140
Embodiment 47: WX101

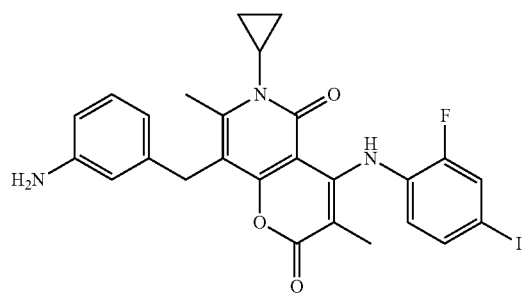 [SMILES: Cc1c(Nc2ccc(I)cc2F)c2c(=O)n(C3CC3)c(C)c(Cc3cccc(N)c3)c2oc1=O]

Synthetic Route:

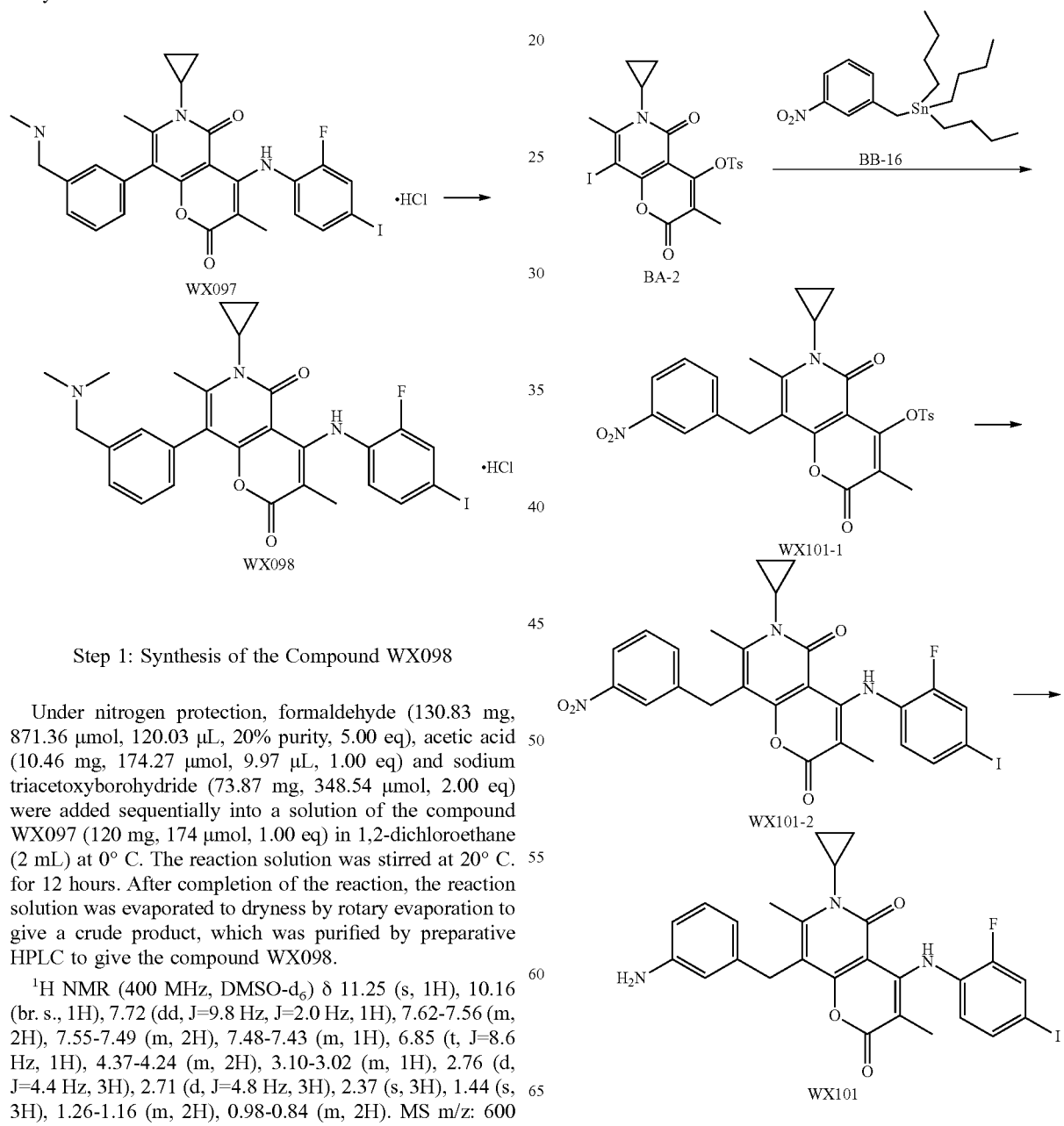

Step 1: Synthesis of the Compound WX098

Under nitrogen protection, formaldehyde (130.83 mg, 871.36 μmol, 120.03 μL, 20% purity, 5.00 eq), acetic acid (10.46 mg, 174.27 μmol, 9.97 μL, 1.00 eq) and sodium triacetoxyborohydride (73.87 mg, 348.54 μmol, 2.00 eq) were added sequentially into a solution of the compound WX097 (120 mg, 174 μmol, 1.00 eq) in 1,2-dichloroethane (2 mL) at 0° C. The reaction solution was stirred at 20° C. for 12 hours. After completion of the reaction, the reaction solution was evaporated to dryness by rotary evaporation to give a crude product, which was purified by preparative HPLC to give the compound WX098.

$^1$H NMR (400 MHz, DMSO-$d_6$) δ 11.25 (s, 1H), 10.16 (br. s., 1H), 7.72 (dd, J=9.8 Hz, J=2.0 Hz, 1H), 7.62-7.56 (m, 2H), 7.55-7.49 (m, 2H), 7.48-7.43 (m, 1H), 6.85 (t, J=8.6 Hz, 1H), 4.37-4.24 (m, 2H), 3.10-3.02 (m, 1H), 2.76 (d, J=4.4 Hz, 3H), 2.71 (d, J=4.8 Hz, 3H), 2.37 (s, 3H), 1.44 (s, 3H), 1.26-1.16 (m, 2H), 0.98-0.84 (m, 2H). MS m/z: 600 [M+H]$^+$

Step 1: Synthesis of the Compound WX101-1

The compound BA-2 (2.00 g, 3.79 mmol, 1.00 eq) and the compound BB-16 (2.42 g, 5.69 mmol, 1.50 eq) were dissolved in N,N-dimethylformamide (10.00 mL), followed by addition of Pd(PPh$_3$)$_4$ (438.27 mg, 379.27 μmol, 0.10 eq) and cesium fluoride (576.11 mg, 3.79 mmol, 1.00 eq) and cuprous iodide (361.16 mg, 1.90 mmol, 0.50 eq). Under nitrogen protection, the reaction temperature was raised to 60° C. and the reaction was stirred for 2 hours. After completion of the reaction, the reaction solution was evaporated to dryness by rotary evaporation to give a crude product. The crude product was purified by column chromatography (PE/EA=10/1-1/1) to give the compound WX101-1. MS m/z: 537.1 [M+H]$^+$

Step 2: Synthesis of the Compound WX101-2

The compound WX101-1 (1.50 g, 749.73 μmol, 1.00 eq) was suspended in ethanol (10.00 mL), 2-fluoro-4-iodoaniline (4.64 g, 19.58 mmol, 26.11 eq) was added sequentially under nitrogen protection. The reaction temperature was raised to 80° C. and the reaction was stirred for 16 hours. After completion of the reaction, the reaction solution was evaporated to dryness by rotary evaporation to give a crude product. The crude product was purified by column chromatography (PE/EA=10/1-1/1) to give the compound WX101-2. MS m/z: 602.2 [M+H]$^+$

Step 3: Synthesis of the Compound WX101

The compound WX101-2 (210.00 mg, 182.98 μmol, 1.00 eq) was suspended in ethanol (4.00 mL) and water (2.00 mL), then iron powder (195.03 mg, 3.49 mmol, 19.08 eq) and ammonium chloride (186.79 mg, 3.49 mmol, 19.08 eq) were added sequentially. Under nitrogen protection, the reaction temperature was raised to 70° C. and the reaction was stirred for 1 hour. After completion of the reaction, the reaction solution was evaporated to dryness by rotary evaporation to give a crude product. The crude product was purified by preparative TLC (PE/EA=1/1) and further purified by preparative HPLC to give the target compound WX101. $^1$H NMR (400 MHz, CDCl$_3$-d) δ 11.20 (s, 1H), 7.46 (dd, J=9.6 Hz, J=2.0 Hz, 1H), 7.41 (d, J=8.4 Hz, 1H), 7.05 (t, J=7.6 Hz, 1H), 6.71 (t, J=7.6 Hz, 1H), 6.58-6.49 (m, 3H), 3.98 (s, 2H), 2.91-2.86 (m, 1H), 2.55 (s, 3H), 1.63 (s, 3H), 1.36-1.30 (m, 2H), 0.90-0.84 (m, 2H). MS m/z: 572.2 [M+H]$^+$

Embodiment 48: WX091&WX095

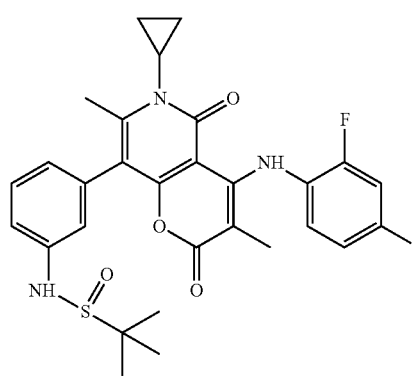

WX091

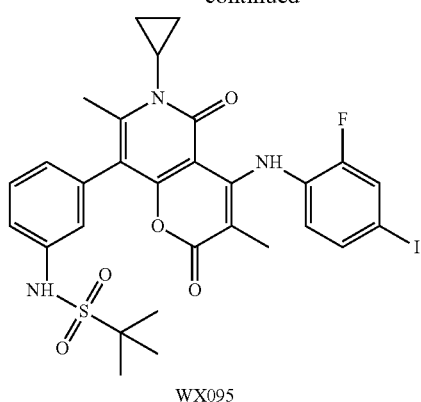

WX095

Synthetic Route:

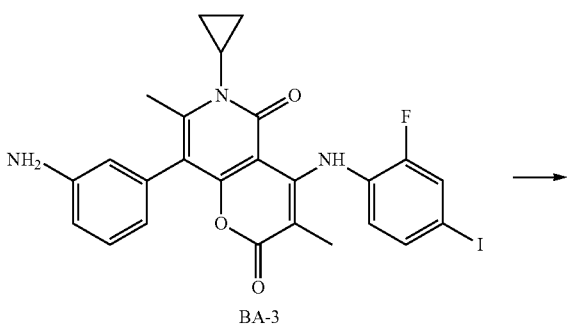

BA-3

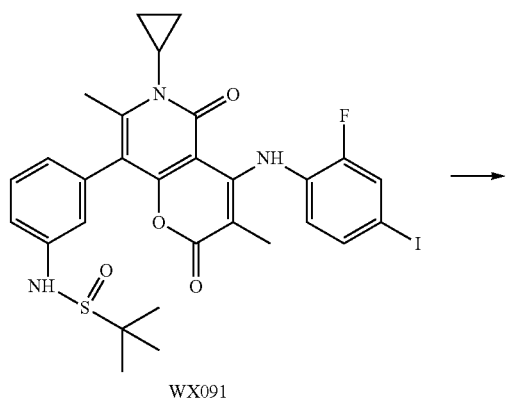

WX091

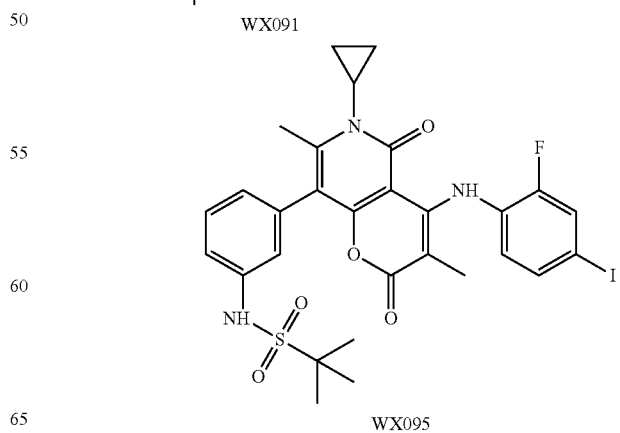

WX095

Step 1: Synthesis of the Compound WX091

The compound BA-3 (300.00 mg, 538.26 μmol, 1.00 eq) was dissolved in dichloromethane (4.00 mL), followed by addition of triethylamine (108.93 mg, 1.08 mol, 2.00 eq), DMAP (131.52 mg, 1.08 μmol, 2.00 eq) and the compound tert-butylsulfinyl chloride (90.83 mg, 645.91 mol, 1.20 eq) were added sequentially at 0° C. The reaction was stirred at 0° C. for 15 minutes. After completion of the reaction, the reaction mixture was added into water (30 mL) and extracted with dichloromethane (60 mL*3). The organic phases were combined and washed with saturated sodium chloride solution (40 mL), dried over anhydrous sodium sulfate, filtered and evaporated to dryness by rotary evaporation to give a crude product. The crude product was purified by preparative TLC (PE/EA=1/2) to give the compound WX091. MS m/z: 662.0 [M+H]$^+$ Step 2: Synthesis of the Compound WX095

The compound WX091 (47.00 mg, 71.05 μmol, 1.00 eq) was dissolved in THF (2.00 mL) and water (2.00 mL), then potassium hydrogen sulfate (174.71 mg, 142.10 μmol, 2.00 eq) was added at 0° C. under nitrogen protection. The reaction was stirred at 20° C. for 6 hours. The reaction mixture was diluted with water (20 mL), and the aqueous phase was extracted with dichloromethane (20 mL*3). The organic phase was collected and washed with saturated sodium chloride solution (10 mL), dried over anhydrous sodium sulfate, filtered and evaporated to dryness by rotary evaporation to give a crude product. The crude product was purified by preparative HPLC and lyophilized to give the target compound WX095. $^1$H NMR (400 MHz, CDCl$_3$-d) δ 11.14 (s, 1H), 7.49-7.42 (m, 1H), 7.38-7.36 (m, 1H), 6.99-6.97 (m, 1H), 6.75-6.72 (m, 1H), 2.96-2.94 (m, 1H), 2.40 (s, 3H), 1.61 (s, 3H), 1.45 (m, 9H), 1.39-1.37 (m, 2H), 0.99 (m, 2H). MS m/z: 677.9 [M+H]$^+$ Referring to the synthesis method of steps 1-2 in Embodiment 48, the embodiments in the following table were synthesized. The structures in the table also represent their possible isomers.

TABLE 3

| | | Structures of the compounds | | |
|---|---|---|---|---|
| Embodiment | Fragment 1 | Fragment 2 | Structure | Compound |
| 49 | BA-3 | oxetane-carboxylic acid (OH, O) | (structure) | WX065 |
| 50 | BA-3 | methanesulfonyl chloride | (structure) | WX066 |
| 51 | BA-3 | methanesulfonyl chloride | (structure) | WX067 |
| 52 | BA-3 | methoxyacetic acid | (structure) | WX080 |

TABLE 3-continued

Structures of the compounds

| Embodiment | Fragment 1 | Fragment 2 | Structure | Compound |
|---|---|---|---|---|
| 53 | BA-3 | (dimethoxyacetic acid) | 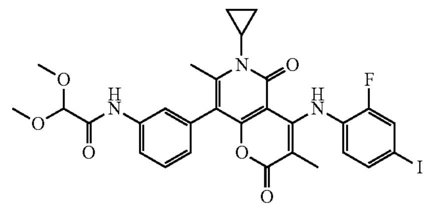 [SMILES: COC(OC)C(=O)Nc1cccc(-c2c(C)n(C3CC3)c(=O)c3c(Nc4ccc(I)cc4F)c(C)c(=O)oc23)c1] | WX081 |
| 54 | BA-3 | (ethanesulfonyl chloride) | 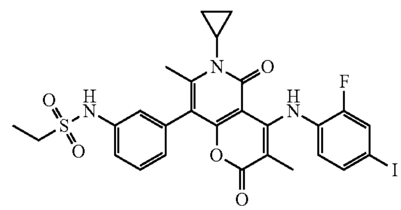 [SMILES: CCS(=O)(=O)Nc1cccc(-c2c(C)n(C3CC3)c(=O)c3c(Nc4ccc(I)cc4F)c(C)c(=O)oc23)c1] | WX082 |
| 55 | BA-3 | BB-8 | 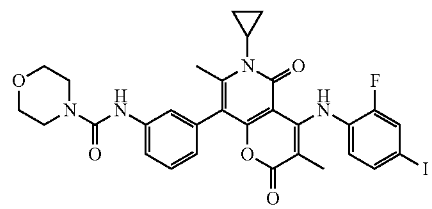 [SMILES: Cc1c(Nc2ccc(I)cc2F)c2c(=O)n(C3CC3)c(C)c(-c3cccc(NC(=O)N4CCOCC4)c3)c2oc1=O] | WX085 |
| 56 | BA-3 | (cyclopropanesulfonyl chloride) | 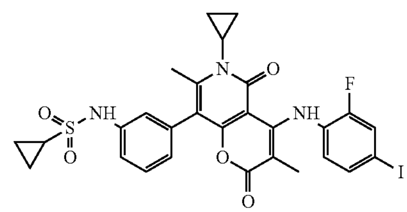 [SMILES: Cc1c(Nc2ccc(I)cc2F)c2c(=O)n(C3CC3)c(C)c(-c3cccc(NS(=O)(=O)C4CC4)c3)c2oc1=O] | WX089 |
| 57 | BA-3 | (methyl chloroformate) | 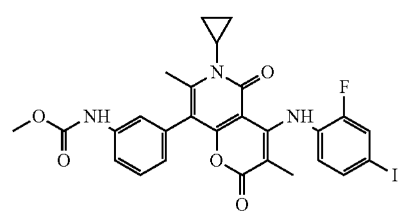 [SMILES: COC(=O)Nc1cccc(-c2c(C)n(C3CC3)c(=O)c3c(Nc4ccc(I)cc4F)c(C)c(=O)oc23)c1] | WX094 |

TABLE 4

NMR and MS data of the embodiments

| Embodiment | Compound | NMR | MS m/z: |
|---|---|---|---|
| 1 | WX040 | $^1$H NMR (400 MHz, DMSO-d$_6$) δ 11.34(s, 1 H), 10.06(s, 1 H), 7.70(dd, J = 10.2 Hz, J = 1.8 Hz, 1 H), 7.60-7.54(m, 2 H), 7.51(d, J = 8.0 Hz, 1 H), 7.40(t, J = 8.0 Hz, 1 H), 6.93(d, J = 7.6 Hz, 1 H), 6.87(t, J = 8.0 Hz, 1 H), 3.58(s, 3 H), 2.24(s, 3 H), 2.04(s, 3 H), 1.44(s, 3H). | 574.1 [M + H]$^+$ |
| 2 | WX049 | $^1$H NMR (400 MHz, DMSO-d$_6$) δ 12.56(s, 1 H), 11.28(s, 1 H), 10.08(s, 1 H),7.73(dd, J = 10.0 Hz, J = 1.6 Hz, 1 H), 7.72-7.53(m, 3 H), 7.40(t, J = 8.8 Hz, 1 H), 6.99(d, J = 7.2 Hz, 1 H), 6.92(t, J = 8.8 Hz, 1 H), 2.11(s, 3 H), 2.06(s, 3 H), 1.45(s, 3 H). | 560.0 [M + H]$^+$ |
| 3 | WX053 | $^1$H NMR (400 MHz, DMSO-d$_6$) δ 11.21(s, 1 H), 7.73(d, J = 10.0 Hz, 1 H), 7.54(d, J = 8.4 Hz, 1 H), 6.90(t, J = 8.4 Hz, 1 H), 6.51(s, 1 H), 5.05(d, J = 4.8 Hz, 1 H), 4.78(t, J = 5.6 Hz, 1 H), 4.27(d, J = 11.2 Hz, 1 H), 3.79-3.92(m, 2 H), 3.39-3.49(m, 2 H), 2.56(s, 3 H), 1.49(s, 3 H). | 501.1 [M + H]$^+$ |

TABLE 4-continued

NMR and MS data of the embodiments

| Embodiment | Compound | NMR | MS m/z: |
|---|---|---|---|
| 4 | WX054 | $^1$H NMR (400 MHz, DMSO-d$_6$) δ 11.18(s, 1 H), 10.19(s, 1 H), 8.64(br. s 1 H), 7.73(d, J = 10.8 Hz, 1 H), 7.68(s, 1 H), 7.56(t, J = 9.2 Hz, 2 H), 7.44(t, J = 8.0 Hz, 1 H), 6.96(d, J = 7.6 Hz, 1 H), 6.90(t, J = 8.0 Hz, 1 H), 4.42(br. s., 2 H), 3.24(br. s., 2 H), 2.55(s, 3 H), 2.32(s, 3 H), 2.07(s, 3 H), 1.48(s, 3 H). | 617.1 [M + H- HCl]$^+$ |
| 5 | WX055 | $^1$H NMR (400 MHz, CDCl$_3$-d) δ 11.16(s, 1 H), 8.22(s, 1 H), 7.78(br. s., 1 H), 7.50-7.43(m, 2 H), 7.27(d, J = 4.8 Hz, 1 H), 7.15(d, J = 8.0 Hz, 1 H), 6.87(d, J = 8.0 Hz, 1 H), 6.75(t, J = 8.8 Hz, 1 H), 4.36(t, J = 6.4 Hz, 2 H), 3.47(t, J = 6.8 Hz, 2 H), 3.00(s, 3 H), 2.84(s, 3 H), 2.34(s, 3 H), 2.05(s, 3 H), 1.62(s, 3 H). | 694.9 [M + H]$^+$ |
| 6 | WX056 | $^1$H NMR (400 MHz, CDCl$_3$-d) δ 11.24(s, 1 H), 8.29(s, 1 H), 7.79(br. s., 1 H), 7.50-7.43(m, 2 H), 7.26(d, J = 4.8 Hz, 1 H), 7.14(d, J = 8.0 Hz, 1 H), 6.86(d, J = 6.8 Hz, 1 H), 6.76(d, J = 8.0 Hz, 1 H), 4.28(d, J = 7.2 Hz, 2 H), 3.64(t, J = 7.2 Hz, 2 H), 3.14(s, 3 H), 2.39(s, 3 H), 2.09(s, 3 H), 2.04(s, 3 H), 1.63(s, 3 H). | 659.0 [M + H]$^+$ |
| 7 | WX057 | $^1$H NMR (400 MHz, DMSO-d$_6$) δ 11.16(s, 1 H), 7.72(dd, J = 10.0 Hz, J = 2.0 Hz, 1 H), 7.53(d, J = 8.0 Hz, 1 H), 6.89(t, J = 8.6 Hz, 1 H), 6.53(s, 1 H), 4.07(t, J = 7.6 Hz, 2 H), 3.39(t, J = 5.8 Hz, 2 H), 3.24(s, 3 H), 2.53(s, 3 H), 1.91-1.83(m, 2 H), 1.47(s, 3 H). | 498.9 [M + H]$^+$ |
| 8 | WX058 | $^1$H NMR (400 MHz, DMSO-d$_6$) δ 11.39(s, 1 H), 10.09(d, J = 4.0 Hz, 1 H), 7.73(dd, J = 10.0 Hz, J = 1.6 Hz, 1 H), 7.62-7.52(m, 3 H), 7.42(t, J = 8.0 Hz, 1 H), 6.97-6.88(m, 2 H), 5.11(d, J = 10.0 Hz, 1 H), 4.80(br. s., 1 H), 4.42-4.34(m, 1 H), 3.95(br. s, 2 H), 3.45(br. s 2 H), 2.33(s, 3 H), 2.06(s, 3 H), 1.47(s, 3 H). | 633.9 [M + H]$^+$ |
| 9 | WX059 | $^1$H NMR (400 MHz, CDCl$_3$-d) δ 11.44(br. s., 1 H), 7.77(br. s., 1 H), 7.51-7.42(m, 2 H), 7.36-7.29(m, 1 H), 7.19(br. s., 1 H), 6.92(d, J = 7.6 Hz, 1 H), 6.80(br. s., 1 H), 4.15(d, J = 11.6 Hz, 2 H), 3.46(t, J = 11.6 Hz, 2 H), 3.20(br. s 1 H), 2.33(s, 3 H), 2.06(s, 3 H), 1.71-1.67(m, 4 H), 1.60(s, 3 H). | 644.2 [M + H]$^+$ |
| 10 | WX060 | $^1$H NMR (400 MHz, DMSO-d$_6$) δ 11.10(s, 1 H), 7.73(dd, J = 10.2 Hz, 2.0 Hz, 2 H), 7.54(d, J = 9.2 Hz, 1 H), 6.90(t, J = 8.8 Hz, 1 H), 6.52(s, 1 H), 4.22(t, J = 5.2 Hz, 2 H), 3.61(t, J = 5.2 Hz, 2 H), 3.24(s, 3 H), 2.54(s, 2 H), 1.48(s, 3 H). | 485.0 [M + H]$^+$ |
| 11 | WX061 | $^1$H NMR (400 MHz, DMSO-d$_6$) δ 11.25(s, 1 H), 10.07(s, 1 H), 7.71(d, J = 10.0 Hz, 1 H), 7.59-7.49(m, 3 H), 7.40(t, J = 7.6 Hz, 1 H), 6.93(d, J = 7.6 Hz, 1 H), 6.88(t, J = 8.4 Hz, 1 H), 4.30(t, J = 5.2 Hz, 2 H), 3.64(t, J = 5.2 Hz, 2 H), 3.23(s, 3 H), 2.29(s, 3 H), 2.04(s, 3 H), 1.44(s, 3 H). | 617.9 [M + H]$^+$ |
| 12 | WX062 | $^1$H NMR (400 MHz, DMSO-d$_6$) δ 11.33(s, 1 H), 10.06(s, 1 H), 7.71(dd, J = 10.4 Hz, J = 2.0 Hz, 1 H), 7.58-7.55(m, 2 H), 7.51(d, J = 8.4 Hz, 1 H), 7.40(t, J = 8.0 Hz, 1 H), 6.95(d, J = 8.0 Hz, 1 H), 6.88(t, J = 8.0 Hz, 1 H), 4.16(t, J = 7.6 Hz, 2 H), 3.40(t, J = 5.8 Hz, 2 H), 3.23(s, 3 H), 2.26(s, 3 H), 2.04(s, 3 H), 1.44(s, 3 H). | 632.0 [M + H]$^+$ |
| 13 | WX109 | $^1$H NMR (400 MHz, DMSO-d$_6$) δ 11.38(s, 1 H), 7.72(d, J = 10.0 Hz, 1 H), 7.52(d, J = 8.4 Hz, 1 H), 7.46(d, J = 8.0 Hz, 1 H), 7.34(t, J = 7.6 Hz, 1 H), 7.18(d, J = 7.6 Hz, 1 H), 6.90(t, J = 8.4 Hz, 1 H), 4.70-4.61(m, 2 H), 3.60(s, 3 H), 3.33(s, 3 H), 3.01(s, 3 H), 2.15(s, 3 H), 1.45(s, 3 H). | 623.0 [M + H]$^+$ |
| 14 | WX110 | $^1$H NMR (400 MHz, DMSO-d$_6$) δ 11.31(s, 1 H), 7.76-7.73(d, J = 9.8 Hz, 1 H), 7.54-7.52(d, J = 7.6 Hz, 1 H), 7.46-7.44(d, J = 7.6 Hz, 1 H), 7.35-7.34(m, 1 H), 7.22-7.20(d, J = 8.0 Hz, 1 H), 7.02(s, 1 H), 4.70-4.61(m, 2 H), 3.10(m, 1 H), 3.01(s, 3 H), 2.21(s, 3 H), 2.14(s, 3 H), 2.01-1.99(d, J = 7.2 Hz, 2 H), 1.23(s, 2 H), 0.93-0.90(d, J = 10.8 Hz, 2 H), 0.69-0.73(t, J = 7.2 Hz, 3 H). | 663.2 [M + H]$^+$ |
| 15 | WX118 | WX118: $^1$H NMR (400 MHz, DMSO-d$_6$) δ 11.33(m, 1 H), 7.72-7.35(m, 1 H), 7.37-7.10(m, 1 H), 6.92(t, J = 8.4 Hz, 1 H), (s, 3 H), 3.01(m, 2 H), 2.50(s, 3 H), 2.06(s, 3 H), 2.00(s, 3 H), 1.43(s, 1 H). | 609.9 [M + H]$^+$ |
| | WX119 | WX119: $^1$H NMR (400 MHz, DMSO-d$_6$) δ 11.35-11.26(m, 1 H), 7.75-7.68(m, 1 H), 7.59-7.25(m, 3 H), 7.10(m, 1 H), 6.89-6.95(m, 1 H), 3.00(s, 3 H), 2.06(s, 3 H), 1.99(s, 3 H), 1.43(s, 3 H) SFC detection method: column: Chiralpak AD-3 100 × 4.6 mm I.D., 3 μm; mobile phase: A: CO$_2$ B: | 610.0 [M + H]$^+$ |

TABLE 4-continued

NMR and MS data of the embodiments

| Embodiment | Compound | NMR | MS m/z: |
|---|---|---|---|
| | | methanol (0.05% DEA); gradient: from 5% B to 40% B at a constant speed in 4.5 minutes, then 40% B for 2.5 minutes, 5% B for 1 minute; flow rate: 2.8 mL/min, column temperature: ° C. The retention times of the compound WX118 and WX119 were 5.934 min and 4.958 min respectively, the ratio was 6:7. | |
| 16 | WX034 | $^1$H NMR (400 MHz, DMSO-d$_6$) δ 11.28(s, 1 H), 10.05(m, 2 H), 7.72-7.69(m, 1 H), 7.56(m, 1 H), 7.52(m, 1 H), 7.40(m, 1 H), 6.97(m, 1 H), 6.86(m, 1 H), 3.03(m, 1 H), 2.31(m, 3 H), 2.04(s, 3 H), 1.44(s, 3 H), 1.19(m, 2 H), 0.90(m, 2 H). | 600.1 [M + H]$^+$ |
| 17 | WX035 | $^1$H NMR (400 MHz, CDCl$_3$-d) δ 10.99(s, 1 H), 7.48-7.42(m, 2 H), 6.74-6.20(m, 1 H), 6.22(s, 1 H), 2.91-2.88(m, 1 H), 2.59(m, 3 H), 1.64(s, 3 H), 1.36-1.34(s, 2 H), 0.94-0.93(s, 2 H). | |
| 18 | WX039 | $^1$H NMR (400 MHz, CDCl$_3$-d) δ 11.04(s, 1 H), 8.27-8.25(s, 1 H), 7.95(m, 1 H), 7.87-7.83(m, 1 H), 7.49-7.47(m, 1 H), 7.46-7.42(m, 1 H), 7.11-7.09(m, 1 H), 6.73-6.70(m, 1 H), 2.98-2.92(s, 1 H), 2.40(s, 3 H), 2.24(s, 3 H), 1.62(m, 3 H), 1.43-1.38(m, 2 H), 0.98-0.97(m, 2 H). | 601.1 [M + H]$^+$ |
| 19 | WX048 | $^1$H NMR (400 MHz, CDCl$_3$-d) δ 11.22(s, 1 H), 10.13(s, 1 H), 7.75-7.72(m, 1 H), 7.65-7.64(m, 2 H), 7.54-7.52(m, 1 H), 7.32(m, 1 H), 6.92-6.90(m, 1 H), 3.08-3.07(m, 1 H), 2.37(s, 3 H), 2.06(s, 3 H), 1.46(s, 3 H), 1.23-1.22(m, 2 H), 0.96-0.88(m, 2 H). | 618.1 [M + H]$^+$ |
| 20 | WX071 | $^1$H NMR (400 MHz, CDCl$_3$-d) δ 11.12(s, 1 H), 7.55-7.42(m, 2 H), 7.35-7.30(m, 2 H), 6.74-6.70(m, 1 H), 4.35-4.28(m, 1 H), 2.98-2.93(m, 1 H), 2.87(s, 3 H), 2.44(s, 3 H), 1.61(s, 3 H), 1.40-1.38(m, 2 H), 0.99-0.90(m, 2 H). | 635.0 [M + H]$^+$ |
| 21 | WX083 | WX083: $^1$H NMR (400 MHz, CDCl$_3$-d) δ 11.03(s, 1 H), 7.42-7.35(m, 2 H), 7.33-7.28(m, 2 H), 7.19-7.12(m, 2 H), 6.64-6.60(m, 1 H), 4.09-3.86(m, 2 H), 2.89-2.85(m, 1 H), 2.40(s, 3 H), 2.33(s, 3 H), 1.52(s, 3 H), 1.30-1.20(m, 2 H), 1.18-1.13(m, 1 H), 0.89-0.88(m, 2 H). | 619.1 [M + H]$^+$ |
| | WX084 | WX084: $^1$H NMR (400 MHz, CDCl$_3$-d) δ 11.08(s, 1 H), 7.49-7.72(m, 2 H), 7.40-7.36(m, 2 H), 7.26-7.19(m, 2 H), 6.72-6.68(s, 1 H), 4.16-3.93(m, 2 H), 2.93(m, 1 H), 2.48(s, 3 H), 2.40(s, 3 H), 1.63-1.59(s, 2 H), 1.38-1.30(m, 2 H), 1.29-1.20(m, 1 H), 0.96(m, 2 H). SFC detection method: column: Chiralpak OD-3 150 × 4.6 mm I.D., 3 µm; mobile phase: A: CO$_2$ B: methanol (0.05% DEA); gradient: from 5% B to 40% B at a constant speed in 4.5 minutes, 40% B for 2.5 minutes, 5% B for 1 minute; flow rate: 2.4 mL/min; column temperature: 40° C. The retention times of the compound WX083 and WX084 were 5.88 min and 6.79 min respectively, the ratio was 1:1. | 619.1 [M + H]$^+$ |
| 22 | WX092 | $^1$H NMR (400 MHz, CDCl$_3$-d) δ 11.19(s, 1 H), 7.50-7.45(m, 5 H), 7.43-7.16(m, 1 H), 6.76-6.71(m, 1 H), 4.91(m, 1 H), 4.83(s, 2 H), 4.39-4.38(s, 2 H), 2.98-2.96(m, 1 H), 2.49(s, 3 H), 1.59(s, 3 H), 1.41(m, 2 H), 1.00(m, 2 H). | 651.1 [M + H]$^+$ |
| 23 | WX100 | $^1$H NMR (400 MHz, CDCl$_3$-d) δ 11.24(s, 1 H), 7.68-7.66(m, 1 H), 7.52(m, 1 H), 7.49-7.44(m, 2 H), 7.43-7.39(m, 1 H), 7.25(m, 1 H), 6.76-6.71(s, 1 H), 4.47-4.31(m, 2 H), 4.01-3.95(s, 3 H), 3.67(s, 1 H), 3.04-2.95(s, 1 H), 2.48(m, 2 H), 1.58(s, 3 H), 1.43-1.38(m, 2 H), 0.98(m, 2 H). | 665.3 [M + H]$^+$ |
| 24 | WX102 | $^1$H NMR (400 MHz, CDCl$_3$-d) δ 11.21(s, 1 H), 7.47-7.44(m, 1 H), 7.40-7.34(m, 3 H), 7.23(s, 1 H), 6.96(m, 1 H), 6.73-6.70(m, 1 H), 4.03(s, 2 H), 2.94-2.88(m, 1 H), 2.60(s, 3 H), 2.16(s, 3 H), 1.62(s, 3 H), 1.37-1.32(m, 2 H), 0.92-0.88(m, 2 H). | 614.2 [M + H]$^+$ |
| 25 | WX103 | $^1$H NMR (400 MHz, CDCl$_3$-d) δ 11.28(s, 1 H), 8.66(m, 1 H), 7.70(m, 1 H), 7.51(s, 1 H), 7.73(m, 3 H), 6.83(m, 2 H), 5.88(m, 2 H), 3.02(m, 1 H), 2.31(s, 3 H), 1.43(s, 3 H), 1.19(m, 2 H), 0.89(m, 2 H). | 650.5 [M + H]$^+$ |
| 26 | WX105 | $^1$H NMR (400 MHz, DMSO-d$_6$) δ 11.18(s, 1 H), 8.34(m, 1 H), 7.72-7.69(m, 1 H), 7.52-7.50(m, 1 H), 6.99-6.98(m, 1 H), 6.90-6.87(m, 1 H), 6.85-6.83(m, 1 H), 3.31(s, 3 H), 3.02(m, 1 H), 2.35(s, 3 H), 1.44(m, 3 H), 1.21- 1.18(m, 2 H), 0.90(m, 2 H). | 637.0 [M + H]$^+$ |
| 27 | WX036 | $^1$H NMR (400 MHz, CDCl$_3$-d) δ 11.26(s, 1 H), 8.08(m, 1 H), 7.65(m, 1 H), 7.49-7.43(m, 2 H), 7.15-7.13(m, 1 H), 7.03-7.01(m, 1 H), 6.78-3.74(m, 1 H), 2.94(s, 1 H), 2.30(s, 3 H), 2.05-2.03(m, 7 H), 1.62(s, 3 H), 1.36(m, 2 H), 0.97-0.95(m, 2 H). | 602.0 [M + H]$^+$ |

TABLE 4-continued

NMR and MS data of the embodiments

| Embodiment | Compound | NMR | MS m/z: |
|---|---|---|---|
| 28 | WX079 | $^1$H NMR (400 MHz, CDCl$_3$-d) δ 11.05(s, 1 H), 8.16(d, J = 5.2 Hz, 1 H), 7.47(dd, J = 9.6 Hz, J = 2.0 Hz, 1 H), 7.42(d, J = 9.6 Hz, 1 H), 6.70(t, J = 8.4 Hz, 1 H), 6.52(d, J = 5.2 Hz, 1 H), 6.39(s, 1 H), 4.67(br. s., 2 H), 2.95-2.91(m, 1 H), 2.41(s, 3 H), 1.61(s, 3 H), 1.41-1.35(m, 2 H), 0.98-0.93(m, 2 H). | 559.0 [M + H]$^+$ |
| 29 | WX086 | $^1$H NMR (400 MHz, CDCl$_3$-d) δ 11.11(s, 1 H), 7.54(d, J = 7.6 Hz, 1 H), 7.46(dd, J = 9.6 Hz, J = 1.6 Hz, 1 H), 7.41(d, J = 8.4 Hz, 1 H), 6.99(d, J = 7.2 Hz, 1 H), 6.70(t, J = 8.4 Hz, 1 H), 6.23(s, 1 H), 3.12(s, 3 H), 2.91-2.98(m, 1 H), 2.30(s, 3 H), 2.08(s, 3 H), 1.59(s, 3 H), 1.38(td, J = 7.2 Hz, J = 2.8 Hz, 2 H), 0.95(q, J = 4.0 Hz, 2 H). | 650.1 [M + H]$^+$ |
| 30 | WX096 | $^1$H NMR (400 MHz, CDCl$_3$-d) δ 11.16(s, 1 H), 7.80(d, J = 8.0 Hz, 1 H), 7.48(d, J = 9.6 Hz, 1 H), 7.43(d, J = 8.4 Hz, 1 H), 7.11(s, 1 H), 6.95(d, J = 7.2 Hz, 1 H), 6.72(t, J = 8.4 Hz, 1 H), 2.99-2.93(m, 1 H), 2.32(s, 3 H), 2.25(s, 3 H), 2.03(s, 3 H), 1.61(s, 3 H), 1.42-1.36(m, 2 H), 1.00-0.95(m, 2 H). | 614.0 [M + H]$^+$ |
| 31 | WX106 | $^1$H NMR (400 MHz, DMSO-d$_6$) δ 11.32(s, 1 H), 7.73(d, J = 10.0 Hz, 1 H), 7.53(d, J = 8.8 Hz, 1 H), 7.46(d, J = 6.0 Hz, 1 H), 7.35(t, J = 7.2 Hz, 1 H), 7.22(d, J = 7.2 Hz, 1 H), 6.89(d, J = 8.0 Hz, 1 H), 4.73-4.58(m, 2 H), 3.09-3.04(m, 1 H), 3.02(s, 3 H), 2.23(s, 3 H), 2.15(s, 3 H), 1.45(s, 3 H), 1.23(brs, 2 H), 1.00-0.85(m, 2 H). | 649.1 [M + H]$^+$ |
| 32 | WX108 | $^1$H NMR (400 MHz, DMSO-d$_6$) δ 11.30(s, 1 H), 7.70(dd, J = 10.4 Hz, J = 2.0 Hz, 1 H), 7.51(d, J = 8.8 Hz, 1 H), 7.47(d, J = 7.6 Hz, 1 H), 7.31(t, J = 10.4 Hz, 1 H), 7.18(d, J = 7.2 Hz, 1 H), 6.86(t, J = 8.8 Hz, 1 H), 4.66(s, 2 H), 3.08-2.98(m, 1 H), 2.78-2.60(m, 1 H), 2.21(s, 3 H), 2.13(s, 3 H), 1.42(s, 3 H), 1.30-1.08(m, 2 H), 1.00-0.85(m, 6 H). | 675.0 [M + H]$^+$ |
| 33 | WX111 | $^1$H NMR (400 MHz, DMSO-d$_6$) δ 11.30(s, 1 H), 7.71(d, J = 8.4 Hz, 1 H), 7.50(br. s., 1 H), 7.36(br. s., 2 H), 7.29(br. s., 1 H), 7.17(br. s., 1 H), 6.86(br. s., 1 H), 3.03(br. s., 1 H), 2.22(s, 3 H), 2.05(s, 3 H), 1.43(s, 3 H), 1.20(br. s., 2 H), 0.91(br. d., J = 12.4 Hz, 2 H). | 556.8 [M + H]$^+$ |
| 34 | WX112 | $^1$H NMR (400 MHz, CDCl$_3$-d) δ 10.97(s, 1 H), 7.69-7.67(d, J = 7.20, 1 H), 7.38-7.32(m, 3 H), 7.02-7.01(d, J = 1.60, 1 H), 7.00(s, 1 H), 6.66-6.64(t, J = 8.00, 1 H), 3.05(s, 3 H), 2.89-2.85(m, 1 H), 2.56(s, 3 H), 1.52(s, 3 H), 1.32-1.29(m, 2 H), 0.90-0.88(s, 2 H). | 586.0 [M + H]$^+$ |
| 35 | WX116 | WX116: $^1$H NMR (400 MHz, CDCl$_3$-d) δ 7.99 -7.94(s, 4 H), 7.41-7.40(m, 3 H), 7.13(m, 1 H), 6.07-6.05(m, 1 H), 4.38-4.37(d, J = 6.00, 2 H), 2.86-2.82(m, 1 H), 2.53(m, 3 H), 2.33(s, 3 H),1.67(s, 3 H), 1.50-1.47(s, 9 H), 0.95-0.90(m, 2 H), 0.87-0.84(m, 2 H). | 670.0 [M + H]$^+$ |
|  | WX117 | WX117: $^1$H NMR (400 MHz, CDCl$_3$-d) δ 10.97(s, 1 H), 7.69-7.67(d, 1 H), 7.38-7.33(m, 3 H), 7.02-7.00(d, 1 H), 6.89-6.83(br.s, 1 H), 6.66-6.64(t, J = 6.00, 1 H), 3.05-3.02(s, 3 H)2.90-2.84(m, 1 H), 2.26(s, 3 H), 1.56-1.52(s, 3 H), 1.32-1.29(m, 2 H), 0.90-0.79(m, 2 H). SFC detection method: Chiral column: AS(250 mm*30 mm, 5 μm); mobile phase: [0.1% NH$_3$H$_2$O EtOH]; B %: 40%-40%, min. The retention times of the compound WX116 and WX117 were 4.522 min and 4.166 min respectively, the ratio was 1:1. | 669.9 [M + H]$^+$ |
| 36 | WX115 | $^1$H NMR (400 MHz, CDCl$_3$-d) δ 10.98(s, 1 H), 9.58(s, 1 H), 8.40(s, 1 H), 7.88(s, 1 H), 7.50-7.43(m, 2 H), 6.72(t, J = 8.6 Hz, 1 H), 2.99-2.95(m, 1 H), 2.42(s, 3 H), 2.30(s, 3 H), 1.62(s, 3 H), 1.45-1.39(m, 2 H), 1.02-0.95(m, 2 H). | 601.8 [M + H]$^+$ |
| 37 | WX113 | WX113: $^1$H NMR (400 MHz, DMSO-d$_6$) δ 11.31(s, 1 H), 9.22(s, 1 H), 7.73(dd, J = 10.0 Hz, J = 1.6 Hz, 1 H), 7.53(d, J = 8.4 Hz, 1 H), 7.43-7.38(m, 1 H), 7.36-7.30(m, 1 H), 7.12(d, J = 7.6 Hz, 1 H), 6.89(t, J = 8.0 Hz, 1 H), 3.08-3.04(m, 1 H), 3.02(s, 3 H), 2.24(s, 3 H), 2.07(s, 3 H), 1.45(s, 3 H), 1.27-1.16(m, 2 H), 1.00-0.86(m, 2 H). | 650.0 [M + H]$^+$ |
|  | WX114 | WX114: $^1$H NMR (400 MHz, DMSO-d$_6$) δ 11.31(s, 1 H), 9.22(s, 1 H), 7.73(dd, J = 10.4 Hz, J = 2.0 Hz, 1 H), 7.53(d, J = 8.8 Hz, 1 H), 7.43-7.38(m, 1 H), 7.36-7.30(m, 1 H), 7.12(d, J = 7.6 Hz, 1 H), 6.89(t, J = 8.4 Hz, 1 H), 3.08-3.04(m, 1 H), 3.02(s, 3 H), 2.24(s, 3 H), 2.07(s, 3 H), 1.45(s, 3 H), 1.27-1.15(m, 2 H), 1.01-0.85(m, 2 H). SFC detection method: column: Chiralpak | 650.0 [M + H]$^+$ |

TABLE 4-continued

NMR and MS data of the embodiments

| Embodiment | Compound | NMR | MS m/z: |
|---|---|---|---|
| | | OJ-3 100 × 4.6 mm I.D., 3 μm; mobile phase: A: $CO_2$ B: methanol (0.05% DEA); gradient: from 5% B to 40% B at a constant speed in 4.5 minutes, 40% B for 2.5sminutes, 5% B for 1 minute; flow rate: 2.8 mL/min; column temperature: 40° C. The retention times of the compound WX113 and WX114 were 4.503 min and 4.166 min respectively, the ratio was 1:1. | |
| 38 | WX088 | $^1$H NMR (400 MHz, CDCl$_3$-d) δ 7.99-7.94(s, 4 H), 7.41-7.40(m, 3 H), 7.13(m, 1 H), 6.07-6.05(m, 1 H), 4.38-4.37(d, J = 6.00, 2 H), 2.86-2.82(m, 1 H), 2.53(m, 3 H), 2.33(m, 3 H), 1.67(s, 3 H), 1.50-1.47(m, 9 H), 0.95-0.90(m, 2 H), 0.87-0.84(m, 2 H). | 551.1 [M + H]$^+$ |
| 39 | WX068 | $^1$H NMR (400 MHz, CDCl$_3$-d) δ 11.12(s, 1 H), 7.52-7.44(m, 2 H), 7.42(d, J = 8.4 Hz, 1 H), 7.38-7.34(m, 1 H), 7.26-7.21(m, 1 H), 7.20(br. s., 1 H), 6.70(t, J = 8.4 Hz, 1 H), 4.17-3.93(m, 2 H), 2.96-2.92(m, 1 H), 2.58(s, 3 H), 2.49(s, 3 H), 2.41(s, 3 H), 1.42-1.34(m, 2 H), 1.01-0.91(m, 2 H). | 619.1 [M + H]$^+$ |
| 40 | WX069 | $^1$H NMR (400 MHz, CDCl$_3$-d) δ 11.09(s, 1 H), 7.40-7.32(m, 3 H), 7.24(d, J = 8.0 Hz, 1 H), 7.07-7.03(m, 2 H), 6.64(t, J = 8.4 Hz, 1 H), 6.12(br. s., 1 H), 4.47-4.33(m, 2 H), 2.89-2.83(m, 1 H), 2.30(s, 3 H), 1.97(s, 3 H), 1.52(s, 3 H), 1.34-1.26(m, 2 H), 0.92-0.84(m, 2 H). | 614.0 [M + H]$^+$ |
| 41 | WX087 | $^1$H NMR (400 MHz, CDCl$_3$-d) δ 11.07(s, 1 H), 7.36(dd, J = 9.6 Hz, J = 2.0 Hz, 1 H), 7.33(d, J = 8.8 Hz, 1 H), 7.16(t, J = 7.6 Hz, 1 H), 6.64-6.58(m, 2 H), 6.45(d, J = 7.2 Hz, 1 H), 6.38(s, 1 H),4.04(br. s., 1 H), 3.56(t, J = 6.4 Hz, 2 H), 3.33(s, 3 H), 3.23(t, J = 5.0 Hz, 2 H), 2.88-2.81(m, 1 H), 2.31(s, 3 H), 1.53(s, 3 H), 1.32-1.24(m, 2 H), 0.91-0.84(m, 2 H). | 616.1 [M + H]$^+$ |
| 42 | WX093 | $^1$H NMR (400 MHz, CDCl$_3$-d) δ 11.18(s, 1 H), 7.48(dd, J = 10.0 Hz, J = 2.0 Hz, 1 H), 7.43(d, J = 9.6 Hz, 1 H), 7.26(d, J = 7.6 Hz, 1 H), 6.76-6.68(m, 2 H), 6.61-6.64(m, 2 H), 3.87(t, J = 5.2 Hz, 2 H), 3.35(t, J = 5.0 Hz, 2 H), 2.98-2.92(m, 1 H), 2.43(s, 3 H), 1.62(s, 3 H), 1.41-1.34(m, 2 H), 1.28(br. s., 1 H), 1.00-0.92(m, 2 H). | 602.0 [M + H]$^+$ |
| 43 | WX097 | $^1$H NMR (400 MHz, DMSO-d$_6$) δ 11.26(s, 1 H), 9.07(br. s., 1 H), 7.72(dd, J = 10.0 Hz, J = 1.6 Hz, 1 H), 7.57(d, J = 4.8 Hz, 1 H), 7.52(d, J = 4.8 Hz, 1 H), 7.48-7.44(m, 1 H), 7.42-7.36(m, 1 H), 7.09(d, J = 7.6 Hz, 1 H), 6.85(t, J = 10.0 Hz, 1 H), 4.22-4.10(m, 2 H), 3.09-3.01(m, 1 H), 2.56(t, J = 5.0 Hz, 3 H), 2.34(s, 3 H), 1.43(s, 3 H), 1.25-1.16(m, 2 H), 0.96-0.84(m, 2 H). | 608.0 [M + Na-HCl]$^+$ |
| 44 | WX099 | $^1$H NMR (400 MHz, DMSO-d$_6$) δ 11.30(s, 1 H), 8.62(s, 1 H), 7.72(d, J = 10.0 Hz, 1 H), 7.52(d, J = 8.0 Hz, 1 H), 7.44-7.36(m, 2 H), 7.33(t, J = 7.6 Hz, 1 H), 6.87(t, J = 8.8 Hz, 1 H), 6.83(d, J = 7.2 Hz, 1 H), 6.05(br. s., 1 H), 3.08-3.00(m, 1 H), 2.64(d, J = 3.2 Hz, 3 H), 2.34(s, 3 H), 1.45(s, 3 H), 1.26-1.16(m, 2 H), 0.98-0.84(m, 2 H). | 615.1 [M + H]$^+$ |
| 45 | WX104 | $^1$H NMR (400 MHz, DMSO-d$_6$) δ 11.28(s, 1 H), 8.36(s, 1 H), 7.70(d, J = 10.4 Hz, 1 H), 7.50(d, J = 8.0 Hz, 1 H), 7.40(s, 1 H), 7.35-7.28(m, 1 H), 7.28-7.22(m, 1 H), 6.85(t, J = 8.8 Hz, 1 H), 6.79(d, J = 6.8 Hz, 1 H), 6.02(s, 1 H), 3.06-2.96(m, 1 H), 2.31(s, 3 H), 1.43(s, 3 H), 1.26(s, 9 H), 1.22-1.14(m, 2 H), 0.95-0.81(m, 2 H). | 657.3 [M + H]$^+$ |
| 46 | WX098 | $^1$H NMR (400 MHz, DMSO-d$_6$) δ 11.25(s, 1 H), 10.16(br. s., 1 H), 7.72 (dd, J = 9.8 Hz, J = 2.0 Hz, 1 H), 7.62-7.56(m, 2 H), 7.55-7.49(m, 2 H), 7.48-7.43(m, 1 H), 6.85(t, J = 8.6 Hz, 1 H), 4.37-4.24(m, 2 H), 3.10-3.02(m, 1 H), 2.76(d, J = 4.4 Hz, 3 H), 2.71(d, J = 4.8 Hz, 3 H), 2.37(s, 3 H), 1.44(s, 3 H), 1.26-1.16(m, 2 H), 0.98-0.84(m, 2 H). | 600.0 [M+H-HCl]$^+$ |
| 47 | WX101 | $^1$H NMR (400 MHz, CDCl$_3$-d) δ 11.20(s, 1 H), 7.46(dd, J = 9.6 Hz, J = 2.0 Hz, 1 H), 7.41(d, J = 8.4 Hz, 1 H), 7.05(t, J = 7.6 Hz, 1 H), 6.71(t, J = 7.6 Hz, 1 H), 6.58-6.49(m, 3 H), 3.98(s, 2 H), 2.91-2.86(m, 1 H), 2.55(s, 3 H), 1.63(s, 3 H), 1.36-1.30(m, 2 H), 0.90-0.84(m, 2 H). | 572.2 [M + H]$^+$ |
| 48 | WX091 | $^1$H NMR (400 MHz, CDCl$_3$-d) δ 11.05(s, 1 H), 7.40-7.31(m, 3 H), 7.11(s, 1 H), 6.89(s, 1 H), 6.81-6.79(d, J = 7.2 Hz, 1 H), 6.71(s, 1 H), 6.64-6.60(t, J = 8.4 Hz, 1 H), 5.38-5.29(d, J = 36.8 Hz, 1 H), 2.89-2.83(m, | 661.9 [M + H]$^+$ |

TABLE 4-continued

NMR and MS data of the embodiments

| Embodiment | Compound | NMR | MS m/z: |
|---|---|---|---|
| | WX095 | 1 H), 2.31(s, 3 H), 1.52(s, 3 H), 1.30-1.28(m, 11 H), 0.88(m, 2 H).<br>$^1$H NMR (400 MHz, CDCl$_3$-d) δ 11.14(s, 1 H), 7.49-7.42(m, 1 H), 7.38-7.36(m, 1 H), 6.99-6.97(m, 1 H), 6.75-6.72(m, 1 H), 2.96-2.94(m, 1 H), 2.40(s, 3 H), 1.61(s, 3 H), 1.45(m, 9 H), 1.39-1.37(m, 2 H), 0.99(m, 2 H). | 677.9 [M + H]$^+$ |
| 49 | WX065 | $^1$H NMR (400 MHz, CDCl$_3$-d) δ 11.36(s, 1 H), 8.72(s, 1 H), 7.98(s, 1 H), 7.52-7.46(t, J = 9.6, 2 H), 7.19-7.15(t, J = 7.6, 2 H), 6.98-6.96(d, J = 7.2, 1 H), 6.84-6.79(t, J = 9.2 Hz, 2 H), 4.94-4.92(d, J = 5.6 Hz, 2 H), 4.76-4.70(m, 2 H), 3.79-3.75(t, J = 7.6 Hz, 1 H), 2.95(s, 1 H), 2.39(s, 3 H), 1.63(s, 3 H), 1.39-1.37(m, 2 H), 0.98(m, 2 H). | 664.0 [M + Na]$^+$ |
| 50 | WX066 | $^1$H NMR (400 MHz, CDCl$_3$-d) δ 11.14(s, 1 H), 7.48-7.42(m, 1 H), 7.24(s, 1 H), 7.14(m, 1 H), 7.04-7.03(d, J = 7.6, 1 H), 6.72-6.70(t, J = 8.0 Hz, 2 H), 3.10(s, 3 H), 2.95(m, 1 H), 2.42(s, 3 H), 1.60(s, 3 H), 1.39-1.37(m, 2 H), 0.97(m, 2 H). | 658.0 [M + Na]$^+$ |
| 51 | WX067 | $^1$H NMR (400 MHz, CDCl$_3$-d) δ 11.08(s, 1 H), 7.60-7.56(t, J = 8.0 Hz, 1 H), 7.48-7.41(m, 4 H), 7.34-7.33(m, 1 H), 6.73-6.69(t, J = 8.4, 1 H), 3.45(s, 6 H), 2.98-2.92(m, 1 H), 2.47(s, 3H), 1.60(s, 3 H), 1.40-1.38(m, 2 H), 0.98(m, 2 H). | 713.9 [M + H]$^+$ |
| 52 | WX080 | $^1$H NMR (400 MHz, CDCl$_3$-d) δ 11.13(s, 1 H), 8.38(s, 1 H), 7.60(s, 1 H), 7.50-7.40(s, 1 H), 7.50-7.40(m, 4 H), 7.00-6.97(d, J = 7.6 Hz, 1 H), 6.70(s, 1 H), 4.02(s, 2 H), 3.54-3.51(s, 3 H), 2.96-2.90(m, 1 H), 2.39(s, 3 H), 1.60(s, 3 H), 1.38-1.31(m, 2 H), 0.97-0.96(m, 2 H). | 630.0 [M + H]$^+$ |
| 53 | WX081 | $^1$H NMR (400 MHz, CDCl$_3$-d) δ 11.13(s, 1 H), 8.42(s, 1 H), 7.60-7.53(s, 1 H), 7.48-7.47(d, J = 1.6 Hz, 1 H), 7.45-7.40(m, 3 H), 7.01-6.99(d, J = 7.6 Hz, 1 H), 6.72-6.70(d, J = 8.4 Hz, 1 H), 4.83(s, 1 H), 3.51-3.45(s, 6 H), 2.96-2.91(m, 1 H), 2.40(s, 3 H), 1.60(s, 3 H), 1.37-1.35(m, 2 H), 0.97-0.96(m, 2 H). | 660.0 [M + H]$^+$ |
| 54 | WX082 | $^1$H NMR (400 MHz, CDCl$_3$-d) δ 11.13(s, 1 H), 7.48-7.41(m, 3 H), 7.27(s, 1 H), 7.16-7.15(d, J = 1.6 Hz, 1 H), 7.02-7.00(d, J = 8.0 Hz, 1 H), 6.72(m, 1 H), 3.25-3.19(m, 2 H), 2.96-2.93(m, 1 H), 2.42(s, 3 H), 1.60(s, 3 H), 1.41-1.37(m, 5 H), 0.97(s, 3 H). | 650.1 [M + H]$^+$ |
| 55 | WX085 | $^1$H NMR (400 MHz, CDCl$_3$-d) δ 11.20(s, 1 H), 7.50-7.47(d, J = 2.0 Hz, 1 H), 7.45-7.43(d, J = 7.2 Hz, 1 H), 7.35(m, 1 H), 7.25(s, 1 H), 6.90-6.88(d, J = 7.6 Hz, 1 H), 6.75-6.73(m, 2 H), 3.76-3.74(m, 4 H), 3.52-3.49(m, 4 H), 2.96-2.92(s, 1 H), 2.43(s, 3 H), 1.61(s, 3 H), 1.38-1.36(m, 2 H), 0.98(m, 2 H). | 671.1 [M + H]$^+$ |
| 56 | WX089 | $^1$H NMR (400 MHz, CDCl$_3$-d) δ 11.15(s, 1 H), 7.48-7.39(m, 3 H), 7.26(m, 1 H), 7.22-7.20(d, J = 7.6 Hz, 1 H), 7.03-7.01(m, 2 H), 6.74-6.72(t, J = 8.4 Hz, 1 H), 2.95(m, 1 H), 2.59-2.58(s, 1H), 2.41(s, 3 H), 1.59(s, 3 H), 1.38-1.36(s, 3 H), 1.26-1.12(m, 2 H), 1.04-0.97(m, 2 H). | 661.9 [M + H]$^+$ |
| 57 | WX094 | $^1$H NMR (400 MHz, CDCl$_3$-d) δ 11.29(s, 1 H), 9.78(s, 1 H), 7.73-7.71(t, J = 6.4 Hz, 1 H), 7.54-7.49(t, J = 6.4 Hz, 2 H), 7.42-7.38(m., 2 H), 6.95-6.93(m, 1 H), 6.87(m, 1 H), 3.67(s, 3 H), 3.05-3.02(m, 1 H), 2.33(s, 3 H), 1.45(s, 3 H), 1.23-1.20(m, 2 H), 0.92-0.90(m, 2 H). | 616.0 [M + H]$^+$ |

Biological Experiment

Biological Test Method 1: MEK Lance Ultra Experiment

Compounds were serially diluted three-fold to 10 concentrations, two duplicates were set. Final test concentrations of the compounds ranged from 10 μM to 0.51 nM. 0.07 nM activated MEK1 (Millipore #14-429) and 2 nM non-activated ERK (Millipore #14-515) were mixed with the compounds or DMSO, the mixture was incubated at 23° C. for 30 minutes. Then 50 nM ULight labeled MBP (PerkinElmer #TRF0109-M) and 50 μM ATP (Invitrogen #PV3227) were added to initiate the reaction, and the mixture was incubated at 23° C. for 90 minutes. After the reaction was stopped by adding EDTA at a final concentration of 15 mM, 2 nM Eu-labeled anti-phosphorylated antibody (PerkinElmer #TRF0201-M) was added and incubated for 1 hour. The fluorescence signal data (excitation band: 320 nm; emission band: 665 nM/615 nM) was determined by an Envision microplate reader (PerkinElmer). XLfit5 software was used for data analysis and mapping. The experimental results are shown in Table 5.

Biological Test Method 2: Cell Viability Experiment

HT29 and A375 cells were plated in a 96-well cell culture plate at a density of 40,000 cells/well and 20,000 cells/well respectively, and the cells were cultured overnight. The compounds were serially diluted in a gradient of 1:3, the dilutions were added to the cell culture medium, and incubated with the cells in a 37° C. incubator for 3 days. The 96-well cell culture plate was taken from the incubator and equilibrated at room temperature for 30 minutes, then Cell Titer-Glo reagent (Promega Cat #G7573) was added at a ratio of 1:2, and the mixture was mixed thoroughly on a shaker for 2 minutes to promote cell lysis. The cell culture plate was incubated at room temperature for 10 minutes and then read on an Envision microplate reader (PerkinElmer). XLfit5 software was used for data analysis and mapping. The experimental results are shown in Table 5.

TABLE 5

Results of in vitro screening test for the compounds of the present disclosure

| Embodiment | Compound | MEK potency IC$_{50}$ (nM) | HT29 IC$_{50}$ (nM) | A375 IC$_{50}$ (nM) |
|---|---|---|---|---|
| 1 | WX040 | 580.67 | 64.06 | 69.67 |
| 2 | WX049 | 67.03 | 7.40 | 3.08 |
| 3 | WX053 | 92.85 | 9.19 | 3.27 |
| 4 | WX054 | 81.55 | 334.19 | 483.58 |
| 5 | WX055 | 71.12 | 977.78 | 643.04 |
| 6 | WX056 | 54.10 | 2824.07 | 1547.70 |
| 7 | WX057 | 78.01 | 72.48 | 24.15 |
| 8 | WX058 | 82.98 | 102.25 | 91.08 |
| 9 | WX059 | 32.40 | 923.28 | 1645.53 |
| 10 | WX060 | 86.42 | 114.96 | 66.91 |
| 11 | WX061 | 57.55 | 445.61 | 442.09 |
| 12 | WX062 | 67.97 | 744.71 | 631.17 |
| 13 | WX109 | 119.48 | 90.69 | 29.25 |
| 14 | WX110 | 93.64 | 207.47 | 94.50 |
| 15 | WX118 | 32.71 | 1.76 | 0.41 |
|  | WX119 | 18.20 | 19.27 | 5.85 |
| 16 | WX034 | 27.79 | 6.39 | 1.48 |
| 17 | WX035 | 110.61 | 98.80 | 32.89 |
| 18 | WX039 | 51.99 | 4.27 | 1.61 |
| 19 | WX048 | 580.87 | 101.28 | 52.58 |
| 20 | WX071 | 66.05 | 4.05 | 2.99 |
| 21 | WX083 | 146.30 | 10.54 | 8.62 |
|  | WX084 | 175.52 | 17.37 | 6.18 |
| 22 | WX092 | 177.93 | 8.96 | 7.54 |
| 23 | WX100 | 113.66 | 6.84 | 2.11 |
| 24 | WX102 | 12.35 | 2.05 | 0.37 |
| 25 | WX103 | 48.92 | 20.31 | 6.58 |
| 26 | WX105 | 282.44 | 16.16 | 8.19 |
| 27 | WX036 | 44.27 | 68.96 | 33.65 |
| 28 | WX079 | 35.30 | 5.52 | 3.23 |
| 29 | WX086 | 29.62 | 0.62 | 0.40 |
| 30 | WX096 | 8.73 | 10.28 | 2.47 |
| 31 | WX106 | 29.94 | 5.89 | 2.32 |
| 32 | WX108 | 29.60 | 13.12 | 2.30 |
| 33 | WX111 | 14.39 | 14.89 | 3.56 |
| 34 | WX112 | 52.93 | 20.29 | 6.04 |
| 35 | WX116 | 34.45 | 0.82 | 0.39 |
|  | WX117 | 423.53 | 18.72 | 7.18 |
| 36 | WX115 | 40.31 | 15.71 | 5.09 |
| 37 | WX113 | 5.61 | 0.82 | 0.37 |
|  | WX114 | 20.86 | 30.15 | 10.58 |
| 38 | WX088 | 45.42 | 4.59 | 2.13 |
| 39 | WX068 | 34.95 | 9.77 | 3.66 |
| 40 | WX069 | 41.60 | 40.29 | 6.63 |
| 41 | WX087 | 152.20 | 23.66 | 9.42 |
| 42 | WX093 | 109.83 | 23.37 | 8.80 |
| 43 | WX097 | 29.51 | 105.10 | 17.22 |
| 44 | WX099 | 49.12 | 12.36 | 4.72 |
| 45 | WX104 | 118.74 | 28.14 | 10.44 |
| 46 | WX098 | 28.54 | 90.27 | 11.90 |
| 47 | WX101 | 17.40 | 12.62 | 1.76 |
| 48 | WX091 | 127.53 | 35.62 | 10.14 |
|  | WX095 | 48.58 | 1.77 | 0.79 |
| 49 | WX065 | 36.25 | 7.38 | 4.31 |
| 50 | WX066 | 77.27 | 7.44 | 4.58 |
| 51 | WX067 | 198.61 | 75.33 | 25.05 |
| 52 | WX080 | 70.48 | 11.21 | 3.20 |
| 53 | WX081 | 104.50 | 12.96 | 5.26 |
| 54 | WX082 | 97.43 | 3.93 | 1.75 |
| 55 | WX085 | 117.87 | 9.34 | 4.65 |
| 56 | WX089 | 61.07 | 1.32 | 0.47 |
| 57 | WX094 | 45.23 | 18.88 | 5.47 |

Conclusion:

The biological test data shows that the compounds of the present disclosure all have good MEK biological activity and tumor cell growth inhibitory activity.

Biological Test Method 3: In Vivo Pharmacodynamics Study on HT-29 Cell Subcutaneous Xenograft Tumor Model in BALB/c Nude Mouse Human colon cancer HT-29 cells (ATCC-HTB-38) were cultured in monolayer in vitro, with McCoy's 5a medium (Gibco, 1835937) supplemented with 10% fetal bovine serum, 100 U/mL penicillin and 100 μg/mL streptomycin, at 37° C. under 5% $CO_2$. The cells were conventionally digested with trypsin-EDTA and passaged twice a week. When the cell saturation was 80%-90%, the cells were collected, counted and inoculated. 0.1 mL ($5\times10^6$) of HT-29 cells was subcutaneously inoculated into the right back of each nude mouse. When the average tumor volume reached 100-180 mm³, the animals were grouped and administration was started (QD, 14-21 days). The diameter of the tumor was measured twice a week with a vernier caliper. The tumor volume is calculated by the formula: $V=0.5\times a\times b^2$, wherein a and b represent the length and width respectively. The antitumor activity of the compounds was evaluated by TGI (%), which reflects the tumor growth inhibition rate. Calculation of TGI (%): TGI (%)=[(1−(average tumor volume at the end of administration in a treatment group−average tumor volume at the start of treatment in this treatment group))/(average tumor volume at the end of treatment in the solvent control group−average tumor volume at the start of treatment in the solvent control group)]×100%. The experimental results are shown in Table 6.

TABLE 6

Pharmacodynamic test results:

| Embodiment | Compound | Dose (mpk) | TGI (%) | Dosage regimen |
|---|---|---|---|---|
| 16 | WX034 | 3 | 90.6 | QD, 21 days |
| 20 | WX071 | 0.5 | 91 | QD, 21 days |
| 29 | WX086 | 0.5 mpk (0-11 D): 0.35 mpk (12-21 D) | 83.1 | QD, 21 days |
| 37 | WX113 | 0.2 | 82.8 | QD, 25 days (5 days administration, and 2 days break) |
| 50 | WX066 | 0.5 | 89 | QD, 21 days |

Conclusion:

The compounds of the present disclosure have a good tumor growth inhibitory activity.

Biological Test Method 4: Pharmacokinetics Study of the Compounds in C57BL/6 Mice Experimental Materials:

C57BL/6 mice (male, 18-22 g, 7-9 weeks old, Shanghai Lingchang)

Experimental Procedure:

The pharmacokinetic characteristics of the compounds in rodents were determined after intravenous and oral administration of the compounds by standard protocols. In the experiment, candidate compounds were formulated into clear solutions, and intravenously and orally administrated to rats in a single dose. The menstruum for intravenous and oral administration was DMSO, PEG and water at a certain ratio or Solutol, HPMC and SLS aqueous solutions at a certain ratio. The whole blood samples within 24 hours were collected, centrifuged at 3,000 rpm for 15 minutes, and the supernatants were isolated to obtain plasma samples. An acetonitrile solution containing an internal standard with a volume of 4 times as the plasma sample volume was added to precipitate the protein. After centrifugation, the supernatant was collected and an equal volume of water was added. After centrifugation, the supernatant was collected and injected to quantitatively analyze the blood drug concentration by LC-MS/MS analysis method, and the pharmacokinetic parameters were calculated, e.g., peak concentration, peak time, clearance, half-life, area under the drug concentration-time curve, bioavailability, etc.

Experimental Results:

TABLE 7

Pharmacokinetic test results

| Samples (compounds prepared by the corresponding embodiments) | Compound | Half life $T_{1/2}$ (h) | Clearance (mL/min/kg) | Comcentration quadrature AUC (nM · hr) | Bioavailability F (%) |
|---|---|---|---|---|---|
| Embodiment 16 | WX034 | 5.41 | 1.84 | 30472 | 68.7 |
| Embodiment 20 | WX071 | 5.28 | 0.912 | 58155 | 83.0 |
| Embodiment 29 | WX086 | 7.00 | 2.20 | 23364 | 76.8 |
| Embodiment 37 | WX113 | 4.64 | 2.92 | 17588 | 73.1 |
| Embodiment 50 | WX066 | 7.62 | 1.85 | 28564 | 99.2 |

Conclusion: The compounds of the present disclosure have good pharmacokinetic indexes in rats.

What is claimed is:

1. A compound represented by formula (I), a pharmaceutically acceptable salt thereof or a tautomer thereof:

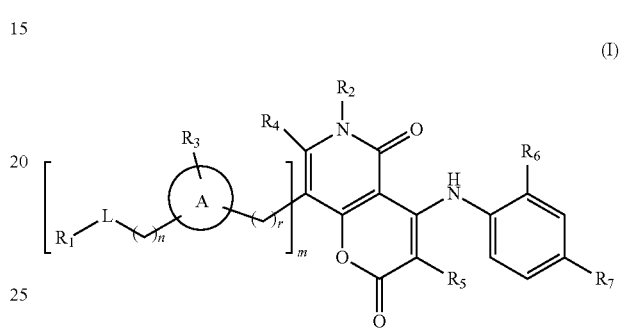

(I)

wherein, n is selected form 0, 1 or 2;

r is selected from 0, 1, 2 or 3;

m is selected from 0 or 1; when m is 0, then

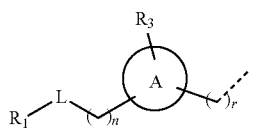

is H;

ring A is selected from phenyl or 5-6 membered heteroaryl;

L is selected from a single bond, —S(=O)—, —S(=O)$_2$—, —C(=O)—, —NH—, —NH—C(=O)—, —NH—C(=O)—O—, —NH—S(=O)$_2$—, —NH—S(=O)— and —NH—C(=O)—NH—, wherein the —NH—, —NH—C(=O)—, —NH—C(=O)—O—, —NH—S(=O)$_2$—, —NH—S(=O)— and —NH—C(=O)—NH— are each optionally substituted by 1, 2 or 3 R;

$R_1$ is selected from H, NH$_2$, $C_{1-6}$ alkyl, 3-6 membered heterocycloalkyl, $C_{3-6}$ cycloalkyl and $C_{1-3}$ heteroalkyl, wherein the $NH_2$, $C_{1-6}$ alkyl, 3-6 membered heterocycloalkyl, $C_{3-6}$ cycloalkyl and $C_{1-3}$ heteroalkyl are each optionally substituted by 1, 2 or 3 R;

$R_2$ is selected from H, $C_{1-6}$ alkyl, $C_{1-6}$ heteroalkyl, $C_{3-6}$ cycloalkyl and 5-6 membered heterocycloalkyl, wherein the $C_{1-6}$ alkyl, $C_{1-6}$ heteroalkyl, $C_{3-6}$ cycloalkyl and 5-6 membered heterocycloalkyl are each optionally substituted by 1, 2 or 3 R;

$R_3$ is selected from H, F, Cl, Br, I, $C_{1-3}$ alkyl, $C_{1-3}$ alkoxy, $C_{2-4}$ alkynyl, $C_{2-4}$ alkenyl and phenyl, wherein the $C_{1-3}$ alkyl, $C_{1-3}$ alkoxy, $C_{2-4}$ alkynyl, $C_{2-4}$ alkenyl and phenyl are each optionally substituted by 1, 2 or 3 R;

$R_4$ and $R_5$ are independently selected from H, F, Cl, Br, I, $NH_2$, OH, $C_{1-6}$ alkyl and $C_{1-3}$ alkoxy, wherein the $C_{1-6}$ alkyl and $C_{1-3}$ alkoxy are each optionally substituted by 1, 2 or 3 R;

$R_6$ and $R_7$ are independently selected from H, F, Cl, Br, I, $CH_3$, Et, $CH_3$—O— and $CH_3$—$CH_2$—O—;

R is selected from F, Cl, Br, I, OH, $NH_2$, $C_{1-3}$ alkyl and $C_{1-3}$ heteroalkyl, wherein the $NH_2$, $C_{1-3}$ alkyl and $C_{1-3}$ heteroalkyl are each optionally substituted by 1, 2 or 3 R';

R' is selected from F, Cl, Br, I, $NH_2$ or $C_{1-3}$ alkyl;

each of the "hetero" in the 5-6 membered heteroaryl, 5-6 membered heterocycloalkyl, 3-6 membered heterocycloalkyl, and $C_{1-3}$ heteroalkyl is independently selected from —NH—, N, —O—, —S(=O)$_2$—, —S(=O)$_2$—NH—, —NH—S(=O)$_2$—NH—, —C(=O)—NH—, —S(=O)—, —C(=O)—, —S(=O)—NH— and —O—C(=O)—NH—;

in any of the above cases, the number of the heteroatom or heteroatomic group is independently selected from 1, 2, 3 or 4.

2. The compound, the pharmaceutically acceptable salt thereof or the tautomer thereof according to claim 1, wherein R' is selected from F, Cl, Br, I, $NH_2$ or $CH_3$.

3. The compound, the pharmaceutically acceptable salt thereof or the tautomer thereof according to claim 1, wherein R is selected from F, Cl, Br, I, OH, $NH_2$, methyl, ethyl, $C_{1-3}$ alkyl-S(=O)$_2$—NH—, $C_{1-3}$ alkyl-S(=O)$_2$—, $C_{1-3}$ alkyl-C(=O)—NH— and $C_{1-3}$ alkyl-O—, wherein the $NH_2$, methyl, ethyl, $C_{1-3}$ alkyl-S(=O)$_2$—NH—, $C_{1-3}$ alkyl-S(=O)$_2$—, $C_{1-3}$ alkyl-C(=O)—NH— and $C_{1-3}$ alkyl-O— are each optionally substituted by 1, 2 or 3 R'.

4. The compound, the pharmaceutically acceptable salt thereof or the tautomer thereof according to claim 3, wherein R is selected from F, Cl, Br, I, OH, $NH_2$, $CH_3$,

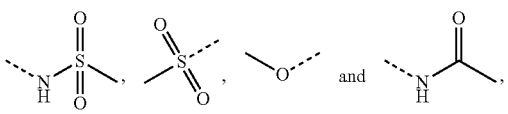

wherein the $NH_2$, $CH_3$,

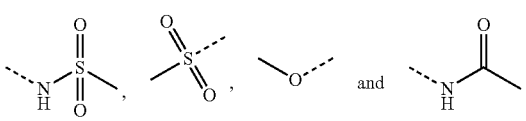

are each optionally substituted by 1, 2 or 3 R'.

5. The compound, the pharmaceutically acceptable salt thereof or the tautomer thereof according to claim 4, wherein R is selected from F, Cl, Br, I, OH, $NH_2$, $CH_3$,

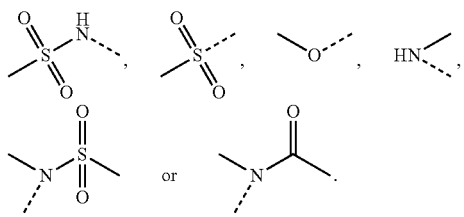

6. The compound, the pharmaceutically acceptable salt thereof or the tautomer thereof according to claim 1, wherein ring A is selected from phenyl, pyridyl or pyrazinyl.

7. The compound, the pharmaceutically acceptable salt thereof or the tautomer thereof according to claim 6, wherein ring A is selected from

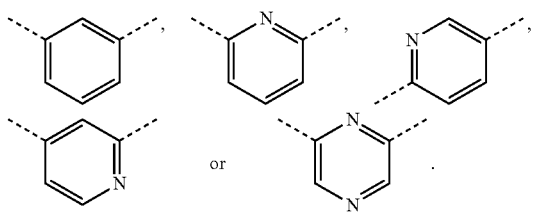

8. The compound, the pharmaceutically acceptable salt thereof or the tautomer thereof according to claim 1, wherein L is selected from a single bond, —NH—, —N($CH_3$)—,

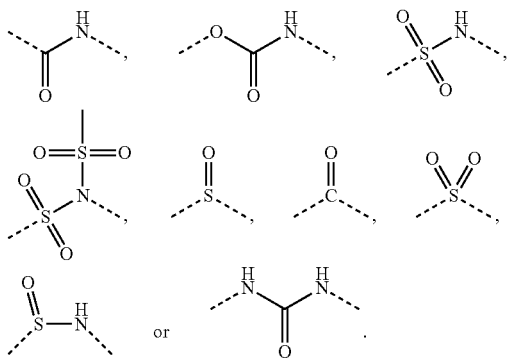

9. The compound, the pharmaceutically acceptable salt thereof or the tautomer thereof according to claim 1, wherein $R_1$ is selected from H, $NH_2$, methyl, ethyl, isobutyl, oxetanyl, morpholinyl, cyclopropyl and $CH_3$—O—, wherein the $NH_2$, methyl, ethyl, isobutyl, oxetanyl, morpholinyl, cyclopropyl and $CH_3$—O— are each optionally substituted by 1, 2 or 3 R.

10. The compound, the pharmaceutically acceptable salt thereof or the tautomer thereof according to claim 1, wherein $R_1$ is selected from H, $NH_2$, Me, Et,

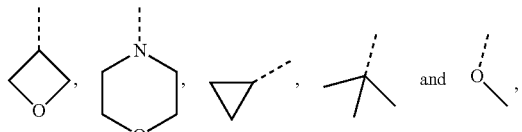

wherein the NH₂, Me, Et,

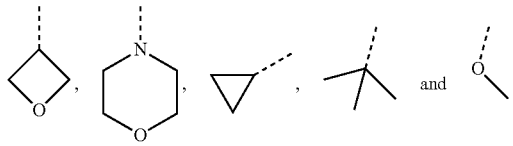

are each optionally substituted by 1, 2 or 3 R.

11. The compound, the pharmaceutically acceptable salt thereof or the tautomer thereof according to claim 10, wherein R₁ is selected from H, NH₂, CH₃, CF₃, Et,

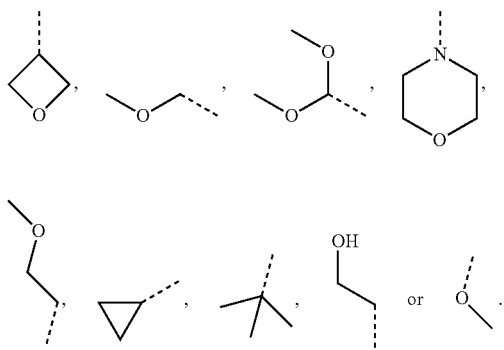

12. The compound, the pharmaceutically acceptable salt thereof or the tautomer thereof according to claim 1, wherein R₂ is selected from H, methyl, ethyl, propyl, cyclopropyl and tetrahydropyranyl, wherein the methyl, ethyl, propyl, cyclopropyl and tetrahydropyranyl are each optionally substituted by 1, 2 or 3 R.

13. The compound, the pharmaceutically acceptable salt thereof or the tautomer thereof according to claim 12, wherein R₂ is selected from H, CH₃,

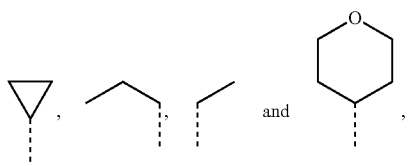

wherein the CH₃,

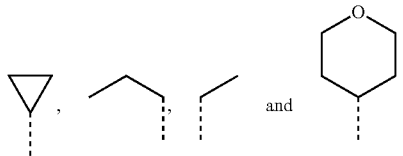

are each optionally substituted by 1, 2 or 3 R.

14. The compound, the pharmaceutically acceptable salt thereof or the tautomer thereof according to claim 13, wherein R₂ is selected from H, CH₃,

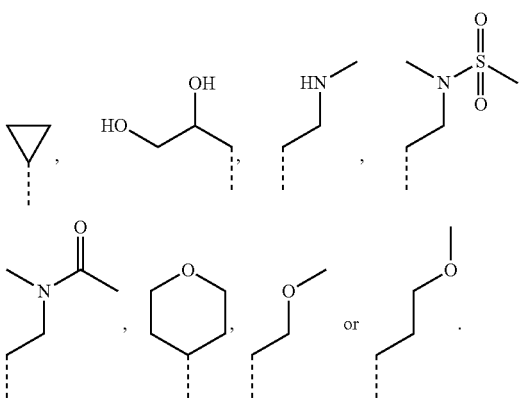

15. The compound, the pharmaceutically acceptable salt thereof or the tautomer thereof according to claim 1, wherein R₃ is selected from H, F, Cl, Br, I, CH₃, CF₃ or CH₃—O—.

16. The compound, the pharmaceutically acceptable salt thereof or the tautomer thereof according to claim 1, wherein R₄ and R₅ are independently selected from H, F, Cl, Br, I, CH₃, CH₃CH₂— and CH₃—O—.

17. The compound, the pharmaceutically acceptable salt thereof or the tautomer thereof according to claim 1, wherein the structural unit

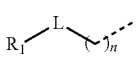

is selected from H, CH₃, NH₂,

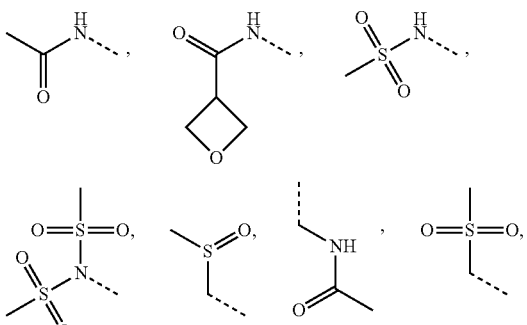

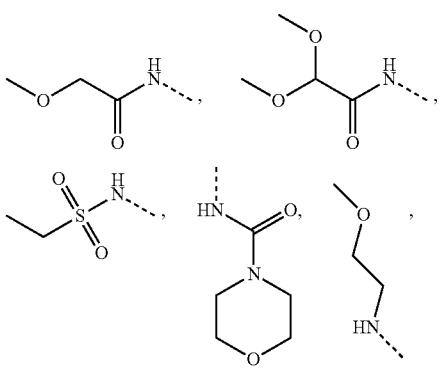

-continued
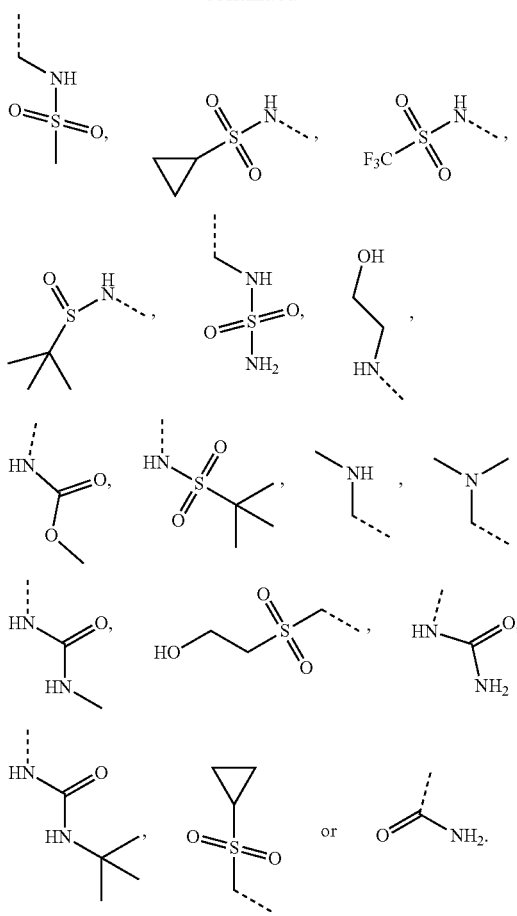
18. The compound, the pharmaceutically acceptable salt thereof or the tautomer thereof according to claim 1, wherein the structural unit
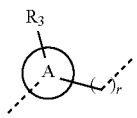
is selected from
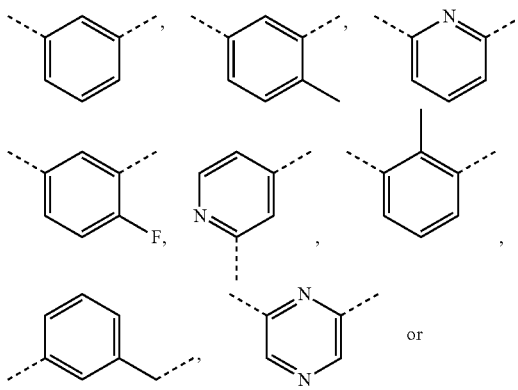
-continued
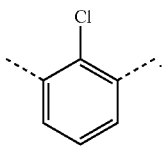
19. The compound, the pharmaceutically acceptable salt thereof or the tautomer thereof according to claim 1, which is selected from
(I-1)
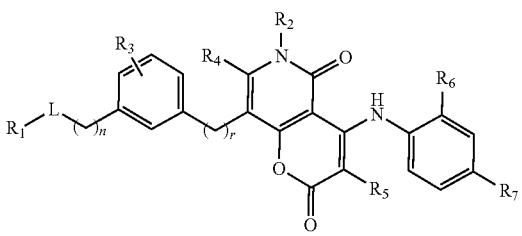
(I-2)
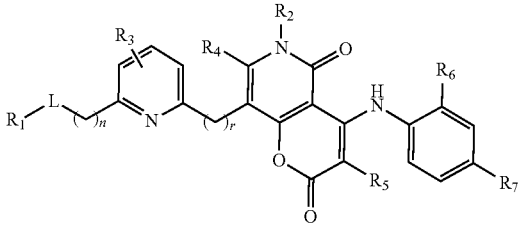
(I-3)
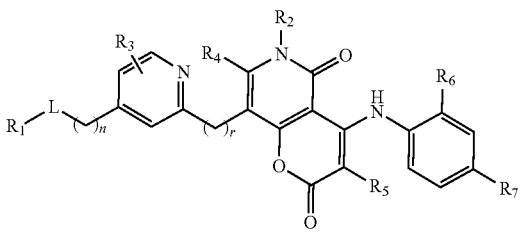
(I-4)
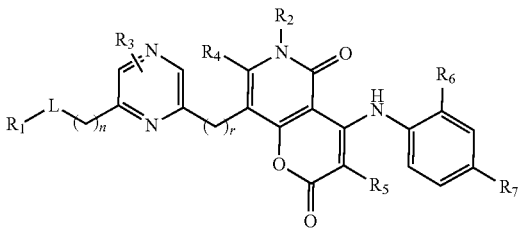
(I-5)
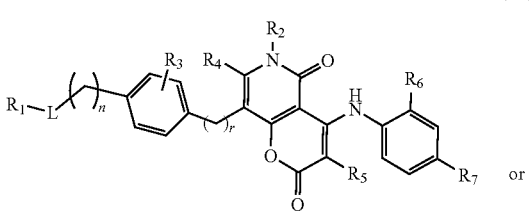
or -continued
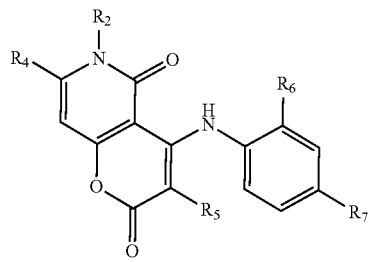
(I-6)
wherein, $R_1$, $R_2$, $R_3$, $R_4$, $R_5$, $R_6$, $R_7$, L, r and n are as defined in claim 1.
20. A compound, a pharmaceutically acceptable salt thereof or a tautomer thereof, wherein the compound is selected from
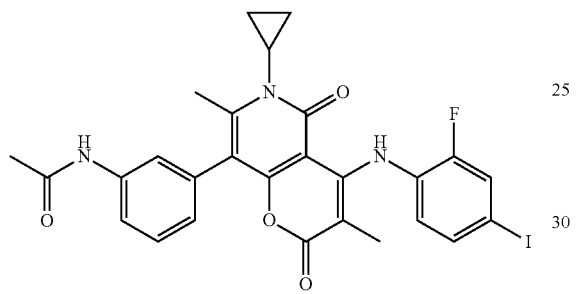
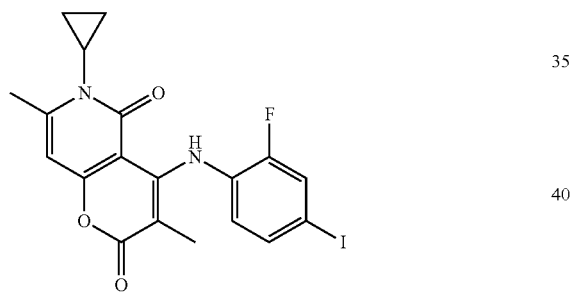
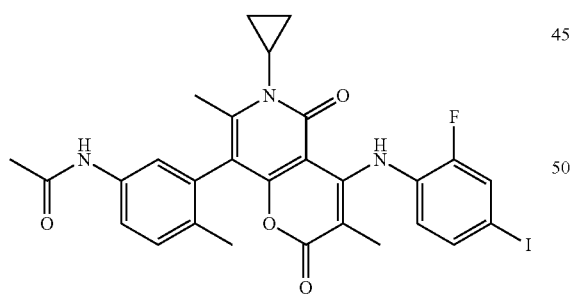
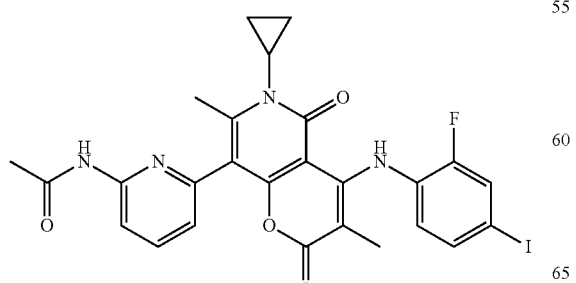
-continued
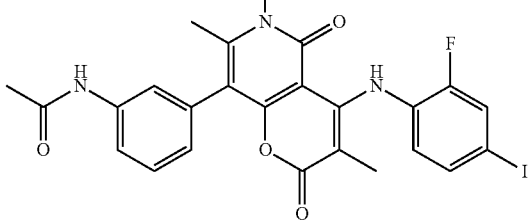
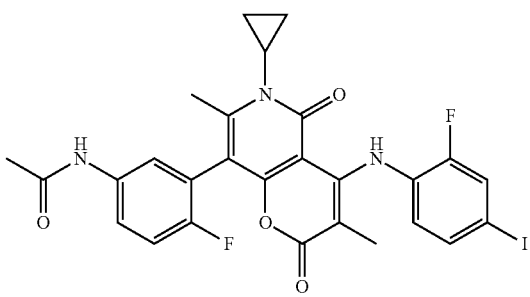
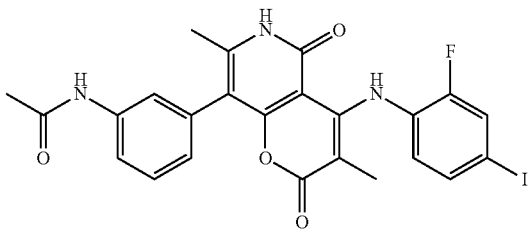
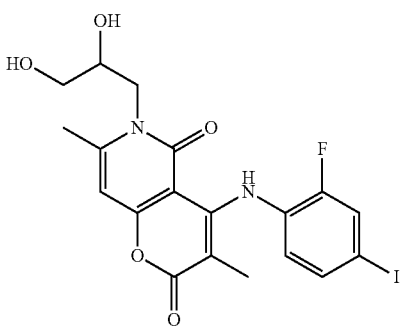
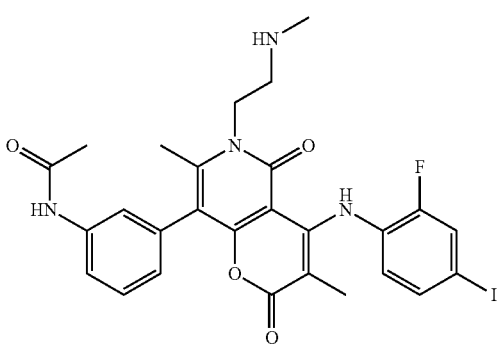

169
-continued
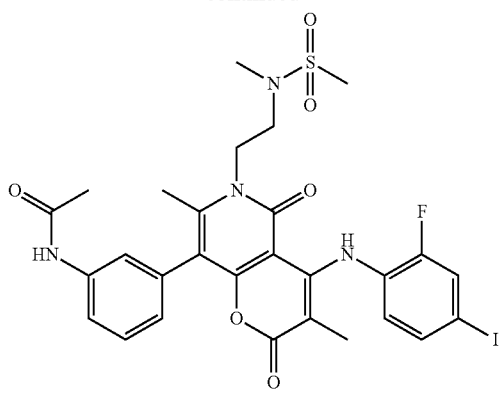
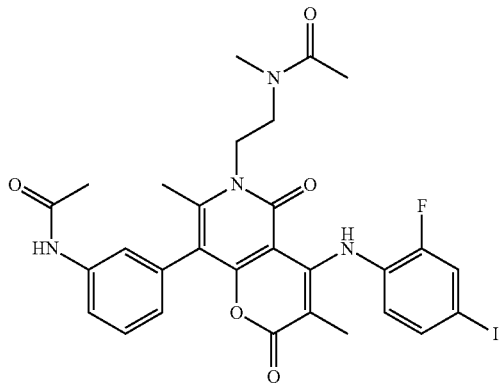
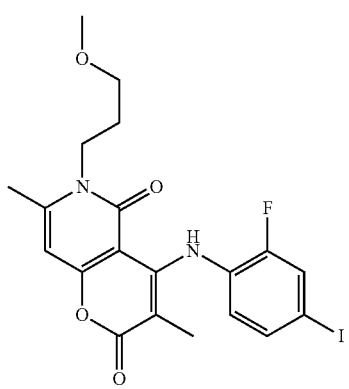
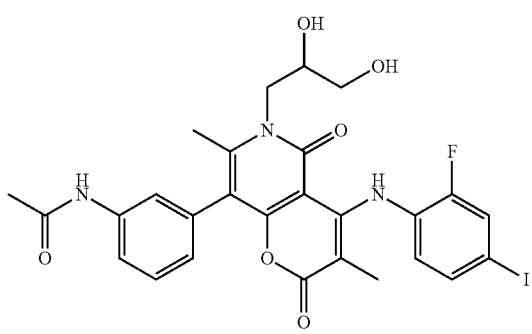
170
-continued
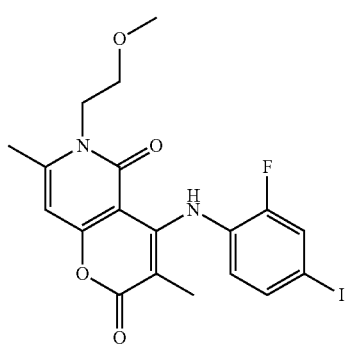
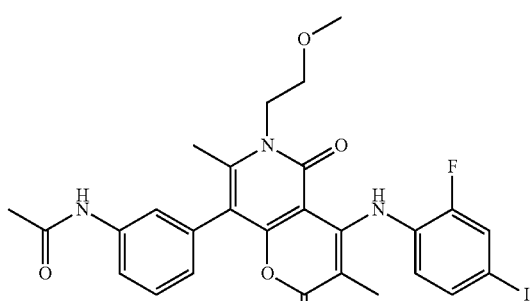
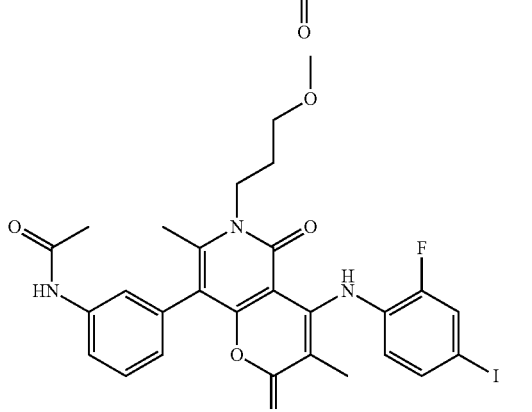
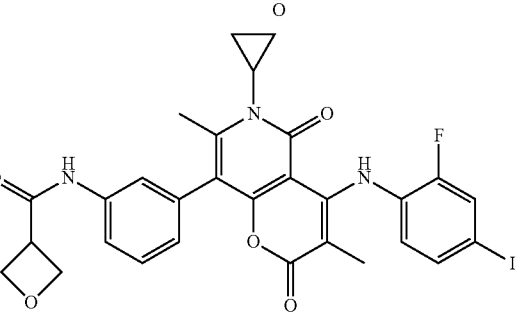

171
-continued
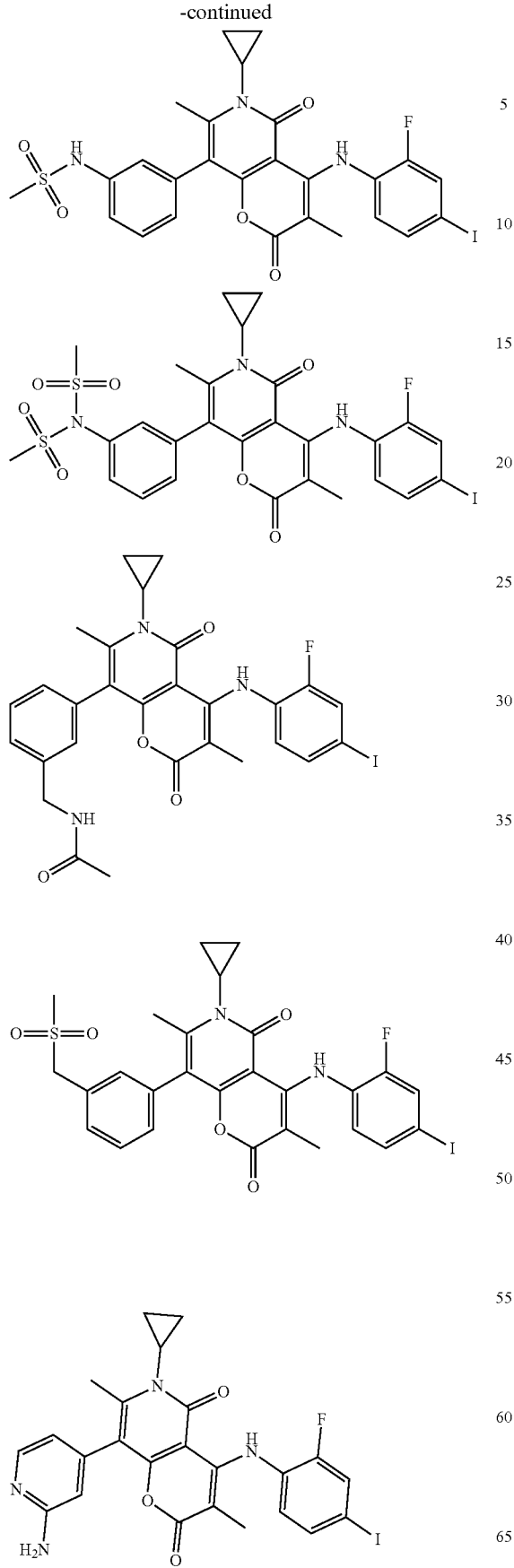
172
-continued
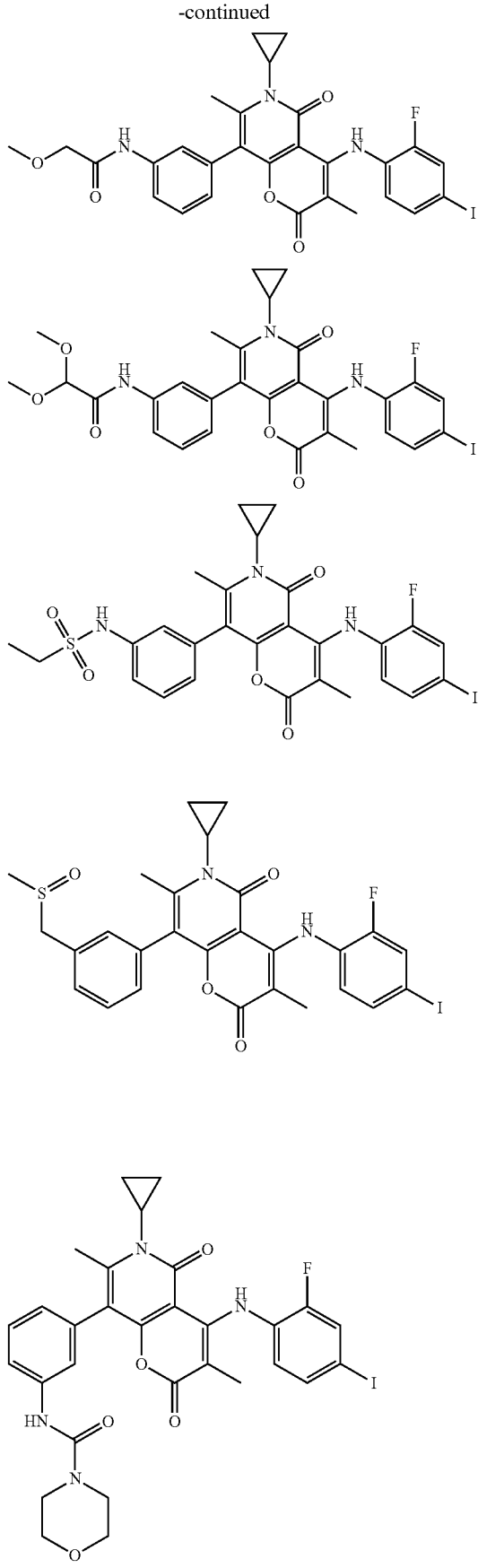

173
-continued
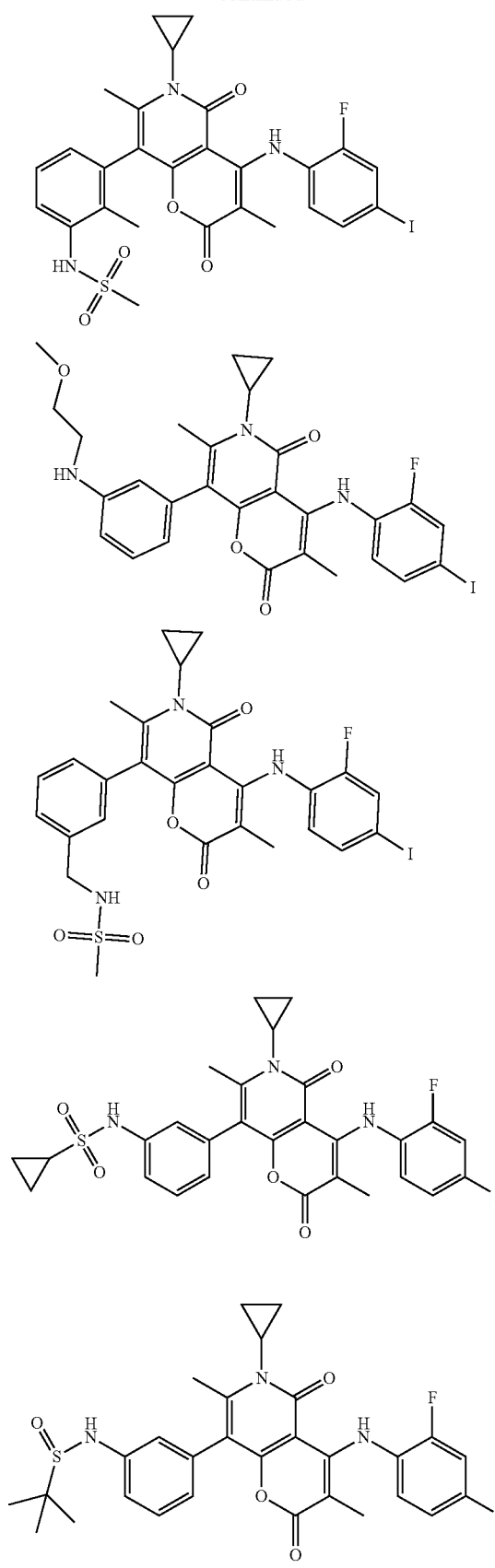
174
-continued
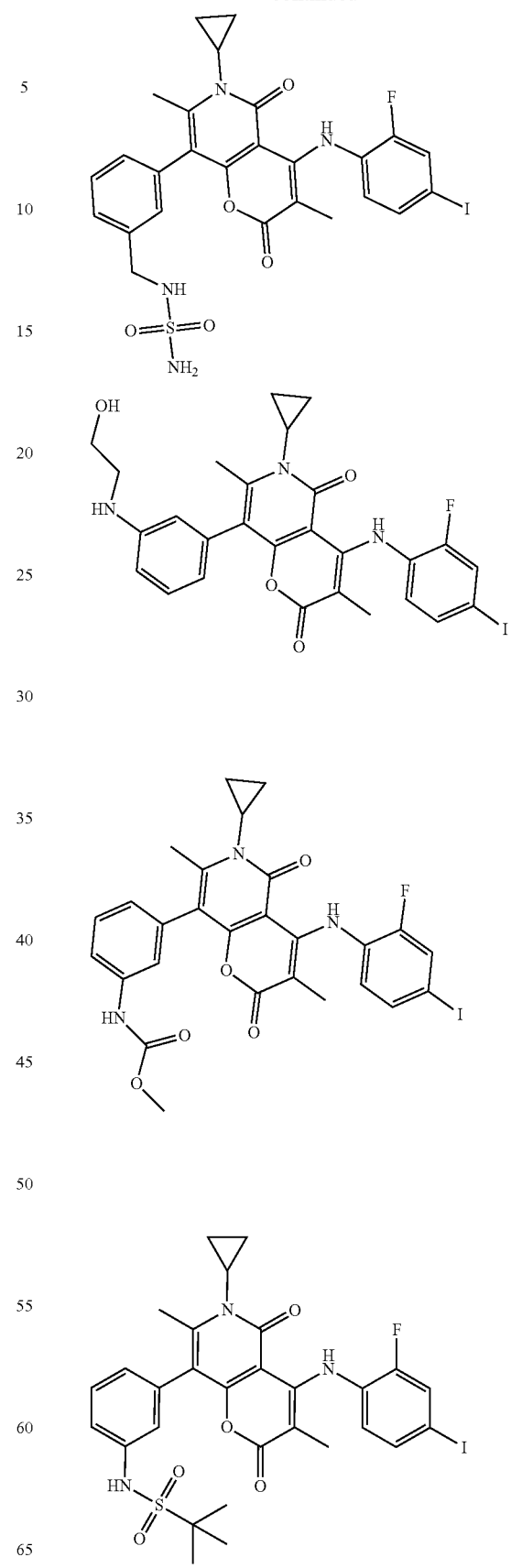

175
-continued
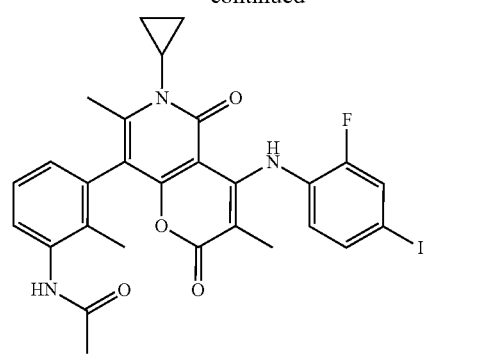
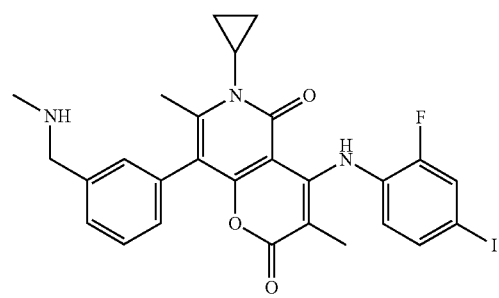
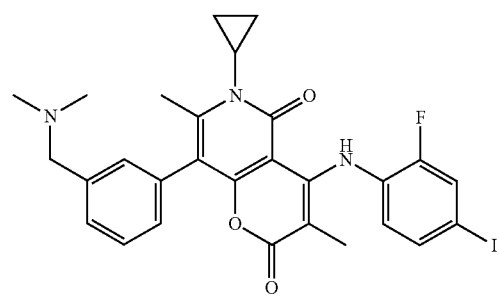
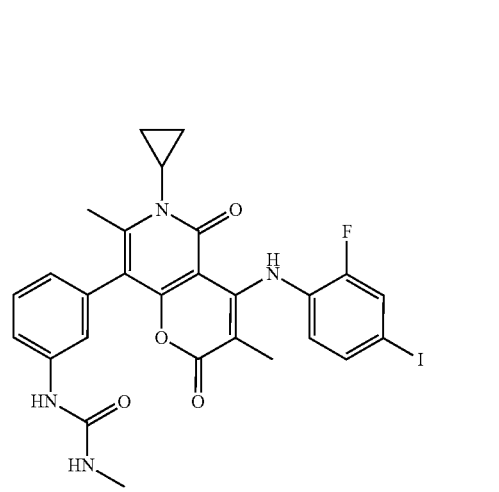
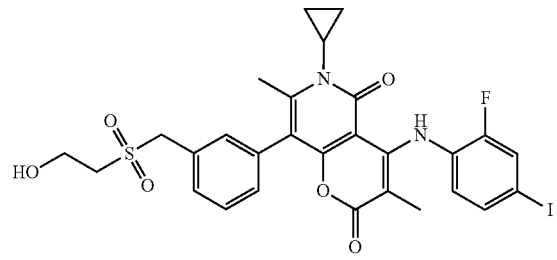
176
-continued
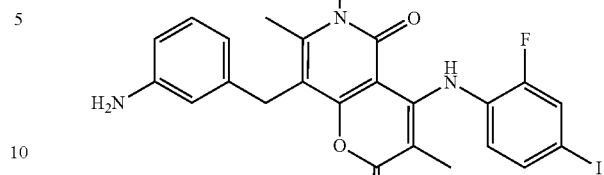
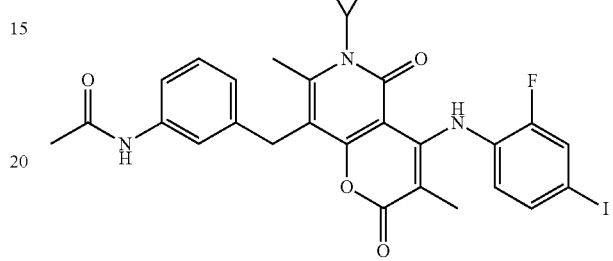
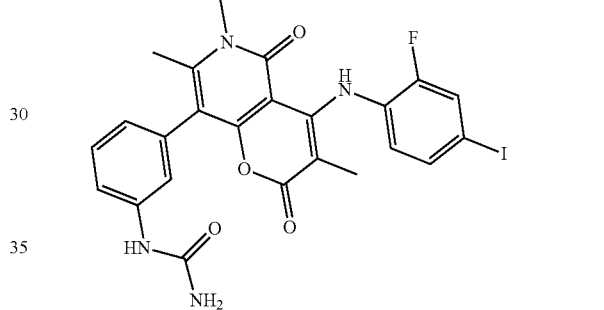
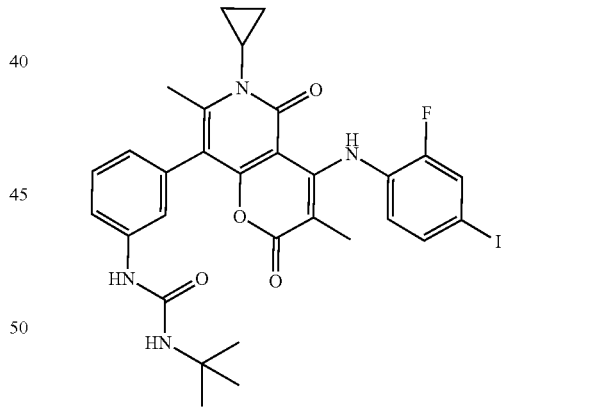
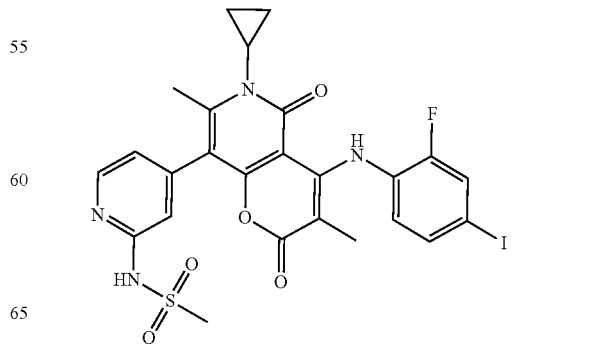

-continued
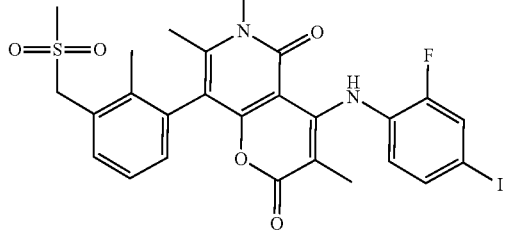
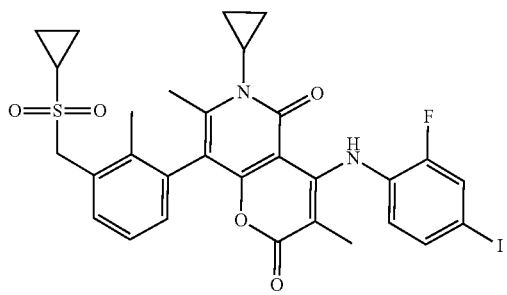
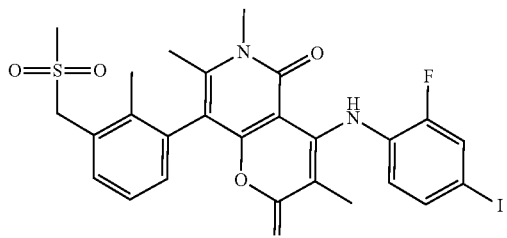
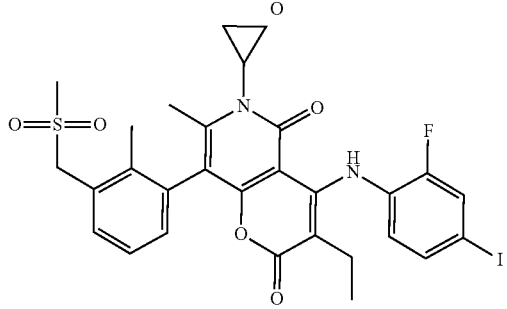
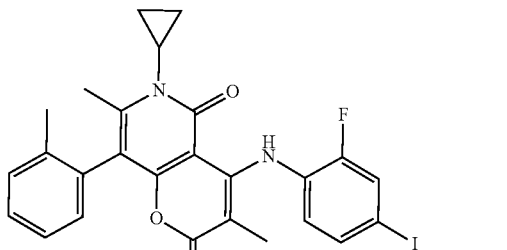
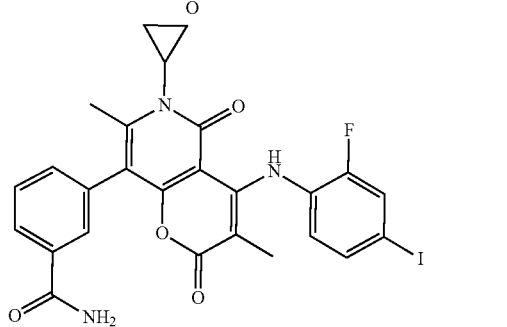
-continued
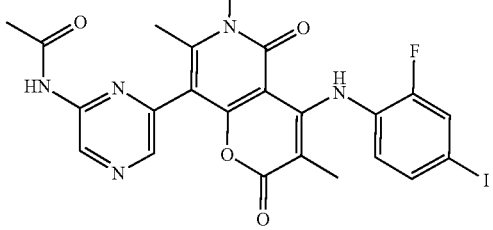
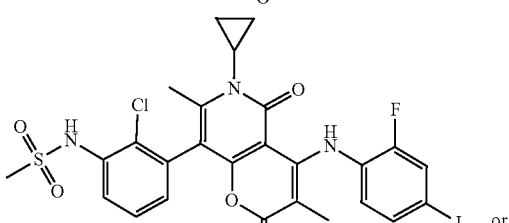
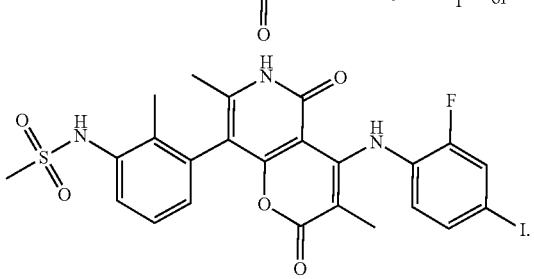 or
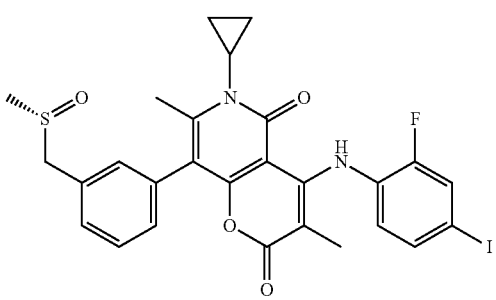
21. The compound according to claim 20, which is selected from
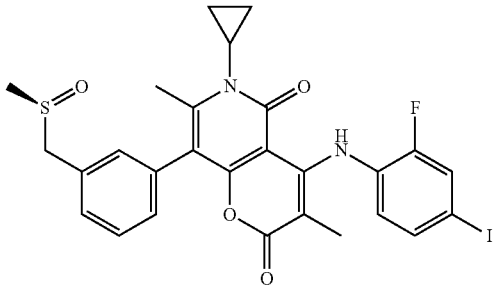
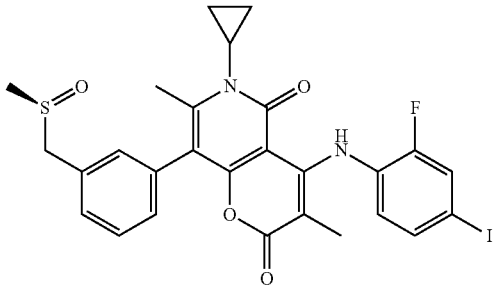

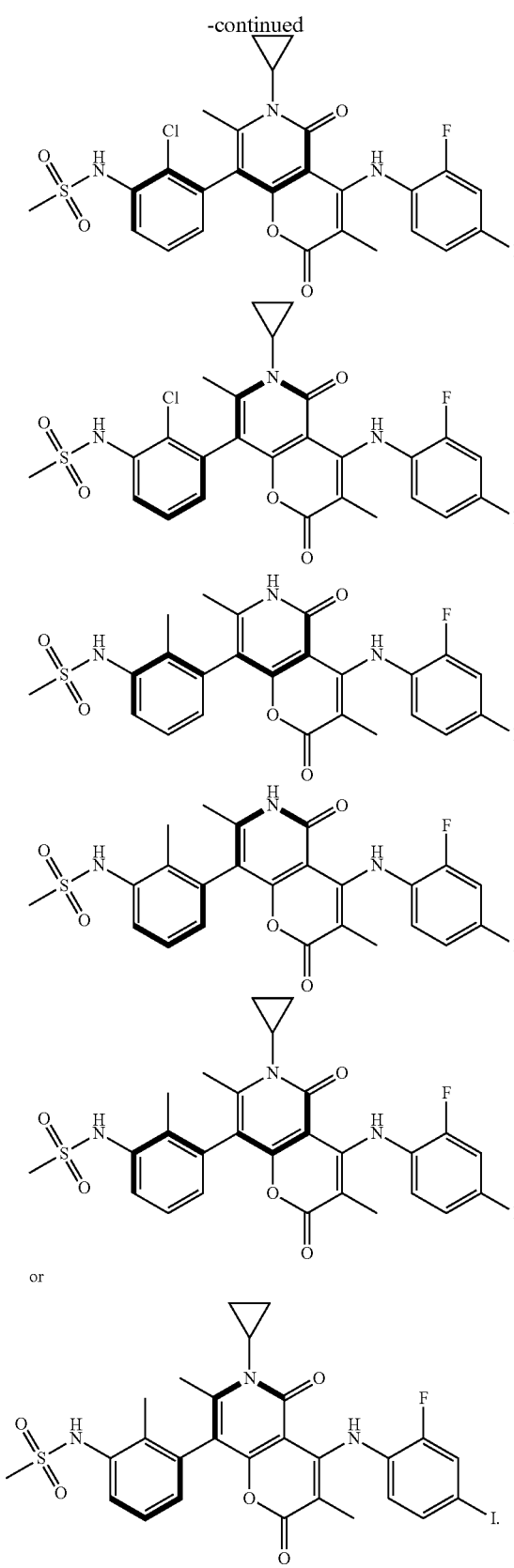

or

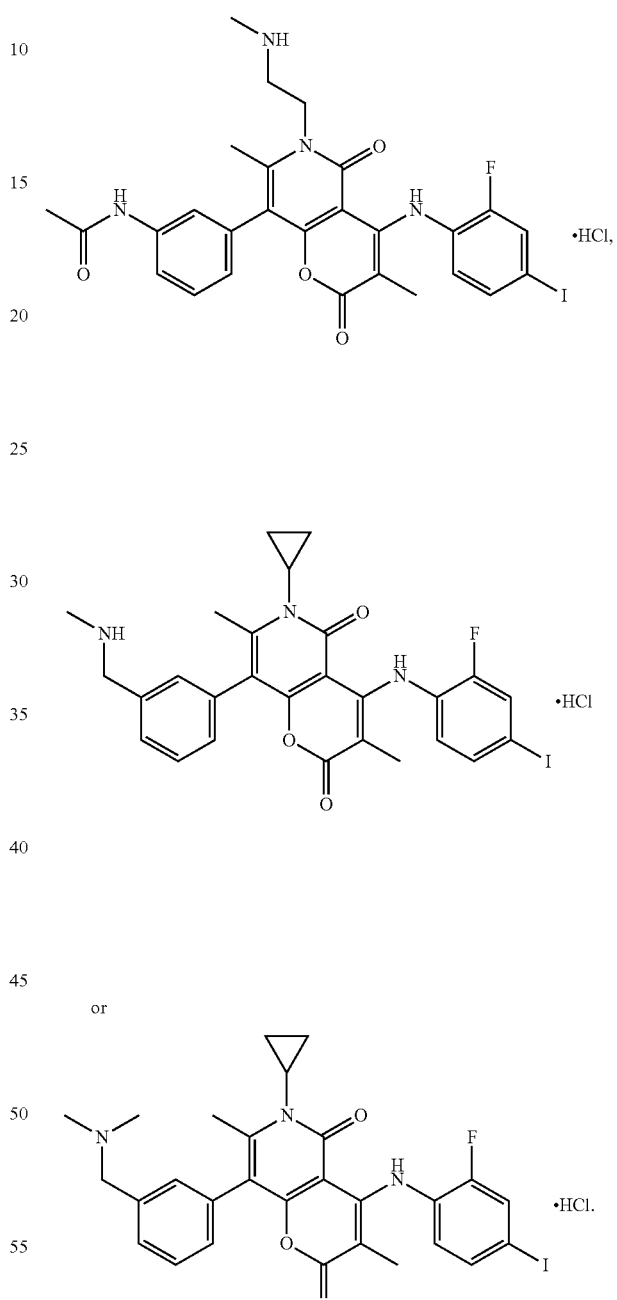

22. The compound, the pharmaceutically acceptable salt thereof or the tautomer thereof according to claim 1, wherein the salt is selected from hydrochloride or formate.

23. The compound, the pharmaceutically acceptable salt thereof or the tautomer thereof according to claim 22, wherein the hydrochloride is selected from or 24. A pharmaceutical composition comprising a therapeutically effective amount of the compound or the pharmaceutically acceptable salt thereof according to claim 1 as an active ingredient and a pharmaceutically acceptable carrier.

* * * * *